United States Patent
Roffler et al.

(10) Patent No.: US 11,369,690 B2
(45) Date of Patent: *Jun. 28, 2022

(54) BI-SPECIFIC ANTIBODIES AND USES THEREOF

(71) Applicants: ACADEMIA SINICA, Taipei (TW); KAOHSIUNG MEDICAL UNIVERSITY, Kaohsiung (TW)

(72) Inventors: Steven R Roffler, Taipei (TW); Tian-Lu Cheng, Kaohsiung (TW); Chien-Han Kao, Kaohsiung (TW); Bing-Mae Chen, Taipei (TW); Yu-Cheng Su, Taipei (TW); Hsin-Yi Tung, Taipei (TW); Kuo-Hsiang Chuang, Taipei (TW)

(73) Assignee: ACADEMIA SINICA & KAOHSIUNG MEDICAL UNIVERSITY, Taipei (TW)

( * ) Notice: Subject to any disclaimer, the term of this patent is extended or adjusted under 35 U.S.C. 154(b) by 797 days.

This patent is subject to a terminal disclaimer.

(21) Appl. No.: 16/111,250

(22) Filed: Aug. 24, 2018

(65) Prior Publication Data

US 2020/0061205 A1 Feb. 27, 2020

Related U.S. Application Data

(63) Continuation of application No. 15/123,243, filed as application No. PCT/US2015/018365 on Mar. 2, 2015, now Pat. No. 10,188,742.

(60) Provisional application No. 61/946,980, filed on Mar. 3, 2014, provisional application No. 61/946,997, filed on Mar. 3, 2014.

(51) Int. Cl.
| | | |
|---|---|---|
| *C07K 16/00* | (2006.01) | |
| *A61K 39/00* | (2006.01) | |
| *A61K 47/68* | (2017.01) | |
| *A61P 35/00* | (2006.01) | |
| *C07K 16/32* | (2006.01) | |
| *A61K 39/395* | (2006.01) | |
| *C07K 16/28* | (2006.01) | |
| *C07K 16/26* | (2006.01) | |
| *A61K 47/14* | (2017.01) | |
| *A61K 47/69* | (2017.01) | |
| *A61K 45/06* | (2006.01) | |

(52) U.S. Cl.
CPC .... *A61K 47/6897* (2017.08); *A61K 39/39558* (2013.01); *A61K 47/14* (2013.01); *A61K 47/6929* (2017.08); *A61P 35/00* (2018.01); *C07K 16/26* (2013.01); *C07K 16/2863* (2013.01); *C07K 16/2869* (2013.01); *C07K 16/2887* (2013.01); *C07K 16/2896* (2013.01); *C07K 16/32* (2013.01); *A61K 45/06* (2013.01); *A61K 2300/00* (2013.01)

(58) Field of Classification Search
CPC .......... A61K 47/6897; A61K 39/39558; A61K 47/6929; A61K 47/6851; A61K 47/6845; A61P 35/00; C07K 16/32; C07K 16/2863
See application file for complete search history.

(56) References Cited

U.S. PATENT DOCUMENTS

2016/0108123 A1* 4/2016 Freeman ................ A61P 35/00
424/85.2

* cited by examiner

*Primary Examiner* — Lei Yao
(74) *Attorney, Agent, or Firm* — Hannah Tien

(57) ABSTRACT

Disclosed herein is a bi-specific antibody that specifically directs a therapeutic agent to a cancer cell by targeting a tumor antigen of the cancer cell, and thereby suppressing the growth of the cancer or blocking the invasion or metastasis of the cancer. The bi-specific antibody of the present disclosure includes a first antigen binding site that binds to polyethylene glycol (PEG); and a second antigen binding site that binds to a target ligand, such as a tumor antigen.

11 Claims, 60 Drawing Sheets

Specification includes a Sequence Listing.

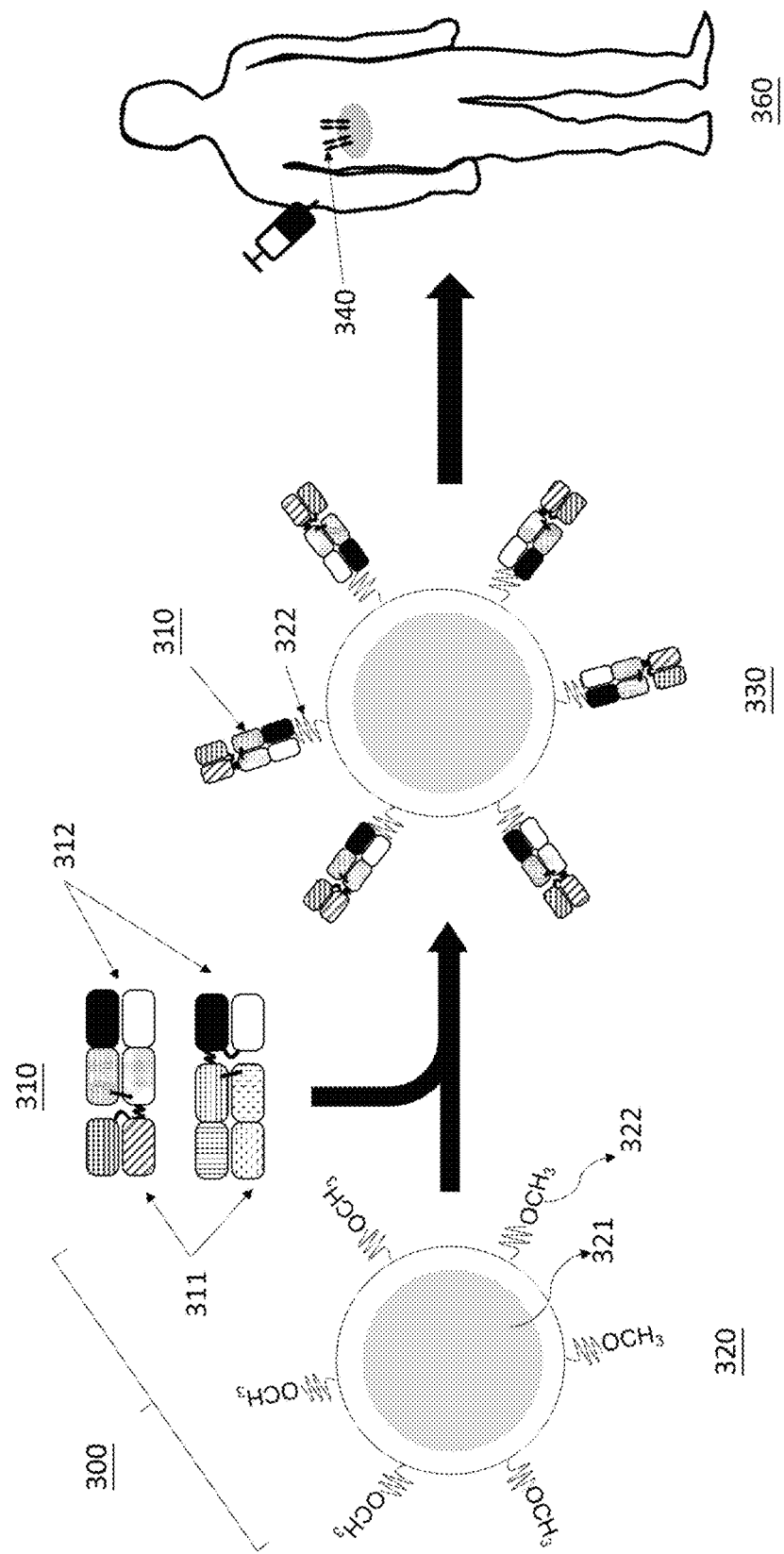

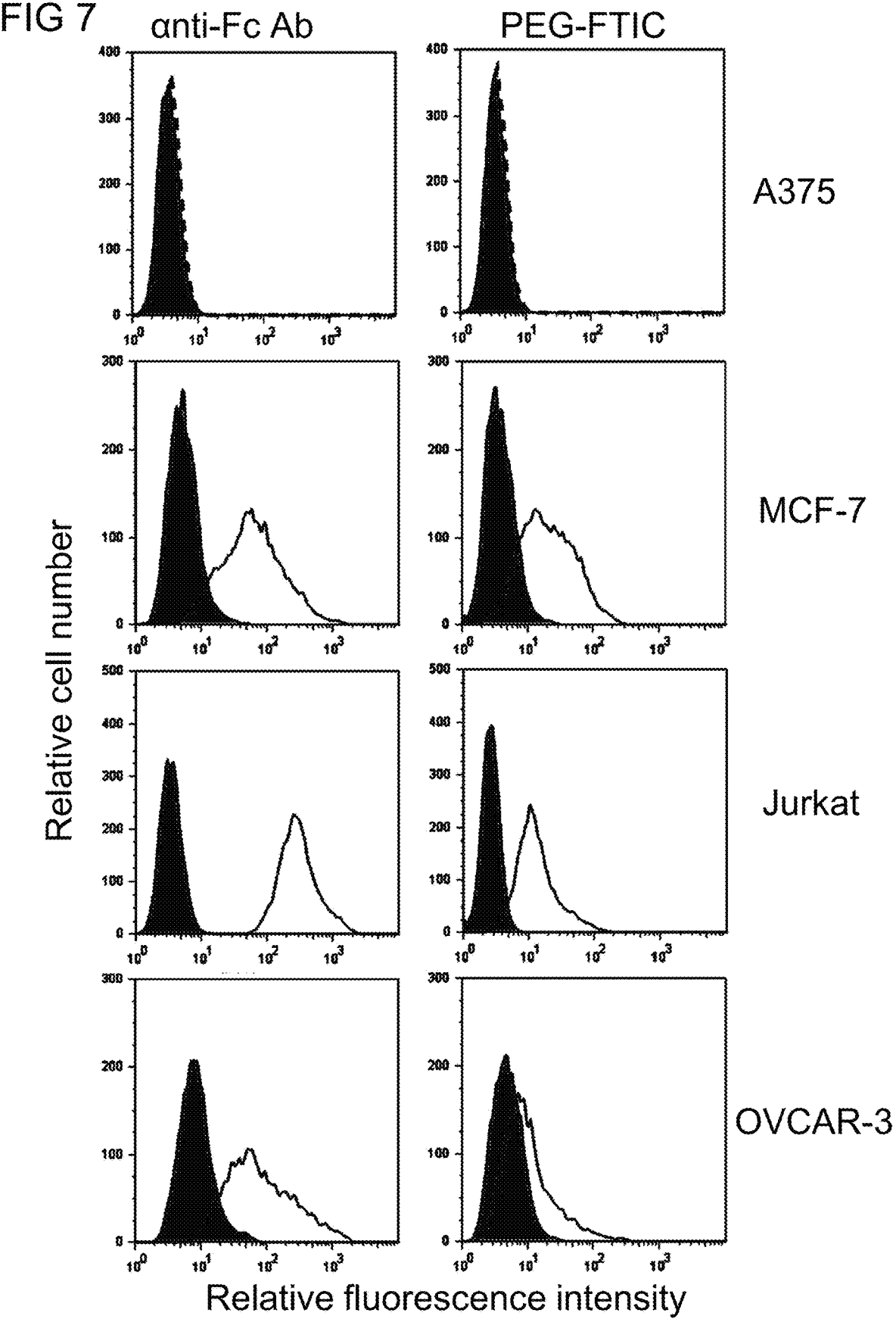

Relative fluorescence intensity (tumor antigen-binding)

Relative fluorescence intensity (PEG-lioposome binding)

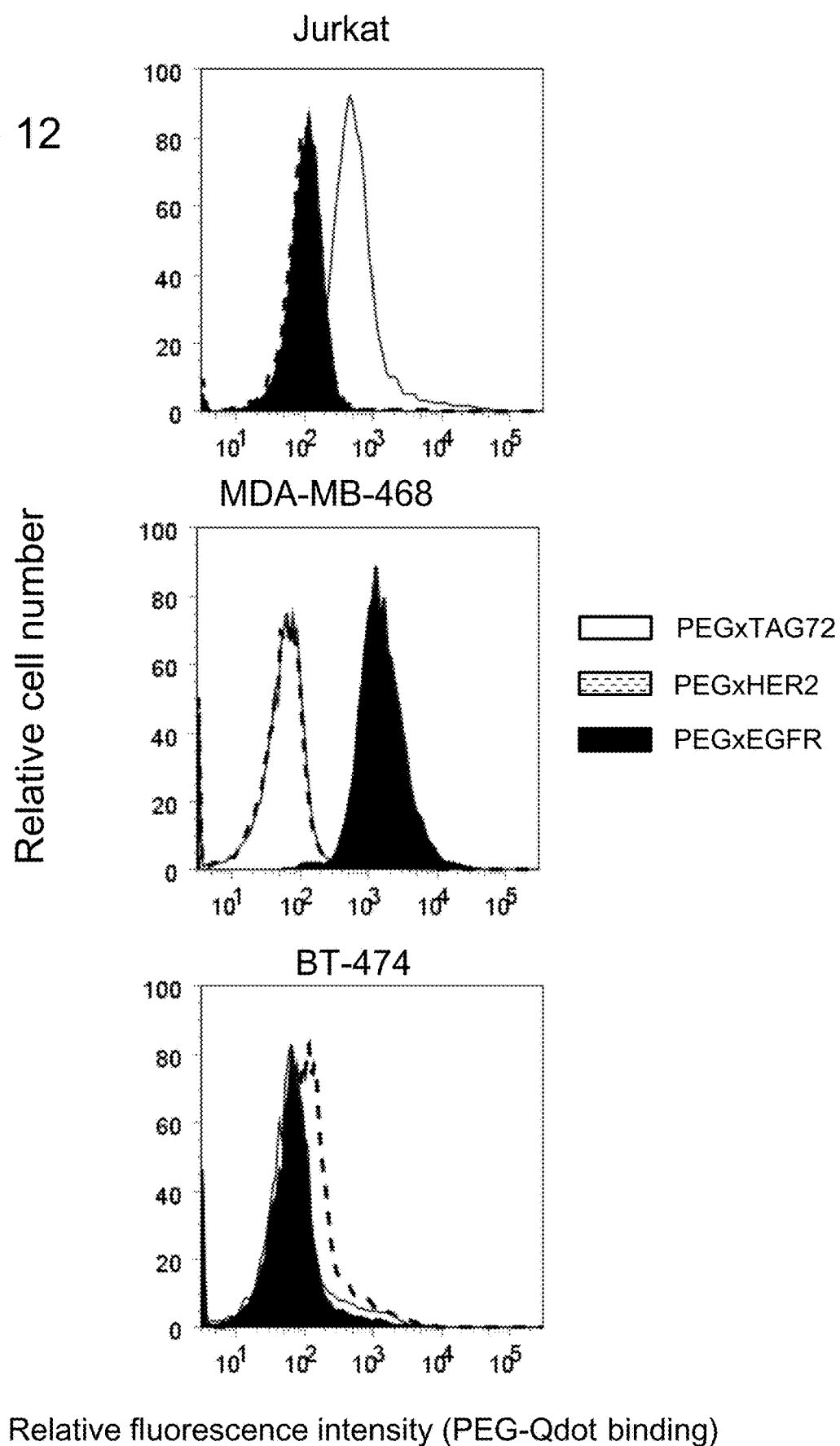

FIG 13A
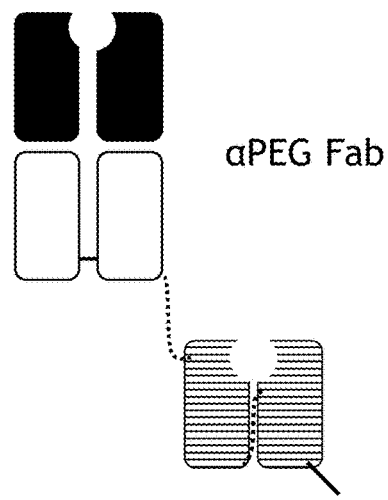
aPEG Fab
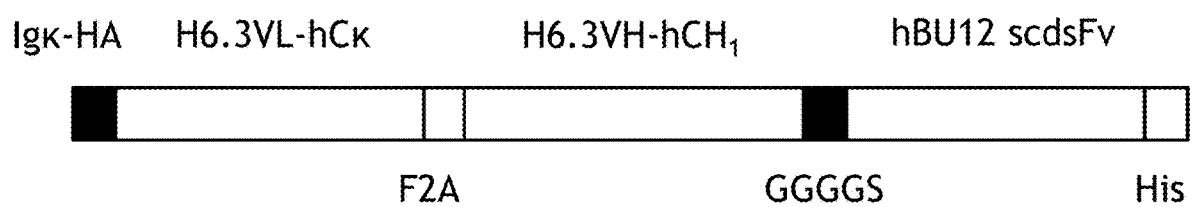
Igκ-HA  H6.3VL-hCκ    H6.3VH-hCH₁    hBU12 scdsFv
F2A            GGGGS          His
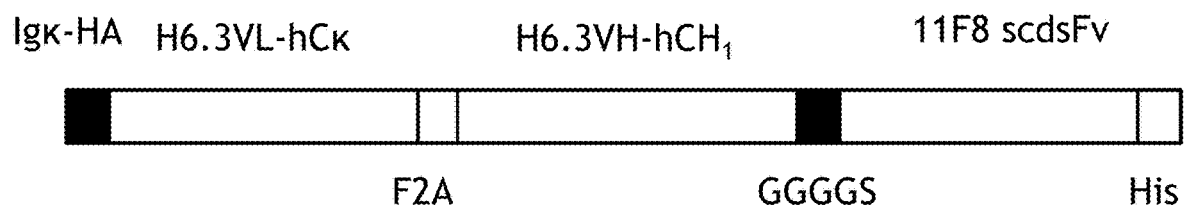
Igκ-HA  H6.3VL-hCκ    H6.3VH-hCH₁    11F8 scdsFv
F2A            GGGGS          His FIG 24B
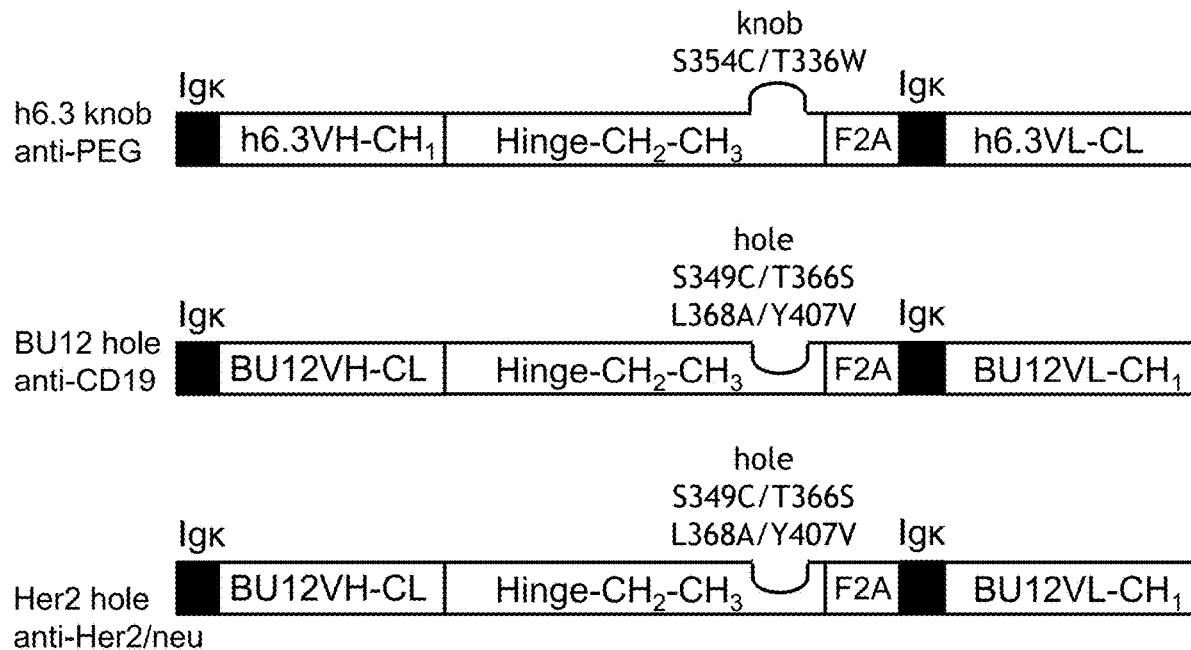
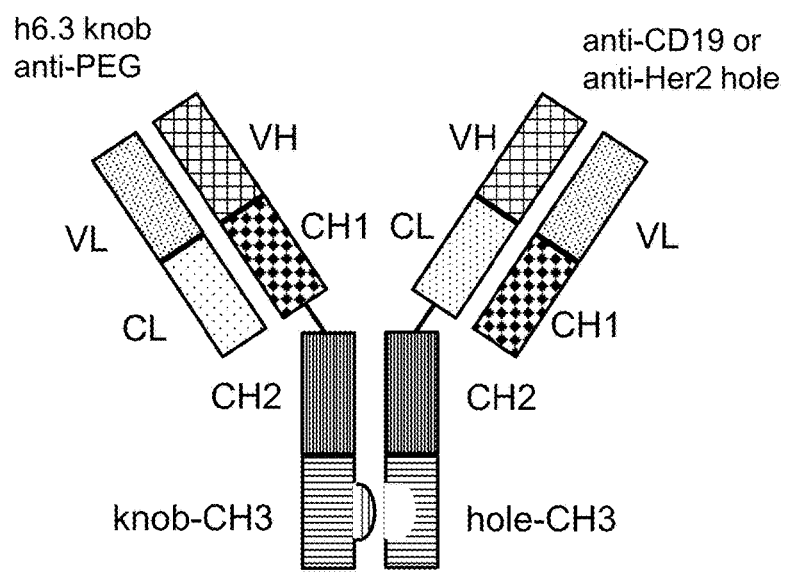

FIG 29

Herceptin/h-α PEG

| LS | HA | anti-HER2 L | F2A | anti-HER2 H | L | anti-mPEG scFv |

Erbitux/h-α PEG

| LS | HA | anti-EGFR L | F2A | anti-EGFR H | L | anti-mPEG scFv |

SEQUENCE LISTING

```
<160> NUMBER OF SEQ ID NOS: 226

<210> SEQ ID NO 1
<211> LENGTH: 219
<212> TYPE: PRT
<213> ORGANISM: Artificial Sequence
<220> FEATURE:
<223> OTHER INFORMATION: Humanized E11 VL-Ck

<400> SEQUENCE: 1

Asp Val Val Met Thr Gln Ser Pro Leu Ser Leu Pro Val Thr Leu Gly
1               5                   10                  15

Gln Pro Ala Ser Ile Ser Cys Arg Ser Ser Lys Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Lys Arg Met Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Ser His Val Pro Pro Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 2
<211> LENGTH: 217
```

```
<212> TYPE: PRT
<213> ORGANISM: Artificial Sequence
<220> FEATURE:
<223> OTHER INFORMATION: Humanized E11 VH-CH1

<400> SEQUENCE: 2
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Met Asn Trp Val Arg Gln Ala Pro Gly Gln Gly Leu Glu Trp Met
        35                  40                  45

Gly Tyr Ile Ile Pro Ser Ser Gly Tyr Val Asp Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Ser Leu Asp Gly Tyr Phe Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val
    210                 215

```
<210> SEQ ID NO 3
<211> LENGTH: 232
<212> TYPE: PRT
<213> ORGANISM: Artificial Sequence
<220> FEATURE:
<223> OTHER INFORMATION: Hinge CH2-CH3

<400> SEQUENCE: 3
```

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 4
<211> LENGTH: 23
<212> TYPE: PRT
<213> ORGANISM: Artificial Sequence
<220> FEATURE:
<223> OTHER INFORMATION: Peptide Linker

<400> SEQUENCE: 4

Val Asp Leu Val Thr Val Ser Ser Ala Ser Thr Gly Gly Ser Gly
1               5                   10                  15

Gln Leu Gly Gly Gly Gly Ser
            20

<210> SEQ ID NO 5
<211> LENGTH: 243
<212> TYPE: PRT
<213> ORGANISM: Artificial Sequence
<220> FEATURE:
<223> OTHER INFORMATION: Hcc49 dsFv

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Cys Leu Glu Trp Met
            35                  40                  45

Gly Tyr Phe Ser Pro Gly Asn Asp Asp Phe Lys Tyr Ser Gln Lys Phe
        50                  55                  60

Gln Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Ile Met Gln Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Ser Pro Asp Ser Leu Ala Val Ser
    130                 135                 140

Leu Gly Glu Arg Ala Thr Ile Asn Cys Lys Ser Ser Gln Ser Val Leu
```

```
                145                 150                 155                 160
Tyr Ser Ser Asn Asn Lys Asn Tyr Leu Ala Trp Tyr Gln Gln Lys Pro
                    165                 170                 175

Gly Gln Pro Pro Lys Leu Leu Ile Tyr Trp Ala Ser Thr Arg Glu Ser
                180                 185                 190

Gly Val Pro Asp Arg Phe Ser Gly Ser Gly Ser Gly Thr Asp Phe Thr
                195                 200                 205

Leu Thr Ile Ser Ser Leu Gln Ala Glu Asp Val Ala Val Tyr Tyr Cys
            210                 215                 220

Gln Gln Tyr Tyr Ser Tyr Pro Leu Thr Phe Gly Cys Gly Thr Lys Val
225                 230                 235                 240

Glu Ile Lys

<210> SEQ ID NO 6
<211> LENGTH: 8
<212> TYPE: PRT
<213> ORGANISM: Artificial Sequence
<220> FEATURE:
<223> OTHER INFORMATION: 6xHis Tag

<400> SEQUENCE: 6

Thr Arg His His His His His His
1               5

<210> SEQ ID NO 7
<211> LENGTH: 243
<212> TYPE: PRT
<213> ORGANISM: Artificial Sequence
<220> FEATURE:
<223> OTHER INFORMATION: 11F8 anti-EGFR dsFv

<400> SEQUENCE: 7

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln Pro Pro Gly Lys Cys Leu Glu
            35                  40                  45

Trp Ile Gly Tyr Ile Tyr Tyr Ser Gly Ser Thr Asp Tyr Asn Pro Ser
        50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Glu Ile Val Met Thr Gln Ser Pro
            130                 135                 140

Ala Thr Leu Ser Leu Ser Pro Gly Glu Arg Ala Thr Leu Ser Cys Arg
145                 150                 155                 160

Ala Ser Gln Ser Val Ser Ser Tyr Leu Ala Trp Tyr Gln Gln Lys Pro
                165                 170                 175

Gly Gln Ala Pro Arg Leu Leu Ile Tyr Asp Ala Ser Asn Arg Ala Thr
                180                 185                 190

Gly Ile Pro Ala Arg Phe Ser Gly Ser Gly Ser Gly Thr Asp Phe Thr
```

```
                195                 200                 205
Leu Thr Ile Ser Ser Leu Glu Pro Glu Asp Phe Ala Val Tyr Tyr Cys
            210                 215                 220
His Gln Tyr Gly Ser Thr Pro Leu Thr Phe Gly Cys Gly Thr Lys Ala
225                 230                 235                 240
Glu Ile Lys

<210> SEQ ID NO 8
<211> LENGTH: 255
<212> TYPE: PRT
<213> ORGANISM: Artificial Sequence
<220> FEATURE:
<223> OTHER INFORMATION: C6ML3-9 anti-HER2 dsFv

<400> SEQUENCE: 8

Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Asn Cys Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gln Ser Val Leu Thr Gln Pro Pro Ser Val Ser Ala Ala Pro Gly Gln
145                 150                 155                 160

Lys Val Thr Ile Ser Cys Ser Gly Ser Ser Ser Asn Ile Gly Asn Asn
                165                 170                 175

Tyr Val Ser Trp Tyr Gln Gln Leu Pro Gly Thr Ala Pro Lys Leu Leu
            180                 185                 190

Ile Tyr Asp His Thr Asn Arg Pro Ala Gly Val Pro Asp Arg Phe Ser
        195                 200                 205

Gly Ser Lys Ser Gly Thr Ser Ala Ser Leu Ala Ile Ser Gly Phe Arg
    210                 215                 220

Ser Glu Asp Glu Ala Asp Tyr Tyr Cys Ala Ser Trp Asp Tyr Thr Leu
225                 230                 235                 240

Ser Gly Trp Val Phe Gly Gly Gly Thr Lys Leu Thr Val Leu Gly
                245                 250                 255

<210> SEQ ID NO 9
<211> LENGTH: 155
<212> TYPE: PRT
<213> ORGANISM: Artificial Sequence
<220> FEATURE:
<223> OTHER INFORMATION: Humanized 6.3 VL-Ck

<400> SEQUENCE: 9

Asp Ile Val Met Thr Gln Ser Pro Asp Ser Leu Ala Val Ser Leu Gly
```

```
   1               5                  10                 15
Glu Arg Ala Thr Ile Asn Cys Lys Ser Ser Gln Ser Val Leu Tyr Ser
                20                 25                 30

Ser Asn Gln Met Asn Tyr Leu Ala Trp Tyr Gln Gln Lys Pro Gly Gln
                35                 40                 45

Pro Pro Lys Leu Leu Ile Tyr Trp Ala Ser Thr Arg Glu Ser Gly Val
    50                 55                 60

Pro Asp Arg Phe Ser Gly Ser Gly Ser Gly Thr Asp Phe Thr Leu Thr
65                  70                 75                  80

Ile Ser Ser Leu Gln Ala Glu Asp Val Ala Val Tyr Tyr Cys Leu Gln
                85                 90                 95

Tyr Leu Ser Ser Trp Thr Phe Gly Gly Gly Thr Lys Leu Glu Ile Lys
                100                105                110

Thr Tyr Ser Leu Ser Ser Thr Leu Thr Leu Ser Lys Ala Asp Tyr Glu
                115                120                125

Lys His Lys Leu Tyr Ala Cys Glu Val Thr His Gln Gly Leu Ser Ser
                130                135                140

Pro Val Thr Lys Ser Phe Asn Arg Gly Glu Cys
145                 150                155
```

<210> SEQ ID NO 10
<211> LENGTH: 219
<212> TYPE: PRT
<213> ORGANISM: Artificial Sequence
<220> FEATURE:
<223> OTHER INFORMATION: Humanized 6.3 VH-CH1

<400> SEQUENCE: 10

```
Gln Val Gln Leu Val Gln Ser Gly Ser Glu Leu Lys Lys Pro Gly Ala
1               5                  10                 15

Ser Val Lys Val Ser Cys Lys Ala Ser Gly Tyr Thr Phe Lys Asn Tyr
                20                 25                 30

Gly Met Asn Trp Val Arg Gln Ala Pro Gly Gln Gly Leu Glu Trp Met
                35                 40                 45

Gly Trp Ile Asn Thr Tyr Thr Gly Gln Pro Ile Tyr Ala Asn Asp Phe
    50                 55                 60

Lys Gly Arg Phe Val Phe Ser Leu Asp Thr Ser Val Ser Thr Ala Tyr
65                  70                 75                  80

Leu Gln Ile Ser Ser Leu Lys Ala Glu Asp Thr Ala Val Tyr Tyr Cys
                85                 90                 95

Ala Arg Asp Trp Gly Pro Tyr Trp Gly Gln Gly Thr Leu Val Thr Val
                100                105                110

Ser Ser Ala Ser Thr Lys Gly Pro Ser Val Phe Pro Leu Ala Pro Ser
                115                120                125

Ser Lys Ser Thr Ser Gly Gly Thr Ala Ala Leu Gly Cys Leu Val Lys
                130                135                140

Asp Tyr Phe Pro Glu Pro Val Thr Val Ser Trp Asn Ser Gly Ala Leu
145                 150                155                160

Thr Ser Gly Val His Thr Phe Pro Ala Val Leu Gln Ser Ser Gly Leu
                165                170                175

Tyr Ser Leu Ser Ser Val Val Thr Val Pro Ser Ser Ser Leu Gly Thr
                180                185                190

Gln Thr Tyr Ile Cys Asn Val Asn His Lys Pro Ser Asn Thr Lys Val
                195                200                205

Asp Lys Arg Val Glu Pro Lys Ser Cys Asp Lys
```

<210> SEQ ID NO 11
<211> LENGTH: 242
<212> TYPE: PRT
<213> ORGANISM: Artificial Sequence
<220> FEATURE:
<223> OTHER INFORMATION: hBU12 dsFv

<400> SEQUENCE: 11

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Cys Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Glu Ile Val Leu Thr Gln Ser Pro Ala
        130                 135                 140

Thr Leu Ser Leu Ser Pro Gly Glu Arg Ala Thr Leu Ser Cys Ser Ala
145                 150                 155                 160

Ser Ser Ser Val Ser Tyr Met His Trp Tyr Gln Gln Lys Pro Gly Gln
                165                 170                 175

Ala Pro Arg Leu Leu Ile Tyr Asp Thr Ser Lys Leu Ala Ser Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Val Ala Val Tyr Tyr Cys Phe Gln
    210                 215                 220

Gly Ser Val Tyr Pro Phe Thr Phe Gly Cys Gly Thr Lys Leu Glu Ile
225                 230                 235                 240

Lys Arg
```

<210> SEQ ID NO 12
<211> LENGTH: 214
<212> TYPE: PRT
<213> ORGANISM: Artificial Sequence
<220> FEATURE:
<223> OTHER INFORMATION: Humanized 15-2b VL-Ck

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ser
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
```

```
                    50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln Tyr Ile Asn Tyr Pro Tyr
                     85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 13
<211> LENGTH: 215
<212> TYPE: PRT
<213> ORGANISM: Artificial Sequence
<220> FEATURE:
<223> OTHER INFORMATION: Humanized 15-2b VH-CH1

<400> SEQUENCE: 13

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Thr Phe Ser Asn Tyr
                 20                  25                  30

Trp Met Asn Trp Val Arg Gln Ala Ser Gly Lys Gly Leu Glu Trp Val
             35                  40                  45

Gly Glu Ile Arg Ser Lys Ser Asn Asn Tyr Ala Thr His Tyr Ala Glu
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Ser Asn Arg Tyr Tyr Trp Gly Gln Gly Thr Leu Val Thr Val
                100                 105                 110

Ser Ser Ala Ser Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Asn Phe Gly Thr
            180                 185                 190

Gln Thr Tyr Thr Cys Asn Val Asp His Lys Pro Ser Asn Thr Lys Val
```

-continued

```
                   195                 200                 205
Asp Lys Thr Val Glu Arg Lys
    210                 215

<210> SEQ ID NO 14
<211> LENGTH: 28
<212> TYPE: PRT
<213> ORGANISM: Artificial Sequence
<220> FEATURE:
<223> OTHER INFORMATION: G-MYC-(G4S)3 Linker

<400> SEQUENCE: 14

Gly Glu Gln Lys Leu Ile Ser Glu Glu Asp Leu Gly Gly Gly Gly Ser
1               5                   10                  15

Gly Gly Gly Gly Ser Gly Gly Gly Gly Ser Gln Leu
            20                  25

<210> SEQ ID NO 15
<211> LENGTH: 255
<212> TYPE: PRT
<213> ORGANISM: Artificial Sequence
<220> FEATURE:
<223> OTHER INFORMATION: C6ML3-9 (Anti-HER2) scFv

<400> SEQUENCE: 15

Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gln Ser Val Leu Thr Gln Pro Pro Ser Val Ser Ala Ala Pro Gly Gln
145                 150                 155                 160

Lys Val Thr Ile Ser Cys Ser Gly Ser Ser Ser Asn Ile Gly Asn Asn
                165                 170                 175

Tyr Val Ser Trp Tyr Gln Gln Leu Pro Gly Thr Ala Pro Lys Leu Leu
            180                 185                 190

Ile Tyr Asp His Thr Asn Arg Pro Ala Gly Val Pro Asp Arg Phe Ser
        195                 200                 205

Gly Ser Lys Ser Gly Thr Ser Ala Ser Leu Ala Ile Ser Gly Phe Arg
    210                 215                 220

Ser Glu Asp Glu Ala Asp Tyr Tyr Cys Ala Ser Trp Asp Tyr Thr Leu
225                 230                 235                 240

Ser Gly Trp Val Phe Gly Gly Gly Thr Lys Leu Thr Val Leu Gly
                245                 250                 255
```

<210> SEQ ID NO 16
<211> LENGTH: 247
<212> TYPE: PRT
<213> ORGANISM: Artificial Sequence
<220> FEATURE:
<223> OTHER INFORMATION: h528 (Anti-EGFR) scFv

<400> SEQUENCE: 16

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Asn
            20                  25                  30

Asn Gly Ile Thr Tyr Leu Glu Trp Tyr Leu Gln Lys Pro Gly Gln Ser
        35                  40                  45

Pro Gln Leu Leu Ile Tyr Lys Val Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Pro Thr Phe Gly Gln Gly Thr Lys Val Glu Ile Lys
            100                 105                 110

Arg Ala Gly Gly Gly Gly Ser Gly Gly Gly Gly Ser Gly Gly Gly Gly
        115                 120                 125

Ser Gln Val Gln Leu Val Gln Ser Gly Ala Glu Val Lys Lys Pro Gly
    130                 135                 140

Ala Ser Val Lys Val Ser Cys Lys Ala Ser Gly Tyr Thr Phe Thr Ser
145                 150                 155                 160

Tyr Trp Met His Trp Val Arg Gln Ala Pro Gly Gln Gly Leu Glu Trp
                165                 170                 175

Met Gly Asn Ile Tyr Pro Gly Ser Gly Gly Thr Asn Tyr Ala Glu Lys
            180                 185                 190

Phe Lys Asn Arg Val Thr Met Thr Arg Asp Thr Ser Ile Ser Thr Ala
        195                 200                 205

Tyr Met Glu Leu Ser Arg Leu Arg Ser Asp Asp Thr Ala Val Tyr Tyr
    210                 215                 220

Cys Ala Arg Ser Gly Gly Pro Tyr Phe Phe Asp Tyr Trp Gly Gln Gly
225                 230                 235                 240

Thr Leu Val Thr Val Ser Ser
                245

<210> SEQ ID NO 17
<211> LENGTH: 227
<212> TYPE: PRT
<213> ORGANISM: Artificial Sequence
<220> FEATURE:
<223> OTHER INFORMATION: Humanized 15-2b scFv

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ser
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

-continued

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln Tyr Ile Asn Tyr Pro Tyr
                 85                  90                  95

Thr Phe Gly Gln Gly Thr Lys Leu Glu Ile Lys Arg Gly Gly Gly Gly
            100                 105                 110

Ser Glu Val Gln Leu Val Glu Ser Gly Gly Gly Leu Val Gln Pro Gly
            115                 120                 125

Gly Ser Leu Lys Leu Ser Cys Ala Ala Ser Gly Phe Thr Phe Ser Asn
130                 135                 140

Tyr Trp Met Asn Trp Val Arg Gln Ala Ser Gly Lys Gly Leu Glu Trp
145                 150                 155                 160

Val Gly Glu Ile Arg Ser Lys Ser Asn Asn Tyr Ala Thr His Tyr Ala
                165                 170                 175

Glu Ser Val Lys Gly Arg Phe Thr Ile Ser Arg Asp Asp Ser Lys Asn
            180                 185                 190

Thr Ala Tyr Leu Gln Met Asn Ser Leu Lys Thr Glu Asp Thr Ala Val
            195                 200                 205

Tyr Tyr Cys Thr Asn Arg Tyr Tyr Trp Gly Gln Gly Thr Leu Val Thr
210                 215                 220

Val Ser Ser
225

<210> SEQ ID NO 18
<211> LENGTH: 219
<212> TYPE: PRT
<213> ORGANISM: Artificial Sequence
<220> FEATURE:
<223> OTHER INFORMATION: hHB12b (Anti-CD19) VH-CH1

<400> SEQUENCE: 18

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Ser
             20                  25                  30

Trp Met Asn Trp Val Arg Gln Ala Pro Gly Lys Gly Leu Glu Trp Val
         35                  40                  45

Gly Arg Ile Tyr Pro Gly Asp Gly Asp Thr Asn Tyr Asn Gly Lys Phe
     50                  55                  60

Lys Gly Arg Phe Thr Ile Ser Arg Asp Asp Ser Lys Asn Ser Leu Tyr
 65                  70                  75                  80

Leu Gln Met Asn Ser Leu Lys Thr Glu Asp Thr Ala Val Tyr Tyr Cys
                 85                  90                  95

Ala Arg Ser Gly Phe Ile Thr Thr Val Leu Asp Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

Pro Ser Ser Leu Gly Thr Gln Thr Tyr Ile Cys Asn Val Asn His
    195                 200                 205

Lys Pro Ser Asn Thr Lys Val Asp Lys Arg Val
    210                 215

<210> SEQ ID NO 19
<211> LENGTH: 217
<212> TYPE: PRT
<213> ORGANISM: Artificial Sequence
<220> FEATURE:
<223> OTHER INFORMATION: hHB12b (Anti-CD19) VL-Ck

<400> SEQUENCE: 19

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Phe Gln Gln Lys Pro Asp Gln Ser Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 20
<211> LENGTH: 239
<212> TYPE: PRT
<213> ORGANISM: Artificial Sequence
<220> FEATURE:
<223> OTHER INFORMATION: 2F2 (Anti-CD20) VH-CH1

<400> SEQUENCE: 20

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asn Asp Tyr Ala Met His Trp Val Arg Gln Ala Pro Gly Lys Gly Leu

```
                    50                  55                  60
Glu Trp Val Ser Thr Ile Ser Trp Asn Ser Gly Ser Ile Gly Tyr Ala
 65                  70                  75                  80

Asp Ser Val Lys Gly Arg Phe Thr Ile Ser Arg Asp Asn Ala Lys Lys
                     85                  90                  95

Ser Leu Tyr Leu Gln Met Asn Ser Leu Arg Ala Glu Asp Thr Ala Leu
                100                 105                 110

Tyr Tyr Cys Ala Lys Asp Ile Gln Tyr Gly Asn Tyr Tyr Tyr Gly Met
                115                 120                 125

Asp Val Trp Gly Gln Gly Thr Thr Val Thr Val Ser Ser Ala Ser Thr
            130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Arg Val
225                 230                 235

<210> SEQ ID NO 21
<211> LENGTH: 233
<212> TYPE: PRT
<213> ORGANISM: Artificial Sequence
<220> FEATURE:
<223> OTHER INFORMATION: 2F2 (Anti-CD20) VL-Ck

<400> SEQUENCE: 21

Met Glu Ala Pro Ala Gln Leu Leu Phe Leu Leu Leu Leu Trp Leu Pro
  1               5                  10                  15

Asp Thr Thr Gly Glu Ile Val Leu Thr Gln Ser Pro Ala Thr Leu Ser
                 20                  25                  30

Leu Ser Pro Gly Glu Arg Ala Thr Leu Ser Cys Arg Ala Ser Gln Ser
                 35                  40                  45

Val Ser Ser Tyr Leu Ala Trp Tyr Gln Gln Lys Pro Gly Gln Ala Pro
 50                  55                  60

Arg Leu Leu Ile Tyr Asp Ala Ser Asn Arg Ala Thr Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln Gln Arg Ser
                100                 105                 110

Asn Trp Pro Ile Thr Phe Gly Gln Gly Thr Arg Leu Glu Ile Lys Thr
                115                 120                 125

Val Ala Ala Pro Ser Val Phe Ile Phe Pro Pro Ser Asp Glu Gln Leu
            130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
```

```
              180                 185                 190
Ser Leu Ser Ser Thr Leu Thr Leu Ser Lys Ala Asp Tyr Glu Lys His
            195                 200                 205

Lys Leu Tyr Ala Cys Glu Val Thr His Gln Gly Leu Ser Ser Pro Val
            210                 215                 220

Thr Lys Ser Phe Asn Arg Gly Glu Cys
225                 230

<210> SEQ ID NO 22
<211> LENGTH: 232
<212> TYPE: PRT
<213> ORGANISM: Artificial Sequence
<220> FEATURE:
<223> OTHER INFORMATION: Knob Hinge CH2-CH3

<400> SEQUENCE: 22

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Cys Arg Asp Glu Leu Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 23
<211> LENGTH: 207
<212> TYPE: PRT
<213> ORGANISM: Artificial Sequence
<220> FEATURE:
<223> OTHER INFORMATION: hBU12 VL-crossover CH1

<400> SEQUENCE: 23

Glu Ile Val Leu Thr Gln Ser Pro Ala Thr Leu Ser Leu Ser Pro Gly
1               5                   10                  15
```

```
Glu Arg Ala Thr Leu Ser Cys Ser Ala Ser Ser Val Ser Tyr Met
                 20                  25                  30

His Trp Tyr Gln Gln Lys Pro Gly Gln Ala Pro Arg Leu Leu Ile Tyr
         35                  40                  45

Asp Thr Ser Lys Leu Ala Ser Gly Ile Pro Ala Arg Phe Ser Gly Ser
     50                  55                  60

Gly Ser Gly Thr Asp Phe Thr Leu Thr Ile Ser Ser Leu Glu Pro Glu
 65                  70                  75                  80

Asp Val Ala Val Tyr Tyr Cys Phe Gln Gly Ser Val Tyr Pro Phe Thr
                 85                  90                  95

Phe Gly Gln Gly Thr Lys Leu Glu Ile Lys Arg Ser Ser Ala Ser Thr
             100                 105                 110

Lys Gly Pro Ser Val Phe Pro Leu Ala Pro Ser Ser Lys Ser Thr Ser
         115                 120                 125

Gly Gly Thr Ala Ala Leu Gly Cys Leu Val Lys Asp Tyr Phe Pro Glu
 130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                 165                 170                 175

Val Val Thr Val Pro Ser Ser Ser Leu Gly Thr Gln Thr Tyr Ile Cys
             180                 185                 190

Asn Val Asn His Lys Pro Ser Asn Thr Lys Val Asp Lys Lys Val
         195                 200                 205
```

<210> SEQ ID NO 24
<211> LENGTH: 227
<212> TYPE: PRT
<213> ORGANISM: Artificial Sequence
<220> FEATURE:
<223> OTHER INFORMATION: hBU12 VH-crossover Ck

<400> SEQUENCE: 24

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Thr Ser
                 20                  25                  30

Gly Met Gly Val Gly Trp Ile Arg Gln His Pro Gly Lys Gly Leu Glu
             35                  40                  45

Trp Ile Gly His Ile Trp Trp Asp Asp Lys Arg Tyr Asn Pro Ala
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Met Glu Leu Trp Ser Tyr Tyr Phe Asp Tyr Trp Gly Gln
             100                 105                 110

Gly Thr Leu Val Thr Val Ser Ser Ala Ser Val Ala Ala Pro Ser Val
         115                 120                 125

Phe Ile Phe Pro Pro Ser Asp Glu Gln Leu Lys Ser Gly Thr Ala Ser
 130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                 165                 170                 175
```

```
Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Leu Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 25
<211> LENGTH: 227
<212> TYPE: PRT
<213> ORGANISM: Artificial Sequence
<220> FEATURE:
<223> OTHER INFORMATION: hole hinge-CH2-CH3

<400> SEQUENCE: 25

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 26
<211> LENGTH: 211
<212> TYPE: PRT
<213> ORGANISM: Artificial Sequence
<220> FEATURE:
<223> OTHER INFORMATION: C6ML3-9 VL-crossover CH1

<400> SEQUENCE: 26

Gln Ser Val Leu Thr Gln Pro Pro Ser Val Ser Ala Ala Pro Gly Gln
1               5                   10                  15
```

```
Lys Val Thr Ile Ser Cys Ser Gly Ser Ser Asn Ile Gly Asn Asn
             20                  25                  30

Tyr Val Ser Trp Tyr Gln Gln Leu Pro Gly Thr Ala Pro Lys Leu Leu
         35                  40                  45

Ile Tyr Asp His Thr Asn Arg Pro Ala Gly Val Pro Asp Arg Phe Ser
 50                      55                  60

Gly Ser Lys Ser Gly Thr Ser Ala Ser Leu Ala Ile Ser Gly Phe Arg
 65                  70                  75                  80

Ser Glu Asp Glu Ala Asp Tyr Tyr Cys Ala Ser Trp Asp Tyr Thr Leu
                 85                  90                  95

Ser Gly Trp Val Phe Gly Gly Thr Lys Leu Thr Val Leu Gly Ser
             100                 105                 110

Ser Ala Ser Thr Lys Gly Pro Ser Val Phe Pro Leu Ala Pro Ser Ser
             115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
             165                 170                 175

Ser Leu Ser Ser Val Val Thr Val Pro Ser Ser Ser Leu Gly Thr Gln
             180                 185                 190

Thr Tyr Ile Cys Asn Val Asn His Lys Pro Ser Asn Thr Lys Val Asp
             195                 200                 205

Lys Lys Val
    210

<210> SEQ ID NO 27
<211> LENGTH: 236
<212> TYPE: PRT
<213> ORGANISM: Artificial Sequence
<220> FEATURE:
<223> OTHER INFORMATION: C6ML3-9 VH-crossover Ck

<400> SEQUENCE: 27

Gln Val Gln Leu Leu Gln Ser Gly Ala Glu Val Lys Lys Pro Gly Glu
1               5                  10                  15

Ser Leu Lys Ile Ser Cys Lys Gly Ser Gly Tyr Ser Phe Thr Ser Tyr
             20                  25                  30

Trp Ile Ala Trp Val Arg Gln Met Pro Gly Lys Gly Leu Glu Tyr Met
         35                  40                  45

Gly Leu Ile Tyr Pro Gly Asp Ser Asp Thr Lys Tyr Ser Pro Ser Phe
 50                  55                  60

Gln Gly Gln Val Thr Ile Ser Val Asp Lys Ser Val Ser Thr Ala Tyr
 65                  70                  75                  80

Leu Gln Trp Ser Ser Leu Lys Pro Ser Asp Ser Ala Val Tyr Phe Cys
                 85                  90                  95

Ala Arg His Asp Val Gly Tyr Cys Ser Ser Asn Cys Ala Lys Trp
             100                 105                 110

Pro Glu Tyr Phe Gln His Trp Gly Gln Gly Thr Leu Val Thr Val Ser
             115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160
```

```
Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
    195                 200                 205

Glu Lys His Lys Leu Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 28
<211> LENGTH: 39
<212> TYPE: DNA
<213> ORGANISM: Artificial Sequence
<220> FEATURE:
<223> OTHER INFORMATION: CH1 primer F

<400> SEQUENCE: 28
ctggtcaccg tctcctcagc ctccaccaag ggaccatcg                       39

<210> SEQ ID NO 29
<211> LENGTH: 25
<212> TYPE: DNA
<213> ORGANISM: Artificial Sequence
<220> FEATURE:
<223> OTHER INFORMATION: CH1 primer R

<400> SEQUENCE: 29
gtcgactttg tcacaagatt tgggc                                      25

<210> SEQ ID NO 30
<211> LENGTH: 39
<212> TYPE: DNA
<213> ORGANISM: Artificial Sequence
<220> FEATURE:
<223> OTHER INFORMATION: Ck primer F

<400> SEQUENCE: 30
accaaggtgg agatcaaacg gactgtggct gcaccatct                       39

<210> SEQ ID NO 31
<211> LENGTH: 26
<212> TYPE: DNA
<213> ORGANISM: Artificial Sequence
<220> FEATURE:
<223> OTHER INFORMATION: Ck primer R

<400> SEQUENCE: 31
ctcgaggcac tctcccctgt tgaagc                                     26

<210> SEQ ID NO 32
<211> LENGTH: 34
<212> TYPE: DNA
<213> ORGANISM: Artificial Sequence
<220> FEATURE:
<223> OTHER INFORMATION: Fc primer F

<400> SEQUENCE: 32
ggtggacaag agagttgagc ccaaatcttg tgac                            34

<210> SEQ ID NO 33
<211> LENGTH: 27
```

```
<212> TYPE: DNA
<213> ORGANISM: Artificial Sequence
<220> FEATURE:
<223> OTHER INFORMATION: Fc primer R

<400> SEQUENCE: 33
caattgtcca ctgccacccc cgcttga                                         27

<210> SEQ ID NO 34
<211> LENGTH: 33
<212> TYPE: DNA
<213> ORGANISM: Artificial Sequence
<220> FEATURE:
<223> OTHER INFORMATION: hE11VL primer F

<400> SEQUENCE: 34
ggcccagccg gccgatgttg tgatgactca gtc                                  33

<210> SEQ ID NO 35
<211> LENGTH: 35
<212> TYPE: DNA
<213> ORGANISM: Artificial Sequence
<220> FEATURE:
<223> OTHER INFORMATION: hE11VL- partial Ck primer R

<400> SEQUENCE: 35
gtgcagccac agtccgtttg atctccacct tggtc                                35

<210> SEQ ID NO 36
<211> LENGTH: 31
<212> TYPE: DNA
<213> ORGANISM: Artificial Sequence
<220> FEATURE:
<223> OTHER INFORMATION: h6-3VL primer F

<400> SEQUENCE: 36
ggcccagccg gccgacatcg tgatgaccca g                                    31

<210> SEQ ID NO 37
<211> LENGTH: 35
<212> TYPE: DNA
<213> ORGANISM: Artificial Sequence
<220> FEATURE:
<223> OTHER INFORMATION: h6-3VL-partial Ck primer R

<400> SEQUENCE: 37
gtgcagccac agtccgtttg atttccacct tggtc                                35

<210> SEQ ID NO 38
<211> LENGTH: 31
<212> TYPE: DNA
<213> ORGANISM: Artificial Sequence
<220> FEATURE:
<223> OTHER INFORMATION: h15-2bVL primer F

<400> SEQUENCE: 38
ggcccagccg gccgacatcc agatgaccca g                                    31

<210> SEQ ID NO 39
<211> LENGTH: 35
<212> TYPE: DNA
<213> ORGANISM: Artificial Sequence
<220> FEATURE:
<223> OTHER INFORMATION: h15-2bVL- partial Ck primer R

<400> SEQUENCE: 39
```
gtgcagccac agtccgtttg atctccagct tggtc                              35

<210> SEQ ID NO 40
<211> LENGTH: 24
<212> TYPE: DNA
<213> ORGANISM: Artificial Sequence
<220> FEATURE:
<223> OTHER INFORMATION: hE11VH primer F

<400> SEQUENCE: 40
agatctcagg tgcagctggt gcag                                          24

<210> SEQ ID NO 41
<211> LENGTH: 35
<212> TYPE: DNA
<213> ORGANISM: Artificial Sequence
<220> FEATURE:
<223> OTHER INFORMATION: hE11VH- partial CH1 primer R

<400> SEQUENCE: 41
tcccttggtg gaggctgagg agacggtgac caggg                              35

<210> SEQ ID NO 42
<211> LENGTH: 26
<212> TYPE: DNA
<213> ORGANISM: Artificial Sequence
<220> FEATURE:
<223> OTHER INFORMATION: h6-3VLH primer F

<400> SEQUENCE: 42
agatctcagg tgcagctggt gcaatc                                        26

<210> SEQ ID NO 43
<211> LENGTH: 34
<212> TYPE: DNA
<213> ORGANISM: Artificial Sequence
<220> FEATURE:
<223> OTHER INFORMATION: h6-3VH-partial CH1 primer R

<400> SEQUENCE: 43
gtcccttggt ggaggctgag gagacggtga ccag                               34

<210> SEQ ID NO 44
<211> LENGTH: 24
<212> TYPE: DNA
<213> ORGANISM: Artificial Sequence
<220> FEATURE:
<223> OTHER INFORMATION: h15-2bVH primer F

<400> SEQUENCE: 44
agatctgagg tgcagctggt ggag                                          24

<210> SEQ ID NO 45
<211> LENGTH: 35
<212> TYPE: DNA
<213> ORGANISM: Artificial Sequence
<220> FEATURE:
<223> OTHER INFORMATION: h15-2bVH- partial CH1 primer R

<400> SEQUENCE: 45
gcccttggtg gaggctgagg agacggtgac caggg                              35

<210> SEQ ID NO 46
<211> LENGTH: 48
<212> TYPE: DNA
<213> ORGANISM: Artificial Sequence

```
<220> FEATURE:
<223> OTHER INFORMATION: hBU12 dsFv primer P1

<400> SEQUENCE: 46
caattgcagg ttcagctgca agagtctggc cctgggttgg ttaagccc                    48

<210> SEQ ID NO 47
<211> LENGTH: 49
<212> TYPE: DNA
<213> ORGANISM: Artificial Sequence
<220> FEATURE:
<223> OTHER INFORMATION: hBU12 dsFv primer P2

<400> SEQUENCE: 47
cagtacaagt cagactgagg gtctgggagg gcttaaccaa cccagggcc                   49

<210> SEQ ID NO 48
<211> LENGTH: 49
<212> TYPE: DNA
<213> ORGANISM: Artificial Sequence
<220> FEATURE:
<223> OTHER INFORMATION: hBU12 dsFv primer P3

<400> SEQUENCE: 48
cagtctgact tgtactgtgt ctgggggttc aatcagcact tctggtatg                   49

<210> SEQ ID NO 49
<211> LENGTH: 48
<212> TYPE: DNA
<213> ORGANISM: Artificial Sequence
<220> FEATURE:
<223> OTHER INFORMATION: hBU12 dsFv primer P4

<400> SEQUENCE: 49
ctgggtgctg cctaatccag cctacaccca taccagaagt gctgattg                    48

<210> SEQ ID NO 50
<211> LENGTH: 50
<212> TYPE: DNA
<213> ORGANISM: Artificial Sequence
<220> FEATURE:
<223> OTHER INFORMATION: hBU12 dsFv primer P5

<400> SEQUENCE: 50
ggattaggca gcacccaggg aagtgtctgg agtggattgg acacatttgg                  50

<210> SEQ ID NO 51
<211> LENGTH: 47
<212> TYPE: DNA
<213> ORGANISM: Artificial Sequence
<220> FEATURE:
<223> OTHER INFORMATION: hBU12 dsFv primer P6

<400> SEQUENCE: 51
aacagtaata gacagcaaca tcctctggct ccaggctgct gattgtg                     47

<210> SEQ ID NO 52
<211> LENGTH: 51
<212> TYPE: DNA
<213> ORGANISM: Artificial Sequence
<220> FEATURE:
<223> OTHER INFORMATION: hBU12 dsFv primer P7

<400> SEQUENCE: 52
caagagatat aacccagccc tgaagagcag agtgacaatc tctgtggata c                51
```

<210> SEQ ID NO 53
<211> LENGTH: 50
<212> TYPE: DNA
<213> ORGANISM: Artificial Sequence
<220> FEATURE:
<223> OTHER INFORMATION: hBU12 dsFv primer P8

<400> SEQUENCE: 53
gacagcttga ggctaaactg gttcttggag gtatccacag agattgtcac                50

<210> SEQ ID NO 54
<211> LENGTH: 49
<212> TYPE: DNA
<213> ORGANISM: Artificial Sequence
<220> FEATURE:
<223> OTHER INFORMATION: hBU12 dsFv primer P9

<400> SEQUENCE: 54
gtttagcctc aagctgtcca gtgtgacagc tgcagatact gctgtctac                 49

<210> SEQ ID NO 55
<211> LENGTH: 48
<212> TYPE: DNA
<213> ORGANISM: Artificial Sequence
<220> FEATURE:
<223> OTHER INFORMATION: hBU12 dsFv primer P10

<400> SEQUENCE: 55
aaacagtaat agacagcaac atcctctggc tccaggctgc tgattgtg                  48

<210> SEQ ID NO 56
<211> LENGTH: 47
<212> TYPE: DNA
<213> ORGANISM: Artificial Sequence
<220> FEATURE:
<223> OTHER INFORMATION: hBU12 dsFv primer P11

<400> SEQUENCE: 56
ggaactttgg tcctactatt ttgactactg gggccaaggc acccttg                   47

<210> SEQ ID NO 57
<211> LENGTH: 53
<212> TYPE: DNA
<213> ORGANISM: Artificial Sequence
<220> FEATURE:
<223> OTHER INFORMATION: hBU12 dsFv primer P12

<400> SEQUENCE: 57 gcccctgac ccgccacctc ctgaggagac tgtgacaagg gtgccttggc ccc             53

<210> SEQ ID NO 58
<211> LENGTH: 53
<212> TYPE: DNA
<213> ORGANISM: Artificial Sequence
<220> FEATURE:
<223> OTHER INFORMATION: hBU12 dsFv primer P13

<400> SEQUENCE: 58
ggtggatcgg ggggtggcgg atctgaaatt gttctcaccc agtctccagc aac            53

<210> SEQ ID NO 59
<211> LENGTH: 52
<212> TYPE: DNA
<213> ORGANISM: Artificial Sequence
<220> FEATURE:
<223> OTHER INFORMATION: hBU12 dsFv primer P14

<400> SEQUENCE: 59
cagggtagcc ctttcccctg gagagagaga cagggttgct ggagactggg tg    52

<210> SEQ ID NO 60
<211> LENGTH: 52
<212> TYPE: DNA
<213> ORGANISM: Artificial Sequence
<220> FEATURE:
<223> OTHER INFORMATION: hBU12 dsFv primer P15

<400> SEQUENCE: 60
ggggaaaggg ctaccctgag ctgcagtgcc agctcaagtg taagttacat gc    52

<210> SEQ ID NO 61
<211> LENGTH: 52
<212> TYPE: DNA
<213> ORGANISM: Artificial Sequence
<220> FEATURE:
<223> OTHER INFORMATION: hBU12 dsFv primer P16

<400> SEQUENCE: 61
ctgggagcct gccctggctt ctgctggtac cagtgcatgt aacttacact tg    52

<210> SEQ ID NO 62
<211> LENGTH: 51
<212> TYPE: DNA
<213> ORGANISM: Artificial Sequence
<220> FEATURE:
<223> OTHER INFORMATION: hBU12 dsFv primer P17

<400> SEQUENCE: 62
gccagggcag gctcccagac tcctgattta tgacacatcc aaactggctt c     51

<210> SEQ ID NO 63
<211> LENGTH: 52
<212> TYPE: DNA
<213> ORGANISM: Artificial Sequence
<220> FEATURE:
<223> OTHER INFORMATION: hBU12 dsFv primer P18

<400> SEQUENCE: 63
ccagacccac tgccactgaa ccttgctgga ataccagaag ccagtttgga tg    52

<210> SEQ ID NO 64
<211> LENGTH: 50
<212> TYPE: DNA
<213> ORGANISM: Artificial Sequence
<220> FEATURE:
<223> OTHER INFORMATION: hBU12 dsFv primer P19

<400> SEQUENCE: 64
cagtggcagt gggtctggaa cagattttac actcacaatc agcagcctgg        50

<210> SEQ ID NO 65
<211> LENGTH: 50
<212> TYPE: DNA
<213> ORGANISM: Artificial Sequence
<220> FEATURE:
<223> OTHER INFORMATION: hBU12 dsFv primer P20

<400> SEQUENCE: 65
gaaaacagta atagacagca acatcctctg gctccaggct gctgattgtg        50

<210> SEQ ID NO 66

```
<211> LENGTH: 48
<212> TYPE: DNA
<213> ORGANISM: Artificial Sequence
<220> FEATURE:
<223> OTHER INFORMATION: hBU12 dsFv primer P21

<400> SEQUENCE: 66
gctgtctatt actgttttca ggggagtgta tacccattca cttttggc                    48

<210> SEQ ID NO 67
<211> LENGTH: 49
<212> TYPE: DNA
<213> ORGANISM: Artificial Sequence
<220> FEATURE:
<223> OTHER INFORMATION: hBU12 dsFv primer P22

<400> SEQUENCE: 67
acgcgttctt ttgatttcca actttgtccc gcagccaaaa gtgaatggg                   49

<210> SEQ ID NO 68
<211> LENGTH: 50
<212> TYPE: DNA
<213> ORGANISM: Artificial Sequence
<220> FEATURE:
<223> OTHER INFORMATION: 11F8 dsFv primer P23

<400> SEQUENCE: 68
gtcgaccaat tgggaggtgg cggatcccag gtgcagctgc aggagtcggg                  50

<210> SEQ ID NO 69
<211> LENGTH: 50
<212> TYPE: DNA
<213> ORGANISM: Artificial Sequence
<220> FEATURE:
<223> OTHER INFORMATION: 11F8 dsFv primer P24

<400> SEQUENCE: 69
acagggtctg tgaaggcttc accagtcctg ggcccgactc ctgcagctgc                  50

<210> SEQ ID NO 70
<211> LENGTH: 52
<212> TYPE: DNA
<213> ORGANISM: Artificial Sequence
<220> FEATURE:
<223> OTHER INFORMATION: 11F8 dsFv primer P25

<400> SEQUENCE: 70
agccttcaca gaccctgtcc ctcacctgca ctgtctctgg tggctccatc ag               52

<210> SEQ ID NO 71
<211> LENGTH: 52
<212> TYPE: DNA
<213> ORGANISM: Artificial Sequence
<220> FEATURE:
<223> OTHER INFORMATION: 11F8 dsFv primer P26

<400> SEQUENCE: 71
ggcggatcca actccagtag taatcaccac tgctgatgga gccaccagag ac               52

<210> SEQ ID NO 72
<211> LENGTH: 50
<212> TYPE: DNA
<213> ORGANISM: Artificial Sequence
<220> FEATURE:
<223> OTHER INFORMATION: 11F8 dsFv primer P27

<400> SEQUENCE: 72
```
actggagttg atccgccag cccccaggga agtgcctgga gtggattggg  50

<210> SEQ ID NO 73
<211> LENGTH: 52
<212> TYPE: DNA
<213> ORGANISM: Artificial Sequence
<220> FEATURE:
<223> OTHER INFORMATION: 11F8 dsFv primer P28

<400> SEQUENCE: 73
ggttgtagtc ggtgctccca ctgtaataga tgtacccaat ccactccagg ca  52

<210> SEQ ID NO 74
<211> LENGTH: 52
<212> TYPE: DNA
<213> ORGANISM: Artificial Sequence
<220> FEATURE:
<223> OTHER INFORMATION: 11F8 dsFv primer P29

<400> SEQUENCE: 74
tgggagcacc gactacaacc cgtccctcaa gagtcgagtc accatgtccg ta  52

<210> SEQ ID NO 75
<211> LENGTH: 50
<212> TYPE: DNA
<213> ORGANISM: Artificial Sequence
<220> FEATURE:
<223> OTHER INFORMATION: 11F8 dsFv primer P30

<400> SEQUENCE: 75
accttcaggg aaaactgatt cttggacgtg tctacggaca tggtgactcg  50

<210> SEQ ID NO 76
<211> LENGTH: 50
<212> TYPE: DNA
<213> ORGANISM: Artificial Sequence
<220> FEATURE:
<223> OTHER INFORMATION: 11F8 dsFv primer P31

<400> SEQUENCE: 76 tcagtttttcc ctgaaggtca actctgtgac cgccgcagac acggctgtgt  50

<210> SEQ ID NO 77
<211> LENGTH: 53
<212> TYPE: DNA
<213> ORGANISM: Artificial Sequence
<220> FEATURE:
<223> OTHER INFORMATION: 11F8 dsFv primer P32

<400> SEQUENCE: 77
ccccactcca aaatcgaca ctctcgcaca gtaatacaca gccgtgtctg cgg  53

<210> SEQ ID NO 78
<211> LENGTH: 50
<212> TYPE: DNA
<213> ORGANISM: Artificial Sequence
<220> FEATURE:
<223> OTHER INFORMATION: 11F8 dsFv primer P33

<400> SEQUENCE: 78 tcgattttg gagtggggac atttgactac tggggccagg gcaccctggt  50

<210> SEQ ID NO 79
<211> LENGTH: 54
<212> TYPE: DNA

```
<213> ORGANISM: Artificial Sequence
<220> FEATURE:
<223> OTHER INFORMATION: 11F8 dsFv primer P34

<400> SEQUENCE: 79
accgccccct gacccgccac ctccgcttga gacggtgacc agggtgccct ggcc      54

<210> SEQ ID NO 80
<211> LENGTH: 56
<212> TYPE: DNA
<213> ORGANISM: Artificial Sequence
<220> FEATURE:
<223> OTHER INFORMATION: 11F8 dsFv primer P35

<400> SEQUENCE: 80
ggatcggggg gtggcggatc tgaaattgtg atgacacagt ctccagccac cctgtc    56

<210> SEQ ID NO 81
<211> LENGTH: 52
<212> TYPE: DNA
<213> ORGANISM: Artificial Sequence
<220> FEATURE:
<223> OTHER INFORMATION: 11F8 dsFv primer P36

<400> SEQUENCE: 81
gcaggagagg gtggctcttt cccctggaga caaagacagg gtggctggag ac        52

<210> SEQ ID NO 82
<211> LENGTH: 48
<212> TYPE: DNA
<213> ORGANISM: Artificial Sequence
<220> FEATURE:
<223> OTHER INFORMATION: 11F8 dsFv primer P37

<400> SEQUENCE: 82
agagccaccc tctcctgcag ggccagtcag agtgttagca gctactta             48

<210> SEQ ID NO 83
<211> LENGTH: 48
<212> TYPE: DNA
<213> ORGANISM: Artificial Sequence
<220> FEATURE:
<223> OTHER INFORMATION: 11F8 dsFv primer P38

<400> SEQUENCE: 83
agcctggcca ggtttctgtt ggtaccaggc taagtagctg ctaacact             48

<210> SEQ ID NO 84
<211> LENGTH: 50
<212> TYPE: DNA
<213> ORGANISM: Artificial Sequence
<220> FEATURE:
<223> OTHER INFORMATION: 11F8 dsFv primer P39

<400> SEQUENCE: 84
cagaaacctg gccaggctcc caggctcctc atctatgatg catccaacag           50

<210> SEQ ID NO 85
<211> LENGTH: 52
<212> TYPE: DNA
<213> ORGANISM: Artificial Sequence
<220> FEATURE:
<223> OTHER INFORMATION: 11F8 dsFv primer P40

<400> SEQUENCE: 85
actgccactg aacctggctg ggatgccagt ggccctgttg gatgcatcat ag        52
```

<210> SEQ ID NO 86
<211> LENGTH: 50
<212> TYPE: DNA
<213> ORGANISM: Artificial Sequence
<220> FEATURE:
<223> OTHER INFORMATION: 11F8 dsFv primer P41

<400> SEQUENCE: 86
gccaggttca gtggcagtgg gtctgggaca gacttcactc tcaccatcag            50

<210> SEQ ID NO 87
<211> LENGTH: 50
<212> TYPE: DNA
<213> ORGANISM: Artificial Sequence
<220> FEATURE:
<223> OTHER INFORMATION: 11F8 dsFv primer P42

<400> SEQUENCE: 87
aatacactgc aaaatcttca ggctctaggc tgctgatggt gagagtgaag            50

<210> SEQ ID NO 88
<211> LENGTH: 52
<212> TYPE: DNA
<213> ORGANISM: Artificial Sequence
<220> FEATURE:
<223> OTHER INFORMATION: 11F8 dsFv primer P43

<400> SEQUENCE: 88
gaagattttg cagtgtatta ctgtcaccag tatggtagca cacctctcac tt         52

<210> SEQ ID NO 89
<211> LENGTH: 52
<212> TYPE: DNA
<213> ORGANISM: Artificial Sequence
<220> FEATURE:
<223> OTHER INFORMATION: 11F8 dsFv primer P44

<400> SEQUENCE: 89
acgcgttttg atctccgcct tggtcccgca gccgaaagtg agaggtgtgc ta         52

<210> SEQ ID NO 90
<211> LENGTH: 53
<212> TYPE: DNA
<213> ORGANISM: Artificial Sequence
<220> FEATURE:
<223> OTHER INFORMATION: linker-MfeI-hBU12 VH primer F

<400> SEQUENCE: 90
gtggtggttc aggacaattg ggaggtggcg gatcccaggt tcagctgcaa gag        53

<210> SEQ ID NO 91
<211> LENGTH: 52
<212> TYPE: DNA
<213> ORGANISM: Artificial Sequence
<220> FEATURE:
<223> OTHER INFORMATION: SalI-linker-MfeI-hBU12 VH primer R

<400> SEQUENCE: 91
gtcgacctgg tcaccgtctc ctcagcctcc accggtggtg gttcaggaca at         52

<210> SEQ ID NO 92
<211> LENGTH: 53
<212> TYPE: DNA
<213> ORGANISM: Artificial Sequence
<220> FEATURE:

<223> OTHER INFORMATION: hBU12VL-Mlu 1-6xHis-ClaI primer R

<400> SEQUENCE: 92
atcgatttaa tgatgatgat gatgatgacg cgttcttttg atttccaact ttg          53

<210> SEQ ID NO 93
<211> LENGTH: 39
<212> TYPE: DNA
<213> ORGANISM: Artificial Sequence
<220> FEATURE:
<223> OTHER INFORMATION: MfeI-h11F8 VH primer F

<400> SEQUENCE: 93
caattgggag gtggcggatc ccaggtgcag ctgcaggag                           39

<210> SEQ ID NO 94
<211> LENGTH: 25
<212> TYPE: DNA
<213> ORGANISM: Artificial Sequence
<220> FEATURE:
<223> OTHER INFORMATION: MluI-11F8VL primer R

<400> SEQUENCE: 94
acgcgttttg atctccgcct tggtc                                         25

<210> SEQ ID NO 95
<211> LENGTH: 39
<212> TYPE: DNA
<213> ORGANISM: Artificial Sequence
<220> FEATURE:
<223> OTHER INFORMATION: MfeI-DNSVH primer F

<400> SEQUENCE: 95
caattgggag gtggcggatc cagtgaagtg aagcttgag                           39

<210> SEQ ID NO 96
<211> LENGTH: 24
<212> TYPE: DNA
<213> ORGANISM: Artificial Sequence
<220> FEATURE:
<223> OTHER INFORMATION: MluI-DNSVL primer R

<400> SEQUENCE: 96
acgcgtccgt tttatttcca actt                                          24

<210> SEQ ID NO 97
<211> LENGTH: 39
<212> TYPE: DNA
<213> ORGANISM: Artificial Sequence
<220> FEATURE:
<223> OTHER INFORMATION: MfeI-hCC49VH primer F

<400> SEQUENCE: 97
caattgggag gtggcggatc ccaggtgcag ctggtgcag                           39

<210> SEQ ID NO 98
<211> LENGTH: 25
<212> TYPE: DNA
<213> ORGANISM: Artificial Sequence
<220> FEATURE:
<223> OTHER INFORMATION: MluI-hCC49VL primer R

<400> SEQUENCE: 98
acgcgttttg atctccacct tggtc                                         25

```
<210> SEQ ID NO 99
<211> LENGTH: 24
<212> TYPE: DNA
<213> ORGANISM: Artificial Sequence
<220> FEATURE:
<223> OTHER INFORMATION: 15-2b- knob: VL-Ck primer F

<400> SEQUENCE: 99
agatctgaca tccagatgac ccag                                          24

<210> SEQ ID NO 100
<211> LENGTH: 36
<212> TYPE: DNA
<213> ORGANISM: Artificial Sequence
<220> FEATURE:
<223> OTHER INFORMATION: 15-2b- knob: VL-Ck primer R

<400> SEQUENCE: 100
tatcgatgtt taaacctagc actctcccct gttgaa                             36

<210> SEQ ID NO 101
<211> LENGTH: 31
<212> TYPE: DNA
<213> ORGANISM: Artificial Sequence
<220> FEATURE:
<223> OTHER INFORMATION: 15-2b- knob: VH-CH1 primer F

<400> SEQUENCE: 101
ggcccagccg gccgaggtgc agctggtgga g                                  31

<210> SEQ ID NO 102
<211> LENGTH: 20
<212> TYPE: DNA
<213> ORGANISM: Artificial Sequence
<220> FEATURE:
<223> OTHER INFORMATION: 15-2b- knob: VH-CH1 primer R

<400> SEQUENCE: 102
aagttttttg tcgaccgtgg                                               20

<210> SEQ ID NO 103
<211> LENGTH: 27
<212> TYPE: DNA
<213> ORGANISM: Artificial Sequence
<220> FEATURE:
<223> OTHER INFORMATION: 15-2b- knob: huIgG1-upper hinge primer F

<400> SEQUENCE: 103
gacaaaactc acacatgccc accgtgc                                       27

<210> SEQ ID NO 104
<211> LENGTH: 36
<212> TYPE: DNA
<213> ORGANISM: Artificial Sequence
<220> FEATURE:
<223> OTHER INFORMATION: 15-2b- knob: CH1-partical hinge primer R

<400> SEQUENCE: 104
gcatgtgtga gttttgtcac aagatttggg ctcaac                             36

<210> SEQ ID NO 105
<211> LENGTH: 24
<212> TYPE: DNA
<213> ORGANISM: Artificial Sequence
<220> FEATURE:
<223> OTHER INFORMATION: 15-2b- knob: CH3 primer R
```

<400> SEQUENCE: 105
ctcgagttta cccggagaca ggga                                              24

<210> SEQ ID NO 106
<211> LENGTH: 28
<212> TYPE: DNA
<213> ORGANISM: Artificial Sequence
<220> FEATURE:
<223> OTHER INFORMATION: h6-3- knob:104 VL-Ck primer F

<400> SEQUENCE: 106
agatctgaca tcgtgatgac ccagtctc                                          28

<210> SEQ ID NO 107
<211> LENGTH: 36
<212> TYPE: DNA
<213> ORGANISM: Artificial Sequence
<220> FEATURE:
<223> OTHER INFORMATION: h6-3- knob:104 VL-Ck primer R

<400> SEQUENCE: 107
tatcgatgtt taaacctagc actctcccct gttgaa                                 36

<210> SEQ ID NO 108
<211> LENGTH: 19
<212> TYPE: DNA
<213> ORGANISM: Artificial Sequence
<220> FEATURE:
<223> OTHER INFORMATION: h6-3- knob:104 VH-CH1 primer F

<400> SEQUENCE: 108
caggtgcagc tggtgcaat                                                    19

<210> SEQ ID NO 109
<211> LENGTH: 20
<212> TYPE: DNA
<213> ORGANISM: Artificial Sequence
<220> FEATURE:
<223> OTHER INFORMATION: h6-3- knob:104 VH-CH1 primer R

<400> SEQUENCE: 109
aactctcttg tccaccttgg                                                   20

<210> SEQ ID NO 110
<211> LENGTH: 32
<212> TYPE: DNA
<213> ORGANISM: Artificial Sequence
<220> FEATURE:
<223> OTHER INFORMATION: BU12-hole: VH-Ck-partial hinge primer F

<400> SEQUENCE: 110
agccggccca ggttcagctg caagagtctg gc                                     32

<210> SEQ ID NO 111
<211> LENGTH: 39
<212> TYPE: DNA
<213> ORGANISM: Artificial Sequence
<220> FEATURE:
<223> OTHER INFORMATION: BU12-hole: VH-Ck-partial hinge primer R

<400> SEQUENCE: 111
gcatgtgtga gttttgtcac actctcccct gttgaagct                              39

<210> SEQ ID NO 112
<211> LENGTH: 23

```
<212> TYPE: DNA
<213> ORGANISM: Artificial Sequence
<220> FEATURE:
<223> OTHER INFORMATION: BU12-hole: VL-partial VH-CH1-upper Hinge primer
      F

<400> SEQUENCE: 112
gaaattgttc tcacccagtc tcc                                              23

<210> SEQ ID NO 113
<211> LENGTH: 21
<212> TYPE: DNA
<213> ORGANISM: Artificial Sequence
<220> FEATURE:
<223> OTHER INFORMATION: BU12-hole: VL-partial VH-CH1-upper Hinge primer
      R

<400> SEQUENCE: 113
ttaacaagat ttgggctcaa c                                                21

<210> SEQ ID NO 114
<211> LENGTH: 43
<212> TYPE: DNA
<213> ORGANISM: Artificial Sequence
<220> FEATURE:
<223> OTHER INFORMATION: BU12-hole: partial VL-hCH1 primer F

<400> SEQUENCE: 114
gttggaaatc aaaagatcct cagcctccac caagggccca tcg                        43

<210> SEQ ID NO 115
<211> LENGTH: 37
<212> TYPE: DNA
<213> ORGANISM: Artificial Sequence
<220> FEATURE:
<223> OTHER INFORMATION: a-Her2-hole: VH primer

<400> SEQUENCE: 115
ggcccagccg gcccaggtgc agctgttgca gtctggg                               37

<210> SEQ ID NO 116
<211> LENGTH: 23
<212> TYPE: DNA
<213> ORGANISM: Artificial Sequence
<220> FEATURE:
<223> OTHER INFORMATION: a-Her2-hole: VH-Ck-partial hinge primer F

<400> SEQUENCE: 116
aggtgcagct gttgcagtct ggg                                              23

<210> SEQ ID NO 117
<211> LENGTH: 39
<212> TYPE: DNA
<213> ORGANISM: Artificial Sequence
<220> FEATURE:
<223> OTHER INFORMATION: a-Her2-hole: VH-Ck-partial hinge primer R

<400> SEQUENCE: 117
gcatgtgtga gttttgtcac actctcccct gttgaagct                             39

<210> SEQ ID NO 118
<211> LENGTH: 42
<212> TYPE: DNA
<213> ORGANISM: Artificial Sequence
<220> FEATURE:
<223> OTHER INFORMATION: a-Her2-hole: VL-partial VH primer F
```

<400> SEQUENCE: 118
ctgaccgtcc taggttcctc agcctccacc aagggcccat cg    42

<210> SEQ ID NO 119
<211> LENGTH: 45
<212> TYPE: DNA
<213> ORGANISM: Artificial Sequence
<220> FEATURE:
<223> OTHER INFORMATION: a-Her2-hole: VL-partial VH primer R

<400> SEQUENCE: 119
acctaggacg gtcagcttgg tcccgccgcc gaacacccag cccga    45

<210> SEQ ID NO 120
<211> LENGTH: 29
<212> TYPE: DNA
<213> ORGANISM: Artificial Sequence
<220> FEATURE:
<223> OTHER INFORMATION: a-Her2-hole: VL primer F

<400> SEQUENCE: 120
ctgccagatc tcagtctgtg ttgacgcag    29

<210> SEQ ID NO 121
<211> LENGTH: 45
<212> TYPE: DNA
<213> ORGANISM: Artificial Sequence
<220> FEATURE:
<223> OTHER INFORMATION: a-Her2-hole: VL primer R

<400> SEQUENCE: 121
acctaggacg gtcagcttgg tcccgccgcc gaacacccag cccga    45

<210> SEQ ID NO 122
<211> LENGTH: 21
<212> TYPE: DNA
<213> ORGANISM: Artificial Sequence
<220> FEATURE:
<223> OTHER INFORMATION: a-Her2-hole: CH1-upper hinge primer R

<400> SEQUENCE: 122
ttaacaagat ttgggctcaa c    21

<210> SEQ ID NO 123
<211> LENGTH: 47
<212> TYPE: DNA
<213> ORGANISM: Artificial Sequence
<220> FEATURE:
<223> OTHER INFORMATION: h15-2b Bgl-VH-1 primer F

<400> SEQUENCE: 123
gaagatctga ggtgcagctg gtggagtctg ggggaggctt ggtccag    47

<210> SEQ ID NO 124
<211> LENGTH: 51
<212> TYPE: DNA
<213> ORGANISM: Artificial Sequence
<220> FEATURE:
<223> OTHER INFORMATION: h15-2b VH-2 primer R

<400> SEQUENCE: 124
agaggctgca caggagagtt tcagggaccc cccaggctgg accaagcctc c    51

<210> SEQ ID NO 125
<211> LENGTH: 51

```
<212> TYPE: DNA
<213> ORGANISM: Artificial Sequence
<220> FEATURE:
<223> OTHER INFORMATION: h15-2b VH-3 primer F

<400> SEQUENCE: 125
tcctgtgcag cctctgggtt caccttcagt aactactgga tgaactgggt c        51

<210> SEQ ID NO 126
<211> LENGTH: 51
<212> TYPE: DNA
<213> ORGANISM: Artificial Sequence
<220> FEATURE:
<223> OTHER INFORMATION: h15-2b VH-4 primer R

<400> SEQUENCE: 126
gccaacccac tccagccctt tcccggaagc ctggcggacc cagttcatcc a        51

<210> SEQ ID NO 127
<211> LENGTH: 51
<212> TYPE: DNA
<213> ORGANISM: Artificial Sequence
<220> FEATURE:
<223> OTHER INFORMATION: h15-2b VH-5 primer F

<400> SEQUENCE: 127
ctggagtggg ttggcgaaat tagatcgaaa tctaataatt atgcgacaca t        51

<210> SEQ ID NO 128
<211> LENGTH: 51
<212> TYPE: DNA
<213> ORGANISM: Artificial Sequence
<220> FEATURE:
<223> OTHER INFORMATION: h15-2b VH-6 primer R

<400> SEQUENCE: 128
ggagatggtg aacctcccctt tcacagactc cgcataatgt gtcgcataat t       51

<210> SEQ ID NO 129
<211> LENGTH: 51
<212> TYPE: DNA
<213> ORGANISM: Artificial Sequence
<220> FEATURE:
<223> OTHER INFORMATION: h15-2b VH-7 primer F

<400> SEQUENCE: 129
aggttcacca tctccagaga tgattcaaag aacacggcgt atctgcaaat g        51

<210> SEQ ID NO 130
<211> LENGTH: 51
<212> TYPE: DNA
<213> ORGANISM: Artificial Sequence
<220> FEATURE:
<223> OTHER INFORMATION: h15-2b VH-8

<400> SEQUENCE: 130
gtaatacacg gccgtgtcct cggttttcag gctgttcatt tgcagatacg c        51

<210> SEQ ID NO 131
<211> LENGTH: 51
<212> TYPE: DNA
<213> ORGANISM: Artificial Sequence
<220> FEATURE:
<223> OTHER INFORMATION: h15-2b VH-9 (T93S) primer F

<400> SEQUENCE: 131
```

```
acggccgtgt attactgttc aacagatac tactggggcc aaggaaccct g        51
```

<210> SEQ ID NO 132
<211> LENGTH: 45
<212> TYPE: DNA
<213> ORGANISM: Artificial Sequence
<220> FEATURE:
<223> OTHER INFORMATION: h15-2b VH-10 primer R

<400> SEQUENCE: 132

```
acctttggtg gaggctgagg agacggtgac cagggttcct tggcc             45
```

<210> SEQ ID NO 133
<211> LENGTH: 28
<212> TYPE: DNA
<213> ORGANISM: Artificial Sequence
<220> FEATURE:
<223> OTHER INFORMATION: homo 3' IgG2 CH1-SalI primer R

<400> SEQUENCE: 133

```
acgcgtcgac tttgcgctca actgtctt                                28
```

<210> SEQ ID NO 134
<211> LENGTH: 43
<212> TYPE: DNA
<213> ORGANISM: Artificial Sequence
<220> FEATURE:
<223> OTHER INFORMATION: h15-2b sfi-VL-1 primer F

<400> SEQUENCE: 134

```
tgctggggcc cagccggccg acatccagat gacccagtct cca               43
```

<210> SEQ ID NO 135
<211> LENGTH: 51
<212> TYPE: DNA
<213> ORGANISM: Artificial Sequence
<220> FEATURE:
<223> OTHER INFORMATION: h15-2b VL-2 primer R

<400> SEQUENCE: 135

```
ggtgactctg tctcctacag atgcagacag ggaggatgga gactgggtca t       51
```

<210> SEQ ID NO 136
<211> LENGTH: 51
<212> TYPE: DNA
<213> ORGANISM: Artificial Sequence
<220> FEATURE:
<223> OTHER INFORMATION: h15-2b VL-3 primer F

<400> SEQUENCE: 136

```
ggagacagag tcaccatcac ttgcaaggcc agtcaggatg taaatacttc t       51
```

<210> SEQ ID NO 137
<211> LENGTH: 51
<212> TYPE: DNA
<213> ORGANISM: Artificial Sequence
<220> FEATURE:
<223> OTHER INFORMATION: h15-2b VL-4 primer R

<400> SEQUENCE: 137

```
aggggctttc cctggtttct gctgatacca ggctacagaa gtatttacat c       51
```

<210> SEQ ID NO 138
<211> LENGTH: 51
<212> TYPE: DNA
<213> ORGANISM: Artificial Sequence -continued

```
<220> FEATURE:
<223> OTHER INFORMATION: h15-2b VL-5 primer F

<400> SEQUENCE: 138
ccagggaaag cccctaagct cctgatctac tgggcatcca cccggcacac t          51

<210> SEQ ID NO 139
<211> LENGTH: 51
<212> TYPE: DNA
<213> ORGANISM: Artificial Sequence
<220> FEATURE:
<223> OTHER INFORMATION: h15-2b VL-6 primer R

<400> SEQUENCE: 139
cccagatcca cttccactga accttgatgg gaccccagtg tgccgggtgg a          51

<210> SEQ ID NO 140
<211> LENGTH: 51
<212> TYPE: DNA
<213> ORGANISM: Artificial Sequence
<220> FEATURE:
<223> OTHER INFORMATION: h15-2b VL-7 primer F

<400> SEQUENCE: 140
ggaagtggat ctgggacaga ttttactttc accatcagca gcctgcagcc t          51

<210> SEQ ID NO 141
<211> LENGTH: 51
<212> TYPE: DNA
<213> ORGANISM: Artificial Sequence
<220> FEATURE:
<223> OTHER INFORMATION: h15-2b VL-8 primer R

<400> SEQUENCE: 141
gatatattgc agacagtaat atgttgcaat atcttcaggc tgcaggctgc t          51

<210> SEQ ID NO 142
<211> LENGTH: 51
<212> TYPE: DNA
<213> ORGANISM: Artificial Sequence
<220> FEATURE:
<223> OTHER INFORMATION: h15-2b VL-9 primer F

<400> SEQUENCE: 142
tgtctgcaat atatcaacta tccgtacacg tttggccagg ggaccaagct g          51

<210> SEQ ID NO 143
<211> LENGTH: 42
<212> TYPE: DNA
<213> ORGANISM: Artificial Sequence
<220> FEATURE:
<223> OTHER INFORMATION: h15-2b VL-10 primer R

<400> SEQUENCE: 143
tggtgcagcc acagtccgtt tgatctccag cttggtcccc tg                    42

<210> SEQ ID NO 144
<211> LENGTH: 57
<212> TYPE: DNA
<213> ORGANISM: Artificial Sequence
<220> FEATURE:
<223> OTHER INFORMATION: homo 3' Ck cys-XhoI primer R

<400> SEQUENCE: 144
ccgctcgagg cactctcccc tgttgaagct ctttgtgacg ggcgagctca ggccctg    57
```

```
<210> SEQ ID NO 145
<211> LENGTH: 54
<212> TYPE: DNA
<213> ORGANISM: Artificial Sequence
<220> FEATURE:
<223> OTHER INFORMATION: h528VH01 primer F

<400> SEQUENCE: 145
caggtgcaac tggttcagag cggcgcggaa gtgaaaaagc cgggcgcgtc ggtt      54

<210> SEQ ID NO 146
<211> LENGTH: 48
<212> TYPE: DNA
<213> ORGANISM: Artificial Sequence
<220> FEATURE:
<223> OTHER INFORMATION: h528VH02 primer R

<400> SEQUENCE: 146
aaaggtatag cctgaggctt tgcagctcac tttaaccgac gcgccgg               48

<210> SEQ ID NO 147
<211> LENGTH: 48
<212> TYPE: DNA
<213> ORGANISM: Artificial Sequence
<220> FEATURE:
<223> OTHER INFORMATION: h528VH03 primer F

<400> SEQUENCE: 147
tcaggctata cctttacgag ctactggatg cattgggtgc gccaggcc              48

<210> SEQ ID NO 148
<211> LENGTH: 48
<212> TYPE: DNA
<213> ORGANISM: Artificial Sequence
<220> FEATURE:
<223> OTHER INFORMATION: h528VH04 primer R

<400> SEQUENCE: 148
aatgttaccc atccattcca ggccctgacc cggggcctgg cgcaccca              48

<210> SEQ ID NO 149
<211> LENGTH: 48
<212> TYPE: DNA
<213> ORGANISM: Artificial Sequence
<220> FEATURE:
<223> OTHER INFORMATION: h528VH05 primer F

<400> SEQUENCE: 149
tggatgggta acatttatcc gggcagcggt ggcaccaact atgcggaa              48

<210> SEQ ID NO 150
<211> LENGTH: 48
<212> TYPE: DNA
<213> ORGANISM: Artificial Sequence
<220> FEATURE:
<223> OTHER INFORMATION: h528VH06 primer R

<400> SEQUENCE: 150
atcacgcgtc atggtcacgc ggttcttaaa tttttccgca tagttggt              48

<210> SEQ ID NO 151
<211> LENGTH: 48
<212> TYPE: DNA
<213> ORGANISM: Artificial Sequence
<220> FEATURE:
<223> OTHER INFORMATION: h528VH07 primer F
```

<400> SEQUENCE: 151
accatgacgc gtgataccag catttcgacg gcctatatgg aactgagc                48

<210> SEQ ID NO 152
<211> LENGTH: 48
<212> TYPE: DNA
<213> ORGANISM: Artificial Sequence
<220> FEATURE:
<223> OTHER INFORMATION: h528VH08 primer R

<400> SEQUENCE: 152
gtaatacacg gcggtgtcat cgctacgcag gcggctcagt tccatata                48

<210> SEQ ID NO 153
<211> LENGTH: 48
<212> TYPE: DNA
<213> ORGANISM: Artificial Sequence
<220> FEATURE:
<223> OTHER INFORMATION: h528VH09 primer F

<400> SEQUENCE: 153
accgccgtgt attactgcgc gcgcagtggc ggtccgtatt ttttcgat                48

<210> SEQ ID NO 154
<211> LENGTH: 51
<212> TYPE: DNA
<213> ORGANISM: Artificial Sequence
<220> FEATURE:
<223> OTHER INFORMATION: h528VH10 primer R

<400> SEQUENCE: 154
cgagctcacg gtaaccagcg taccctggcc ccagtaatcg aaaaaatacg g            51

<210> SEQ ID NO 155
<211> LENGTH: 45
<212> TYPE: DNA
<213> ORGANISM: Artificial Sequence
<220> FEATURE:
<223> OTHER INFORMATION: (G4S)2-ahEGFR VH primer F

<400> SEQUENCE: 155
ggcggtggtg gtcgggtgg cggcggatct caggtgcaac tggtt                    45

<210> SEQ ID NO 156
<211> LENGTH: 26
<212> TYPE: DNA
<213> ORGANISM: Artificial Sequence
<220> FEATURE:
<223> OTHER INFORMATION: ahEGFR VH-stop-Cal primer R

<400> SEQUENCE: 156
ccatcgattt acgagctcac ggtaac                                        26

<210> SEQ ID NO 157
<211> LENGTH: 48
<212> TYPE: DNA
<213> ORGANISM: Artificial Sequence
<220> FEATURE:
<223> OTHER INFORMATION: h528VL01 primer F

<400> SEQUENCE: 157
gatattgtga tgacccagag cccgctgagc ctgccggtga ccccaggc                48

<210> SEQ ID NO 158

```
<211> LENGTH: 48
<212> TYPE: DNA
<213> ORGANISM: Artificial Sequence
<220> FEATURE:
<223> OTHER INFORMATION: h528VL02 primer R

<400> SEQUENCE: 158
ctgcgagctg cggcagctaa tcgacgccgg ttcgcctggg gtcaccgg          48

<210> SEQ ID NO 159
<211> LENGTH: 48
<212> TYPE: DNA
<213> ORGANISM: Artificial Sequence
<220> FEATURE:
<223> OTHER INFORMATION: h528VL03 primer F

<400> SEQUENCE: 159
tgccgcagct cgcagaacat cgtgcataat aacggcatta cctatctg          48

<210> SEQ ID NO 160
<211> LENGTH: 48
<212> TYPE: DNA
<213> ORGANISM: Artificial Sequence
<220> FEATURE:
<223> OTHER INFORMATION: h528VL04 primer R

<400> SEQUENCE: 160
cgggctttgg cccggtttct gcagatacca ttccagatag gtaatgcc          48

<210> SEQ ID NO 161
<211> LENGTH: 48
<212> TYPE: DNA
<213> ORGANISM: Artificial Sequence
<220> FEATURE:
<223> OTHER INFORMATION: h528VL05 primer F

<400> SEQUENCE: 161
ccgggccaaa gcccgcagct gttaatttat aaagtgagcg atcgcttt          48

<210> SEQ ID NO 162
<211> LENGTH: 48
<212> TYPE: DNA
<213> ORGANISM: Artificial Sequence
<220> FEATURE:
<223> OTHER INFORMATION: h528VL06 primer R

<400> SEQUENCE: 162
accgctgccc gaaaagcgat ccggcacgcc gctaaagcga tcgctcac          48

<210> SEQ ID NO 163
<211> LENGTH: 48
<212> TYPE: DNA
<213> ORGANISM: Artificial Sequence
<220> FEATURE:
<223> OTHER INFORMATION: h528VL07 primer F

<400> SEQUENCE: 163
ttttcgggca gcggtagtgg caccgatttt acgctgaaaa ttagccgc          48

<210> SEQ ID NO 164
<211> LENGTH: 48
<212> TYPE: DNA
<213> ORGANISM: Artificial Sequence
<220> FEATURE:
<223> OTHER INFORMATION: h528VL08 primer R

<400> SEQUENCE: 164
```
gcagtaatac acgccaacat cctccgcttc cacgcggcta attttcag        48

<210> SEQ ID NO 165
<211> LENGTH: 48
<212> TYPE: DNA
<213> ORGANISM: Artificial Sequence
<220> FEATURE:
<223> OTHER INFORMATION: h528VL09 primer F

<400> SEQUENCE: 165
ggcgtgtatt actgctttca gggcagccat atcccgccaa cctttggc        48

<210> SEQ ID NO 166
<211> LENGTH: 45
<212> TYPE: DNA
<213> ORGANISM: Artificial Sequence
<220> FEATURE:
<223> OTHER INFORMATION: h528VL10 primer R

<400> SEQUENCE: 166
cgcgcgttta atttccactt tggtgccttg gccaaaggtt ggcgg        45

<210> SEQ ID NO 167
<211> LENGTH: 24
<212> TYPE: DNA
<213> ORGANISM: Artificial Sequence
<220> FEATURE:
<223> OTHER INFORMATION: Mfe-ahEGFR VL primer F

<400> SEQUENCE: 167
caattggata ttgtgatgac ccag        24

<210> SEQ ID NO 168
<211> LENGTH: 45
<212> TYPE: DNA
<213> ORGANISM: Artificial Sequence
<220> FEATURE:
<223> OTHER INFORMATION: ahEGFR VL-(G4S)2 primer R

<400> SEQUENCE: 168
cgacccacca ccgcccgagc caccgccacc cgcgcgttta atttc        45

<210> SEQ ID NO 169
<211> LENGTH: 58
<212> TYPE: DNA
<213> ORGANISM: Artificial Sequence
<220> FEATURE:
<223> OTHER INFORMATION: Sal-G-myc-G4S primer F

<400> SEQUENCE: 169
acgcgtcgac ggggaacaaa aactcatctc agaagaggat ctgggaggcg gtggcagt        58

<210> SEQ ID NO 170
<211> LENGTH: 57
<212> TYPE: DNA
<213> ORGANISM: Artificial Sequence
<220> FEATURE:
<223> OTHER INFORMATION: G2S-G4SX2-MfeI primer F

<400> SEQUENCE: 170
ggtggcagtg gtggtggtgg atcaggaggt ggcggatccc aattgcaggt gcagctg        57

<210> SEQ ID NO 171
<211> LENGTH: 27
<212> TYPE: DNA

```
<213> ORGANISM: Artificial Sequence
<220> FEATURE:
<223> OTHER INFORMATION: Her2 scFv-stop-ClaI primer R

<400> SEQUENCE: 171
atcgattcaa cctaggacgg tcagctt                                          27

<210> SEQ ID NO 172
<211> LENGTH: 30
<212> TYPE: DNA
<213> ORGANISM: Artificial Sequence
<220> FEATURE:
<223> OTHER INFORMATION: mfe1-h15-2bVL primer F

<400> SEQUENCE: 172
caattggaca tccagatgac ccagtctcca                                       30

<210> SEQ ID NO 173
<211> LENGTH: 35
<212> TYPE: DNA
<213> ORGANISM: Artificial Sequence
<220> FEATURE:
<223> OTHER INFORMATION: h15-2bscFv-ClaI-Sbfl primer R

<400> SEQUENCE: 173
cccctgcagg catcgattta tgaggagacg gtgac                                 35

<210> SEQ ID NO 174
<211> LENGTH: 43
<212> TYPE: DNA
<213> ORGANISM: Artificial Sequence
<220> FEATURE:
<223> OTHER INFORMATION: NaeI-X+hHB12bVL-1 primer F

<400> SEQUENCE: 174
gccggccgag atcgtgctga cccagagccc cgacttccag agc                        43

<210> SEQ ID NO 175
<211> LENGTH: 53
<212> TYPE: DNA
<213> ORGANISM: Artificial Sequence
<220> FEATURE:
<223> OTHER INFORMATION: hHB12bVL-2 primer R

<400> SEQUENCE: 175
ctctgcaggt gatggtcacc ttctccttgg gggtcacgct ctggaagtcg ggg             53

<210> SEQ ID NO 176
<211> LENGTH: 54
<212> TYPE: DNA
<213> ORGANISM: Artificial Sequence
<220> FEATURE:
<223> OTHER INFORMATION: hHB12bVL-3 primer F

<400> SEQUENCE: 176
gtgaccatca cctgcagagc cagcgagagc gtggacacct cggcatcag cttc             54

<210> SEQ ID NO 177
<211> LENGTH: 52
<212> TYPE: DNA
<213> ORGANISM: Artificial Sequence
<220> FEATURE:
<223> OTHER INFORMATION: hHB12bVL-4 priemr R

<400> SEQUENCE: 177
gctctggtcg ggcttctgct ggaaccagtt catgaagctg atgccgaagg tg              52
```

<210> SEQ ID NO 178
<211> LENGTH: 51
<212> TYPE: DNA
<213> ORGANISM: Artificial Sequence
<220> FEATURE:
<223> OTHER INFORMATION: hHB12bVL-5 primer F

<400> SEQUENCE: 178
gaagcccgac cagagcccca agctgctgat ccacgccgcc agcaaccagg g    51

<210> SEQ ID NO 179
<211> LENGTH: 51
<212> TYPE: DNA
<213> ORGANISM: Artificial Sequence
<220> FEATURE:
<223> OTHER INFORMATION: hHB12bVL-6 primer R

<400> SEQUENCE: 179
cttccgctgc cgctgaatct gctgggcacg ccgctgccct ggttgctggc g    51

<210> SEQ ID NO 180
<211> LENGTH: 52
<212> TYPE: DNA
<213> ORGANISM: Artificial Sequence
<220> FEATURE:
<223> OTHER INFORMATION: hHB12bVL-7 primer F

<400> SEQUENCE: 180
ttcagcggca gcggaagcgg caccgacttc accctgacca tcaacagcct gg    52

<210> SEQ ID NO 181
<211> LENGTH: 54
<212> TYPE: DNA
<213> ORGANISM: Artificial Sequence
<220> FEATURE:
<223> OTHER INFORMATION: hHB12bVL-8 primer R

<400> SEQUENCE: 181
ctctgctggc agtagtaggt tgctgcgtcc tcggcctcca ggctgttgat ggtc    54

<210> SEQ ID NO 182
<211> LENGTH: 52
<212> TYPE: DNA
<213> ORGANISM: Artificial Sequence
<220> FEATURE:
<223> OTHER INFORMATION: hHB12bVL-9 primer F

<400> SEQUENCE: 182
aacctactac tgccagcaga gcaaggaggt gcccttcacc ttcggcggcg gc    52

<210> SEQ ID NO 183
<211> LENGTH: 52
<212> TYPE: DNA
<213> ORGANISM: Artificial Sequence
<220> FEATURE:
<223> OTHER INFORMATION: DraIII+hHB12bVL-10 primer R

<400> SEQUENCE: 183
gacactcggt gcagccacag tcttgatctc caccttggtg ccgccgccga ag    52

<210> SEQ ID NO 184
<211> LENGTH: 44
<212> TYPE: DNA
<213> ORGANISM: Artificial Sequence
<220> FEATURE:

<223> OTHER INFORMATION: HpaI+hHB12bVH-1 primer F

<400> SEQUENCE: 184
gttaacgagg tgcagctggt ggagagcggc ggcggcctgg tgca                    44

<210> SEQ ID NO 185
<211> LENGTH: 54
<212> TYPE: DNA
<213> ORGANISM: Artificial Sequence
<220> FEATURE:
<223> OTHER INFORMATION: hHB12bVH-2 primer R

<400> SEQUENCE: 185
cgctggcggc gcagctcagt ctcaggctgc cgccgggctg caccaggccg ccgc          54

<210> SEQ ID NO 186
<211> LENGTH: 54
<212> TYPE: DNA
<213> ORGANISM: Artificial Sequence
<220> FEATURE:
<223> OTHER INFORMATION: hHB12bVH-3 primer F

<400> SEQUENCE: 186
gctgcgccgc cagcggcttc accttcagca gcagctggat gaactgggtg agac          54

<210> SEQ ID NO 187
<211> LENGTH: 56
<212> TYPE: DNA
<213> ORGANISM: Artificial Sequence
<220> FEATURE:
<223> OTHER INFORMATION: hHB12bVH-4 primer R

<400> SEQUENCE: 187
gattctgccc acccactcca ggcccttgcc gggggcctgt ctcacccagt tcatcc        56

<210> SEQ ID NO 188
<211> LENGTH: 57
<212> TYPE: DNA
<213> ORGANISM: Artificial Sequence
<220> FEATURE:
<223> OTHER INFORMATION: hHB12bVH-5 primrer F

<400> SEQUENCE: 188
gagtgggtgg gcagaatcta ccccggcgac ggcgacacca actacaacgg caagttc       57

<210> SEQ ID NO 189
<211> LENGTH: 56
<212> TYPE: DNA
<213> ORGANISM: Artificial Sequence
<220> FEATURE:
<223> OTHER INFORMATION: hHB12bVH-6 primer R

<400> SEQUENCE: 189
tcttgctgtc gtctctgctg atggtgaatc tgcccttgaa cttgccgttg tagttg        56

<210> SEQ ID NO 190
<211> LENGTH: 52
<212> TYPE: DNA
<213> ORGANISM: Artificial Sequence
<220> FEATURE:
<223> OTHER INFORMATION: hHB12bVH-7 primer F

<400> SEQUENCE: 190
ttcagcggca gcggaagcgg caccgacttc accctgacca tcaacagcct gg            52

```
<210> SEQ ID NO 191
<211> LENGTH: 56
<212> TYPE: DNA
<213> ORGANISM: Artificial Sequence
<220> FEATURE:
<223> OTHER INFORMATION: hHB12bVH-8 primer R

<400> SEQUENCE: 191
atgaagccgc ttctggcgca gtagtacacg gcggtgtcct cggtcttcag gctgtt        56

<210> SEQ ID NO 192
<211> LENGTH: 55
<212> TYPE: DNA
<213> ORGANISM: Artificial Sequence
<220> FEATURE:
<223> OTHER INFORMATION: hHB12bVH-9 primer F

<400> SEQUENCE: 192
cgccagaagc ggcttcatca ccaccgtgct ggacttcgac tactggggcc agggc         55

<210> SEQ ID NO 193
<211> LENGTH: 55
<212> TYPE: DNA
<213> ORGANISM: Artificial Sequence
<220> FEATURE:
<223> OTHER INFORMATION: ApaI+hHB12bVH-10 primer R

<400> SEQUENCE: 193
gggccctttg gtggaggcgc tgctcacggt caccagggtg ccctggcccc agtag         55

<210> SEQ ID NO 194
<211> LENGTH: 50
<212> TYPE: DNA
<213> ORGANISM: Artificial Sequence
<220> FEATURE:
<223> OTHER INFORMATION: NaeI-X-aCD20VL-1 primer F

<400> SEQUENCE: 194
gccggccatg gaagcccag ctcagcttct cttcctcctg ctactctggc                50

<210> SEQ ID NO 195
<211> LENGTH: 62
<212> TYPE: DNA
<213> ORGANISM: Artificial Sequence
<220> FEATURE:
<223> OTHER INFORMATION: aCD20VL-2 primer R

<400> SEQUENCE: 195
ctggagactg tgtcaacaca atttctccgg tggtatctgg gagccagagt agcaggagga    60
ag                                                                    62

<210> SEQ ID NO 196
<211> LENGTH: 59
<212> TYPE: DNA
<213> ORGANISM: Artificial Sequence
<220> FEATURE:
<223> OTHER INFORMATION: aCD20VL-3 primer F

<400> SEQUENCE: 196
aattgtgttg acacagtctc cagccaccct gtctttgtct ccaggggaaa gagccaccc     59

<210> SEQ ID NO 197
<211> LENGTH: 59
<212> TYPE: DNA
<213> ORGANISM: Artificial Sequence
<220> FEATURE:
```

<223> OTHER INFORMATION: aCD20VL-4 primer R

<400> SEQUENCE: 197
caggctaagt agctgctaac actctgactg gccctgcagg agagggtggc tctttcccc    59

<210> SEQ ID NO 198
<211> LENGTH: 58
<212> TYPE: DNA
<213> ORGANISM: Artificial Sequence
<220> FEATURE:
<223> OTHER INFORMATION: aCD20VL-5 primer F

<400> SEQUENCE: 198
tgttagcagc tacttagcct ggtaccaaca gaaacctggc caggctccca ggctcctc    58

<210> SEQ ID NO 199
<211> LENGTH: 57
<212> TYPE: DNA
<213> ORGANISM: Artificial Sequence
<220> FEATURE:
<223> OTHER INFORMATION: aCD20VL-6 primer R

<400> SEQUENCE: 199
ctggctggga tgccagtggc cctgttggat gcatcataga tgaggagcct gggagcc    57

<210> SEQ ID NO 200
<211> LENGTH: 59
<212> TYPE: DNA
<213> ORGANISM: Artificial Sequence
<220> FEATURE:
<223> OTHER INFORMATION: aCD20VL-7 primer F

<400> SEQUENCE: 200
actggcatcc cagccaggtt cagtggcagt gggtctggga cagacttcac tctcaccat    59

<210> SEQ ID NO 201
<211> LENGTH: 65
<212> TYPE: DNA
<213> ORGANISM: Artificial Sequence
<220> FEATURE:
<223> OTHER INFORMATION: aCD20VL-8 primer R

<400> SEQUENCE: 201
ctgacagtaa taaactgcaa aatcttcagg ctctaggctg ctgatggtga gagtgaagtc    60
tgtcc    65

<210> SEQ ID NO 202
<211> LENGTH: 62
<212> TYPE: DNA
<213> ORGANISM: Artificial Sequence
<220> FEATURE:
<223> OTHER INFORMATION: aCD20VL-9 primer F

<400> SEQUENCE: 202
gaagattttg cagtttatta ctgtcagcag cgtagcaact ggccgatcac cttcggccaa    60
gg    62

<210> SEQ ID NO 203
<211> LENGTH: 58
<212> TYPE: DNA
<213> ORGANISM: Artificial Sequence
<220> FEATURE:
<223> OTHER INFORMATION: DraIII-aCD20VL-10 primer R

<400> SEQUENCE: 203
gacactcggt gcagccacag ttttaatctc cagtcgtgtc ccttggccga aggtgatc        58

<210> SEQ ID NO 204
<211> LENGTH: 48
<212> TYPE: DNA
<213> ORGANISM: Artificial Sequence
<220> FEATURE:
<223> OTHER INFORMATION: HpaI+aCD20VH-1 primer F

<400> SEQUENCE: 204
gttaacatgg agttgggact gagctggatt ttccttttgg ctatttta        48

<210> SEQ ID NO 205
<211> LENGTH: 59
<212> TYPE: DNA
<213> ORGANISM: Artificial Sequence
<220> FEATURE:
<223> OTHER INFORMATION: aCD20VH-2 primer R

<400> SEQUENCE: 205
ctccaccagc tgcacttcac actggacacc ttttaaaata gccaaaagga aatccagc        59

<210> SEQ ID NO 206
<211> LENGTH: 54
<212> TYPE: DNA
<213> ORGANISM: Artificial Sequence
<220> FEATURE:
<223> OTHER INFORMATION: aCD20VhH-3 primer F

<400> SEQUENCE: 206
gaagtgcagc tggtggagtc tgggggaggc ttggtacagc ctggcaggtc cctg        54

<210> SEQ ID NO 207
<211> LENGTH: 58
<212> TYPE: DNA
<213> ORGANISM: Artificial Sequence
<220> FEATURE:
<223> OTHER INFORMATION: aCD20VH-4 primer R

<400> SEQUENCE: 207
cataatcatt aaaggtgaat ccagaggctg cacaggagag tctcagggac ctgccagg        58

<210> SEQ ID NO 208
<211> LENGTH: 60
<212> TYPE: DNA
<213> ORGANISM: Artificial Sequence
<220> FEATURE:
<223> OTHER INFORMATION: aCD20VH-5 primer F

<400> SEQUENCE: 208
gcctctggat tcacctttaa tgattatgcc atgcactggg tccggcaagc tccagggaag        60

<210> SEQ ID NO 209
<211> LENGTH: 59
<212> TYPE: DNA
<213> ORGANISM: Artificial Sequence
<220> FEATURE:
<223> OTHER INFORMATION: aCD20VH-6 primer R

<400> SEQUENCE: 209
ggaaccacta ttccaactaa tagttgagac ccactccagg cccttccctg gagcttgcc        59

<210> SEQ ID NO 210
<211> LENGTH: 60
<212> TYPE: DNA

```
<213> ORGANISM: Artificial Sequence
<220> FEATURE:
<223> OTHER INFORMATION: aCD20VH-7 primer F

<400> SEQUENCE: 210
tcaactatta gttggaatag tggttccata ggctatgcgg actctgtgaa gggccgattc      60

<210> SEQ ID NO 211
<211> LENGTH: 56
<212> TYPE: DNA
<213> ORGANISM: Artificial Sequence
<220> FEATURE:
<223> OTHER INFORMATION: aCD20VH-8 primer R

<400> SEQUENCE: 211
gatacaggga cttcttggcg ttgtctctgg agatggtgaa tcggcccttc acagag         56

<210> SEQ ID NO 212
<211> LENGTH: 55
<212> TYPE: DNA
<213> ORGANISM: Artificial Sequence
<220> FEATURE:
<223> OTHER INFORMATION: aCD20VH-9 primer F

<400> SEQUENCE: 212
cgccaagaag tccctgtatc tgcaaatgaa cagtctgaga gctgaggaca cggcc          55

<210> SEQ ID NO 213
<211> LENGTH: 57
<212> TYPE: DNA
<213> ORGANISM: Artificial Sequence
<220> FEATURE:
<223> OTHER INFORMATION: aCD20VH-10 primer R

<400> SEQUENCE: 213
gtagtagttg ccgtactgta tatcttttgc acagtaatac aaggccgtgt cctcagc        57

<210> SEQ ID NO 214
<211> LENGTH: 57
<212> TYPE: DNA
<213> ORGANISM: Artificial Sequence
<220> FEATURE:
<223> OTHER INFORMATION: aCD20VH-11 primer F

<400> SEQUENCE: 214
agatatacag tacggcaact actactacgg tatggacgtc tggggccaag ggaccac        57

<210> SEQ ID NO 215
<211> LENGTH: 49
<212> TYPE: DNA
<213> ORGANISM: Artificial Sequence
<220> FEATURE:
<223> OTHER INFORMATION: ApaI-aCD20VH-12 primer R

<400> SEQUENCE: 215
gggccctttg gtggaggctg aggagacggt gaccgtggtc ccttggccc                 49

<210> SEQ ID NO 216
<211> LENGTH: 12
<212> TYPE: PRT
<213> ORGANISM: Artificial Sequence
<220> FEATURE:
<223> OTHER INFORMATION: Humanized 6.3 VL

<400> SEQUENCE: 216

Gln Ser Val Leu Tyr Ser Ser Asn Gln Met Asn Tyr
```

```
1               5                  10
```

<210> SEQ ID NO 217
<211> LENGTH: 8
<212> TYPE: PRT
<213> ORGANISM: Artificial Sequence
<220> FEATURE:
<223> OTHER INFORMATION: Humanized 6.3 VL

<400> SEQUENCE: 217

```
Leu Gln Tyr Leu Ser Ser Trp Thr
1               5
```

<210> SEQ ID NO 218
<211> LENGTH: 8
<212> TYPE: PRT
<213> ORGANISM: Artificial Sequence
<220> FEATURE:
<223> OTHER INFORMATION: Humanized 6.3 VH

<400> SEQUENCE: 218

```
Gly Tyr Thr Phe Lys Asn Tyr Gly
1               5
```

<210> SEQ ID NO 219
<211> LENGTH: 8
<212> TYPE: PRT
<213> ORGANISM: Artificial Sequence
<220> FEATURE:
<223> OTHER INFORMATION: Humanized 6.3 VH

<400> SEQUENCE: 219

```
Ile Asn Thr Tyr Thr Gly Gln Pro
1               5
```

<210> SEQ ID NO 220
<211> LENGTH: 7
<212> TYPE: PRT
<213> ORGANISM: Artificial Sequence
<220> FEATURE:
<223> OTHER INFORMATION: Humanized 6.3 VH

<400> SEQUENCE: 220

```
Ala Arg Asp Trp Gly Pro Tyr
1               5
```

<210> SEQ ID NO 221
<211> LENGTH: 11
<212> TYPE: PRT
<213> ORGANISM: Artificial Sequence
<220> FEATURE:
<223> OTHER INFORMATION: Humanized 15-2b VL

<400> SEQUENCE: 221

```
Lys Ala Ser Gln Asp Val Asn Thr Ser Val Ala
1               5                  10
```

<210> SEQ ID NO 222
<211> LENGTH: 7
<212> TYPE: PRT
<213> ORGANISM: Artificial Sequence
<220> FEATURE:
<223> OTHER INFORMATION: Humanized 15-2b VL

<400> SEQUENCE: 222

```
Trp Ala Ser Thr Arg His Thr
1               5
```

```
<210> SEQ ID NO 223
<211> LENGTH: 9
<212> TYPE: PRT
<213> ORGANISM: Artificial Sequence
<220> FEATURE:
<223> OTHER INFORMATION: Humanized 15-2b VL

<400> SEQUENCE: 223

Leu Gln Tyr Ile Asn Tyr Pro Tyr Thr
1               5

<210> SEQ ID NO 224
<211> LENGTH: 10
<212> TYPE: PRT
<213> ORGANISM: Artificial Sequence
<220> FEATURE:
<223> OTHER INFORMATION: Humanized 15-2b VH

<400> SEQUENCE: 224

Gly Phe Thr Phe Ser Asn Tyr Trp Met Asn
1               5                   10

<210> SEQ ID NO 225
<211> LENGTH: 19
<212> TYPE: PRT
<213> ORGANISM: Artificial Sequence
<220> FEATURE:
<223> OTHER INFORMATION: Humanized 15-2b VH

<400> SEQUENCE: 225

Glu Ile Arg Ser Lys Ser Asn Asn Tyr Ala Thr His Tyr Ala Glu Ser
1               5                   10                  15

Val Lys Gly

<210> SEQ ID NO 226
<211> LENGTH: 6
<212> TYPE: PRT
<213> ORGANISM: Artificial Sequence
<220> FEATURE:
<223> OTHER INFORMATION: Humanized 15-2b VH

<400> SEQUENCE: 226

Ser Asn Arg Tyr Tyr Trp
1               5
```

BI-SPECIFIC ANTIBODIES AND USES THEREOF

This application contains a Sequence Listing in computer readable form.

The computer readable form is incorporated herein by reference. This application is a Continuation application of the pending U.S. patent application Ser. No. 15/123,243 filed on Sep. 1, 2016, which is the National Stage of International Application No. PCT/US2015/018365 filed on Mar. 2, 2015, which claims priority to U.S. Provisional Application No. 61/946,997, filed Mar. 3, 2014, and U.S. Provisional Appl. No. 61/946,980, filed Mar. 3, 2014. The entire contents of these documents are incorporated herein by reference in their entireties.

BACKGROUND OF THE INVENTION

1. Field of the Invention

The present disclosure relates to treatments of cancers. Specifically, the present disclosure relates to novel bi-specific antibodies and their uses for suppressing the growth or metastasis of cancers; and tracking the development of cancers.

2. Description of Related Art

Covalent attachment of poly(ethylene glycol) (PEGylation) to substances such as proteins, peptides, and nanoparticles (NPs) (e.g., liposomes, micelles, and the like) can increase drug bioavailability, enhance blood circulation half-life and hinder capture by the reticuloendothelial system (RES). These favorable attributes have led to the widespread use of PEGylation in the development of NPs including those available in clinical use, such as liposomal doxorubicin (Caelyx) for the treatment of ovarian and breast carcinomas and Kaposi's sarcoma and Genexol-PM® (Paclitaxel-loaded PEG-PLA micelles), approved for metastatic breast cancer, non-small cell lung cancer and ovarian cancer in South Korea. PEGylated nanoparticles (PEG-NPs) are highly regarded as the second generation of drug delivery systems and the mainstream of therapeutic or imaging agents.

PEGylated substances, particularly, PEG-NPs can accumulate in tumors due to the enhanced permeability and retention (EPR) effect caused by the abnormal structure of endothelial cells in tumors. PEG-NPs, however, often accumulate near tumors but do not penetrate into the tumor mass, and some drugs cannot easily diffuse from PEG-NPs to cancer cells. Therefore, several studies reported that chemical conjugation of antibodies to PEG-NPs increases specific targeting and intracellular uptake which improves therapeutic efficacy and the sensitivity of imaging. However, chemically linking antibodies to PEG-NPs is difficult to achieve. Most functional groups (e.g., amino, carboxyl, thiol groups) are abundant in ligands, which may cause loss of antibody function, or result in heterogeneous orientation of the antibody, thereby rendering it difficult to obtain a reproducible product after chemical conjugation. Further, chemical conjugation may also alter the structure of nano-carriers and encapsulated drugs. These problems limit the clinical applicability of targeted NPs.

In view of the foregoing, there exist in the related art, a need for an improved way of targeting PEGylated substances (e.g., PEG-NPs), which is reproducible and easy to use.

SUMMARY

The present disclosure provides humanized bi-specific antibodies and their uses for treating cancers or for tracking development of cancers.

Accordingly, it is the first object of the present disclosure to provide a bi-specific antibody (BsAb) that bind to two different epitopes, which are a PEG molecule (e.g., the terminal methoxy or hydroxyl group of the PEG, or the backbone of the PEG) and a target ligand (e.g., an epidermal growth factor receptor (EGFR), TAG72, CD19, or CD20). The BsAb of the present disclosure includes a first antigen binding site that binds to PEG and comprises a first light chain variable domain and a first heavy chain variable domain; a second antigen binding site that binds to a target ligand (e.g., a tumor antigen). Preferably, the BsAb of the present disclosure further includes a peptide linker between the first antigen binding site and the second antigen binding site. Optionally, the first antigen binding site may further include a first hinge domain.

The target ligand may be a protein selected from the group consisting of epidermal growth factor receptor (EGFR), human epidermal growth factor receptor (HER2), HER3, tumor-associated glycoprotein 72 (TAG-72), CD19 and, CD20.

In some embodiments, the first antigen binding site of the BsAb binds to the backbone of PEG and comprises a first VL-Cκ domain at least 90% identical to SEQ ID NO: 1, a first VH-CH1 domain at least 90% identical to SEQ ID NO: 2, and a first hinge domain at least 90% identical to SEQ ID NO: 3; while the second antigen binding site of the BsAb binds to any of TAG-72, EGFR, or HER2 and comprises a single chain variable fragment (scFv) at least 90% identical to SEQ ID NO: 5, 7, or 8; and the peptide linker is at least 90% identical to SEQ ID NO: 4.

In some embodiments, the first antigen binding site binds to the backbone of PEG with the first VL-Cκ domain at least 90% identical to SEQ ID NO: 9, and the first VH-CH1 domain at least 90% identical to SEQ ID NO: 10; while the second antigen binding site binds to EGFR or CD19 and comprises a scFv at least 90% identical to SEQ ID NO: 7 or 11; and the peptide linker is at least 90% identical to SEQ ID NO: 4.

In other embodiment, the first antigen binding site binds to the backbone of PEG and comprises a first VL-Cκ domain at least 90% identical to SEQ ID NO: 9, a first VH-CH1 domain at least 90% identical to SEQ ID NO: 10, and a first HR-CH2-CH3 domain at least 90% identical to SEQ ID NO: 22; while the second antigen binding site binds to CD19 or HER2 and comprises a second VL-CH1 domain at least 90% identical to SEQ ID NO: 23 or 26, a second VH-Cκ domain at least 90% identical to SEQ ID NO: 24 or 27, and a second HR-CH2-CH3 domain at least 90% identical to SEQ ID NO:25.

In another embodiment, the first antigen binding site binds to the terminal methoxy or hydroxyl group of PEG and comprises a first VL-Cκ domain at least 90% identical to SEQ ID NO: 12, a first VH-CH1 domain at least 90% identical to SEQ ID NO: 13, and a first HR-CH2-CH3 domain at least 90% identical to SEQ ID NO: 22; while the second antigen binding site binds to CD19 or HER2 and comprises a second VL-CH1 domain at least 90% identical to SEQ ID NO: 23 or 26, a second VH-Cκ domain at least 90% identical to SEQ ID NO: 24 or 27, and a second HR-CH2-CH3 domain at least 90% identical to SEQ ID NO: 25.

In still another embodiment, the first antigen binding site binds to the terminal methoxy or hydroxyl group of polyethylene glycol (PEG) and comprises a first VL-Cκ domain at least 90% identical to SEQ ID NO: 12, a first VH-CH1 domain at least 90% identical to SEQ ID NO: 13, and a first HR-CH2-CH3 domain at least 90% identical to SEQ ID NO: 22; while the second antigen binding site binds to HER2 or EGFR, and comprises a humanized single chain variable fragment (scFv) at least 90% identical to SEQ ID NO: 15 or 16.

In further embodiments, the first antigen binding site binds to the terminal methoxy or hydroxyl group of polyethylene glycol (PEG) and comprises a humanized single chain variable fragment (scFv) at least 90% identical to SEQ ID NO: 17; while the second antigen binding site binds to CD19 or CD20 and comprises a first VL-Cκ domain at least 90% identical to SEQ ID NO: 21, a first VH-CH1 domain at least 90% identical to SEQ ID NO: 20.

It is the second object of the present disclosure to provide a pharmaceutical kit for treating or tracking the development of cancers, including metastatic and/or drug-resistant cancers. The pharmaceutical kit includes at least, two components, which are respectively the bi-specific antibody described above; and a PEGylated substance that is either a therapeutic agent or an imaging agent. The therapeutic agent may be any of a protein, a peptide, or a nanoparticle containing therein a chemotherapeutic drug. The imaging agent may be a quantum dot (QD), a microbubble contrast agent, a fluorescence dye, an iron nanoparticle, a chelated radioisotope or a gold nanoparticle.

In practice, the bi-specific antibody and the PEGylated substance of the pharmaceutical kit are first mixed to form an assembly; and the assembly is then administered to the subject for treating cancers or for tracking cancers.

It is thus the third object of the present disclosure to provide a method of treating a subject suffering from the growth of a cancer. The method includes the steps of, administering the bi-specific antibody described above and a PEGylated substance containing a therapeutic agent, concurrently or sequentially to the subject in a dose sufficient to inhibit the growth or metastasis of the cancer of the subject. Preferably, the method comprises the steps of mixing the bi-specific antibody described above and the PEGylated substance containing a therapeutic agent to form an assembly, and administering the assembly to the subject in a dose sufficient to inhibit the growth or metastasis of the cancer of the subject. The dose administered to the subject is from about 0.1 to 50 mg/Kg body weight of the subject. In certain embodiments, the dose is administered to the subject from about 1 to 40 mg/Kg body weight of the subject, preferably from about 5 to 10 mg/Kg body weight of the subject. The dose can be administered in a single dose, or alternatively in more than one smaller doses.

Cancers, preferably those exhibit increased expression levels of EGFR, HER2, TAG72, CD19 or CD20 are treatable by the method of the present disclosure. In preferred embodiments, the method of the present disclosure is effective for treating a subject having breast cancer, head and neck cancer, colorectal cancer or ovarian cancer.

It is the fourth object of the present disclosure to provide a method of imaging tissues in a live subject. The method includes steps of, administering the bi-specific antibody described above and a PEGylated substance containing a therapeutic agent, concurrently or sequentially to the subject in an amount sufficient to imagine the tissues in the subject. Preferably, the method includes steps of: (a) mixing a first sufficient amount of any of the humanized bi-specific antibody of the present disclosure and a second sufficient amount of a PEGylated substance (e.g., a nanoparticle containing therein an imagine agent such as a quantum dot (PEG-QD) or a fluorescent dye) to form an assembly; (b) injecting the assembly of the step (a) to the subject; and (c) imaging the tissues of the subject by fluorescence imaging, electron spin resonance (ESR) imaging, gamma camera imaging, X-ray imaging, computed tomography (CT), or magnetic resonance imaging (MRI). According to some embodiments, the PEG-QD comprises a quantum dot nanocrystal selected from the group consisting of CdHgTe, CdSe, CdSe/ZnS, CdS, CdTe, CdTe/CdS, PbSe and PbS.

The details of one or more embodiments of the invention are set forth in the accompanying description below. Other features and advantages of the invention will be apparent from the detail descriptions, and from claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects and advantages of the present invention will become better understood with reference to the following description, appended claims and the accompanying drawings, where:

FIG. 3 is a schematic diagram illustrating the one-step targeting and treating cancer by use of the humanized anti-mPEG BsAbs in accordance to one embodiment of the present disclosure;

FIG. 7 illustrates the cancer cell selectivity of the humanized anti-PEG (hE11) BsAbs of example 1.2 in accordance with one embodiment of the present disclosure;

FIG. 12 illustrates the binding activities of the humanized monovalent anti-PEG (hE11) BsAbs of example 2.1 with the PEGylated Quantum Dot (Qdot655) in Jurkat (TAG-72+), MDA-MB-468 (EGFR+) or BT-474 (HER2+) cells in accordance with one embodiment of the present disclosure;

FIG. 13A is a schematic illustration of DNA constructs for humanized monovalent anti-PEG (h6.3) BsAbs of example 2.2 and the structure of the BsAb in accordance with one embodiment of the present disclosure;

FIG. 24B is a schematic illustration of DNA constructs for humanized knob in hole anti-PEG (h6.3) BsAbs of example 3.1 and the structures of the BsAbs in accordance with one embodiment of the present disclosure;

FIG. 29 is a schematic illustration of DNA constructs for BsAbs of example 4.1 in accordance with one embodiment of the present disclosure;

DESCRIPTION

Figure 1:
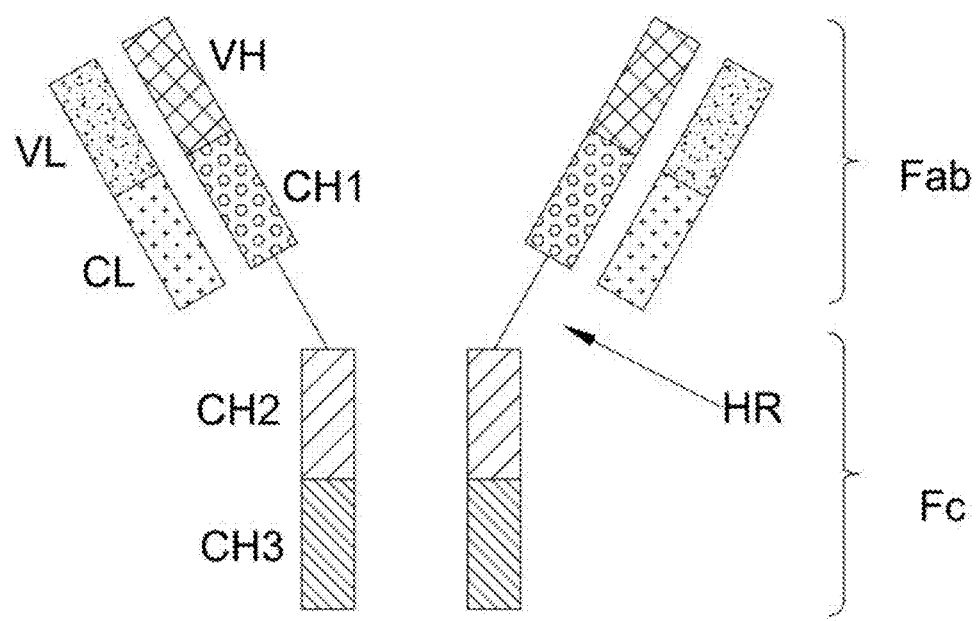
FIG. 1 is a schematic diagram of IgG antibody with the domains indicated.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

The term "antibody" is used in the broadest sense and specifically covers monoclonal antibodies, polyclonal antibodies, multispecific antibodies (e.g., bi-specific antibodies), and antibody fragments so long as they exhibit the desired biological activity, that is, to specifically bind to an antigen when it preferentially recognizes its target antigen in a complex mixture of proteins and/or other molecules.

The term "monoclonal antibody" as used herein refers to an antibody obtained from a population of substantially homogeneous antibodies, and is not to be constructed as requiring production of the antibody by any particular method. In contrast to polyclonal antibodies which typically include different antibodies directed to different epitopes, each monoclonal antibody is directed against a single determinant (i.e., epitope) on the antigen. The monoclonal antibodies of the present disclosure may be made by the hybridoma method or by recombinant DNA methods. The monoclonal antibodies herein specifically include "chimeric" or "recombinant" antibodies, in which a portion of the heavy and/or light chain is identical with or homologous to corresponding sequences in antibodies derived from a particular species or belonging to an antibody class or subclass, while the remainder of the chain identical with or homologous to corresponding sequences in antibodies derived from another species or belonging to another antibody class or subclass, as well as fragments of such antibodies, as long as they exhibit the desired biological activity.

"Humanized" forms of non-human (e.g., murine) antibodies are chimeric antibodies which contain minimal sequence derived from non-human immunoglobulin. Humanized antibodies are human immunoglobulins in which hypervariable region residues are replaced by hypervarible region residues from a non-human species such as mouse, rat, rabbit, or non-human primate having the desired specificity or affinity. In some instances, Fv framework region (FR) residues of the human immunoglobulin are replaced by corresponding non-human residues. In general, the humanized antibody will comprise substantially all of at least one, and typically two, variable domains, in which all or substantially all of the FR regions are those of a human immunoglobulin sequence. The humanized antibody may optionally comprise at least a portion of an immunoglobulin constant region (Fc), typically that of a human immunoglobulin.

An "isolated" antibody is one which has been identified and separated and/or recovered from a component of its nature environment. Containment components of its nature environment are materials which would interfere with therapeutic uses of the antibody of this invention, and may include enzymes, hormones, and other protenaceous or non-proteinaceous solutes. Isolated antibody includes the antibody in situ within recombinant cells. Ordinarily, isolated antibody will be prepared by at least one purification step.

The term "bi-specific antibody (BsAb)" refers to an antibody having specificities for at least two different antigens. For example, BsAb may have one arm having a specificity for one antigenic site, such as a tumor associated antigen, while the other arm recognizes a different target, for example, a haptan that is bound to a lethal agent (e.g., INF-α or a liposome containing an anti-cancer agent such as vinca alkaloid) or an imaging agent (e.g., a microbubble containing a contrast agent or a quantum dot or fluorescent dye). In preferred embodiments, the BsAb of the present disclosure has two antigen-binding sites, in which one is directed against a tumor antigen (e.g., TAG72, CD19, EGFR or HER2), while the other is directed against a hydrophilic polymer (e.g., polyethylene oxide (PEG)), that is bound to a nanoparticle containing a cancer therapeutic agent therein (e.g., Lipo/DOX).

The term "valent" as used herein refers to the presence of a specified number of binding sites in an antibody molecule.

As such, the term "monovalent", "divalent", "trivalent" and tetravalent" refer to the presence of 1, 2, 3, and 4 binding sites, respectively in an antibody molecule. The BsAb of the present disclosure is at least "divalent", and may be multivalent, such as tetravalent.

The term "linker" and "peptide linker" are interchangeably used in the present disclosure and refers to a peptide having natural or synthetic amino acid residues for connecting two polypeptides. For example, the peptide linker may be used to connect the VH and the VL to form the single chain variable fragment (e.g., scFv); or to connect the scFv to the full length antibody to form a BsAb of the present disclosure. Preferably, the linker is a peptide having at least 5 amino acid residues in length, such as 5 to 100 amino acid residues in length, more preferably 10 to 30 amino acid residues in length. The linker within scFv is a peptide of at least 5 amino acid residues in length, preferably 15 to 20 amino acid residues in length. In one example, the linker comprises a sequence of $(G_nS)_m$, with G=glycine, S=serine, n is a number between 1 to 4, and m is 1, 2 or 3. Preferably, the linker comprises a sequence of $(G_4S)_3$; or a sequence of $(G_3S)$ and $(G_3S_2)$.

The term "PEGylated substance" as used herein refers to a substance coated with polyethylene glycol (PEG), which includes but is not limited to, a protein (e.g., a chemokine), a peptide (e.g., leuprolide) and a nanoparticle (NP) containing therein a therapeutic agent or an imagine agent. Materials known in the state of the art that may give rise to the nanoparticle includes mesoporpous silica, as well as the material that has a hydrophilic portion and a hydrophobic portion that forms a micelle structure capable of including a therapeutic agent (e.g., anti-cancer agent) or an imaging agent (e.g., a fluorescence dye, a quantum dot, a chelated radioisotope, a paramagnetic iron, gold nanoparticle or a contrast agent) within its structure. Suitable materials for forming nanoparticles in the present disclosure include, but are not limited to, mesoporpous silica; phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination; biodegrable polymer such as polylactic acid (PLA), polyglycolic acid (PGA) poly(lactic-co-glycolic acid) (PLGA), polycaprolactone (PCL), polydioxanone (PDO), polyanhydrides, polyorthoesters, chitosan and the like, alone or in combination. Preferably, the PEGylated substance, such as a PEGylated NP, further contains a cancer therapeutic agent or an imagine agent within the micelle structure.

The terms "cancer" and "tumor" are used alternatively in the present disclosure and preferably refer to the physiological condition in mammals and especially in humans that is typically characterized by un-regulated cell growth. Cancers in this respect include metastases cancers, and/or drug-resistant cancers. Cancers, preferably those exhibit increased expression levels of TAG72, EGFR, HER2, CD19, and CD20. Accordingly, cancers or tumors treatable by the present disclosure are breast, lung, colon, colorectal, spleen, kidney, liver, bladder, head and neck, ovary, prostate, brain, pancreas, skin, bone, blood, thymus, uterus, testicles, cervix, and neuron. More specifically, the cancer is selected from the group consisting of breast cancer, colorectal cancer, head and neck cancer, colon cancer, hepatic cancer, non-Hodgkin's lymphoma, lymphoma, pancreatic cancer, lung cancer, gastric cancer, prostate cancer, brain tumor, retinoblastoma, ovarian cancer, cervical cancer, hematopoietic malignances, esophageal cancer, renal cell carcinoma, squamous cell carcinoma, glioma, and leukemia The term "therapeutic agent(s)" as used herein refers to an agent utilized to treat, combat, ameliorate, prevent or improve a disease or a condition, such as a cancer, in a patient. Accordingly, therapeutic agent(s) for treating cancer preferably refers to cytotoxic agents that are known to improve the therapeutic effects of a cancer treatment; accordingly, cytotoxic agents as used in the present disclosure include, but are not limited to, radiation, chemotherapeutic agents, antibodies, and the like.

The term "drug-resistant cancer" as used herein refers to a cancer whose growth is not suppressed or retarded by the application of a well-known cytotoxic agent, which may be a chemotherapeutic agent, an antibody, a peptide or a combination thereof. In some embodiments, the drug is a chemotherapeutic agent. Examples of chemotherapeutic agent include alkylating agent such as nitrosoureas, cisplatin, or dacarbazine; antimetabolites such as folic acid, purine or pyrimidine antagonists; mitotic inhibitors such as vinca alkaloids; cytotoxic antibiotics and camptothecin derivatives. Preferred chemotherapeutic agent includes adriamycin, amifostine, bleomycin, busulfan, cisplatin, and/or other platinum compounds, preferably including carboplatin and/or oxaliplatin, camptothecin, CPT-11, cytosine arabinoside, chlorambucil, cyclophosphamide, cytarabine, daunorubicin, doxorubicin, docetaxel, dacarbazine, dactinomycin, etoposide, 5-fluorouracil (5-FU), fluoxuridine, gemcitabine, hydroxyurea, ifosfamide, idarubicin, interferon beta, irinotecan, L-asparaginase, L-aspartic acid, lomustine, mechlorethamine, mitomycin, methotrexate, mitoxantrone, megestrol, melphalan, mercaptopurine, mitotane, paclitaxel (taxol), plicamycin, pentostatin, streptozocin, topotecan, tamoxifen, teniposide, thioguanine, vinblastine, vincristine, and a combination thereof. In other embodiments, the drug is a chemokine (e.g., CC chemokine, CXC chemokine, C chemokine and $CX_3C$ chemokine) or a cytokine (e.g., interferone, interleukin, lymphokine, and tumor necrosis factor). In further embodiments, the drug is a peptide, preferably a peptide with cytotoxicity effects toward cancer cells. Preferably, the anti-cancer peptide is selected from the group consisting of leuprolide, goserelin, octreotide, histrelin, abarelix, cetrorelix, degarelix, cilengtide, ATN-161, and IM862.

The term "therapeutically effective amount" as used herein refers to an amount effective, at dosages, and for periods of time necessary, to achieve the desired therapeutically desired result with respect to the treatment of cancers, including metastatic and/or drug-resistant cancers.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "administered", "administering" or "administration" are used interchangeably herein to refer means either directly administering a bi-specific antibody or a composition of the present disclosure.

The term "subject" or "patient" refers to an animal including the human species that is treatable with the compositions and/or methods of the present disclosure. The term "subject" or "patient" intended to refer to both the male and female gender unless one gender is specifically indicated. Accordingly, the term "subject" or "patient" comprises any mammal which may benefit from treatment of cancer. Examples of a "subject" or "patient" include, but are not limited to, a human, rat, mouse, guinea pig, monkey, pig, goat, cow, horse, dog, cat, bird and fowl. In an exemplary embodiment, the patient is a human.

The term "identical" or "percent identity" as used herein refers to two or more sequences or subsequences that are the same or have a specified percentage of amino acid residues that are the same, when compared and aligned for maximum correspondence. To determine the percent identity, the sequences are aligned for optimal comparison purposes (e.g., gaps can be introduced in the sequence of a first amino acid sequence for optimal alignment with a second amino acid sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=number of identical positions/total number of positions (e.g., overlapping positions)×100). In certain embodiments, the two sequences are the same length.

The singular forms "a", "and", and "the" are used herein to include plural referents unless the context clearly dictates otherwise.

II. Description of the Invention

Accordingly, it is the first aspect of the present disclosure to provide bi-specific antibodies (BsAbs) that convert a non-targeted PEGylated substance to tumor-targeted PEGylated substance and thereby suppress the growth of a cancer or blocking the invasion or metastasis of a cancer, including drug-resistant cancer.

1. The Structures of BsAbs of the Present Disclosure

Antibodies belong to the immunoglobulin class of proteins that includes IgG, IgA, IgE, IgM, and IgD. The most abundant immunoglobulin found in serum is IgG, whose schematic structure is illustrated in FIG. 1. The IgG structure has four chains, two light chains and two heavy chains; each light chain has two domains and each heavy chain has four domains. The antigen-binding site is located in the fragment antigen binding (Fab) region that contains a variable light (VL) and variable heavy (VH) chain domains as well as a constant light (CL) and constant heavy (CH1) domains. The CH2 and CH3 domain region of the heavy chain is called fragment crystallizable (Fc) region. A full length antibody heavy chain is therefore a polypeptide consisting of, from N-terminus to C-terminus, a VH, a CH1, a hinge region (HR), a CH2, and a CH3; abbreviated as VH-CH1-HR-CH2-CH3. A full length antibody light chain is a polypeptide consisting in N-terminus to C-terminus direction of a VL and a CL, abbreviated as VL-CL, in which the CL can be κ (kappa) or λ (lambda). The IgG is regarded as a heterotetramer having two heavy chains that are held together by disulfide bonds (—S—S—) between the CL domain and the CH1 domain and between the hinge regions of the two heavy chains.

As stated above in the "definition" section, the BsAbs refer to Abs having specificities for at least two different antigens; hence, BsAbs of the present disclosure is a recombinant Ab engineered to contain sequences capable of binding to different antigens. Accordingly, various recombinant bi-specific antibody formats have been developed in the present disclosure, and the schematic structures of these BsAbs are illustrated in FIGS. 2A to 2E.

Figure 2A:
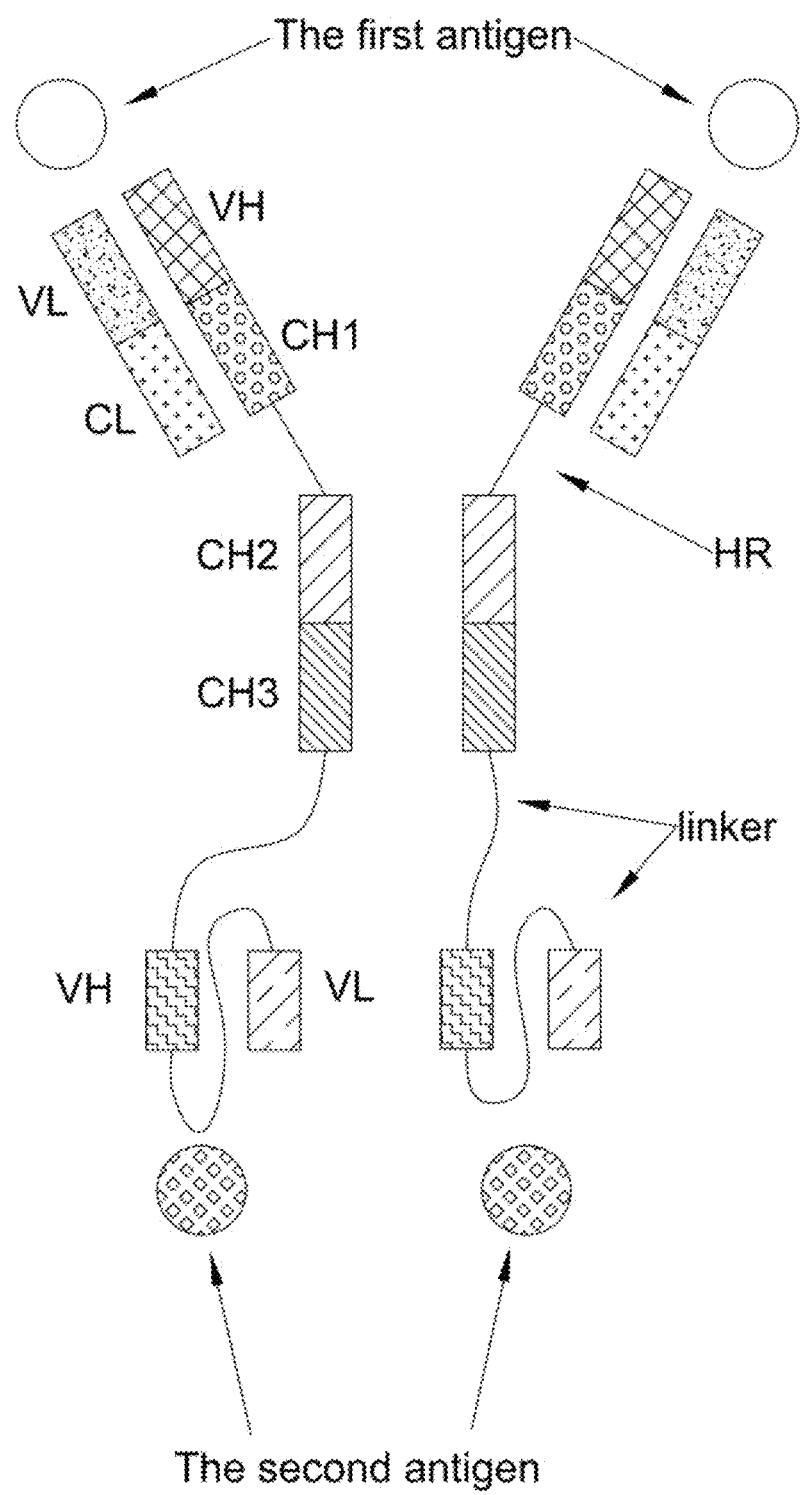
FIG. 2A is a schematic diagram of a dimeric BsAb structure in accordance to one embodiment of the present disclosure.

In some embodiments, the BsAb of the present disclosure is a dimeric, tetravalent bi-specific antibody, in which the two heavy chains of a full length IgG directed to the first antigens are respectively fused to single chain variable fragments (e.g., scFv) directed to the second antigens via peptide linkers (FIG. 2A). The scFv, preferably a disulfide-stabilized scFv, consists of an antibody heavy chain variable domain (VH) and an antibody light chain variable domain (VL), and a linker; abbreviated as VH-linker-VL.

Figure 2B:
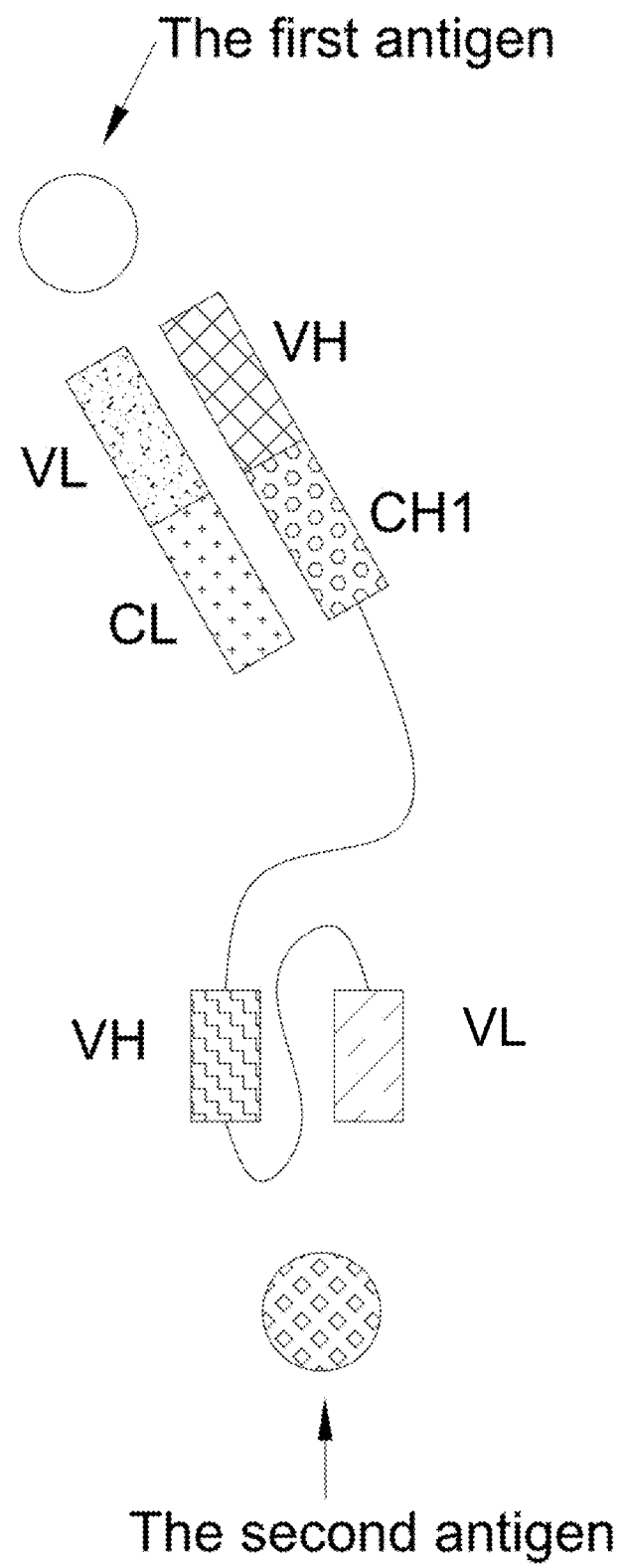
FIG. 2B is a schematic diagram of a monomeric BsAb structure in accordance to one embodiment of the present disclosure.

Alternatively, the BsAb of the present disclosure may be a monomeric, divalent bi-specific antibody, in which a VH-CH1 domain and a light chain VL-CL domain directed to a first antigen is fused via a peptide linker to a disulfide stabilized single chain domain directed to a second antigen (FIG. 2B).

Figure 2C:
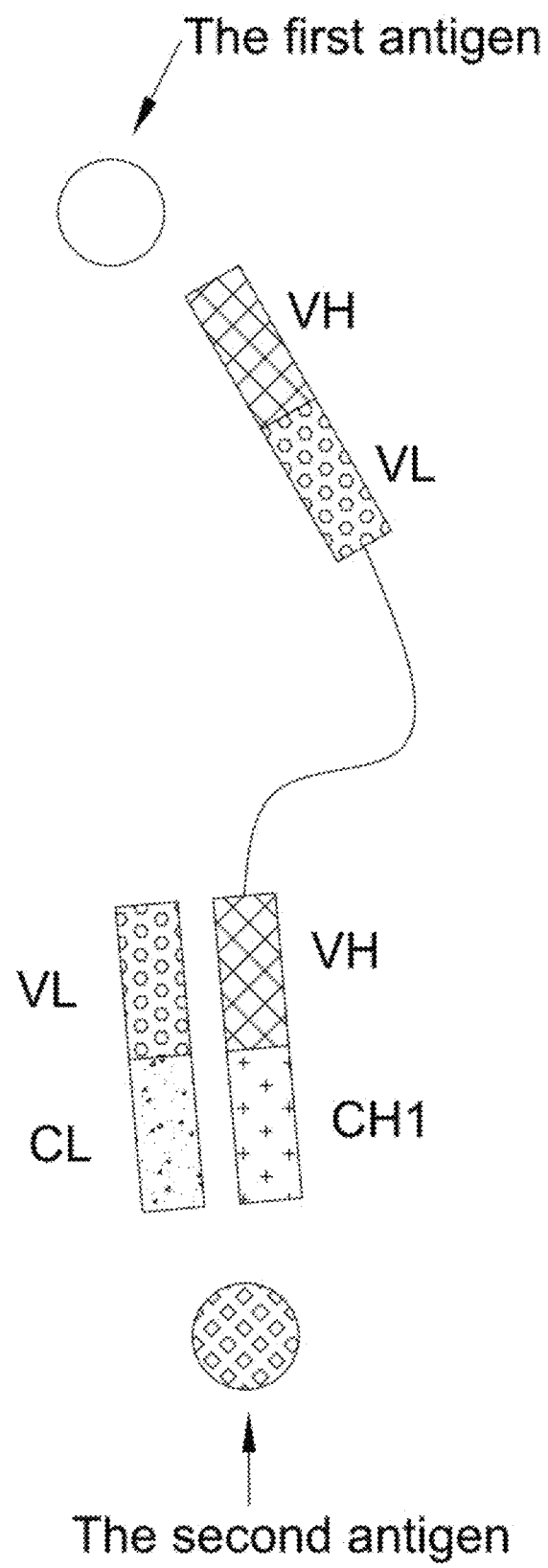
FIG. 2C is a schematic diagram of a monomeric BsAb structure in accordance to another embodiment of the present disclosure.

In some embodiments, the BsAb of the present disclosure is a monomeric, divalent bi-specific antibody, in which a disulfide stabilized single chain domain directed to the first antigen is connected to a monomeric antibody directed to a second antigen via a peptide linker (FIG. 2C).

In other embodiments, the BsAb of the present disclosure has a "knob into hole" structure, in which a knob in the CH3 domain of the first heavy chain is created by replacing several amino acids with alternative amino acids, and a hole in the juxtaposed position at the CH3 domain of the second heavy chain is created by replacing appropriate amino acid with alternative ones. In addition, cysteine residues are introduced to form a disulfide bond linkage between the heavy chains. A schematically presentation of the "knob into hole" BsAb structure is as depicted in FIG. 2D.

Figure 2D:
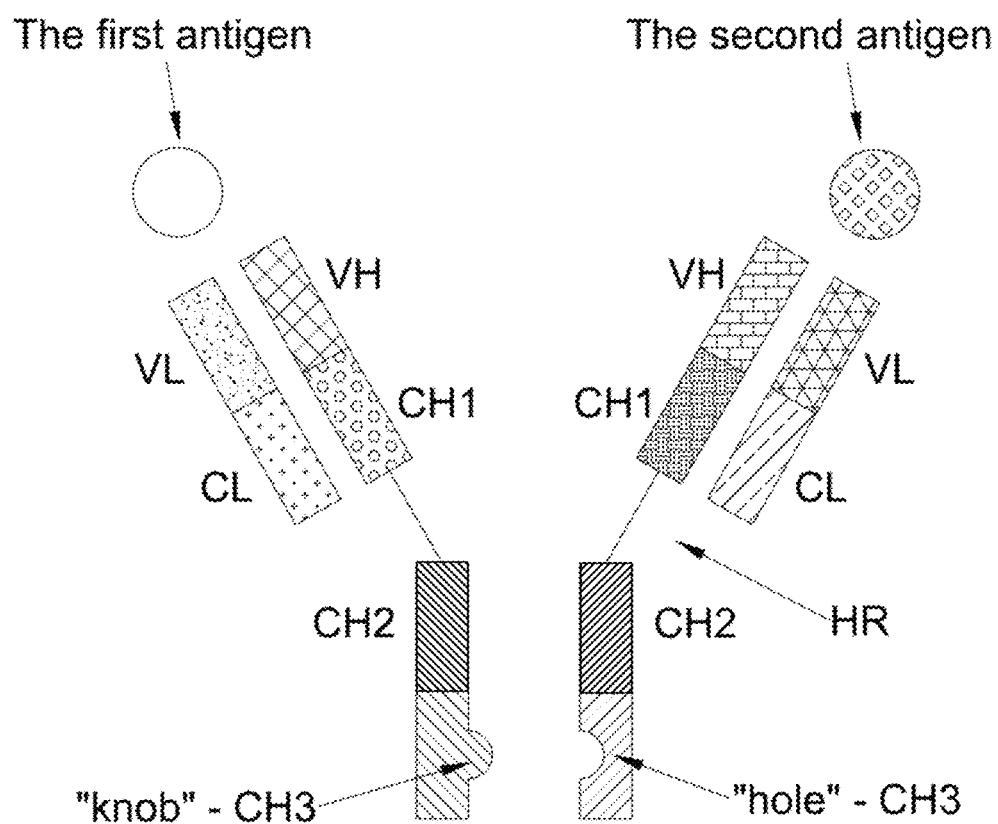
FIG. 2D is a schematic diagram of a "knob in hole" BsAb structure in accordance to one embodiment of the present disclosure.
Figure 2E:
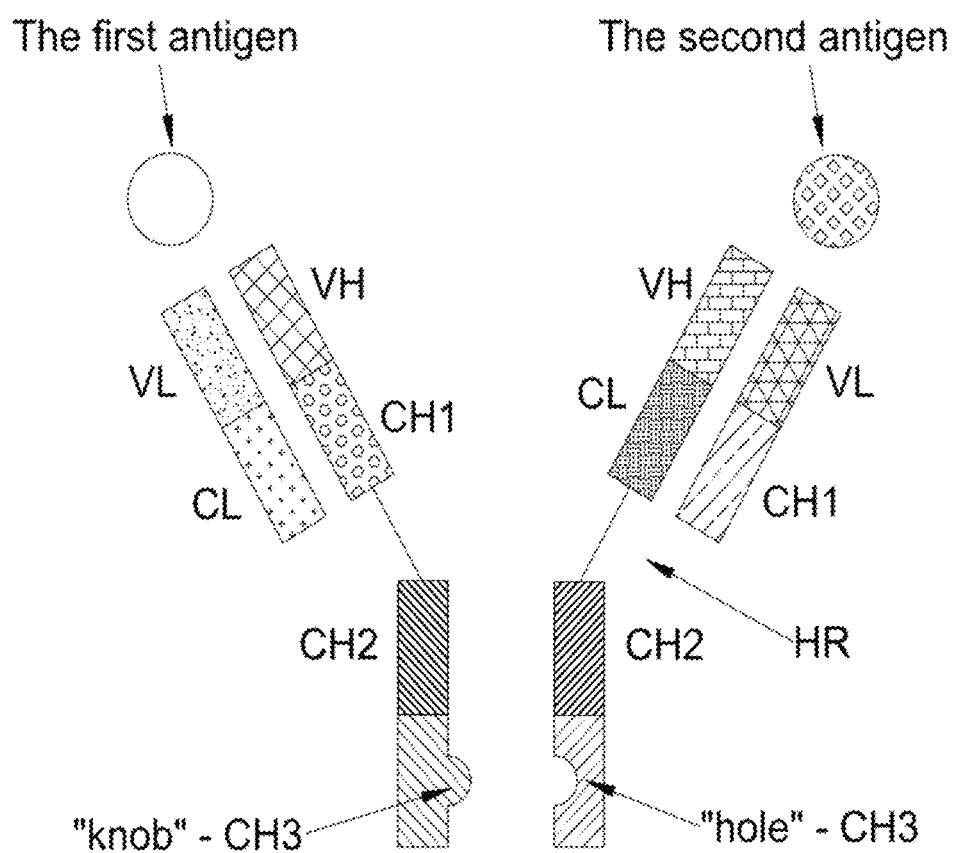
FIG. 2E is a schematic diagram depicting the modified "knob in hole" BsAb structure having crossover heavy and light chains in accordance to one embodiment of the present disclosure.

In further embodiments, the "knob in hole" BsAb as depicted in FIG. 2D is further modified, in which a monomeric antibody heavy chain is crossovered with its light chain during transcription, and thereby creating a modified antibody heavy chain hetero-polypeptide consisting in N-terminus to C-terminus direction of a VH, a CL, a hinge region (HR), a CH2, and a knob-CH3; abbreviated as VH-CL-HR-CH2-knob-CH3; and a modified antibody light chain hetero-polypeptide consisting in N-terminus to C-terminus direction of a VL and a CH1; abbreviated as VL-CH1. FIG. 2E is a schematic drawing of this modified "knob into hole" BsAb structure, in which one monomeric antibody heavy chain is crossovered with its light chain, while the other monomeric antibody structure remains unchanged.

2. Antibody Preparation

Methods for preparing the BsAbs of the present disclosure are described in the Examples. In order to prepare a humanized BsAb, a non-human (e.g., murine) antibody is prepared and used as a starting material; relevant technology is briefly described in the following section.

2.1 Production of Murine Anti-mPEG Antibody

To produce the desired monoclonal antibodies, animals such as mice, rats or rabbits are first immunized with mPEG-derivatized proteins (i.e., the PEG molecule has a terminal methoxy group) molecule or PEG-derivatized proteins (i.e., the PEG molecule has a terminal hydroxyl group) at a suitable dose. Generally, adjuvant and the mPEG- or PEG-derivatized protein solution are mixed together when immunizing the animals with mPEG- or PEG-derivatized proteins. Examples of adjuvants useful for this invention include Freund's complete adjuvant (FCA), Freund's incomplete adjuvant (FIA), and aluminum hydroxide adjuvant. Immunization is generally carried out mainly by intravenous, subcutaneous, intraperitoneal or intramuscular injection of the antigen. The immunization interval is not particularly limited. Immunization may be carried out at intervals of several days to several weeks, preferably 2 to 3 weeks, for 1 to 10 times, preferably 2 to 5 times. Once antibody titers in serum samples diluted by 1000 fold reaches 2 or more in the absorbance level as the result of immunization, the animals are left for about 1 month Then, re-immunization is carried out for at least once. Several days, preferably 3 to 5 days, after the final immunization, splenic cells and regional lymph nodes are removed. Blood samples are taken regularly after immunization and subject to centrifugation to separate sera. The resultant sera are then subject to measurement of antibody titers by any suitable method, which includes, and is not limited to, enzyme linked immunosorbent assay (ELISA), enzyme immunoassay (EIA), or radio immunoassay (RIA). In one preferred example, antibody titers are measured by ELISA. Then, final immunization is given to those animals showing high antibody titers to mPEG- or PEG-derived protein isoforms.

Antibody-producing cells are prepared from splenic cells and regional lymph nodes or the like of the immunized animals. In the preparation of antibody-producing cells, it is preferably to remove tissue debris and erythrocytes as much as possible. Commercial erythrocyte remover may be used to this purpose. Alternatively, a buffer ammonium chloride and Tris may be prepared and used.

The thus prepared antibody-producing cells should be immediately fused with immortal cells such as myeloma cells to produce hybridoma cells, which semi-eternally continue to proliferate while producing antibodies. Commonly available cell strains derived from an animal such as a mouse may be used. A preferable cell strain to be used in this invention should be those that fuse efficiently, support stable high level production of antibody and are sensitive to HAT selection medium, which contains hypoxanthine, thymidine and aminopterin, and should survive there only when fused with antibody-producing cells. Examples of myeloma cells include, but are not limited to, mouse myeloma cell line (such as myeloma FO cells) and human myeloma cell line (such as Karpas 707H).

Cell fusion is usually carried out by mixing splenic cells or lymph node cells with a commercial available myeloma cells in the presence of a cell-fusion promoter, such as PEG having an average molecular weight from about 200 to 20,000 daltons or the like. Alternatively, cell fusion may be carried out in a commercial cell fusion device utilizing electric stimulation such as electro-fusion. After the fusion, the resultant cells are then diluted and cultured in HAT medium.

Hybridomas of interest are then selected from the fused cells. The fused cells surviving cultured in HAT medium would form colonies. The supernatant of each culture well is then collected and examined for the presence or absence of antibody titers to mPEG- or PEG-derivatizeded proteins. As a method of confirmation, ELISA, EIA or RIA may be used, in which $CH_3$-$PEG_{750}$-$NH_2$ or $NH_2$-$PEG_{3000}$-$NH_2$ is coated onto the plates and used as a screening criteria.

Once antibody-positive wells are identified, cells are then cultured in a HT medium, which does not contain aminopterin. After culturing for a while, antibody titers in the culture supernatant are confirmed again. Cells that are finally selected are then subject to cloning to obtain single cells. Clones that exhibit high specificity to mPEG- or PEG-derived proteins are selected, and are proliferated to some extent to establish hybridomas.

According to preferred embodiments of the present disclosure, 3 hybridomas, E11, 15-2b and 6-3, were selected. The 15-2b hybridoma produced an anti-mPEG monoclonal antibody that specifically bound to terminal methoxy or hydroxyl group, but not the backbone, of PEG. By contrast, the E11 and 6-3 hybridomas, produced anti-PEG backbone monoclonal antibodies that bound to the backbone, instead of the end methoxy or hydroxyl group of PEG.

In some embodiments, the anti-mPEG monoclonal antibodies were selected over the anti-PEG backbone monoclonal antibodies due to space homogeneity rendered by anti-mPEG Abs once they were bound with PEGylated nanoparticles. In other embodiments, the anti-PEG backbone monoclonal antibodies were selected over the anti-mPEG monoclonal antibodies.

The thus produced anti-mPEG or anti-PEG monoclonal antibodies may be isolated or prepared by any known method. For example, antibodies may be prepared from cultured supernatant obtained by culturing hybridomas in a medium with low serum concentration. Alternatively, hybridomas may be injected into abdominal cavities of animals and the resultant abdominal dropsies are collected to prepare antibodies. Antibodies may be purified or isolated by methods that employ affinity column, gel filtration chromatography, ion exchange chromatography or the like. Any of these known methods may be appropriately selected or used in combination.

Alternatively, anti-mPEG or anti-PEG monoclonal antibodies may be produced by DNA cloning. DNA encoding anti-mPEG or anti-PEG mAbs may be easily isolated and sequenced by use of conventional procedures, such as using oliognucleotide probes that are capable of binding specifically to genes encoding the heavy and light chains of the monoclonal antibodies. The hybridoma cells (e.g., E11, 6-3 or 15-2b hybridoma) serve as a preferred source of such DNA. Once isolated, the DNA may be placed into expression vectors, which are then transfected into host cells such as *E. Coli* cells, simian COS cells or Chinese hamster ovary (CHO) cells or myeloma cells that do not produce immunoglobulin proteins, to synthesize the desired monoclonal antibodies in the recombinant host cells.

The monoclonal antibodies thus produced and the DNA encoding such antibodies can then be used to produce chimeric antibodies (e.g., bi-specific antibodies), humanized antibodies and/or antibody fragments derived thereof.

2.2 Production of Humanized Anti-mPEG (15-2) or Anti-PEG (E11 or 6.3) Antibody

The major concern of a non-human origin monoclonal antibody is its immunogenicity to the recipient, in some cases, caused dangerous allergic reactions. Most monoclonal antibodies are of murine origin, and have been found to be immunogenic when injected to human. To reduce the immunogenicity of anti-mPEG or anti-PEG mAbs of this invention, humanized antibodies are produced by attaching variable domains in the heavy and light chains of murine anti-mPEG or anti-PEG Abs onto the constant regions of human antibodies.

To create humanized anti-mPEG or anti-PEG antibodies, the DNA encoding such antibodies was isolated and sequenced in accordance with methods described above in section 2.1, and then used to create humanized constructs. Detailed production method is set forth in the Examples.

According to preferred embodiments of the present disclosure, CDR (complementary determining region) grafting is employed, in which the CDR regions in the VH and VL genes of a human antibody are replaced with the appropriate CDR coding segments (such as those DNA segments in anti-mPEG or anti-PEG Abs that code amino acid segments responsible for binding PEG). The resulting antibodies therefore have variable regions in which only the CDRs are from the original mouse antibodies, while the framework regions in the VH and VL genes as well as the constant region genes (i.e., Cκ or CH1-H-CH2-CH3) are those of human IgG.

In preferred embodiments, the humanized anti-mPEG or anti-PEG Ab comprises a heavy chain variable domain and a light chain variable domain. Once produced, the humanized anti-mPEG or anti-PEG Abs may be purified according to standard procedures in the art, including cross-flow filtration, affinity column chromatography, gel filtration and the like. It should be understood that the humanized antibodies shall perform in a manner identical or substantially similar to that of murine anti-mPEG Abs. Preferably, the humanized anti-mPEG or anti-PEG Abs (either in the form of Fab or full length IgG) shall be more advantages to use in a human subject, as compared to the murine version. In some embodiments, the humanized anti-mPEG Abs are used in the production of bi-specific antibodies of the present disclosure. In other embodiments, the humanized anti-PEG Abs are used in the production of bi-specific antibodies of the present disclosure.

2.3 Production of Bi-Specific Monoclonal Antibodies (BsAbs)

To produce BsAbs, the humanized anti-mPEG or anti-PEG Abs (either in the form of Fab or a full length IgG) described above in Section 2.2 are further linked with antibodies or scFv that bind tumor antigens, so as to confer cancer targeting effect. Detailed production method is set forth in the Examples.

In general, DNA sequences of the above humanized anti-mPEG or anti-PEG Abs including the heavy and light chains of humanized anti-mPEG or anti-PEG sequences are ligated with DNA sequence of a desired antibody or scFv that binds a tumor antigen via use of a linker, then the chimeric sequence is cloned into an expression vector for transfecting a host cell, and subsequently purified in accordance with similar steps described above in section 2.2. The thus produced BsAbs may then be used to treat cancers or to track the developments of cancers with an aid of an imaging system.

Accordingly, humanized monomeric and dimeric antibodies are produced, with bi-specificities to both PEGylated molecules and tumor antigens, which include, but are not limited to, TAG72, EGFR, HER2, CD19, and CD20.

In some embodiments, monomeric BsAbs including PEG×EGFR (anti-PEG anti-EGFR), PEG×TAG72 (anti-PEG anti-TAG72), and PEG×HER2 (anti-PEG anti-HER2) are produced, with the anti-PEG portion derived from the hE11 Fab fragment. In another embodiment, monomeric h6.3Fab×EGFR (anti-PEG anti-EGFR) and h6.3Fab×CD19 (anti-PEG anti-CD19) are produced, in which h6.3 Fab, instead of hE11 Fab, is fused with scFv against EGFR or CD19. In a further embodiment, monomeric h15-2b Fab× EGFR scFv (anti-PEG anti-EGFR), h15-2b Fab×HER2 scFv (anti-PEG anti-HER2), are produced, in which h15-2b Fab is fused with scFv against EGFR or HER2. In still further embodiments, monomeric h15-2b scFv×CD19 Fab (anti-PEG anti-CD19) and h15-2b scFv×CD20 Fab (anti-PEG anti-CD20) are produced, in which h15-2b scFv is fused with Fab against CD19 or CD20.

In other embodiments, dimeric BsAbs, including PEG2× EGFR (anti-PEG anti-EGFR), PEG2×TAG72 (anti-PEG anti-TAG72), and PEG2×HER2 (anti-PEG anti-HER2) are produced. Unlike the monomeric BsAb, each dimeric BsAb includes a full length IgG, with each heavy chain being linked to the scFv that binds a tumor antigen (e.g., TAG 72, EGFR or HER2). Further, monomeric BsAbs of PEG× EGFR, PEG×HER2, and PEG×TAG72 of the present disclosure differ from their counterparts in the dimeric forms (i.e., PEG2×EGFR, PEG2×HER2, and PEG2×TAG72) in that they do not possess HR-CH2-CH3 domains in their respective structures.

In still some other embodiments, "knob in hole" BsAbs are created, in which DNA sequences encoding antibody heavy chains, particularly the CH3 domains of the two heavy chains, are designed to introduce specific and complementary interactions at the interface of the respective CH3 domains of the two heavy chains. For example, several amino acids are substituted with alternative amino acids in the first heavy chain CH3 domain to create a "knob" structure, and several amino acids in the second heavy chain CH3 domain are altered to create a "hole" such that antibody heavy chains expressed from these DNA sequences are unlikely to form a combination of just the first pairs or just the second pairs, but rather the "knob in hole" heavy chain pairs. The knob-in-hole technique is well known to those skilled in the art, and can be readily applied in forming the BsAbs of the present disclosure. Additionally, the "knob in hole" BsAbs may be further modified by crossing over the antibody heavy chain and the antibody light chain, and thereby creating an antibody heavy chain hetero-polypeptide consisting in N-terminus to C-terminus direction of a VH, a CL, a hinge region (HR), a CH2, and a knob-CH3; abbreviated as VH-CL-HR-CH2-knob-CH3; and an antibody light chain hetero-polypeptide consisting in N-terminus to C-terminus direction of a VL and a CH1; abbreviated as VL-CH1.

Accordingly, in one specific embodiment, a "knob in hole" anti-mPEG, anti-CD19 BsAb is produced. Specifically, two point mutations, S354C and T366W are introduced into the CH3 region of one h15-2b (anti-mPEG) heavy chain to create a knob structure; whereas additional four point mutations at S349C, T366S, L368A, and Y407V are introduced into the CH3 region of one BU12 (anti-CD19) heavy chain to generate a hole structure. In addition to creating the knob and hole structures on respective heavy chains, the Bu12-hole heavy chain may be further modified by crossing over with its light chain to generate a hetero heavy chain polypeptide and a hetero light chain polypeptide as described above. Therefore, each arms of the Y-shape h15-2b knob/Bu12-hole BsAb respectively recognize different antigens, that is, a PEGylated molecule and CD19. In one specific embodiment, h15-2b knob/HER2-hole BsAb is provided, in which the two arms of the Y-shape h15-2b knob/HER2-hole BsAb respectively recognize a PEGylated molecule and HER2.

The components and their respective amino acid sequences of BsAbs of the present disclosure are summarized in Tables 1 to 13.

TABLE 1

Amino Acid Sequence of PEG2 × TAG72

| Name | Amino Acid Sequence | SEQ ID NO |
|---|---|---|
| Humanized E11 VL-Cκ | DVVMTQSPLSLPVTLGQPASISCRSSKSIVHSNGNTYLEWFQQR PGQSPRRLIYKVSKRMSGVPDRFSGSGSGTDFTLKISRVEAEDV GVYYCSQGSHVPPTFGGGTKVEIKRTVAAPSVFIFPPSDEQLKS GTASVVCLLNNFYPREAKVQWKVDNALQSGNSQESVTEQDSK DSTYSLSSTLTLSKADYEKHKLYACEVTHQGLSSPVTKSFNRGEC | 1 |
| Humanized E11 VH-CH1 | QVQLVQSGAEVKKPGASVKVSCKASGYTFTTYTMNWVRQAP GQGLEWMGYIIPSSGYVDYNQKFKGRVTMTRDTSTSTVYMEL SSLRSEDTAVYYCVRSLDGYFWFAYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV DKRV | 2 |
| Hinge CH2-CH3 | EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSRDELTKNQVSLTCLVKGFYPSDIAVEWESNGQPE NNYKTTPPVLDSDGSFFLYSKLTVDKSRWQQGNVFSCSVMHE ALHNHYTQKSLSLSPGK | 3 |
| Peptide Linker | VDLVTVSSASTGGGSGQLGGGGS | 4 |
| Hcc49 dsFv | QVQLVQSGAEVKKPGASVKVSCKASGYTFTDHAIHWVRQAPG QCLEWMGYFSPGNDDFKYSQKFQGRVTITADKSASTAYMELSS LRSEDTAVYYCARSWIMQYWGQGTLVTVSSGGGGSGGGGSG GGGSDIVMTQSPDSLAVSLGERATINCKSSQSVLYSSNNKNYLA WYQQKPGQPPKLLIYWASTRESGVPDRFSGSGSGTDFTLTISSL QAEDVAVYYCQQYYSYPLTFGCGTKVEIK | 5 |
| 6xHis Tag | TRHHHHHH | 6 |

TABLE 2

Amino Acid Sequence of PEG2 × EGFR

| Name | Amino Acid Sequence | SEQ ID NO |
|---|---|---|
| Humanized E11 VL-Cκ | DVVMTQSPLSLPVTLGQPASISCRSSKSIVHSNGNTYLEWFQQR PGQSPRRLIYKVSKRMSGVPDRFSGSGSGTDFTLKISRVEAEDV GVYYCSQGSHVPPTFGGGTKVEIKRTVAAPSVFIFPPSDEQLKS GTASVVCLLNNFYPREAKVQWKVDNALQSGNSQESVTEQDSK DSTYSLSSTLTLSKADYEKHKLYACEVTHQGLSSPVTKSFNRGEC | 1 |
| Humanized E11 VH-CH1 | QVQLVQSGAEVKKPGASVKVSCKASGYTFTTYTMNWVRQAP GQGLEWMGYIIPSSGYVDYNQKFKGRVTMTRDTSTSTVYMEL SSLRSEDTAVYYCVRSLDGYFWFAYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV DKRV | 2 |
| Hinge CH2-CH3 | EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSRDELTKNQVSLTCLVKGFYPSDIAVEWESNGQPE NNYKTTPPVLDSDGSFFLYSKLTVDKSRWQQGNVFSCSVMHE ALHNHYTQKSLSLSPGK | 3 |
| Peptide Linker | VDLVTVSSASTGGGSGQLGGGGS | 4 |
| 11F8 anti-EGFR dsFv | QVQLQESGPGLVKPSQTLSLTCTVSGGSISSGDYYWSWIRQPPG KCLEWIGYIYYSGSTDYNPSLKSRVTMSVDTSKNQFSLKVNSV TAADTAVYYCARVSIFGVGTFDYWGQGTLVTVSSGGGGSGGG GSGGGGSEIVMTQSPATLSLSPGERATLSCRASQSVSSYLAWYQ QKPGQAPRLLIYDASNRATGIPARFSGSGSGTDFTLTISSLEPEDF AVYYCHQYGSTPLTFGCGTKAEIK | 7 |
| 6xHis Tag | TRHHHHHH | 6 |

TABLE 3

Amino Acid Sequence of PEG2 × HER2

| Name | Amino Acid Sequence | SEQ ID NO |
|---|---|---|
| Humanized E11 VL-Cκ | DVVMTQSPLSLPVTLGQPASISCRSSKSIVHSNGNTYLEWFQQR PGQSPRRLIYKVSKRMSGVPDRFSGSGSGTDFTLKISRVEAEDV GVYYCSQGSHVPPTFGGGTKVEIKRTVAAPSVFIFPPSDEQLKS GTASVVCLLNNFYPREAKVQWKVDNALQSGNSQESVTEQDSK DSTYSLSSTLTLSKADYEKHKLYACEVTHQGLSSPVTKSFNRGEC | 1 |
| Humanized E11 VH-CH1 | QVQLVQSGAEVKKPGASVKVSCKASGYTFTTYTMNWVRQAP GQGLEWMGYIIPSSGYVDYNQKFKGRVTMTRDTSTSTVYMEL SSLRSEDTAVYYCVRSLDGYFWFAYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV DKRV | 2 |
| Hinge CH2-CH3 | EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSRDELTKNQVSLTCLVKGFYPSDIAVEWESNGQPE NNYKTTPPVLDSDGSFFLYSKLTVDKSRWQQGNVFSCSVMHE ALHNHYTQKSLSLSPGK | 3 |
| Peptide Linker | VDLVTVSSASTGGGSGQLGGGGS | 4 |
| C6ML3-9 anti-HER2 dsFv | QVQLLQSGAEVKKPGESLKISCKGSGYSFTSYWIAVVVRQMPG KGLEYMGLIYPGDSDTKYSPSFQGQVTISVDKSVSTAYLQWS SLKPSDSAVYFCARHDVGYCSSSNCAKWPEYFQHWGQGTLV TVSSGGGGSGGGGSGGGGSQSVLTQPPSVSAAPGQKVTISC SGSSSNIGNNYVSVVYQQLPGTAPKLLIYDHTNRPAGVPDRFS GSKSGTSASLAISGFRSEDEADYYCASWDYTLSGVVVFGGGT KLTVLG | 8 |
| 6xHis Tag | TRHHHHHH | 6 |

TABLE 4

Amino Acid Sequence of h6.3Fab × EGFR

| Name | Amino Acid Sequence | SEQ ID NO |
|---|---|---|
| Humanized 6.3 VL-Cκ | DIVMTQSPDSLAVSLGERATINCKSSQSVLYSSNQMNYLAWYQ QKPGQPPKLLIYWASTRESGVPDRFSGSGSGTDFTLTISSLQAED VAVYYCLQYLSSWTFGGGTKLEIKTYSLSSTLTLSKADYEKHK LYACEVTHQGLSSPVTKSFNRGEC | 9 |
| Humanized 6.3 VH-CH1 | QVQLVQSGSELKKPGASVKVSCKASGYTFKNYGMNWVRQAP GQGLEWMGWINTYTGQPIYANDFKGRFVFSLDTSVSTAYLQIS SLKAEDTAVYYCARDWGPYWGQGTLVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKRVE PKSCDK | 10 |
| Peptide Linker | VDLVTVSSASTGGGSGQLGGGGS | 4 |
| 11F8 anti-EGFR dsFv | QVQLQESGPGLVKPSQTLSLTCTVSGGSISSGDYYWSWIRQPPG KCLEWIGYIYYSGSTDYNPSLKSRVTMSVDTSKNQFSLKVNSV TAADTAVYYCARVSIFGVGTFDYWGQGTLVTVSSGGGGSGGG GSGGGGSEIVMTQSPATLSLSPGERATLSCRASQSVSSYLAWYQ QKPGQAPRLLIYDASNRATGIPARFSGSGSGTDFTLTISSLEPEDF AVYYCHQYGSTPLTFGCGTKAEIK | 7 |
| 6xHis Tag | TRHHHHHH | 6 |

TABLE 5

Amino Acid Sequence of h6.3Fab × CD19

| Name | Amino Acid Sequence | SEQ ID NO |
|---|---|---|
| Humanized 6.3 VL-Cκ | DIVMTQSPDSLAVSLGERATINCKSSQSVLYSSNQMNYLAWYQQKPGQPPKLLIYWASTRESGVPDRFSGSGSGTDFTLTISSLQAEDVAVYYCLQYLSSWTFGGGTKLEIKTYSLSSTLTLSKADYEKHKLYACEVTHQGLSSPVTKSFNRGEC | 9 |
| Humanized 6.3 VH-CH1 | QVQLVQSGSELKKPGASVKVSCKASGYTFKNYGMNWVRQAPGQGLEWMGWINTYTGQPIYANDFKGRFVFSLDTSVSTAYLQISSLKAEDTAVYYCARDWGPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDK | 10 |
| Peptide Linker | VDLVTVSSASTGGGSGQLGGGGS | 4 |
| hBU12 dsFv | QVQLQESGPGLVKPSQTLSLTCTVSGGSISTSGMGVGWIRQHPGKCLEWIGHIWWDDDKRYNPALKSRVTISVDTSKNQFSLKLSSVTAADTAVYYCARMELWSYYFDYWGQGTLVTVSSGGGGSGGGGSGGGGSEIVLTQSPATLSLSPGERATLSCSASSSVSYMHWYQQKPGQAPRLLIYDTSKLASGIPARFSGSGSGTDFTLTISSLEPEDVAVYYCFQGSVYPFTFGCGTKLEIKR | 11 |
| 6xHis Tag | TRHHHHHH | 6 |

TABLE 6

Amino Acid Sequence of h15-2b Fab × HER2 scFv

| Name | Amino Acid Sequence | SEQ ID NO |
|---|---|---|
| Humanized 15-2b VL-Cκ | DIQMTQSPSSLSASVGDRVTITCKASQDVNTSVAVVYQQKPGKAPKLLIYWASTRHTGVPSRFSGSGSGTDFTFTISSLQPEDIATYYCLQYINYPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKLYACEVTHQGLSSPVTKSFNRGEC | 12 |
| Humanized 15-2b VH-CH1 | EVQLVESGGGLVQPGGSLKLSCAASGFTFSNYWMNVVVRQASGKGLEVVVGEIRSKSNNYATHYAESVKGRFTISRDDSKNTAYLQMNSLKTEDTAVYYCSNRYYWGQGTLVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERK | 13 |
| G-MYC-(G4S)3 Linker | GEQKLISEEDLGGGGSGGGGSGGGGSQL | 14 |
| C6ML3-9 (Anti-HER2) scFv | QVQLLQSGAEVKKPGESLKISCKGSGYSFTSYWIAVVVRQMPGKGLEYMGLIYPGDSDTKYSPSFQGQVTISVDKSVSTAYLQWSSLKPSDSAVYFCARHDVGYCSSSNCAKWPEYFQHWGQGTLVTVSSGGGGSGGGGSGGGGSQSVLTQPPSVSAAPGQKVTISCSGSSSNIGNNYVSVVYQQLPGTAPKLLIYDHTNRPAGVPDRFSGSKSGTSASLAISGFRSEDEADYYCASWDYTLSGVVVFGGGTKLTVLG | 15 |

TABLE 7

Amino Acid Sequence of h15-2b Fab × EGFR scFv

| Name | Amino Acid Sequence | SEQ ID NO |
|---|---|---|
| Humanized 15-2b VL-Cκ | DIQMTQSPSSLSASVGDRVTITCKASQDVNTSVAVVYQQKPGKAPKLLIYWASTRHTGVPSRFSGSGSGTDFTFTISSLQPEDIATYYCLQYINYPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKLYACEVTHQGLSSPVTKSFNRGEC | 12 |

TABLE 7-continued

Amino Acid Sequence of h15-2b Fab x EGFR scFv

| Name | Amino Acid Sequence | SEQ ID NO |
|---|---|---|
| Humanized 15-2b VH-CH1 | EVQLVESGGGLVQPGGSLKLSCAASGFTFSNYWMNVVRQAS GKGLEVVVGEIRSKSNNYATHYAESVKGRFTISRDDSKNTAYL QMNSLKTEDTAVYYCSNRYYWGQGTLVTVSSASTKGPSVFPL APCSRSTSESTAALGCLVKDYFPEPVTVSWNSGALTSGVHTF PAVLQSSGLYSLSSVVTVPSSNFGTQTYTCNVDHKPSNTKVD KTVERK | 13 |
| G-MYC-(G4S)3 Linker | GEQKLISEEDLGGGGSGGGGSGGGGSQL | 14 |
| h528 (Anti-EGFR) scFv | DIVMTQSPLSLPVTPGEPASISCRSSQNIVHNNGITYLEVVYLQK PGQSPQLLIYKVSDRFSGVPDRFSGSGSGTDFTLKISRVEAED VGVYYCFQGSHIPPTFGQGTKVEIKRAGGGGSGGGGSGGGG SQVQLVQSGAEVKKPGASVKVSCKASGYTFTSYWMHVVVRQ APGQGLEWMGNIYPGSGGTNYAEKFKNRVTMTRDTSISTAYM ELSRLRSDDTAVYYCARSGGPYFFDYWGQGTLVTVSS | 16 |

TABLE 8

Amino Acid Sequence of h15-2b scFv x CD19 Fab

| Name | Amino Acid Sequence | SEQ ID NO |
|---|---|---|
| Humanized 15-2b scFv | DIQMTQSPSSLSASVGDRVTITCKASQDVNTSVAVVYQQKPGK APKLLIYWASTRHTGVPSRFSGSGSGTDFTFTISSLQPEDIATY YCLQYINYPYTFGQGTKLEIKRGGGGSEVQLVESGGGLVQPG GSLKLSCAASGFTFSNYWMNVVRQASGKGLEVVVGEIRSKSN NYATHYAESVKGRFTISRDDSKNTAYLQMNSLKTEDTAVYYCT NRYYWGQGTLVTVSS | 17 |
| G-MYC-(G4S)3 Linker | GEQKLISEEDLGGGGSGGGGSGGGGSQL | 14 |
| hHB12b (Anti-CD19) VH-CH1 | EVQLVESGGGLVQPGGSLRLSCAASGFTFSSSWMNVVRQAP GKGLEVVVGRIYPGDGDTNYNGKFKGRFTISRDDSKNSLYLQM NSLKTEDTAVYYCARSGFITTVLDFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKPS NTKVDKRV | 18 |
| hHB12b (Anti-CD19) VL-Cκ | EIVLTQSPDFQSVTPKEKVTITCRASESVDTFGISFMNWFQQK PDQSPKLLIHAASNQGSGVPSRFSGSGSGTDFTLTINSLEAED AATYYCQQSKEVPFTFGGGTKVEIKTVAAPSVFIFPPSDEQLK SGTASVVCLLNNFYPREAKVQWKVDNALQSGNSQESVTEQD SKDSTYSLSSTLTLSKADYEKHKLYACEVTHQGLSSPVTKSFN RGEC | 19 |

TABLE 9

Amino Acid Sequence of h15-2b scFv x CD20 Fab

| Name | Amino Acid Sequence | SEQ ID NO |
|---|---|---|
| Humanized 15-2b scFv | DIQMTQSPSSLSASVGDRVTITCKASQDVNTSVAVVYQQKPGK APKLLIYWASTRHTGVPSRFSGSGSGTDFTFTISSLQPEDIATY YCLQYINYPYTFGQGTKLEIKRGGGGSEVQLVESGGGLVQPG GSLKLSCAASGFTFSNYWMNVVRQASGKGLEVVVGEIRSKSN NYATHYAESVKGRFTISRDDSKNTAYLQMNSLKTEDTAVYYCT NRYYWGQGTLVTVSS | 17 |
| G-MYC-(G4S)3 Linker | GEQKLISEEDLGGGGSGGGGSGGGGSQL | 14 |

TABLE 9-continued

Amino Acid Sequence of h15-2b scFv × CD20 Fab

| Name | Amino Acid Sequence | SEQ ID NO |
|---|---|---|
| 2F2 (Anti-CD20) VH-CH1 | MELGLSWIFLLAILKGVQCEVQLVESGGGLVQPGRSLRLSCAA SGFTFNDYAMHVVVRQAPGKGLEVVVSTISWNSGSIGYADSVK GRFTISRDNAKKSLYLQMNSLRAEDTALYYCAKDIQYGNYYYG MDVWGQGTTVTVSSASTKGPSVFPLAPSSKSTSGGTAALGCL VKDYFPEPVTVSWNSGALTSGVHTFPAVLQSSGLYSLSSVVT VPSSSLGTQTYICNVNHKPSNTKVDKRV | 20 |
| 2F2 (Anti-CD20) VL-Cκ | MEAPAQLLFLLLLWLPDTTGEIVLTQSPATLSLSPGERATLSCR ASQSVSSYLAVVYQQKPGQAPRLLIYDASNRATGIPARFSGSG SGTDFTLTISSLEPEDFAVYYCQQRSNWPITFGQGTRLEIKTVA APSVFIFPPSDEQLKSGTASVVCLLNNFYPREAKVQWKVDNAL QSGNSQESVTEQDSKDSTYSLSSTLTLSKADYEKHKLYACEV THQGLSSPVTKSFNRGEC | 21 |

TABLE 10

Amino Acid Sequence of 15-2b knob/Bu12 hole

| Name | Amino Acid Sequence | SEQ ID NO |
|---|---|---|
| 15-2b knob heavy chain | | |
| Humanized 15-2b VL-Cκ | DIQMTQSPSSLSASVGDRVTITCKASQDVNTSVAWYQQKPGKA PKLLIYWASTRHTGVPSRFSGSGSGTDFTFTISSLQPEDIATYYC LQYINYPYTFGQGTKLEIKRTVAAPSVFIFPPSDEQLKSGTASVV CLLNNFYPREAKVQWKVDNALQSGNSQESVTEQDSKDSTYSLS STLTLSKADYEKHKLYACEVTHQGLSSPVTKSFNRGEC | 12 |
| Humanized 15-2b VH-CH1 | EVQLVESGGGLVQPGGSLKLSCAASGFTFSNYWMNWVRQASG KGLEWVGEIRSKSNNYATHYAESVKGRFTISRDDSKNTAYLQM NSLKTEDTAVYYCTNRYYWGQGTLVTVSSASTKGPSVFPLAPC SRSTSESTAALGCLVKDYFPEPVTVSWNSGALTSGVHTFPAVLQ SSGLYSLSSVVTVPSSNFGTQTYTCNVDHKPSNTK | 13 |
| Knob Hinge CH2-CH3 | EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPCRDELTKNQVSLWCLVKGFYPSDIAVEWESNGQP ENNYKTTPPVLDSDGSFFLYSKLTVDKSRWQQGNVFSCSVMHE ALHNHYTQKSLSLSPGK | 22 |
| hBU12 hole | | |
| hBU12 VL-crossover CH1 | EIVLTQSPATLSLSPGERATLSCSASSSVSYMHWYQQKPGQAPR LLIYDTSKLASGIPARFSGSGSGTDFTLTISSLEPEDVAVYYCFQ GSVYPFTFGQGTKLEIKRSSASTKGPSVFPLAPSSKSTSGGTAAL GCLVKDYFPEPVTVSWNSGALTSGVHTFPAVLQSSGLYSLSSV VTVPSSSLGTQTYICNVNHKPSNTKVDKKV | 23 |
| hBU12 VH-crossover Cκ | QVQLQESGPGLVKPSQTLSLTCTVSGGSISTSGMGVGWIRQHPG KGLEWIGHIWWDDDKRYNPALKSRVTISVDTSKNQFSLKLSSV TAADTAVYYCARMELWSYYFDYWGQGTLVTVSSASVAAPSV FIFPPSDEQLKSGTASVVCLLNNFYPREAKVQWKVDNALQSGN SQESVTEQDSKDSTYSLSSTLTLSKADYEKHKLYACEVTHQGLS SPVTKSFNRGEC | 24 |
| hole hinge-CH2-CH3 | DKTHTCPPCPAPELLGGPSVFLFPPKPKDTLMISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVCT LPPSRDELTKNQVSLSCAVKGFYPSDIAVEWESNGQPENNYKT TPPVLDSDGSFFLVSKLTVDKSRWQQGNVFSCSVMHEALHNH YTQKSLSLSPGK | 25 |

TABLE 11

Amino Acid Sequence of 15-2b knob/anti-HER2 hole

| Name | Amino Acid Sequence | SEQ ID NO |
|---|---|---|
| 15-2b knob heavy chain | | |
| Humanized 15-2b VL-Cκ | DIQMTQSPSSLSASVGDRVTITCKASQDVNTSVAWYQQKPGKA PKLLIYWASTRHTGVPSRFSGSGSGTDFTFTISSLQPEDIATYYC LQYINYPYTFGQGTKLEIKRTVAAPSVFIFPPSDEQLKSGTASVV CLLNNFYPREAKVQWKVDNALQSGNSQESVTEQDSKDSTYSLS STLTLSKADYEKHKLYACEVTHQGLSSPVTKSFNRGEC | 12 |
| Humanized 15-2b VH-CH1 | EVQLVESGGGLVQPGGSLKLSCAASGFTFSNYWMNVVRQAS GKGLEVVVGEIRSKSNNYATHYAESVKGRFTISRDDSKNTAYL QMNSLKTEDTAVYYCSNRYYWGQGTLVTVSSASTKGPSVFPL APCSRSTSESTAALGCLVKDYFPEPVTVSWNSGALTSGVHTF PAVLQSSGLYSLSSVVTVPSSNFGTQTYTCNVDHKPSNTKVD KTVERK | 13 |
| Knob Hinge CH2-CH3 | EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPCRDELTKNQVSLWCLVKGFYPSDIAVEWESNGQP ENNYKTTPPVLDSDGSFFLYSKLTVDKSRWQQGNVFSCSVMHE ALHNHYTQKSLSLSPGK | 22 |
| Anti-HER2 hole | | |
| C6ML3-9VL-crossover CH1 | QSVLTQPPSVSAAPGQKVTISCSGSSSNIGNNYVSWYQQLPGTA PKLLIYDHTNRPAGVPDRFSGSKSGTSASLAISGFRSEDEADYY CASWDYTLSGWVFGGGTKLTVLGSSASTKGPSVFPLAPSSKSTS GGTAALGCLVKDYFPEPVTVSWNSGALTSGVHTFPAVLQSSGL YSLSSVVTVPSSSLGTQTYICNVNHKPSNTKVDKKV | 26 |
| C6ML3-9 VH-crossover Cκ | QVQLLQSGAEVKKPGESLKISCKGSGYSFTSYWIAWVRQMPGK GLEYMGLIYPGDSDTKYSPSFQGQVTISVDKSVSTAYLQWSSLK PSDSAVYFCARHDVGYCSSSNCAKWPEYFQHWGQGTLVTVSS ASVAAPSVFIFPPSDEQLKSGTASVVCLLNNFYPREAKVQWKV DNALQSGNSQESVTEQDSKDSTYSLSSTLTLSKADYEKHKLYA CEVTHQGLSSPVTKSFNRGEC | 27 |
| hole hinge-CH2-CH3 | DKTHTCPPCPAPELLGGPSVFLFPPKPKDTLMISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVCT LPPSRDELTKNQVSLSCAVKGFYPSDIAVEWESNGQPENNYKT TPPVLDSDGSFFLVSKLTVDKSRWQQGNVFSCSVMHEALHNH YTQKSLSLSPGK | 25 |

TABLE 12

Amino Acid Sequence of h6.3 knob/BU12 hole

| Name | Amino Acid Sequence | SEQ ID NO |
|---|---|---|
| h6.3 knob heavy chain | | |
| Humanized 6.3 VL-Cκ | DIVMTQSPDSLAVSLGERATINCKSSQSVLYSSNQMNYLAWYQ QKPGQPPKLLIYWASTRESGVPDRFSGSGSGTDFTLTISSLQAED VAVYYCLQYLSSWTFGGGTKLEIKTYSLSSTLTLSKADYEKHK LYACEVTHQGLSSPVTKSFNRGEC | 9 |
| Humanized 6.3 VH-CH1 | QVQLVQSGSELKKPGASVKVSCKASGYTFKNYGMNWVRQAP GQGLEWMGWINTYTGQPIYANDFKGRFVFSLDTSVSTAYLQIS SLKAEDTAVYYCARDWGPYWGQGTLVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKRVE PKSCDK | 10 |

TABLE 12-continued

Amino Acid Sequence of h6.3 knob/BU12 hole

| Name | Amino Acid Sequence | SEQ ID NO |
|---|---|---|
| Knob Hinge CH2-CH3 | EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPCRDELTKNQVSLWCLVKGFYPSDIAVEWESNGQP ENNYKTTPPVLDSDGSFFLYSKLTVDKSRWQQGNVFSCSVMHE ALHNHYTQKSLSLSPGK | 22 |

BU12 hole

| Name | Amino Acid Sequence | SEQ ID NO |
|---|---|---|
| hBU12 VL-crossover CH1 | EIVLTQSPATLSLSPGERATLSCSASSSVSYMHWYQQKPGQAPR LLIYDTSKLASGIPARFSGSGSGTDFTLTISSLEPEDVAVYYCFQ GSVYPFTFGQGTKLEIKRSSASTKGPSVFPLAPSSKSTSGGTAAL GCLVKDYFPEPVTVSWNSGALTSGVHTFPAVLQSSGLYSLSSV VTVPSSSLGTQTYICNVNHKPSNTKVDKKV | 23 |
| hBU12 VH-crossover Cκ | QVQLQESGPGLVKPSQTLSLTCTVSGGSISTSGMGVGWIRQHPG KGLEWIGHIWWDDDKRYNPALKSRVTISVDTSKNQFSLKLSSV TAADTAVYYCARMELWSYYFDYWGQGTLVTVSSASVAAPSV FIFPPSDEQLKSGTASVVCLLNNFYPREAKVQWKVDNALQSGN SQESVTEQDSKDSTYSLSSTLTLSKADYEKHKLYACEVTHQGLS SPVTKSFNRGEC | 24 |
| hole hinge-CH2-CH3 | DKTHTCPPCPAPELLGGPSVFLFPPKPKDTLMISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVCT LPPSRDELTKNQVSLSCAVKGFYPSDIAVEWESNGQPENNYKT TPPVLDSDGSFFLVSKLTVDKSRWQQGNVFSCSVMHEALHNH YTQKSLSLSPGK | 25 |

TABLE 13

Amino Acid Sequence of h6.3 knob/anti-HER2 hole

| Name | Amino Acid Sequence | SEQ ID NO |
|---|---|---| h6.3 knob heavy chain

| Name | Amino Acid Sequence | SEQ ID NO |
|---|---|---|
| Humanized 6.3 VL-Cκ | DIVMTQSPDSLAVSLGERATINCKSSQSVLYSSNQMNYLAWYQ QKPGQPPKLLIYWASTRESGVPDRFSGSGSGTDFTLTISSLQAED VAVYYCLQYLSSWTFGGGTKLEIKTYSLSSTLTLSKADYEKHK LYACEVTHQGLSSPVTKSFNRGEC | 9 |
| Humanized 6.3 VH-CH1 | QVQLVQSGSELKKPGASVKVSCKASGYTFKNYGMNWVRQAP GQGLEWMGWINTYTGQPIYANDFKGRFVFSLDTSVSTAYLQIS SLKAEDTAVYYCARDWGPYWGQGTLVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKRVE PKSCDK | 10 |
| Knob Hinge CH2-CH3 | EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPCRDELTKNQVSLWCLVKGFYPSDIAVEWESNGQP ENNYKTTPPVLDSDGSFFLYSKLTVDKSRWQQGNVFSCSVMHE ALHNHYTQKSLSLSPGK | 22 |

Anti-HER2 hole

| Name | Amino Acid Sequence | SEQ ID NO |
|---|---|---|
| C6ML3-9V L-crossover CH1 | QSVLTQPPSVSAAPGQKVTISCSGSSSNIGNNYVSWYQQLPGTA PKLLIYDHTNRPAGVPDRFSGSKSGTSASLAISGFRSEDEADYY CASWDYTLSGWVFGGGTKLTVLGSSASTKGPSVFPLAPSSKSTS GGTAALGCLVKDYFPEPVTVSWNSGALTSGVHTFPAVLQSSGL YSLSSVVTVPSSSLGTQTYICNVNHKPSNTKVDKKV | 26 |

TABLE 13-continued

Amino Acid Sequence of h6.3 knob/anti-HER2 hole

| Name | Amino Acid Sequence | SEQ ID NO |
|---|---|---|
| C6ML3-9 VH-crossover CK | QVQLLQSGAEVKKPGESLKISCKGSGYSFTSYWIAWVRQMPGK GLEYMGLIYPGDSDTKYSPSFQGQVTISVDKSVSTAYLQWSSLK PSDSAVYFCARHDVGYCSSSNCAKWPEYFQHWGQGTLVTVSS ASVAAPSVFIFPPSDEQLKSGTASVVCLLNNFYPREAKVQWKV DNALQSGNSQESVTEQDSKDSTYSLSSTLTLSKADYEKHKLYA CEVTHQGLSSPVTKSFNRGEC | 27 |
| hole hinge-CH2-CH3 | DKTHTCPPCPAPELLGGPSVFLFPPKPKDTLMISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVCT LPPSRDELTKNQVSLSCAVKGFYPSDIAVEWESNGQPENNYKT TPPVLDSDGSFFLVSKLTVDKSRWQQGNVFSCSVMHEALHNH YTQKSLSLSPGK | 25 |

3. Pharmaceutical Kit

It is the second aspect of the present disclosure to provide a pharmaceutical kit for treating or imaging cancers, including metastatic and/or drug-resistant cancers. The pharmaceutical kit includes at least two components, the first component being the BsAbs of the present disclosure; and the second component being a PEGylated substance, which includes a cancer therapeutic agent (e.g., vinca alkaloid) or an imaging agent (e.g., a microbubble containing therein a contrast agent, or a quantum dot) inside the PEGylated substance. Typically, each component is contained in respective separate container. Preferably, the first and second components can be respectively present in the container in a dry solid form or as a suspension in a physiologically acceptable aqueous carrier. The kit may optionally include a physiologically acceptable aqueous carrier such as a saline for reconstitution of the dry components before injection. The two components will be reconstituted separately with the respective carriers, then mixed to form an assembly, which is administered to the subject (e.g., by injection).

4. One-Step Method of Targeting and Treating Cancer

Accordingly, it is the third aspect of the present disclosure to provide a one-step method of targeting and treating cancers, including metastatic and/or drug-resistant cancers. The method takes advantages of the pharmaceutical kit described in Section 3, in which the isolated humanized anti-PEG bi-specific antibody (BsAbs) as described in Section 2 is mixed with a PEGylated substance to form an assembly before being administered to the subject. Alternatively, the humanized BsAbs as described in Section 2 is injected to the test subject (e.g., human) first, then followed by the injection of a PEGylated substance (data not shown).

FIG. 3 is a schematic drawing illustrating the one-step targeting and treating cancer by use of the pharmaceutical kit 300 of the present disclosure. The pharmaceutical kit 300 includes a humanized anti-PEG BsAb 310 and a PEGylated substance 320. The humanized anti-PEG BsAb 310 is composed of a first antigen binding site 311 that selectively binds to PEGylated substance 320, which contains a cancer therapeutic agent within its structure; and a second antigen binding site 312 that selectively binds to a target protein, such as a tumor antigen 340. In this embodiment, the PEGylated substance 320 is depicted as a liposome or micelle, and is characterized in having a cancer therapeutic agent 321 within the liposome or micelle structure and a plurality of PEG molecules 322 extended from the surface of the liposome or micelle. Upon binding to the PEGylated substance 320, the first antigen binding site 311 of the BsAb 310 allows the BsAb 310 to orient the second antigen binding site 312 outward from the surface of the PEGylated substance 320, thereby converting the non-targeted PEGylated substance 320 to tumor cell-targeted PEGylated substance.

In practice, to achieve one-step targeting and treating purpose, the humanized anti-PEG BsAb 310 is mixed with the PEGylated substance 320 to form an assembly 330, the assembly 330 is then immediately administered (e.g., injection) to a subject (e.g., a human 360 as depicted in FIG. 3).

Accordingly, it is the third aspect of the present disclosure to provide a method of treating cancers. The method includes the step of, administering to the subject, the BsAb of the present disclosure and a PEGylated substance containing a cancer therapeutic agent therein, in a dose sufficient to inhibit the growth or metastasis of the cancer of the subject. The dose administered to the subject is from about 0.1 to 50 mg/Kg body weight of the subject. In certain embodiments, the dose is administered to the subject from about 1 to 40 mg/Kg body weight of the subject, such as 10 to 30 mg/Kg body weight of the subject. The dose can be administered in a single dose, or alternatively in more than one smaller doses.

The BsAb of the present disclosure and the PEGylated substance may be administered to a mammal, preferably human, by any route that may effectively transports the cancer therapeutic agent contained in the PEGylated substance to the appropriate or desired site of action, such as oral, nasal, pulmonary, transdermal, such as passive or iontophoretic delivery, or parenteral, e.g., rectal, depot, subcutaneous, intravenous, intramuscular, intranasal, intracerebella, ophthalmic solution or an ointment. It will be appreciated that the dosage of the present disclosure will vary from patient to patient not only for the cancer therapeutic agent selected, the route of administration, and the ability of the BsAb in combination with a PEGylated substance, to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the cancer therapeutic agent are outweighed by the therapeutically beneficial effects. Preferably, the BsAb and the PEGylated substance of the present disclosure are administered at a dosage and for a time such that the number and/or severity of the symptoms are decreased.

5. Method of Imaging a Targeted Tissues

The fourth aspect of the present disclosure is to provide a method of imaging tissues, particularly the cancerous tissues, of a live subject. The method also takes advantages of the pharmaceutical kit described in Section 3, in which the isolated humanized anti-PEG bi-specific antibody (BsAbs) as described in Section 2 is mixed with a PEGylated substance to form an assembly before being administered to the subject.

The method includes the steps of, (a) mixing a first sufficient amount of the humanized BsAb of the present disclosure and a second sufficient amount of a PEGylated quantum dot (PEG-QD) or a PEGylated liposome containing a fluorescent dye, to form an assembly; (b) injecting the assembly of the step (a) to a body portion of the subject; and (c) imaging the body portion of the subject by fluorescence imaging, electron spin resonance (ESR) imaging, X-ray imaging, computed tomography (CT), or magnetic resonance imaging (MRI). The PEG-QD includes a quantum dot nanocrystal selected from the group consisting of CdHgTe, CdSe, CdSe/ZnS, CdS, CdTe, CdTe/CdS, PbSe and PbS.

The 6.3 antibody comprises the sequence of VL-Cκ domain (SEQ ID NO: 9) and the sequence of VH-CH1 domain (SEQ ID NO: 10), wherein the sequence of VL-Cκ domain comprises a CDR1 having the sequence of SEQ ID NO: 216; a CDR2 having the sequence of Trp-Ala-Ser; and a CDR3 having the sequence of SEQ ID NO: 217, wherein the sequence of VH-CH1 domain comprises a CDR1 having the sequence of SEQ ID NO: 218; a CDR2 having the sequence of SEQ ID NO: 219; and a CDR3 having the sequence of SEQ ID NO: 220.

The h15-2b antibody comprises the sequence of VL-Cκ domain (SEQ ID NO: 12) and the sequence of VH-CH1 domain (SEQ ID NO: 13), wherein the sequence of VL-Cκ domain comprises a CDR1 having the sequence of SEQ ID NO: 221; a CDR2 having the sequence of SEQ ID NO: 222; and a CDR3 having the sequence of SEQ ID NO: 223, wherein the sequence of VH-CH1 domain comprises a CDR1 having the sequence of SEQ ID NO: 224; a CDR2 having the sequence of SEQ ID NO: 225; and a CDR3 having the sequence of SEQ ID NO: 226.

The present invention further provides a humanized bi-specific antibody against the terminal methoxy or hydroxyl group of polyethylene glycol (PEG) and a target ligand on a cancer cell, comprising, a first antigen binding site that binds to the PEG, wherein the first antigen binding site comprises a first VL-Cκ domain and a first VH-CH1 domain; and a second antigen binding site that binds to the target ligand on the cancer cell, wherein, the first VL-Cκ domain comprises a CDR1 having the sequence of SEQ ID NO: 221; a CDR2 having the sequence of SEQ ID NO: 222; and a CDR3 having the sequence of SEQ ID NO: 223; and the first VH-CH1 domain comprises a CDR1 having the sequence of SEQ ID NO: 224; a CDR2 having the sequence of SEQ ID NO: 225; and a CDR3 having the sequence of SEQ ID NO: 226.

In one embodiment, the first VL-Cκ domain has the sequence of SEQ ID NO: 12, and the first VH-CH1 domain has the sequence of SEQ ID NO: 13.

In another embodiment, the first antigen binding site further comprises a Knob Hinge CH2-CH3 domain connecting to the first VH-CH1 domain, wherein the Knob Hinge CH2-CH3 domain has the sequence of SEQ ID NO: 22.

In one embodiment, the first antigen binding site and the second antigen binding site are Fab or single chain variable fragment (scFv).

In another embodiment, the target ligandis EGFR, HER2, TAG-72, CD19 or CD20.

The present invention will now be described more specifically with reference to the following embodiments, which are provided for the purpose of demonstration rather than limitation.

EXAMPLES

Materials and Methods.
Cells and Animals

Breast cancer cell line MCF-7, human T lymphocyte cell line Jurkat, ovarian cancer cell line OVCAR-3, epidermoid carcinoma cell line A431 (EGFR$^+$) (ATCC CRL1555), B lymphocyte cell line Raji (CD19$^+$) (ATCC CCL86), malignant melanoma cell line A-375, 293FT cells, B-lymphoblastoid cell line Ramos (CD19$^+$) (ATCC CRL-1596), SW480 (EGFR$^+$), SW620 human colon carcinoma cells, human breast adenocarcinoma cell line SKBR3 (HER2$^+$), human breast adenocarcinoma cell line MDA-MB-468, BALB 3T3 cells, and GP2-293 retrovirus packaging cells were used in the present disclosure. In general, cells were cultured in Dulbecco's modified Eagle's medium (Sigma, St Louis, Mo., USA) supplemented with 10% fetal calf serum (HyClone, Logan, Utah), 100 U/mL penicillin and 100 μg/mL streptomycin at 37° C. in an atmosphere of 5% $CO_2$ in air. A431, Raji and Ramos cells were grown in RPMI-1640 containing the same supplements but with 10% bovine serum source.

Female BALB/c nude mice (6-8 weeks old) were obtained from the National Laboratory Animal Center, Taipei, Taiwan. All animal experiments were performed in accordance with institutional guidelines and approved by the Laboratory Animal Facility and Pathology Core Committee of IBMS, Academia Sinica.

Generating Murine Anti-PEG Antibodies (Abs)

Hybridoma cells secreting anti-PEG Ab were generated by immunizing female BALB/c mice with mPEG-derived proteins or PEG-derived proteins as described previously (Su et al., Bioconjugate Chemistry (2010) 21(7), 1264-1270). The hybridomas were then screened by ELISA. Specifically, 96-well plates were coated with 1 μg/well CH3-PEG$_{750}$-NH2, NH2-PEG$_{3000}$-NH2 (Sigma-Aldrich), or CH3-PEG$_{5000}$-NH2 in 5 μL/well 0.1M NaHCO$_3$/Na$_2$CO$_3$ for 3 hr at 37° C. and then blocked with 200 μL/well dilution buffer (2% skim mile in PBS) at 4° C. overnight. Graded concentrations of antibodies in 50 μL 2% skim milk were added to plates at room temperature for 1 hr. The plates were washed with PBS-T (PBS containing 0.05% Tween-20) 3 times and with PBS 2 times. HRP-conjugated goat anti-mouse IgMμchain (2 μg/mL) or HRP-conjugated donkey antimouse IgG Fc (2 μg/mL) in 50 μL dilution buffer were added for 1 hr. The plates were washed and peroxidase activity was measured by adding 100 μL/well TMB substrate solution (BioLegend, San Diego, Calif.) for 30 min at room temperature. After adding stop buffer (2N $H_2SO_4$, 50 μL/well), the absorbance (405 nm) were read. Selected hybridomas were cloned three times by limiting dilution in 96-well plates containing thymocyte feeder cells in HT medium (Sigma-Aldrich) supplemented with 15% fetal calf serum (Hyclone), and then three hybridoma cells, E11, 6-3, and 15-2b were produced, in which E11 and 6-3 secreted anti-PEG backbone Abs, whereas 15-2b secreted anti-mPEG Abs.

Construction of DNA Plasmids for PEG2×EGFR, PEG2×TAG72, PEG2×HER2, h6.3Fab×EGFR, and h6.3Fab×CD19

To generate the anti-PEG Fab or IgG based BsAbs, the mouse $V_L$ and $V_H$ domains of the anti-PEG antibodies were cloned from cDNA respectively prepared from the E11, 6-3, and 15-2b hybridoma cells. The humanized $V_L$ and $V_H$ domains of the anti-PEG (hE11, h6-3) and anti-mPEG (h15-2b) antibodies, generated by grafting the DNA sequences coding the complementarity-determining regions (CDRs) of the light and heavy chain variable region genes of E11, h6-3 and 15-25 into the framework regions of human IgG VL and VH genes, then were fused with the DNA sequence encoding the remaining human IgG1 constant region genes.

The Cκ, $CH_1$, and partial $CH_1$-hinge-$CH_2$—$CH_3$ (Fc), constant domains of human $IgG_1$ were cloned from extracted human PBMC cDNA by using the primers in Table 14.

TABLE 14

Primers For Cloning Human $CH_1$, Cκ and $F_c$ Fragments

| Name | Sequence (5'-3') | SEQ ID NO |
|---|---|---|
| $CH_1$ | ctggtcaccgtctcctcagcctccaccaagggaccatcg (forward) | 28 |
| | gtcgactttgtcacaagatttgggc (reverse) | 29 |
| Cκ | accaaggtggagatcaaacggactgtggctgcaccatct (forward) | 30 |
| | ctcgaggcactctcccctgttgaagc (reverse) | 31 |
| $F_c$ | ggtggacaagagagttgagcccaaatcttgtgac (forward) | 32 |
| | caattgtccactgccaccccgcttga (reverse) | 33 |

The humanized variable domains ($V_L$ or $V_H$) and human antibody constant domains (Cκ, $CH_1$, or Hinge-$CH_2$—$CH_3$) were joined by overlap PCR. To this aim, all the humanized $V_L$ fragments were amplified by PCR to introduce a partial Cκ fragment at the C-terminus using primers in Table 15.

TABLE 15

Primers For Cloning the $V_L$ Domains of humanized E11, 6-3, 15-2b anti-PEG fragments

| Name | Sequence (5'-3') | SEQ ID NO |
|---|---|---|
| hE11$V_L$ (forward) | ggcccagccggccgatgttgtgatgactcagtc | 34 |
| hE11$V_L$-partial Cκ (reverse) | gtgcagccacagtccgtttgatctccaccttggtc | 35 |
| h6-3$V_L$ (forward) | ggcccagccggcc gacatcgtgatgacccag | 36 |
| h6-3$V_L$-partial Cκ (reverse) | gtgcagccacagtccgtttgatttccaccttggtc | 37 |
| h15-2b$V_L$ (forward) | ggcccagccggccgacatccagatgacccag | 38 |
| h15-2b$V_L$-partial Cκ (reverse) | gtgcagccacagtccgtttgatctccagcttggtc | 39 |

The $V_L$-partial Cκ and Cκ fragments were again joined by overlap PCR to generate $V_L$-Cκ fragments using the forward primers of $V_L$ domains and the Cκ reverse primer as shown above in Tables 14 and 15.

Likewise, all the humanized $V_H$ fragments were amplified by PCR to introducing partial $CH_1$ fragment at the C-terminus using primers shown in Table 16.

TABLE 16

Primers For Cloning the $V_H$ Domains of humanized E11, 6-3, 15-2b anti-PEG Fragments

| Name | Sequence (5'-3') | SEQ ID NO |
|---|---|---|
| hE11$V_H$ (forward) | agatctcaggtgcagctggtgcag | 40 |
| hE11$V_H$-partial CH$_1$ (reverse) | tcccttggtggaggctgaggagacggtgaccaggg | 41 |
| h6-3$V_L$H (forward) | agatctcaggtgcagctggtgcaatc | 42 |
| h6-3$V_H$-partial CH$_1$ (reverse) | gtcccttggtggaggctgaggagacggtgaccag | 43 |
| h15-2b$V_H$ (forward) | agatctgaggtgcagctggtggag | 44 |
| h15-2b$V_H$-partial CH$_1$ (reverse) | gcccttggtggaggctgaggagacggtgaccaggg | 45 |

The $V_H$-partial CH$_1$, CH$_1$ and Fc fragments were joined by overlap PCR to generate $V_H$-CH$_1$ or $V_H$-CH$_1$-hinge-CH$_2$—CH$_3$ fragments using the forward primers of $V_H$ domains, and the CH1 and Fc reverse primers as indicated above in Tables 14 and 16.

The hBU12 dsFv DNA fragment was synthesized by assembly PCR based on the $V_H$ and $V_L$ sequences of hBU12 described in U.S. Pat. No. 7,968,687 B2, the entirety of which is incorporated herein by reference. PCR was carried out as follows: 95° C. for 3 min; 10 cycles at 95° C. for 30 s, 63 to 53° C. touchdown for 1 min (decrease 1° C. every cycles), 72° C. for 1 min; 25 cycles at 95° C. for 30 s, 53° C. for 1 min, 72° C. for 1 min; 72° C. for 10 min. The $V_H$ and $V_L$ fragments were joined and amplified using P1 and P22 primers described in Table 17. The 11F8 dsFv DNA fragment was synthesized by assembly PCR based on the $V_H$ and $V_L$ sequences of 11F8 described in EP2332990 A1, the entirety of which is incorporated herein by reference. PCR was carried out as described above. The $V_H$ and $V_L$ fragments were assembled by assembly PCR using primers P23 to P34 and primers P35 to P44, respectively described in Table 18. The hCC49 scFv and DNS scFv DNA fragments were amplified by PCR using the primers as described in our previous studies (K C Chen et al., Bioconjugate Chemistry 22: 938-948, 2011). The production of C6ML3-9 dsFv plasmid was described in EP2258726A1. We next generated SalI-linker-MfeI-hBU12 scdsFv-MluI-6×His-ClaI by PCR using primers set forth in Table 19; whereas MfeI-linker-11F8 dsFv-MluI, MfeI-linker-DNS dsFv-MluI and MfeI-linker-hCC49 dsFv-MluI are generated by PCR using primers as described in Table 20.

TABLE 17

Primers For Cloning hBU12 dsFv

| Primer name | Primer Sequence (5'-xxxxxxx-3') | SEQ ID NO |
|---|---|---|
| P1 | CAATTGCAGGTTCAGCTGCAAGAGTCTGGCCCTGGGTTGGTTAAGCCC | 46 |
| P2 | CAGTACAAGTCAGACTGAGGGTCTGGGAGGGCTTAACCAACCCAGGGCC | 47 |
| P3 | CAGTCTGACTTGTACTGTGTCTGGGGGTTCAATCAGCACTTCTGGTATG | 48 |
| P4 | CTGGGTGCTGCCTAATCCAGCCTACACCCATACCAGAAGTGCTGATTG | 49 |
| P5 | GGATTAGGCAGCACCCAGGGAAGTGTCTGGAGTGGATTGGACACATTTGG | 50 |
| P6 | AACAGTAATAGACAGCAACATCCTCTGGCTCCAGGCTGCTGATTGTG | 51 |
| P7 | CAAGAGATATAACCCAGCCCTGAAGAGCAGAGTGACAATCTCTGTGGATAC | 52 |
| P8 | GACAGCTTGAGGCTAAACTGGTTCTTGGAGGTATCCACAGAGATTGTCAC | 53 |
| P9 | GTTTAGCCTCAAGCTGTCCAGTGTGACAGCTGCAGATACTGCTGTCTAC | 54 |
| P10 | AAACAGTAATAGACAGCAACATCCTCTGGCTCCAGGCTGCTGATTGTG | 55 |
| P11 | GGAACTTTGGTCCTACTATTTTGACTACTGGGGCCAAGGCACCCTTG | 56 |
| P12 | GCCCCCTGACCCGCCACCTCCTGAGGAGACTGTGACAAGGGTGCCTTGGCCCC | 57 |
| P13 | GGTGGATCGGGGGGTGGCGGATCTGAAATTGTTCTCACCCAGTCTCCAGCAAC | 58 |

TABLE 17-continued

Primers For Cloning hBU12 dsFv

| Primer name | Primer Sequence (5'-xxxxxxx-3') | SEQ ID NO |
|---|---|---|
| P14 | CAGGGTAGCCCTTTCCCCTGGAGAGAGAGACAGGGTTGCTGGAGACTGGGTG | 59 |
| P15 | GGGGAAAGGGCTACCCTGAGCTGCAGTGCCAGCTCAAGTGTAAGTTACATGC | 60 |
| P16 | CTGGGAGCCTGCCCTGGCTTCTGCTGGTACCAGTGCATGTAACTTACACTTG | 61 |
| P17 | GCCAGGGCAGGCTCCCAGACTCCTGATTTATGACACATCCAAACTGGCTTC | 62 |
| P18 | CCAGACCCACTGCCACTGAACCTTGCTGGAATACCAGAAGCCAGTTTGGATG | 63 |
| P19 | CAGTGGCAGTGGGTCTGGAACAGATTTTACACTCACAATCAGCAGCCTGG | 64 |
| P20 | GAAAACAGTAATAGACAGCAACATCCTCTGGCTCCAGGCTGCTGATTGTG | 65 |
| P21 | GCTGTCTATTACTGTTTTCAGGGGAGTGTATACCCATTCACTTTTGGC | 66 |
| P22 | ACGCGTTCTTTTGATTTCCAACTTTGTCCCGCAGCCAAAAGTGAATGGG | 67 |

TABLE 18

Primers For Cloning 11F8 dsFv

| Primer name | primer sequence (5'-xxxxxxx-3') | SEQ ID NO |
|---|---|---|
| P23 | GTCGACCAATTGGGAGGTGGCGGATCCCAGGTGCAGCTGCAGGAGTCGGG | 68 |
| P24 | ACAGGGTCTGTGAAGGCTTCACCAGTCCTGGGCCCGACTCCTGCAGCTGC | 69 |
| P25 | AGCCTTCACAGACCCTGTCCCTCACCTGCACTGTCTCTGGTGGCTCCATCAG | 70 |
| P26 | GGCGGATCCAACTCCAGTAGTAATCACCACTGCTGATGGAGCCACCAGAGAC | 71 |
| P27 | ACTGGAGTTGGATCCGCCAGCCCCCAGGGAAGTGCCTGGAGTGGATTGGG | 72 |
| P28 | GGTTGTAGTCGGTGCTCCCACTGTAATAGATGTACCCAATCCACTCCAGGCA | 73 |
| P29 | TGGGAGCACCGACTACAACCCGTCCCTCAAGAGTCGAGTCACCATGTCCGTA | 74 |
| P30 | ACCTTCAGGGAAAACTGATTCTTGGACGTGTCTACGGACATGGTGACTCG | 75 |
| P31 | TCAGTTTTCCCTGAAGGTCAACTCTGTGACCGCCGCAGACACGGCTGTGT | 76 |
| P32 | CCCCACTCCAAAAATCGACACTCTCGCACAGTAATACACAGCCGTGTCTGCGG | 77 |
| P33 | TCGATTTTTGGAGTGGGGACATTTGACTACTGGGGCCAGGGCACCCTGGT | 78 |
| P34 | ACCGCCCCTGACCCGCCACCTCCGCTTGAGACGGTGACCAGGGTGCCCTGGCC | 79 |
| P35 | GGATCGGGGGGTGGCGGATCTGAAATTGTGATGACACAGTCTCCAGCCACCCTGTC | 80 |
| P36 | GCAGGAGAGGGTGGCTCTTTCCCCTGGAGACAAAGACAGGGTGGCTGGAGAC | 81 |
| P37 | AGAGCCACCCTCTCCTGCAGGGCCAGTCAGAGTGTTAGCAGCTACTTA | 82 |
| P38 | AGCCTGGCCAGGTTTCTGTTGGTACCAGGCTAAGTAGCTGCTAACACT | 83 |
| P39 | CAGAAACCTGGCCAGGCTCCCAGGCTCCTCATCTATGATGCATCCAACAG | 84 |
| P40 | ACTGCCACTGAACCTGGCTGGGATGCCAGTGGCCCTGTTGGATGCATCATAG | 85 |
| P41 | GCCAGGTTCAGTGGCAGTGGGTCTGGGACAGACTTCACTCTCACCATCAG | 86 |
| P42 | AATACACTGCAAAATCTTCAGGCTCTAGGCTGCTGATGGTGAGAGTGAAG | 87 |
| P43 | GAAGATTTTGCAGTGTATTACTGTCACCAGTATGGTAGCACACCTCTCACTT | 88 |
| P44 | ACGCGTTTTGATCTCCGCCTTGGTCCCGCAGCCGAAAGTGAGAGGTGTGCTA | 89 |

TABLE 19

Primers For Cloning SalI-linker-MfeI-hBU12 scFv-MluI-6xHis-ClaI

| Name | Sequence (5'-3') | SEQ ID NO |
|---|---|---|
| linker-MfeI-hBU12 $V_H$ (forward) | gtggtggttcaggacaattgggaggtggcggatcccaggttcagctgcaagag | 90 |
| SalI-linker-MfeI-hBU12 $V_H$ (forward) | gtcgacctggtcaccgtctcctcagcctccaccggtggtggttcaggacaat | 91 |
| hBU12$V_L$-MluI-6xHis-ClaI (reverse) | atcgatttaatgatgatgatgatgatgacgcgttatttgatttccaactttg | 92 |

TABLE 20

Primers For Cloning MfeI-linker-11F8 dsFv-MluI, MfeI-linker-DNS dsFv-MluI and MfeI-linker-hCC49 dsFv-MluI

| Name | Sequence (5'-3') | SEQ ID NO |
|---|---|---|
| MfeI-h11F8 $V_H$ (forward) | caattgggaggtggcggatcccaggtgcagctgcaggag | 93 |
| MluI-11F8$V_L$ (reverse) | acgcgttttgatctccgccttggtc | 94 |
| MfeI-DNS$V_H$ (forward) | caattgggaggtggcggatccagtgaagtgaagcttgag | 95 |
| MluI-DNS$V_L$ (reverse) | acgcgtccgttttatttccaactt | 96 |
| MfeI-hCC49$V_H$ (forward) | caattgggaggtggcggatcccaggtgcagctggtgcag | 97 |
| MluI-hCC49$V_L$ (reverse) | acgcgttttgatctccaccttggtc | 98 |

The pLNCX-SfiI-mAGP3 $V_L$-Cκ-XhoI-F2A-BglII-mAGP3 VH-CH$_1$-SalI-eB7-ClaI plasmid was used as template for further sub-cloning. These SfiI-$V_L$-Cκ-XhoI or BglII-VH-CH$_1$-SalI or BglII-VH-CH$_1$-hinge-CH$_2$—CH$_3$-SalI fragments were sub-cloned into the template DNA plasmid described above by digesting with proper restriction enzyme to generate pLNCX-SfiI-anti-PEG $V_L$-Cκ-XhoI-F2A-BglII-anti-PEG $V_H$-CH$_1$-SalI-eB7-ClaI orpLNCX-SfiI-anti-PEG$V_L$-Cκ-XhoI-F2A-BglII-anti-PEG$V_H$-CH1-hinge-CH2-CH3-SalI-eB7-ClaI plasmids. Furthermore, the single chain variable fragments (scFv or scdsFv) were sub-cloned into these plasmids by using SalI and ClaI or followed by MfeI and ClaI enzyme digestion.

Construction of DNA Plasmids for 15-2b Knob/Bu12 Hole, 15-2Bknob/Anti-HER2 Hole, h6.3 Knob/Bu12 Hole, and h6.3 Knob/Anti-HER2 Hole To construct the knob into hole BsAbs, $V_H$-CH$_1$ of h15-2b or h6-3 was fused with the modified human IgG$_1$ CH$_2$—CH$_3$ domain to form the heavy chain of h15-2b-knob or h6-3-knob by assembly PCR. The heavy chain sequence, which is followed by a sequence derived from furin-2A (F2A) and the light chain sequence of h15-2b or h6-3, was cloned into lentival vector pLKOAS3W-hyg (RNAi core, Academia Sinica, Taipei, Taiwan) by use of NheI and PmeI restriction sites. We adopted the immunoglobulin domain crossover approach, alone with modifications of the locations of the $C_H1$ and hinge regions, to generate BU12-hole and α-Her2-hole. In brief, $V_H$-partial CH$_1$-Cκ-partial hinge, with a human influenza virus hemagglutinin (HA) tag protein fused at the N terminal of the heavy chain was fused with human IgG1 CH$_2$—CH$_3$ domain to form the new heavy chain. $V_L$-CH1-partial hinge sequences of α-Her2 Ab or BU12 were connected with the new heavy chain sequences by a F2A sequence and cloned into lentiviral vector pLKOAS3W-pur (RNAi core, Academia Sinica, Taipei, Taiwan) by use of SfiI and PmeI restriction sites. Primers used for cloning were as described in Table 21.

TABLE 21

Primers For Cloning knob into hole BsAbs

| Name | Sequence (5'-3') | SEQ ID NO |
|---|---|---|
| 15-2b-knob: | | |
| $V_L$-C$_κ$ (forward) | agatctgacatccagatgacccag | 99 |

TABLE 21-continued

Primers For Cloning knob into hole BsAbs

| Name | Sequence (5'-3') | SEQ ID NO |
|---|---|---|
| | tatcgatgtttaaacctagcactctccctgttgaa (reverse) | 100 |
| $V_H$-$CH_1$ | ggcccagccggccgaggtgcagctggtggag (forward) | 101 |
| | aagttttttgtcgaccgtgg (reverse) | 102 |
| huIgG1-upper hinge | gacaaaactcacacatgcccaccgtgc (forward) | 103 |
| $CH_1$-partical hinge | gcatgtgtgagttttgtcacaagatttgggctcaac (reverse) | 104 |
| $CH_3$ | ctcgagtttacccggagacaggga (reverse) | 105 |
| h6-3-knob: 104 | | |
| $V_L$-$C_\kappa$ | agatctgacatcgtgatgacccagtctc (forward) | 106 |
| | tatcgatgtttaaacctagcactctccctgttgaa (reverse) | 107 |
| $V_H$-$CH_1$ | caggtgcagctggtgcaat (forward) | 108 |
| | aactctcttgtccaccttgg (reverse) | 109 |
| BU12-hole: | | |
| $V_H$-$C_\kappa$-partial hinge | agccggcccaggttcagctgcaagagtctggc (forward) | 110 |
| | gcatgtgtgagttttgtcacactctccctgttgaagct (reverse) | 111 |
| $V_L$-partial $V_H$-$CH_1$-upperHinge | gaaattgttctcacccagtctcc (forward) | 112 |
| | ttaacaagatttgggctcaac (reverse) | 113 |
| partial $V_L$-$hCH_1$ | gttggaaatcaaaagatcctcagcctccaccaagggcccatcg (forward) | 114 |
| α-Her2-hole: | | |
| $V_H$ | ggcccagccggcccaggtgcagctgttgcagtctggg (forward) | 115 |
| $V_H$-$C_\kappa$-partial hinge | aggtgcagctgttgcagtctggg (forward) | 116 |
| | gcatgtgtgagttttgtcacactctccctgttgaagct (reverse) | 117 |
| $V_L$-partial $V_H$ | ctgaccgtcctaggttcctcagcctccaccaagggcccatcg (forward) | 118 |
| | acctaggacggtcagcttggtcccgccgccgaacacccagcccga (reverse) | 119 |
| $V_L$ | ctgccagatctcagtctgtgttgacgcag (forward) | 120 |
| | acctaggacggtcagcttggtcccgccgccgaacacccagcccga (reverse) | 121 |
| $CH_1$-upper hinge | ttaacaagatttgggctcaac (reverse) | 122 |

Constructing DNA Plasmids for 15-2b FabxHER2 scFv, 15-2b FabxEGFR scFv, 15-2b scFvxCD19 Fab, and 15-2b scFvxCD20 Fab The $V_L$-Cκ and $V_H$-$C_{H1}$ domains of the anti-mPEG antibody were cloned from the cDNA of the 15-2b hybridoma and humanized as described previously (Chuang K-H et al., J. Nucl. Med. 2010 (51): 933-941). The humanized anti-mPEG $V_L$ and $V_H$ segments were synthesized by assembly polymerase chain reaction (PCR) and were subcloned into retroviral vector pLNCX-anti-PEG-eB7) in the unique BglII, SalI, SfiI, and XhoI restriction enzyme sites, respectively. Primers for cloning 15-2b Fab sequence are given in Table 22. The human anti-EGFR scFv was cloned based on the h528Fv DNA sequence (Makabe et al., (2008) J. Biol. Chem, 283, 1156-1166). Therefore, h528Fv DNA sequence was generated by assembly PCR. Primers used in the cloning of anti-EGFR $V_H$ and $V_L$ are given in Table 23. Then, using Mfe-ahEGFR VL primer, ahEGFR $V_L$-(G4S)2 primer, (G4S)2-ahEGFR $V_H$ primer and ahEGFR $V_H$-stop-Cal primer to create human anti-EGFR scFv, which contained a myc tag and fifteen amino acid (GGGGS)3 flexible linker in front of the sequence.

A human anti-HER2 scFv and anti-DNS scFv were cloned from the pBub-YCMC plasmid (Shahied et al., (2004) J. Biol. Chem. 279, 53907-53914) and pLNCX-DNS-B7 (Chuang et al., (2006) Bioconjugate Chemistry 17, 707-714), respectively. Primers for cloning human anti-HER2 scFv and anti-DNS scFv are given in Tables 24 and 25, respectively. A myc tag and fifteen amino acid (GGGGS)3 flexible linker was placed between the anti-mPEG Fab and scFv genes to generate pLNCX-PEG×EGFR, pLNCX-PEG×HER2 and pLNCX-PEG×DNS plasmids by using SalI and CalI restriction enzyme sites.

TABLE 22

Primers For Cloning h15-2b Fab Sequence

| Name of Primer | Sequence | SEQ ID NO |
|---|---|---|
| h15-2b VH-CH1 | | |
| h15-2b Bgl-VH-1 (forward) | 5'-gaagatctgaggtgcagctggtggagtctgggggaggcttggtccag-3' | 123 |
| h15-2b VH-2 (reverse) | 5'-agaggctgcacaggagagtttcagggacccccaggctggaccaagcctcc-3' | 124 |
| h15-2b VH-3 (forward) | 5'-tcctgtgcagcctctgggttcaccttcagtaactactggatgaactgggtc-3' | 125 |
| h15-2b VH-4 (reverse) | 5'-gccaacccactccagcccttcccggaagcctggcggacccagttcatcca-3' | 126 |
| h15-2b VH-5 (forward) | 5'-ctggagtgggttggcgaaattagatcgaaatctaataattatgcgacacat-3' | 127 |
| h15-2b VH-6 (reverse) | 5'-ggagatggtgaacctccctttcacagactccgcataatgtgtcgcataatt-3' | 128 |
| h15-2b VH-7 (forward) | 5'-aggttcaccatctccagagatgattcaaagaacacggcgtatctgcaaatg-3' | 129 |
| h15-2b VH-8 (reverse) | 5'-gtaatacacggccgtgtcctcggttttcaggctgttcatttgcagatacgc-3' | 130 |
| h15-2b VH-9 (T93S) (forward) | 5'-acggccgtgtattactgttccaacagatactactggggccaaggaaccctg-3' | 131 |
| h15-2b VH-10 (reverse) | 5'-acctttggtggaggctgaggagacggtgaccagggttccttggcc-3' | 132 |
| homo 3' IgG2 CH1-SalI (reverse) | 5'-acgcgtcgactttgcgctcaactgtctt-3' | 133 |
| h15-2b VL-Cκ | | |
| h15-2b sfi-VL-1 (forward) | 5'-tgctggggcccagccggccgacatccagatgacccagtctcca-3' | 134 |
| h15-2b VL-2 (reverse) | 5'-ggtgactctgtctcctacagatgcagacagggaggatggagactgggtcat-3' | 135 |
| h15-2b VL-3 (forward) | 5'-ggagacagagtcaccatcacttgcaaggccagtcaggatgtaaatacttct-3' | 136 |
| h15-2b VL-4 (reverse) | 5'-aggggctttccctggtttctgctgataccaggctacagaagtatttacatc-3' | 137 |
| h15-2b VL-5 (forward) | 5'-ccagggaaagcccctaagctcctgatctactgggcatccacccggcacact-3' | 138 |
| h15-2b VL-6 (reverse) | 5'-cccagatccacttccactgaaccttgatgggaccccagtgtgccgggtgga-3' | 139 |
| h15-2b VL-7 (forward) | 5'-ggaagtggatctgggacagattttactttcaccatcagcagcctgcagcct-3' | 140 |
| h15-2b VL-8 (reverse) | 5'-gatatattgcagacagtaatatgttgcaatatcttcaggctgcaggctgct-3' | 141 |

TABLE 22-continued

Primers For Cloning h15-2b Fab Sequence

| Name of Primer | Sequence | SEQ ID NO |
|---|---|---|
| h15-2b VL-9 (forward) | 5'-tgtctgcaatatatcaactatccgtacacgtttggccaggggaccaagctg-3' | 142 |
| h15-2b VL-10 (reverse) | 5'-tggtgcagccacagtccgtttgatctccagcttggtcccctg-3' | 143 |
| homo 3' CKcys-XhoI (reverse) | 5'-ccgctcgaggcactctcccctgttgaagctctttgtgacgggcgagctcaggccctg-3' | 144 |

TABLE 23

Primers for the cloning of h528 (Anti-EGFR) scFv

| Name of Primer | Sequence | SEQ ID NO |
|---|---|---|
| h528VH01 (forward) | 5'-caggtgcaactggttcagagcggcgcggaagtgaaaaagccgggcgcgtcggtt-3' | 145 |
| h528VH02 (reverse) | 5'-aaaggtatagcctgaggctttgcagctcactttaaccgacgcgcccgg-3' | 146 |
| h528VH03 (forward) | 5'-tcaggctataccttttacgagctactggatgcattgggtgcgccaggcc-3' | 147 |
| h528VH04 (reverse) | 5'-aatgttacccatccattccaggccctgacccggggcctggcgcaccca-3' | 148 |
| h528VH05 (forward) | 5'-tggatgggtaacatttatccgggcagcggtggcaccaactatgcggaa-3' | 149 |
| h528VH06 (reverse) | 5'-atcacgcgtcatggtcacgcggttcttaaattttttccgcatagttggt-3' | 150 |
| h528VH07 (forward) | 5'-accatgacgcgtgataccagcatttcgacggcctatatggaactgagc-3' | 151 |
| h528VH08 (reverse) | 5'-gtaatacacggcggtgtcatcgctacgcaggcggctcagttccatata-3' | 152 |
| h528VH09 (forward) | 5'-accgccgtgtattactgcgcgcgcagtggcggtccgtattttttcgat-3' | 153 |
| h528VH10 (reverse) | 5'-cgagctcacggtaaccagcgtaccctggccccagtaatcgaaaaaatacgg-3' | 154 |
| (G4S)2-ahEGFR VH (forward) | 5'-ggcggtggtgggtcgggtggcggcggatctcaggtgcaactggtt-3' | 155 |
| ahEGFR VH-stop-CaI (reverse) | 5'-ccatcgatttacgagctcacggtaac-3' | 156 |
| h528VL01 (forward) | 5'-gatattgtgatgacccagagcccgctgagcctgccggtgaccccaggc-3' | 157 |
| h528VL02 (reverse) | 5'-ctgcgagctgcggcagctaatcgacgccggttcgcctggggtcaccgg-3' | 158 |
| h528VL03 (forward) | 5'-tgccgcagctcgcagaacatcgtgcataataacggcattacctatctg-3' | 159 |
| h528VL04 (reverse) | 5'-cgggctttggcccggtttctgcagataccattccagataggtaatgcc-3' | 160 |
| h528VL05 (forward) | 5'-ccgggccaaagcccgcagctgttaatttataaagtgagcgatcgcttt-3' | 161 |
| h528VL06 (reverse) | 5'-accgctgcccgaaaagcgatccggcacgccgctaaagcgatcgctcac-3' | 162 |

TABLE 23-continued

Primers for the cloning of h528 (Anti-EGFR) scFv

| Name of Primer | Sequence | SEQ ID NO |
|---|---|---|
| h528VL07 (forward) | 5'-ttttcgggcagcggtagtggcaccgattttacgctgaaaattagccgc-3' | 163 |
| h528VL08 (reverse) | 5'-gcagtaatacacgccaacatcctccgcttccacgcggctaattttcag-3' | 164 |
| h528VL09 (forward) | 5'-ggcgtgtattactgctttcagggcagccatatcccgccaacctttggc-3' | 165 |
| h528VL10 (reverse) | 5'-cgcgcgtttaatttccactttggtgccttggccaaaggttggcgg-3' | 166 |
| Mfe-ahEGFR VL (forward) | 5'-caattggatattgtgatgacccag-3' | 167 |
| ahEGFR VL-(G4S)2 (reverse) | 5'-cgacccaccaccgcccgagccaccgccacccgcgcgtttaatttc-3' | 168 |

TABLE 24

Primers for the cloning of C6ML3-9 (Anti-HER2) scFv

| Name of Primer | Sequence | SEQ ID NO |
|---|---|---|
| Sal-G-myc-G4S (forward) | 5'-acgcgtcgacggggaacaaaaactcatctcagaagaggatctgggaggcggtggcagt-3' | 169 |
| G2S-G4SX2-MfeI (forward) | 5'-ggtggcagtggtggtggtggatcaggaggtggcggatcccaattgcaggtgcagctg-3' | 170 |
| Her2 scFv-stop-ClaI (reverse) | 5'-atcgattcaacctaggacggtcagctt-3' | 171 |

TABLE 25

Primers for the cloning of h15-2b scFv

| Name of Primer | Sequence | SEQ ID NO |
|---|---|---|
| mfe1-h15-2bVL (forward) | 5'-caattggacatccagatgacccagtctcca-3' | 172 |
| h15-2bscFv-ClaI-SbfI (reverse) | 5'-cccctgcaggcatcgatttatgaggagacggtgac-3' | 173 |

Primers for cloning Human anti-CD19 VH and VL are given in Tables 26. The cloned human anti-CD19 VH and VL sequences (Table 13) were then fused with DNA sequence of h15-2b scFv to generate DNA construct for expressing BsAbs of PEG×CD19. Similarly, human anti-CD20 VH and VL were cloned by primers given in Table 27 and the cloned human anti-CD20 and anti-CD22 sequences were then fused with DNA sequence of h15-2b scFv to produce constructs for expressing BsAbs of PEG×CD20 and PEG×CD22, respectively.

TABLE 26

Primers for the cloning of hHB12b (Anti-CD19) VL and VH

| Name of Primer | Sequence | SEQ ID NO |
|---|---|---|
| hHB12b VL | | |
| NaeI-X + hHB12bVL-1 (forward) | 5'-gccggccgagatcgtgctgacccagagccccgacttccagagc-3' | 174 |
| hHB12bVL-2 (reverse) | 5'-ctctgcaggtgatggtcaccttctccttgggggtcacgctctggaagtcgggg-3' | 175 |
| hHB12bVL-3 (forward) | 5'-gtgaccatcacctgcagagccagcgagagcgtggacaccttcggcatcagcttc-3' | 176 |
| hHB12bVL-4 (reverse) | 5'-gctctggtcgggcttctgctggaaccagttcatgaagctgatgccgaaggtg-3' | 177 |
| hHB12bVL-5 (forward) | 5'-gaagcccgaccagagccccaagctgctgatccacgccgccagcaaccaggg-3' | 178 |

TABLE 26-continued

Primers for the cloning of hHB12b (Anti-CD19) VL and VH

| Name of Primer | Sequence | SEQ ID NO |
|---|---|---|
| hHB12bVL-6 (reverse) | 5'-cttccgctgccgctgaatctgctgggcacgccgctgccctggttgctggcg-3' | 179 |
| hHB12bVL-7 (forward) | 5'-ttcagcggcagcggaagcggcaccgacttcaccctgaccatcaacagcctgg-3' | 180 |
| hHB12bVL-8 (reverse) | 5'-ctctgctggcagtagtaggttgctgcgtcctcggcctccaggctgttgatggtc-3' | 181 |
| hHB12bVL-9 (forward) | 5'-aacctactactgccagcagagcaaggaggtgcccttcaccttcggcggcggc-3' | 182 |
| DraIII + hHB12bVL-10 (reverse) | 5'-gacactcggtgcagccacagtcttgatctccaccttggtgccgccgccgaag-3' | 183 |
| hHB12b VH | | |
| HpaI + hHB12bVH-1 (forward) | 5'-gttaacgaggtgcagctggtggagagcggcggcggcctggtgca-3' | 184 |
| hHB12bVH-2 (reverse) | 5'-cgctggcggcgcagctcagtctcaggctgccgccgggctgcaccaggccgccgc-3' | 185 |
| hHB12bVH-3 (forward) | 5'-gctgcgccgccagcggcttcaccttcagcagcagctggatgaactgggtgagac-3' | 186 |
| hHB12bVH-4 (reverse) | 5'-gattctgcccacccactccaggcccttgccggggcctgtctcacccagttcatcc-3' | 187 |
| hHB12bVH-5 (forward) | 5'-gagtgggtgggcagaatctaccccggcgacggcgacaccaactacaacggcaagttc-3' | 188 |
| hHB12bVH-6 (reverse) | 5'-tcttgctgtcgtctctgctgatggtgaatctgcccttgaacttgccgttgtagttg-3' | 189 |
| hHB12bVH-7 (forward) | 5'-ttcagcggcagcggaagcggcaccgacttcaccctgaccatcaacagcctgg-3' | 190 |
| hHB12bVH-8 (reverse) | 5'-atgaagccgcttctggcgcagtagtacacggcggtgtcctcggtcttcaggctgtt-3' | 191 |
| hHB12bVH-9 (forward) | 5'-cgccagaagcggcttcatcaccaccgtgctggacttcgactactggggccagggc-3' | 192 |
| ApaI + hHB12bVH-10 (reverse) | 5'-gggcccttggtggaggcgctgctcacggtcaccagggtgccctggccccagtag-3' | 193 |

TABLE 27

Primers for the cloning of F2F (Anti-CD20) VL and VH

| Name of Primer | Sequence | SEQ ID NO |
|---|---|---|
| F2F VL | | |
| NaeI-X-aCD20VL-1 (forward) | 5'-gccggccatggaagcccagctcagcttctcttcctcctgctactctggc-3' | 194 |
| aCD20VL-2 (reverse) | 5'-ctggagactgtgtcaacacaatttctccggtggtatctgggagccagagtagcaggaggaag-3' | 195 |
| aCD20VL-3 (forward) | 5'-aattgtgttgacacagtctccagccaccctgtctttgtctccaggggaaagagccaccc-3' | 196 |

TABLE 27-continued

Primers for the cloning of F2F (Anti-CD20) VL and VH

| Name of Primer | Sequence | SEQ ID NO |
|---|---|---|
| aCD20VL-4 (reverse) | 5'-caggctaagtagctgctaacactctgactggccctgcaggagagggtggctcttctccc-3' | 197 |
| aCD20VL-5 (forward) | 5'-tgttagcagctacttagcctggtaccaacagaaacctggccaggctcccaggctcctc-3' | 198 |
| aCD20VL-6 (reverse) | 5'-ctggctgggatgccagtggccctgttggatgcatcatagatgaggagcctgggagcc-3' | 199 |
| aCD20VL-7 (forward) | 5'-actggcatcccagccaggttcagtggcagtgggtctgggacagacttcactctcaccat-3' | 200 |
| aCD20VL-8 (reverse) | 5'-ctgacagtaataaactgcaaaatcttcaggctctaggctgctgatggtgagagtgaagtctgtcc-3' | 201 |
| aCD20VL-9 (forward) | 5'-gaagattttgcagtttattactgtcagcagcgtagcaactggccgatcaccttcggccaagg-3' | 202 |
| DraIII - aCD20VL-10 (reverse) | 5'-gacactcggtgcagccacagttttaatctccagtcgtgtcccttggccgaaggtgatc-3' | 203 |

F2F VH

| Name of Primer | Sequence | SEQ ID NO |
|---|---|---|
| HpaI + aCD20VH-1 (forward) | 5'-gttaacatggagttgggactgagctggattttccttttggctattta-3' | 204 |
| aCD20VH-2 (reverse) | 5'-ctccaccagctgcacttcacactggacaccttttaaaatagccaaaaggaaaatccagc-3' | 205 |
| aCD20VhH-3 (forward) | 5'-gaagtgcagctggtggagtctgggggaggcttggtacagcctggcaggtccctg-3' | 206 |
| aCD20VH-4 (reverse) | 5'-cataatcattaaaggtgaatccagaggctgcacaggagagtctcagggacctgcagg-3' | 207 |
| aCD20VH-5 (forward) | 5'-gcctctggattcacctttaatgattatgccatgcactgggtccggcaagctccagggaag-3' | 208 |
| aCD20VH-6 (reverse) | 5'-ggaaccactattccaactaatagttgagacccactccaggcccttccctggagcttgcc-3' | 209 |
| aCD20VH-7 (forward) | 5'-tcaactattagttggaatagtggttccataggctatgcggactatgtgaagggccgattc-3' | 210 |
| aCD20VH-8 (reverse) | 5'-gatacagggacttcttggcgttgtctctggagatggtgaatcggcccttcacagag-3' | 211 |
| aCD20VH-9 (forward) | 5'-cgccaagaagtccctgtatctgcaaatgaacagtctgagagctgaggacacggcc-3' | 212 |
| aCD20VH-10 (reverse) | 5'-gtagtagttgccgtactgtatatcttttgcacagtaatacaaggccgtgtcctcagc-3' | 213 |
| aCD20VH-11 (forward) | 5'-agatatacagtacggcaactactactacggtatggacgtaggggccaagggaccac-3' | 214 |
| ApaI - aCD20VH-12 (reverse) | 5'-gggccattggtggaggctgaggagacggtgaccgtggtcccttggccc-3' | 215 |

Production of Recombinant PEG2×TAG72, PEG2×EGFR, PEG2-HER2, PEG×TAG72, PEG×EGFR and PEG×HERBsAbs CHO-K1/PEG2×TAG72 and CHO-K1/PEG2×DNS cells that stably secrete PEG2×TAG72 and PEG2×DNS BsAbs were generated by retroviral transduction of CHO-K1 Chinese hamster ovary cells. PEG2×TAG72, PEG2×EGFR, PEG2-HER2, PEG×TAG72, PEG×EGFR and PEG×HER BsAbs were produced by transient transfection of 293FT cells with corresponding plasmids. 293FT/h6.3FabxCD19 and 293FT/h6.3FabxEGFR cells that stably secreted h6.3FabxCD19 and h6.3FabxEGFR BsAbs were generated by lentiviral transduction. Recombinant lentiviral particles were packaged by co-transfection of pAS3w. Ppuro-pAS3w.Ppuro-h6.3FabxCD19 and pAS3w.Ppuro-h6.3FabxEGFR (7.5 µg) with pCMVΔR8.91 (6.75 µg) and pMD.G (0.75 µg) using TransIT-LT1 transfection reagent (Mirus Bio, Madison, Wis.) (45 µL) in 293FT cells grown in a 10 cm culture dish (90% confluency). After 48 hr, lentiviral particles were harvested and concentrated by ultracentrifugation (Beckman SW 41 Ti Ultracentrifuge Swing Bucket Rotor, 50,000 g, 1.5 hr, 4° C.). Lentiviral particles were suspended in culture medium containing 5 µg/mL polybrene and filtered through a 0.45 µm filter. 293FT cells were seeded in 6-well plates ($1 \times 10^5$ cells/well) one day before viral infection. Lentivirus containing medium was added to cells and then centrifuged for 1.5 hr (500 g, 32° C.). The cells were selected in puromycin (5 µg/mL) to generate stable cell lines. These anti-PEG BsAbs were purified by affinity chromatography on a TALON column. Briefly, the medium was harvested from CELLine adhere 1000 bioreactors (INTEGRA Biosciences AG, Switzerland) every 7-10 days. Poly-histidine-tagged BsAbs were purified on a $Co^{2+}$-TALON column (GE Healthcare Life Sciences, Piscataway, N.J.). The columns were washed by 5-fold bed volumes of binding buffer (0.3 M NaCl/20 mM phosphate/HCl, pH 7.4) and followed by 10-fold bed volumes of washing buffer (0.3 M NaCl/20 mM phosphate/5 mM imidazole/HCl, pH 7.4). These poylhistidine-tagged BsAbs were eluted by elution buffer (0.3 M NaCl/20 mM phosphate/150 mM imidazole/HCl, pH 7.4). The eluted proteins were desalted on Sephadex G-25, equilibrated with PBS and concentrated by ultrafiltration. Protein concentrations were determined by the bicinchoninic acid protein assay (Pierce, Rockford, Ill., U.S.A.).

Production of PEG×EGFR, PEG×HER2 and PEG×DNS BsAbs

To produce desired BsAbs, the BALB 3T3 producer cells were transfected with plasmids of this invention as described above, and were subsequently sorted by FACS on a MoFlo™ XDP (Beckman coulter, Inc., Brea, Calif.) at 4° C. and then incubated into CELLine (INTEGRA Biosciences AG, Zizers, Switzerland) with 1% CCS DMEM. After collecting the culture medium, BsAbs were purified by mPEG affinity chromatography, which was made by coupling 36 mg of o-(2-aminoethyl)-o'-methylpolyethylene glycol 750 (Fluka-Sigma-Aldrich, St. Louis, Mo.) on 1 g of CNBr-activated Sepharose™ 4B (GE Healthcare, Little Chalfont, UK). This procedure was performed by following the instruction manual of CNBr-activated Sepharose™ 4B (GE Healthcare).

Purification of Knob in Hole BsAbs

293FT cells stably expressing BsAbs were cultured in Cell Line adhere 1000 (Integra Biosciences AG, Zizers, Switzerland) in DMEM with 10% low bovine IgG medium (serum was pre-absorbed with protein A resin) at a starting cell number of $5 \times 10^7$. Culture supernatant was harvested every week. The pooled supernatant was centrifuged at 800 g for 10 min at 4° C. to remove cells and subsequently centrifuged at 15000 rpm for 25 min at 4° C. to remove cell debris. Later on, the supernatant was passed through a 0.45 µM filter and G25 column in phosphate saline buffer (PBS), and finally the bsAb was affinity purified using protein A sepharose. After protein A purification, the purified products were further purified by affinity chromatography by CNBr-activated Sepharose™ 4B (Sigma-Aldrich Chemical Co, St. Louis, Mo., USA) conjugated with 35 mg of methyl-$PEG_{1000}$-NH2 per gram of CNBr activated Sepharose™ 4B. Subsequently, the purified bsAb were further purified by affinity chromatography using Pierce anti-HA agarose (Thermo Scientific, MA, USA). Purified bsAb fractions were dialyzed against 1000 volumes of PBS three times and concentrated using Amicon Ultra (30 kD cutoff) (Millipore).

Analysis of the Purified BsAbs

Five microgram of BsAbs (such as PEG2×TAG72, PEG2×DNS, mPEG×EGFR, mPEG×HER2, mPEG×DNS, 15-2b/BU12, h6.3/BU12, h6.3Fab×EGFR, and h6.3Fab×CD19 BsAbs) were electrophoresed in 10% SDS-PAGE gels under reducing or non-reducing conditions and then stained by Coomassie Blue.

ELISA

The anti-PEG binding specificity of BsAbs was measured by adding graded concentrations of PEG2×TAG72, PEG2×DNS, hCC49 scFv, h6.3Fab×EGFR or h6.3Fab×CD19 in 50 µL 2% skim milk to the mucin, BSA-PEG5000, $NH_2$-$PEG_{3k}$-$NH_2$ or BSA coated plates at RT for 1 h. The plates were washed with PBS-T (PBS containing 0.05% Tween-20) three times. Rabbit anti-6×His (2 µg/mL) supplemented with HRP-conjugated goat anti-rabbit (2 µg/mL) or HRP-conjugated goat Ig anti human IgG Fab (2 µg/mL) (Jackson ImmunoResearch Laboratories, West Grove, Pa.) in 50 µL dilution buffer were added for 1 h at room temperature. The plates were washed with PBS-T (PBS containing 0.05% Tween-20) three times and with PBS two times. Bound peroxidase activity was measured by adding 150 µL/well ABTS substrate solution (BioLegend, San Diego, Calif.) for 30 min at room temperature. The absorbance (405 nm) of wells was measured in a microplate reader (Molecular Device, Menlo Park, Calif.).

Flow Cytometer Analysis

PEG2×TAG72 or control PEG2×DNS BsAbs (10 µg/mL) were incubated with A-375(TAG72−), MCF-7(TAG72+), Jurkat (TAG72+) or OVCAR-3(TAG72+) cells at 4° C. for 30 min followed by FITC-labeled goat anti-human immunoglobulin second antibody (2 µg/mL) (Jackson ImmunoResearch Laboratories, West Grove, Pa.) or FITC-labeled 4arm-PEG (2 µg/mL). Tumor-specific targeting of PEGylated compounds was also examined by staining A431 ($EGFR^{high}$), and Raji ($CD19^{high}$) cell lines with 10 µg/mL of h6.3Fab×EGFR or h6.3Fab×CD19 BsAbs in PBS containing 0.05% BSA (staining buffer) at 4° C. for 30 min. The cells were washed with cold PBS for 3 times. PEG-Qdot655 (8 nM) (Invitrogen, Grand Island, N.Y.) or PEG-liposomal Texas-Red (100 nm size, 50 µM, lipid conc.) (FormuMax Scientific, Palo Alto, Calif.) in staining buffer was added to cells for 30 min at 4° C. Raji cells (CD19+) or SKBR3 cells (HER2+) were incubated with 10 µg/ml h15-2b-knob/BU12-hole, h15-2b-knob/anti-Her2-hole, h6-3-knob/BU12-hole or h6-3-knob/anti-Her2-hole BsAbs, washed and incubated with 0.25 µg/ml FITC-labeled goat anti-human IgG or 10 nM methoxy-PEG Qdot 655 at 4° C. for 30 min. After washing with cold PBS, the surface fluorescence of $10^4$ viable cells was measured by FACScaliber flow cytometer (Becton Dickinson, Mountain View, Calif., USA) then analyzed with Flowjo (Tree Star Inc., San Carlos, Calif., USA).

Confocal Microscopy of BsAb-Targeted Nano-Particles

The coverslips (30 mm) in POC chambers were coated with 10 µg/mL poly-L-lysine in PBS for 30 min at room temperature. The coverslips were washed twice with PBS and then $5 \times 10^4$ cells/chamber of A431 ($EGFR^+$) tumor cells were seeded on the coverslips. A431 cells were incubated with 10 µg/mL of h6.3Fab×EGFR or h6.3Fab×CD19 BsAbs at 37° C. for 30 min containing 1 µg/mL of Hoechst 33342 and 100 nM of LysoTracker® Red DND-99 (Invitrogen Life Technologies Corporation, NY, USA). The cells were washed with culture medium for 2 times. Cell imaging was recorded with an Axiovert 200M Confocal Microscope (Carl Ziess Inc., Thornwood, N.Y.) after adding 16 nM of PEG-Qdot655 solution (Invitrogen Life Technologies Corporation, NY, USA).

Cytotoxicity Assay

A431 ($EGFR^{high}$) and Raji ($CD19^{high}$) cells (5000 cells/well) were seeded in 96-well plates overnight. Fifteen microgram per mL of h6.3Fab×EGFR or h6.3Fab×CD19 BsAbs were added to the cells for 30 min at 37° C. and followed by graded concentrations of free doxorubicin or PEGylated liposomal doxorubicin (Doxisome®, Taiwan Liposome Company Ltd., Taipei, Taiwan) was added to the cells in triplicate at 37° C. for 4 h. The cells were subsequently washed once and incubated for an additional 48 h in fresh culture medium and then pulsed for 16 h with $^3$H-thymidine (1 µCi/well). Results are expressed as percent inhibition of $^3$H-thymidine incorporation into cellular DNA in comparison to untreated cells.

In Vivo Optical Imaging of PEG-NIR797 Probes

BALB/c nude mice bearing Ramos (CD19+) and A431 (EGFR+) tumor (~250 mm$^3$) in their hind leg regions were intravenously injected with h6.3Fab×EGFR (50 µg) and PEG-NIR791 (50 µg). Pentobarbital anesthetized mice were sequentially imaged with an IVIS spectrum optical imaging system (excitation, 745 nm; emission, 840 nm; Perkin-Elmer, Inc., MA, USA) at 45 min, 24 and 48 hr after injection.

Detecting the Expressed Level of Tumor Markers on Colon and Breast Cancer Cells

EGFR expression was measured by staining SW480 or SW620 cells with 1 mg/ml Erbitux followed by 1 mg/ml FITC conjugated goat anti-human IgG Fc (Jackson Immuno-Research Laboratories, Westgrove, Pa.) at 4° C. The same procedure were used to measure HER2 expression of SK-BR-3 or MDA-MB-468 cells, which were stained by 1 mg/ml Herceptin followed by 1 mg/ml FITC conjugated goat anti-human IgG Fc. After extensive washing with ice cold PBS, the surface immunofluorescence of viable cells was measured with a FACScan flow cytometer (BD Biosciences, San Diego, Calif.) and fluorescence intensities were analyzed with Cellquest pro software (BD Biosciences).

Bi-Functional Assay of PEG×EGFR and PEG×HER2

Ninety-six well plates were coated with 2 µg/well of poly-L-lysine (40 µg/ml) in PBS for 5 min at room temperature, washed twice with PBS and then coated with 2×10$^5$ cells/well of SW480 (EGFR$^+$) or SK-BR-3 (HER2$^+$) tumor cells. PEG×EGFR, PEG×HER2 and PEG×DNS (10 µg/ml) were added to the wells at room temperature for 1 h. The wells were then washed three times with DMEM and 200 ng/ml of Lipo/DOX, 66.7 ng/ml of Lipo/IR780, 100 ng/ml of SN38/PM, 600 ng/ml of FeOdots, 0.5 nM of AuNP and 0.5 nM of Qdot$_{565nm}$ were added to the wells for 20 mins. After extensive washing with DMEM, the concentrations of PEG-NPs were determined by adding 5 µg/ml of anti-PEG backbone Ab (6-3 Ab from 6-3 hybridoma) for 1 hr, and then DMEM washing three times. In order to amplifying the signals, 0.4 µg/ml of goat anti-mouse IgG Fc-HRP (Jackson ImmunoResearch Laboratories, Inc., PA, USA) was added to the wells. Washing wells fourth times with DMEM, followed by ABTS substrate before absorbance values at 405 nm were measured in a microplate reader (Molecular Device, Menlo Park, Calif., USA).

Non-Covalent Modification of PEG-NPs with PEG×EGFR and PEG×HER2

BsAbs were added to the PEG-NPs in BSA/PBS buffer (0.05% BSA in 1×PBS buffer) at 4° C. for 1 h at protein/PEG-NP ratios of 380-570 µg BsAb/µmol doxorubicin (for Lipo/DOX), 550 µg BsAbs/µmol FeOdot and 140 ng BsAbs/pmol Qdots. After PEG×EGFR or PEG×HER2 modification, PEG-NPs became αEGFR-NPs or αHER2-NPs.

Confirm the Conversion of Non-Targeted NPs to Targeted NPs

Ninety-six well plates were coated with 2 µg/well of poly-L-lysine (40 µg/ml) in PBS for 5 min at room temperature, washed twice with PBS and then coated with 2×10$^5$ cells/well of SW480 (EGFR+), SW620 (EGFR$^-$), SK-BR-3 (HER2$^+$) or MDA-MB-468 (HER2$^-$) tumor cells. SW480 (EGFR$^+$) and SW620 (EGFR$^-$) cells were incubated with 4 µg/ml of αEGFR-Lipo/DOX, 1 µg/ml of αEGFR-Lipo/IR780 and 4 µg/ml of FeOdots for 20 mins. After extensive washing with DMEM, the concentrations of PEGylated NPs were determined by adding 5 µg/ml of anti-PEG backbone Ab (6-3 Ab) for 1 hr, and then DMEM washing three times. In order to amplifying the signals, 0.4 µg/ml of goat anti-mouse IgG Fc-HRP (Jackson ImmunoResearch Laboratories, Inc., Pa., USA) was added to the wells. Washing wells with DMEM, followed by adding ABTS substrate before absorbance values at 405 nm were measured in a microplate reader (Molecular Device, Menlo Park, Calif., USA). The same procedure was used to examine SK-BR-3 (HER2$^+$) and MDA-MB-468 (HER2$^-$) cells that were stained with 4 µg/ml of αHER2-Lipo/DOX, 4 µg/ml of FeOdots and 2 nM of αEGFR-Qdot$_{565\ nm}$ for 20 mins.

Confocal Microscopy of BsAb-Targeted NPs

Circular coverslips (18 mm) in 12 wells plate were coated with 20 µg/well of poly-L-lysine (40 µg/ml) in PBS for 5 min at room temperature. The coverslips were washed twice with PBS and then 4×10$^4$ cells/well of SW480 (EGFR$^+$), SW620 (EGFR$^-$), SK-BR-3 (HER2$^+$) or MDA-MB-468 (HER2$^-$) tumor cells were coated on the coverslips. SW480 (EGFR$^+$) and SW620 cells (EGFR$^-$) were incubated with 300 ng/ml of αEGFR-Lipo/Rho and αDNS-Lipo/Rho at 37° C. for 1 h. The cells were fixed with 2% paraformaldehyde in PBS for 30 min at 4° C. and were stained with DAPI for 45 min at 4° C. Then, the coverslips were washed 4 times with PBS, and then mounted with fluorescent mounting medium (Dako, Glostrup, Denmark) on glass microscope slide. The fluorescent signals of αEGFR-Lipo/Rho and αDNS-Lipo/Rhowere recorded with an Olympus FluoView™ FV1000 Confocal Microscope (Olympus Imaging America Inc., Center Valley, Pa.). The same procedure was used to image SK-BR-3 (HER2$^+$) and MDA-MB-468 (HER2$^-$) cells which were stained with 4 nM of αHER2-Qdot$_{565nm}$ and αDNS-Qdot$_{565nm}$, respectively.

Targeting of BsAb-Targeted FeOdots by MR Imaging

MR imaging was performed with a clinical 3.0 T MR imager (Signa; GE Healthcare, Little Chalfont, UK). 1×10$^7$ SW480 (EGFR$^+$) or SW620 (EGFR$^-$) cells were incubated with different concentrations of αEGFR-FeOdots or αDNS-FeOdots (7 µM, 14 µM and 28 µM) at 4° C. for 30 min. The cells were washed with PBS 3 times and then the accumulation of BsAbs-FeOdots were scanned by T2-weighted fast spin-echo sequence (TR/TE=2500 ms/60 ms). The same protocol was used to examine localization of αHER2-FeOdots and αDNS-FeOdots at SK-BR-3 (HER2$^+$) and MDA-MB-468 (HER2$^-$) cells.

In Vitro Cytotoxicity of BsAb-Targeted Lipo/DOX

SW480 (EGFR$^+$) and SW620 (EGFR$^-$) cells (3×10$^3$/well) were seeded in 96-wells plates. 2 µg/ml or 4 µg/ml of αEGFR-Lipo/DOX, αDNS-Lipo/DOX, and Lipo/DOX were added to each well and incubated at 37° C. for 1 h. The medium was replenished and the cells were incubated for 72 h before cell viability was measured with the ATPlite™ Luminescence Assay System (Perkin-Elmer, Inc., Waltham, Mass.). Cell viability for SK-BR-3 (HER2$^+$) or MDA-MB-468 (HER2$^-$) cells incubated with αHER2-Lipo/DOX, αDNS-Lipo/DOX, or Lipo/DOX at 37° C. for 3 h were measured in accordance with the same procedures. Results were expressed as percent inhibition of luminescence as compared with untreated cells by the following formula: % inhibition=100×(treated luminescence/untreated luminescence). The standard deviation for each data point was averaged over three samples (n=3).

In Vivo Optical Imaging of BsAb-Lipo/IR780 and Lipo/IR780

BALB/c nude mice bearing SW480 (EGFR$^+$) and SW620 (EGFR$^-$) tumor (approximately 100 mm$^3$) in their hind leg regions, were intravenously injected with αEGFR-Lipo/IR780, αDNS-Lipo/IR780, and Lipo/IR780 (100 μg per mouse), respectively. Pentobarbital anesthetized mice were sequentially imaged with an IVIS spectrum optical imaging system (excitation, 745 nm; emission, 840 nm; Perkin-Elmer, Inc., Waltham, Mass.) at 24, 48 and 72 h after injection.

Treatment of EGFR$^+$ and EGFR$^-$ Tumors with BsAb-Lipo/DOX and Lipo/DOX

BALB/c nude mice (n=6) were inoculated s.c. with 4×10$^6$ SW480 (EGFR$^+$) cells and 1×10$^6$ SW620 (EGFR$^-$) cells in their hind leg regions. After tumor sizes reached to about 20 mm$^3$, Lipo/DOX, αDNS-Lipo/DOX and αEGFR-Lipo/DOX were i.v. administered at 5 mg DOX/kg once weekly for 3 weeks, for a total dose of 15 mg DOX/kg. Other treatment groups included saline. Tumor measurements were performed 3 times a week using a caliper, and tumor sizes were calculated using the equation: (length×width×high)/2. Mice were weighted once a week to examine the toxicity.

Statistic Analysis.

Statistical significance of differences between mean values was estimated with JMP 9.0 software (SAS Institute, Inc., Cary, N.C.) using the nonparametric Mann-Whitney test. P-values in the cytotoxicity assay and in vivo toxicity<0.05 and the P-values in the in vivo treatment<0.01 were considered to be statistically significant.

Example 1 Production and Characterization of Dimeric Humanized Bi-Specific Antibodies (BsAbs)

1.1 Production of Murine Anti-mPEG or Anti-PEG Abs

In order to produce humanized BsAbs, three hybridoma cells, E11, 15-2b and 6-3, were identified, and their respective monoclonal Abs were collected by affinity chromatography. The binding specificity of the collected antibodies toward immobilized PEG was then determined. An exemplary binding specificity between monoclonal antibody produced by hybridoma 15-2b and PEG is illustrated in FIG. 4.

Figure 4:
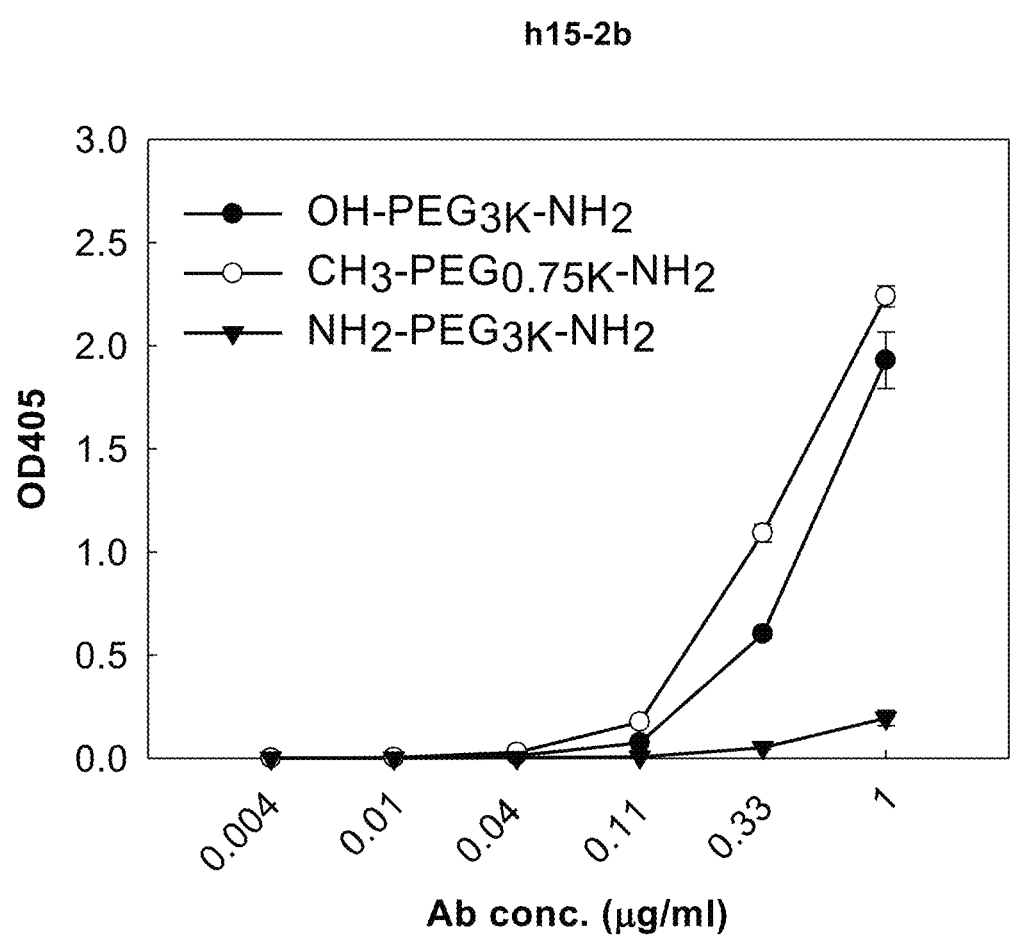
FIG. 4 depicts the binding of anti-mPEG antibody secreted by hybridoma 15-2b to immobilized PEG molecules in accordance with one example of the present disclosure.

As evident from FIG. 4, monoclonal antibody produced by hybridoma 15-2b bound with CH$_3$-PEG$_{750}$-NH2, instead of NH$_2$-PEG$_{3000}$-NH2; which indicates that such monoclonal antibody specifically recognized the terminal methoxy group of the CH$_3$-PEG molecules or the terminal hydroxyl group of PEG molecules (FIG. 4), and is thus termed anti-mPEG Ab; whereas the antibody produced by hybridoma 6-3 or E11 specifically recognized the backbone portion and not the terminal methoxy or hydroxyl group or the PEG molecules, and is thus termed anti-PEG Ab.

DNA encoding the anti-mPEG or anti-PEG Abs was then isolated and sequenced using conventional procedures (i.e., by using oligonucleotide probes that are capable of binding specifically to genes encoding the heavy and light chains of the monoclonal Abs).

1.2 Production of Dimeric Humanized Anti-PEG (hE11) Anti-TAG72 BsAb

To produce humanized Abs with bispecificity, the DNA sequence of murine anti-mPEG mAb of example 1.1 was humanized and fused with a humanized single-chain antibody fragment gene against tumor-associated glycoprotein 72 (TAG-72) antigen (hcc49 scFv) or a dansyl (DNS) hapten in accordance with procedures described in the Materials and Methods section.

Figure 5A:
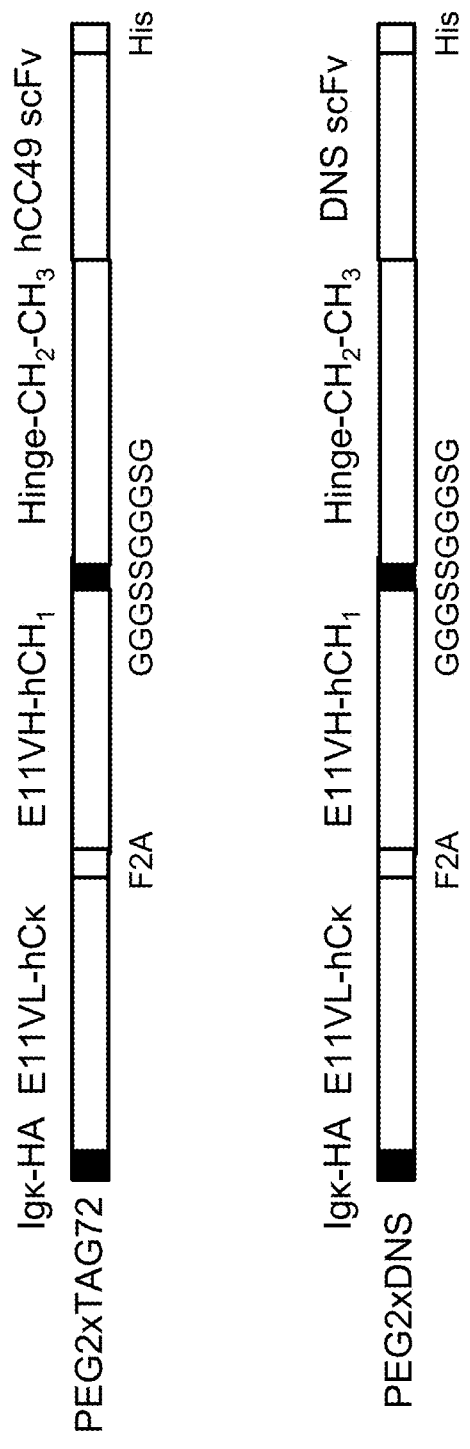
FIG. 5A is a schematic illustration of DNA constructs for humanized anti-PEG (hE11) BsAbs of example 1.2 in accordance with one embodiment of the present disclosure.
Figure 5B:
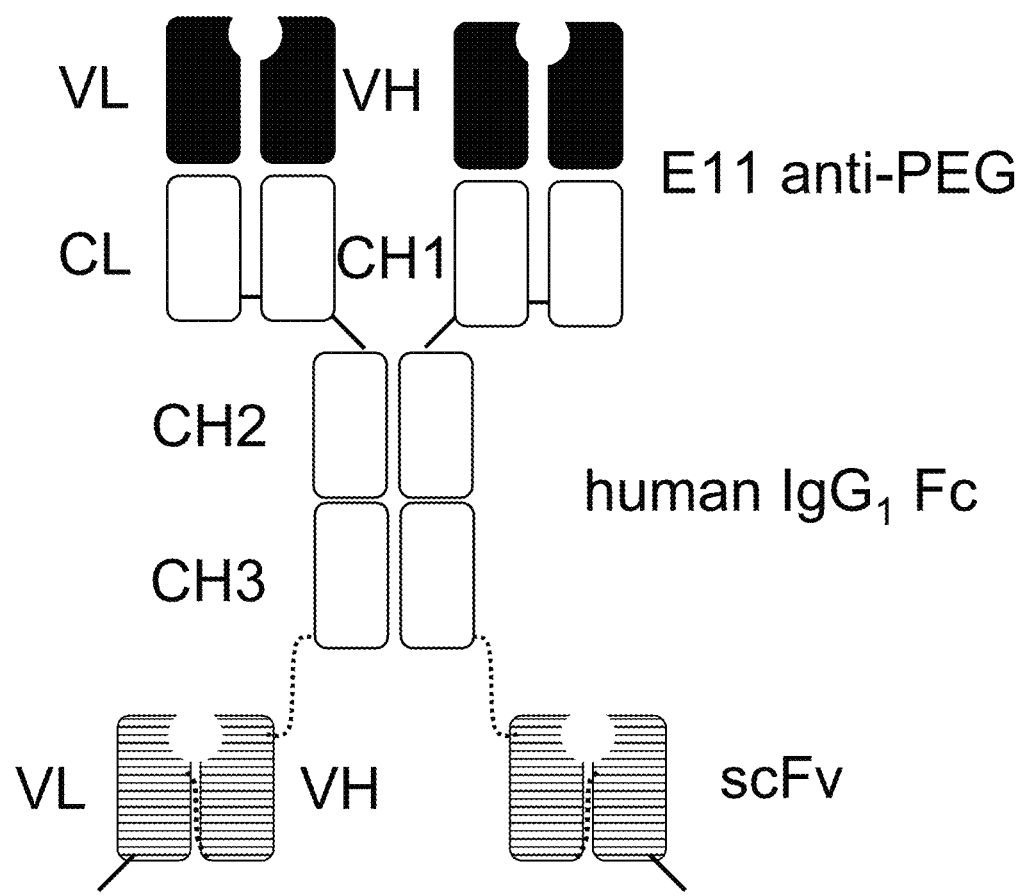
FIG. 5B is a schematic drawing of the structure of the humanized anti-PEG (hE11) BsAbs of example 1.2.
Figure 5C:
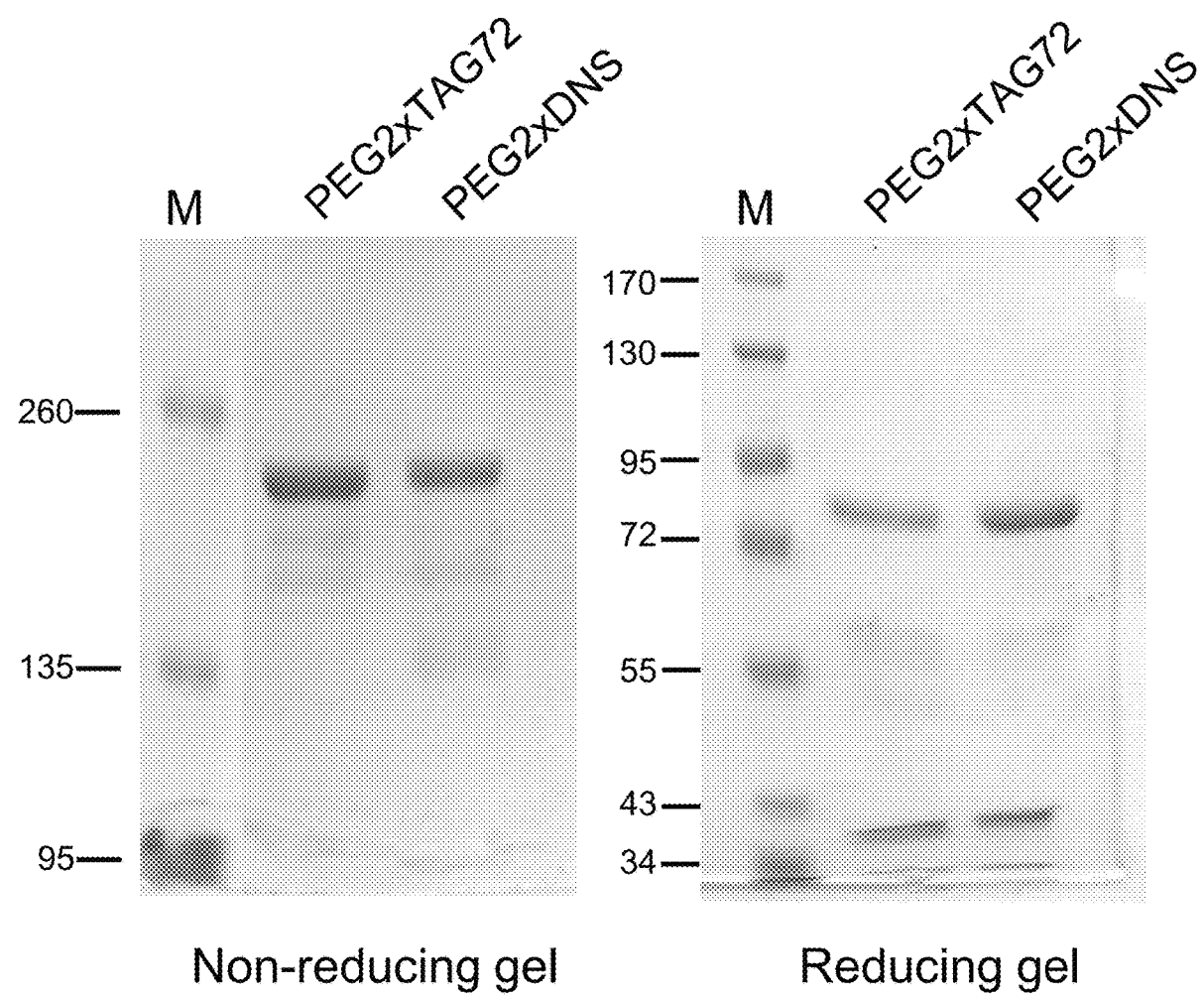
FIG. 5C illustrates the SDS-PAGE analysis of the humanized anti-PEG (hE11) BsAbs of example 1.2 in reducing or non-reducing conditions in accordance with one embodiment of the present disclosure.
Figure 5D:
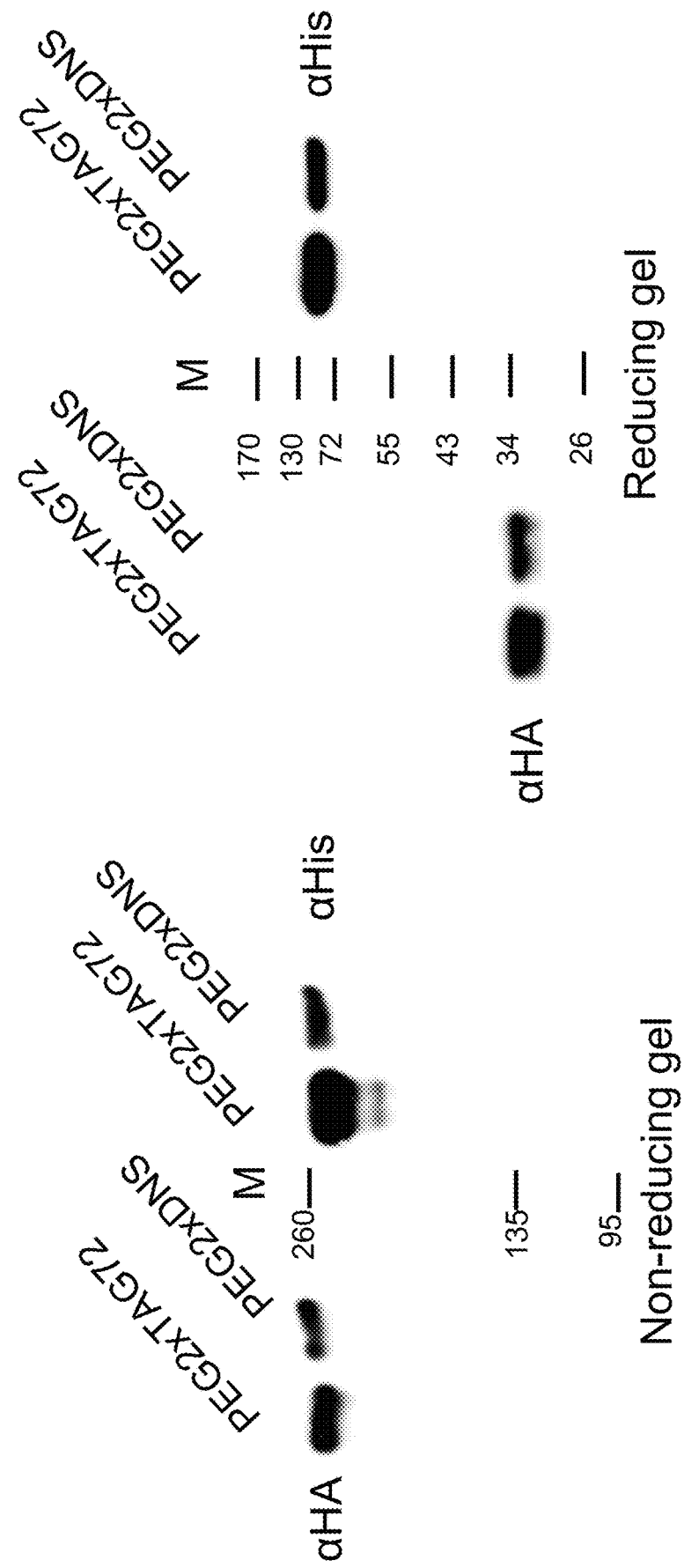
FIG. 5D illustrates the western blot analysis of the humanized anti-PEG (hE11) BsAbs of example 1.2 in accordance with one embodiment of the present disclosure.

FIG. 5A is a schematic illustration of the DNA constructs of the humanized bi-specific Abs prepared in this example. In general, each construct encoded in sequence, HA epitope tag (HA), the hE11 anti-PEG light chain, a F2A bicistronic element, the hE11 anti-PEG heavy chain, a hinge-CH$_2$—CH$_3$ domain, a linker peptide (L), an anti-tumor scFv sequence (e.g., hcc49 scFv for PEG2×TAG72 plasmid, and anti-dansyl scFv for the control PEG2×DNS plasmid), and a histidine tag. FIG. 5B is a schematic illustration of the dimeric humanized anti-PEG BsAb of this example. Accordingly, BsAbs including PEG2×TAG72 and PEG2×DNS were produced. SDS-PAGE analysis indicated that BsAbs were composed by a VH-CH1-H-CH2-CH3-scFv fragment (72 kDa) and light chain (35 kDa) under reducing condition (FIG. 5C, right panel); by contrast, a 230 kDa disulfide-linked BsAbs was observed under non-reducing condition (FIG. 5C, left panel). The result was further confirmed by a western blot analysis, in which the HA epitope tag on the N-terminus of the hE11 anti-PEG light chain and the His epitope tag present on the C-terminus of the scFv attached to the hE11 anti-PEG heavy chain were detected, demonstrating that the bispecific antibody was present in the expected conformation (FIG. 5D).

1.3 Characterizing the Function of BsAbs of Example 1.2

Bi-functional activity of the humanized hE11 BsAbs of example 1.2 was examined in this example.

Figure 6A:
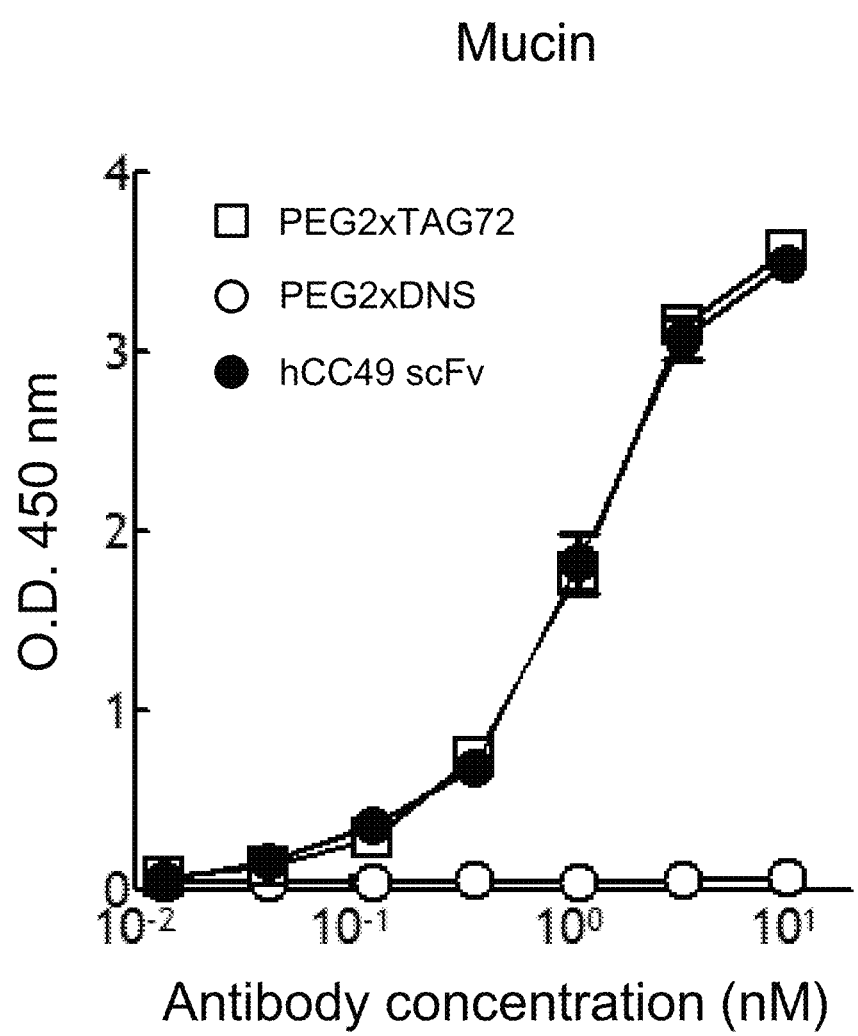
FIGS. 6A to 6C respectively illustrate the antigen-binding activity of the humanized anti-PEG (hE11) BsAbs of example 1.2 towards (A) mucin, (B) BSA-PEG$_{5,000}$ or (C) BSA in accordance with one embodiment of the present disclosure.
Figure 6B:
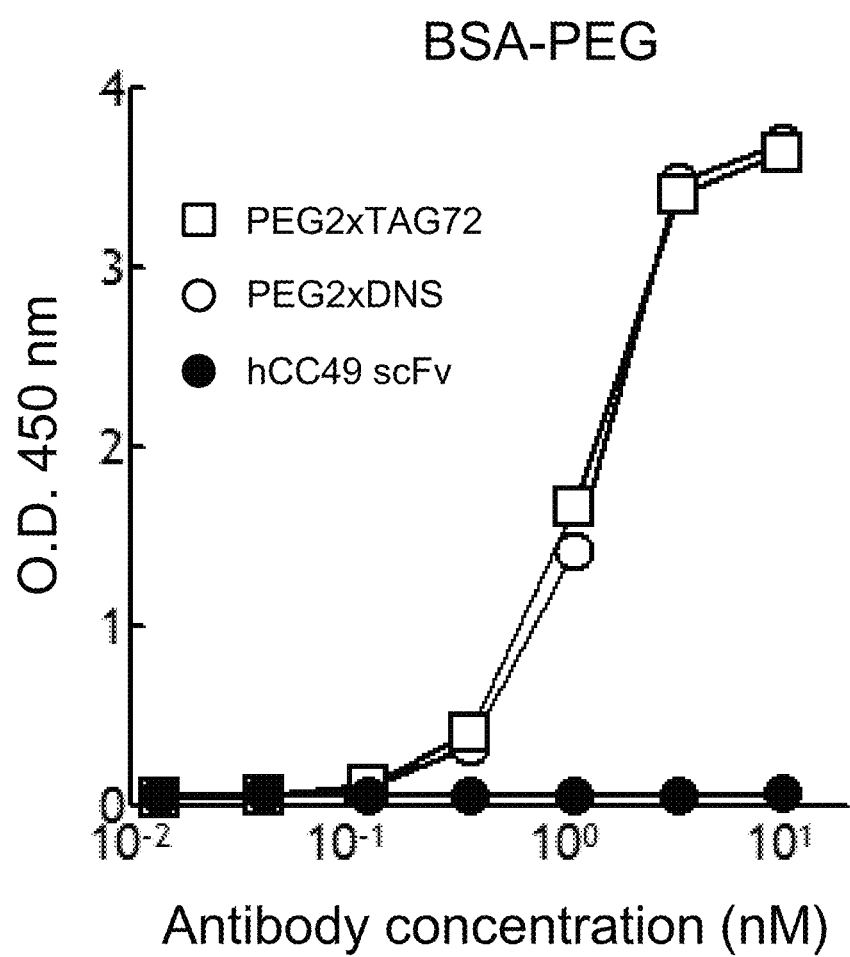
Figure 6C:
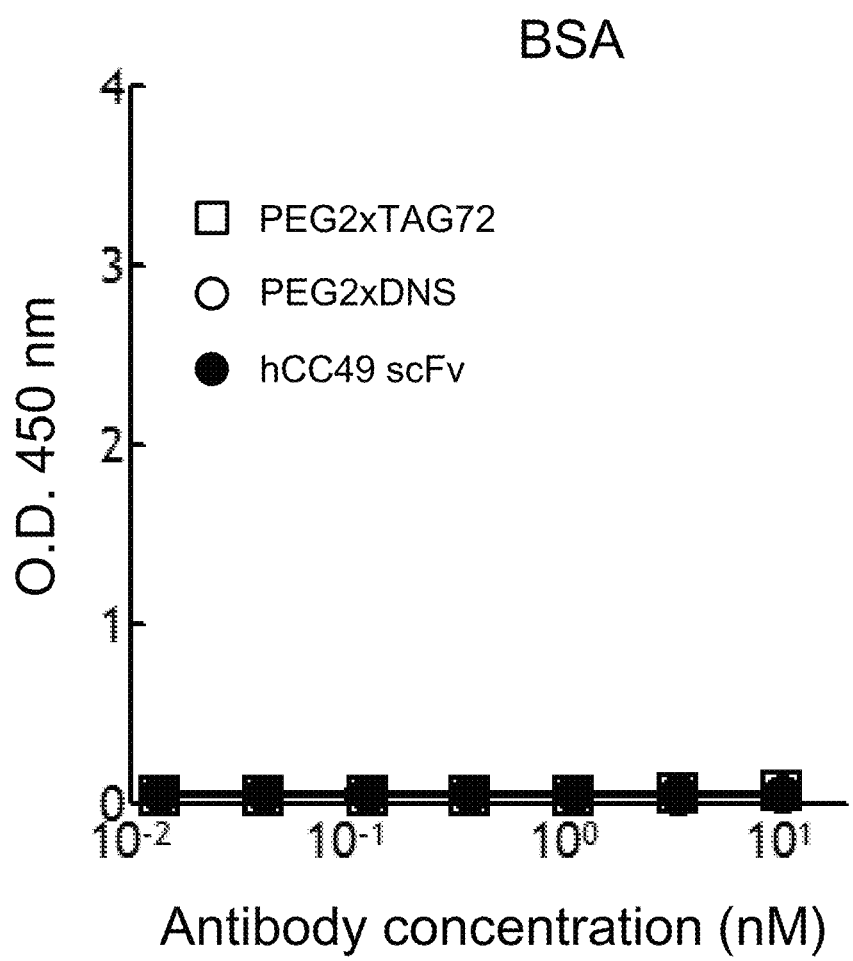

Binding of the BsAbs was detected by ELISA. Microtiter plates were first coated with antigens and then PEG2×TAG72, PEG2×DNS BsAbs or hCC49 (anti-TAG72) single chain antibody was added. After the plates were extensively washed to remove unbound antibodies, the remaining bound antibodies in each well were detected with HRP-conjugated secondary antibody. The PEG2×TAG72 BsAb was able to bind to both mucin (TAG-72 tumor antigen) (FIG. 6A) as well as BSA-PEG (FIG. 6B) but not to BSA (FIG. 6C), demonstrating that PEG2×TAG72 displayed dual antigen specificity to both PEG and mucin. By contrast, the control PEG2×DNS BsAb bound to BSA-PEG but not to mucin. Likewise, the hcc49 scFv bound to mucin but not to BSA-PEG. In sum, PEG2×TAG72 anti-PEG (hE11) BsAb of example 1.2 can bind both PEG and tumor antigens.

To determine if the hE11 BsAbs of example 1.2 could bind target cells, MCF-7 breast cancer, Jurkat T cells and OVCAR-3 ovarian cancer cells, which express the TAG-72 antigen recognized by the hCC49 antibody, were incubated with PEG2×TAG72 and PEG2×DNS BsAbs. A-375 malignant melanoma cells, which do not express the TAG-72 antigen, were used as a negative control cell line. After washing unbound BsAbs from the cells, the BsAbs that remained bound to cells were detected with FITC-conjugated anti-human immunoglobulin antibody. Detection of surface immunofluorescence in a flow cytometer demonstrated that TAG-72 positive cells bound PEG2×TAG72 BsAb but not the control PEG2×DNS BsAb (FIG. 7, left panels). To test if PEG2×TAG72 could simultaneously bind to cancer cells and PEGylated molecules, the cells were first incubated with BsAbs, washed and then incubated with FITC-labeled PEG molecules. TAG-72 positive cells incubated with PEG2×TAG72 BsAb but not the control PEG2×DNS BsAb could bind PEG-FITC, demonstrating that PEG2×TAG72 acted as a true BsAb which could simultaneously bind tumor antigens and PEG molecules (FIG. 7, right panels).

1.4 Production and Characterization of Dimeric Humanized Anti-PEG (hE11) Anti-EGFR or Anti-HER BsAbs To assess whether other cellular targets could be targeted by anti-PEG BsAbs, single-chain antibody fragment genes against epidermal growth factor receptor (EGFR) and the HER2 antigen was fused to the C-terminus of the heavy chain $C_H3$ region gene of the humanized E11 antibody to generate PEG2×EGFR and PEG2×HER2, respectively in accordance with similar procedures of example 1.2.

Figure 8A:
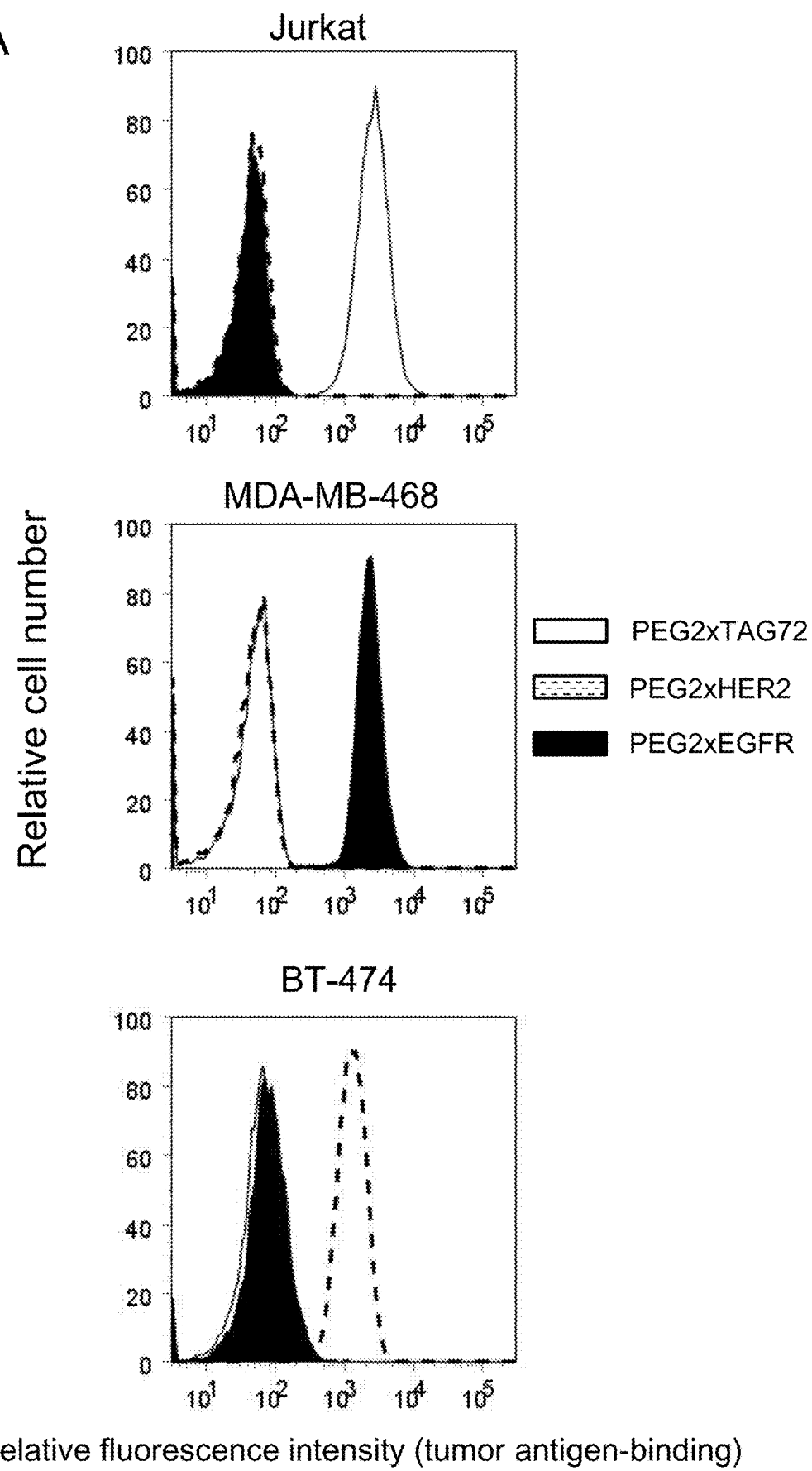
FIG. 8A illustrates the cancer cell selectivity of the dimeric humanized anti-PEG (hE11) BsAbs of example 1.4 in Jurkat (TAG-72+), MDA-MB-468 (EGFR+) or BT-474 (HER2+) cells in accordance with one embodiment of the present disclosure.

Assessment of the ability of these BsAbs to bind cancer cells indicated that PEG2×TAG72 bound with Jurkat T cells (Tag-72 positive) but not MDA-MB-468 cells or BT-474 cells. By contrast, PEG2×EGFR BsAb bound to MDA-MB-468 cells (EGFR positive) but not the other two cells, whereas PEG2×HER2 BsAbs bound specifically with BT-474 cells (HER2 positive) (FIG. 8A). Thus, these BsAbs bound to respective target cells in an antigen-dependent manner.

Figure 8B:
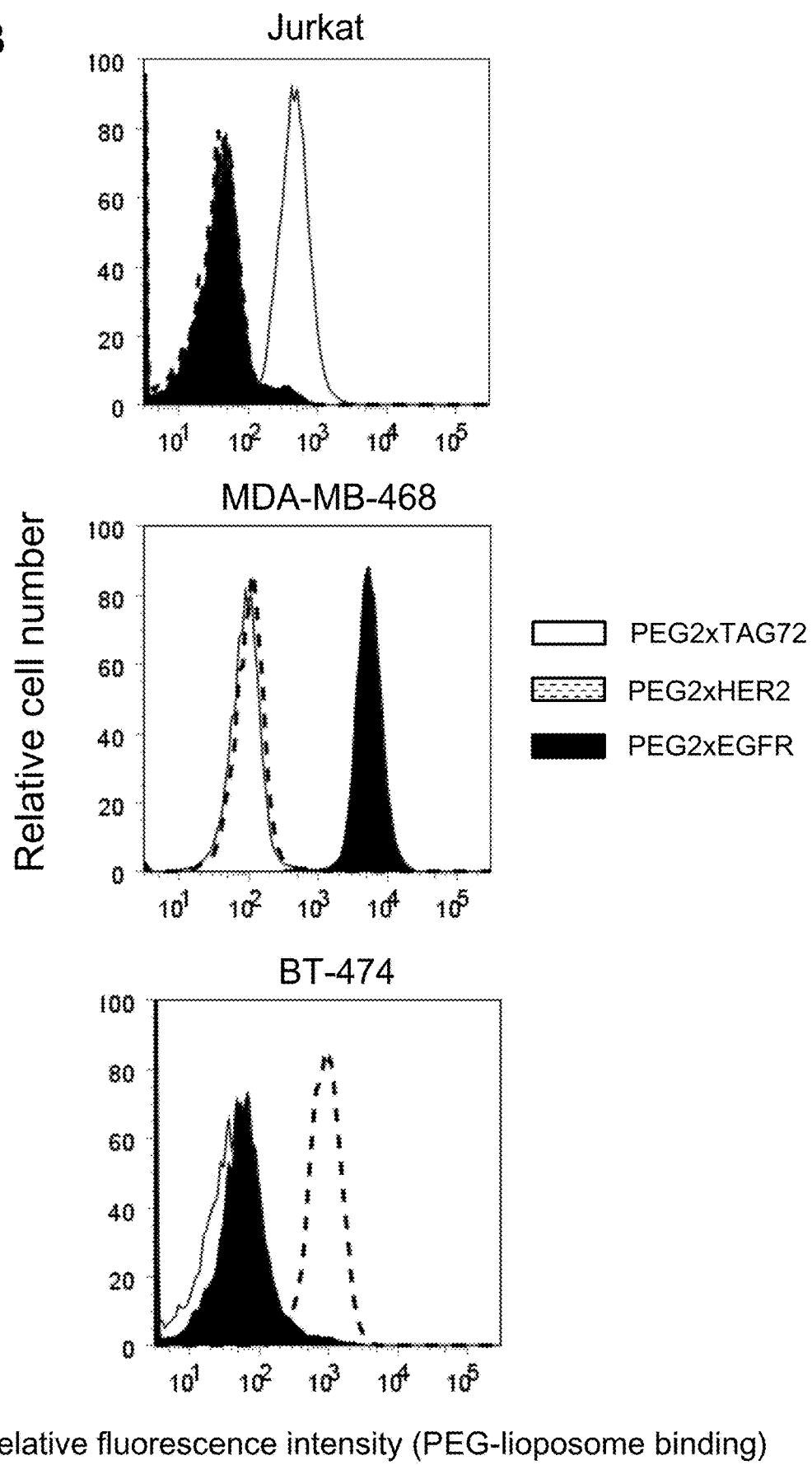
FIG. 8B illustrates the binding activities of the dimeric humanized anti-PEG (hE11) BsAbs of example 1.4 with the PEGylated liposomal Texas Red in Jurkat (TAG-72+), MDA-MB-468 (EGFR+) or BT-474 (HER2+) cells in accordance with one embodiment of the present disclosure.
Figure 8C:
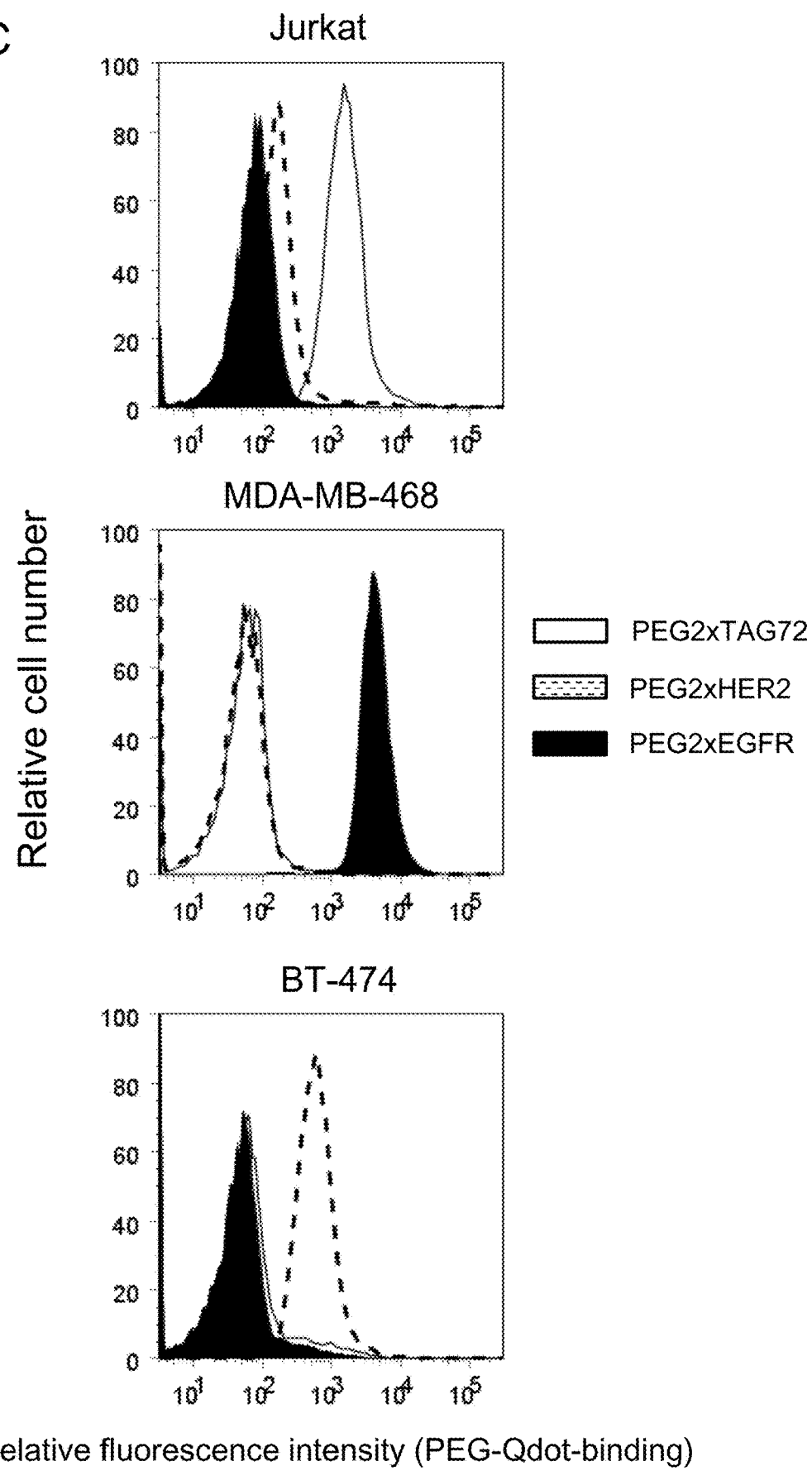
FIG. 8C illustrates the binding activities of the dimeric humanized anti-PEG (hE11) BsAbs of example 1.4 with the PEGylated Quantum Dot (Qdot655) in Jurkat (TAG-72+), MDA-MB-468 (EGFR+) or BT-474 (HER2+) cells in accordance with one embodiment of the present disclosure.

The ability of the bispecific antibodies to simultaneously bind cancer cells and PEGylated compounds was further investigated by first incubating cells with BsAbs, washing unbound antibody from the cells and then adding PEG-liposomal Texas Red or PEG-Qdot655 (PEGylated quantum dots). Each BsAb selectively accumulated PEGylated liposomes (FIG. 8B) or PEGylated nanoparticles (FIG. 8C) at cells that expressed the corresponding target antigen on their surface.

In sum, the anti-PEG BsAbs of this example can simultaneously bind to target antigens and PEGylated substances to selectively accumulate PEGylated compounds and nanoparticles on their respective target cells.

Example 2 Production and Characterization of Monovalent Humanized BsAbs 2.1 Production and Characterization of Monovalent Anti-PEG (E11) BsAbs Monovalent anti-PEG BsAbs were generated by fusing the Fab fragment of a humanized antibody derived from the anti-PEG antibody E11 to single chain antibodies with specificity for tumor-associated antigens.

Figure 9:
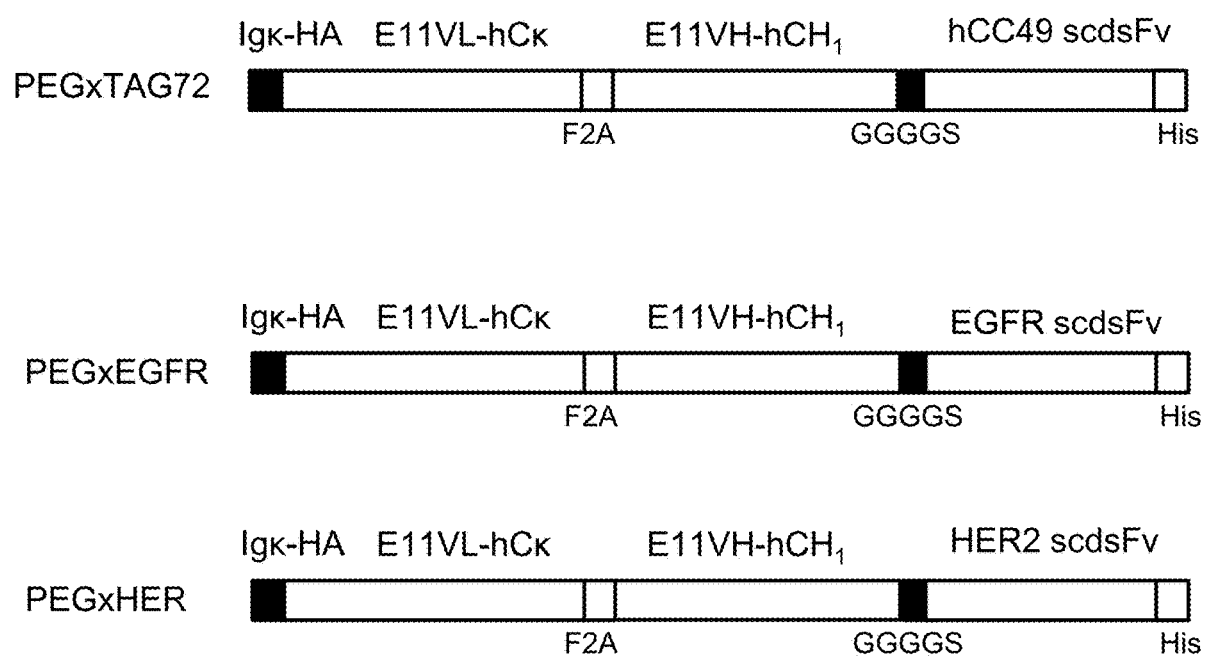
FIG. 9 is a schematic illustration of DNA constructs for humanized monovalent anti-PEG (hE11) BsAbs of example 2.1 and the structure of the monovalent BsAb in accordance with one embodiment of the present disclosure.

Specifically, the hE11 Fab fragment was fused a single-chain antibody fragment (scFv) derived from anti-TAG72, anti-EGFR (epidermal growth factor receptor) or anti-HER2/Neu antibodies (FIG. 9). CHO cells that stably expressed the monovalent BsAbs were generated and culture medium from each expression cell line was collected.

Figure 10:
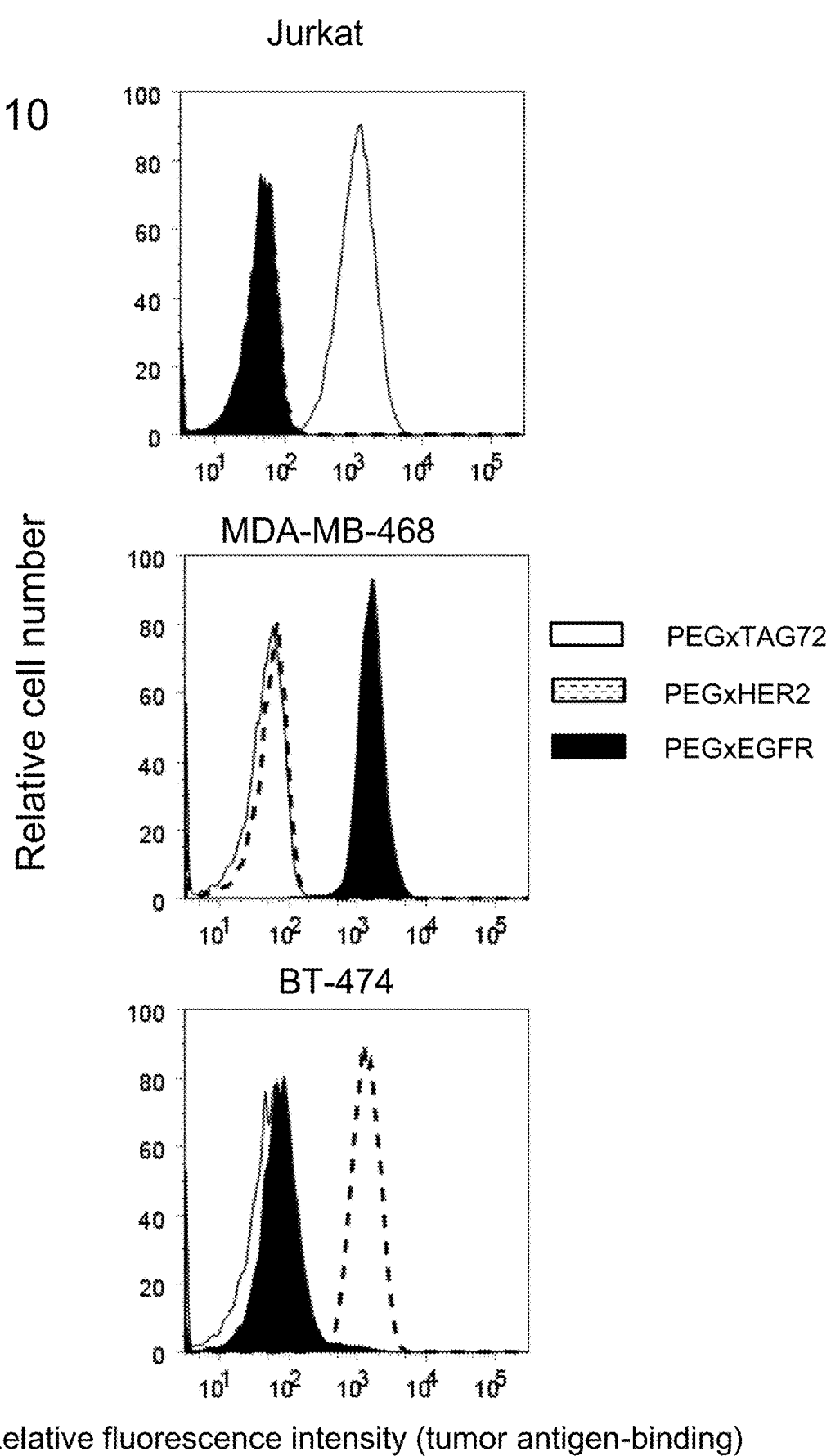
FIG. 10 illustrates the cancer cell selectivity of the humanized monovalent anti-PEG (hE11) BsAbs of example 2.1 in Jurkat (TAG-72+), MDA-MB-468 (EGFR+) or BT-474 (HER2+) cells in accordance with one embodiment of the present disclosure.

The binding specificity of monovalent BsAbs with their target proteins was measured by collecting the culture medium of BsAbs producing cells, adding the collected medium to cells that expressed the target protein, then determining the binding by ELSA. After washing the cells, the bound BsAbs were detected by FITC-labeled goat anti-human immunoglobulin second antibody. It was found that PEG×TAG72 bound to Jurkat T cells (Tag-72 positive), but not MDA-MB-468 cells or BT-474 cells. By contrast, PEG×EGFR BsAb bound to MDA-MB-468 cells (EGFR positive) but not the other two cells; whereas PEG×HER2 BsAb was found to bind with BT-474 cells (HER2 positive) specifically (FIG. 10). Thus, monovalent anti-PEG (hE11) BsAbs bound to target cells in an antigen-dependent and selective manner.

Figure 11:
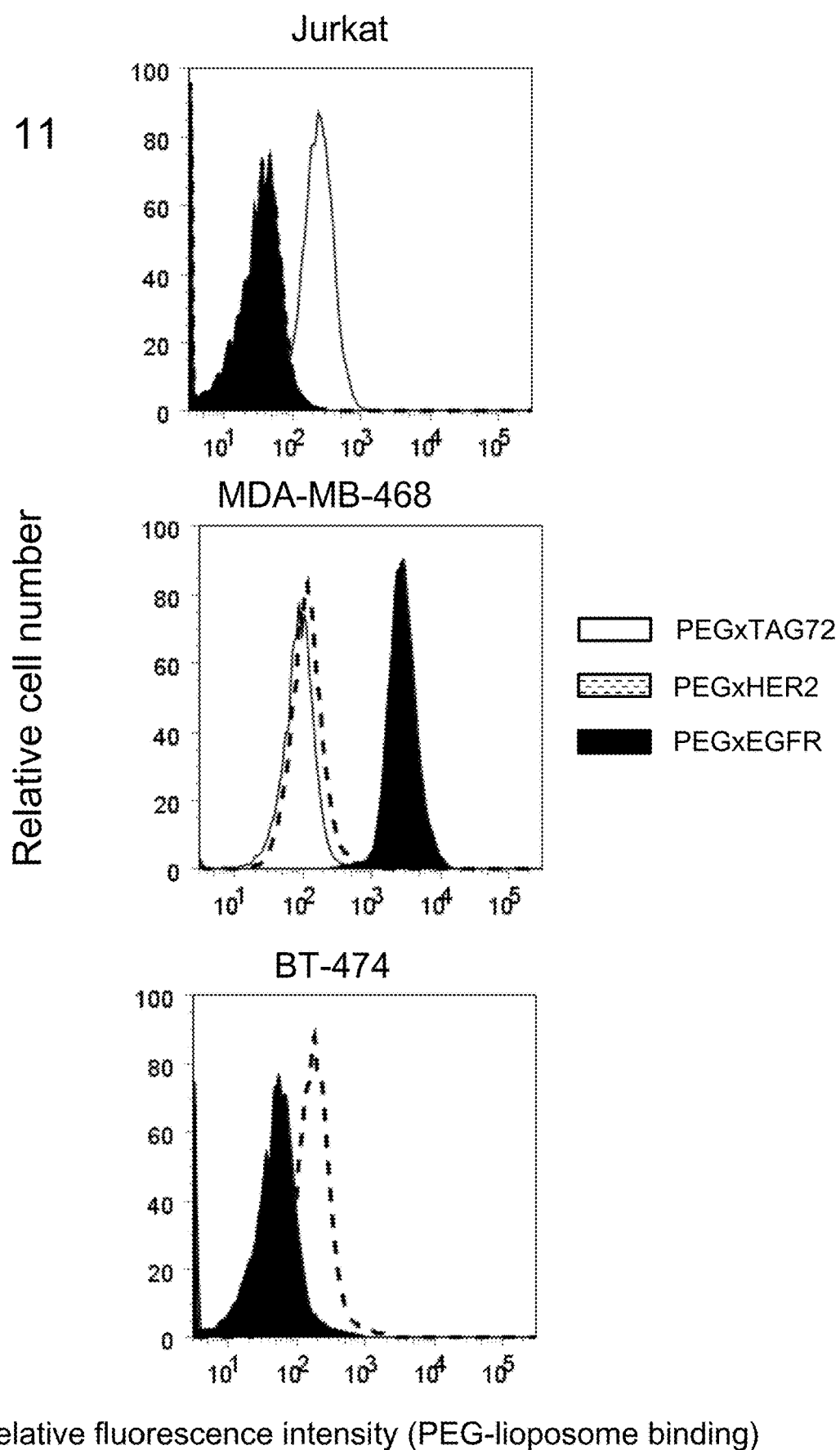
FIG. 11 illustrates the binding activities of the humanized monovalent anti-PEG (hE11) BsAbs of example 2.1 with the PEGylated liposomal Texas Red in Jurkat (TAG-72+), MDA-MB-468 (EGFR+) or BT-474 (HER2+) cells in accordance with one embodiment of the present disclosure.

The ability of the monovalent BsAb to simultaneously bind with cancer cells and PEGylated compounds was examined by incubating target cells with BsAbs and PEGylated substances. After washing out the unbound antibody from the cells, PEG-liposomal Texas Red or PEG-Qdot655 (PEGylated quantum dots) were then added. Each BsAb selectively accumulated PEGylated liposomes (FIG. 11) or PEGylated nanoparticles (FIG. 12) at cells that expressed the corresponding target antigen on their surface. Thus, monovalent anti-PEG (hE11) BsAbs can simultaneously bind to target antigens and PEGylated substances to selectively accumulate PEGylated compounds and nanoparticles on the surface of the target cells.

2.2 Production and Characterization of Monovalent Anti-PEG (h6.3) BsAbs

Figure 13B:
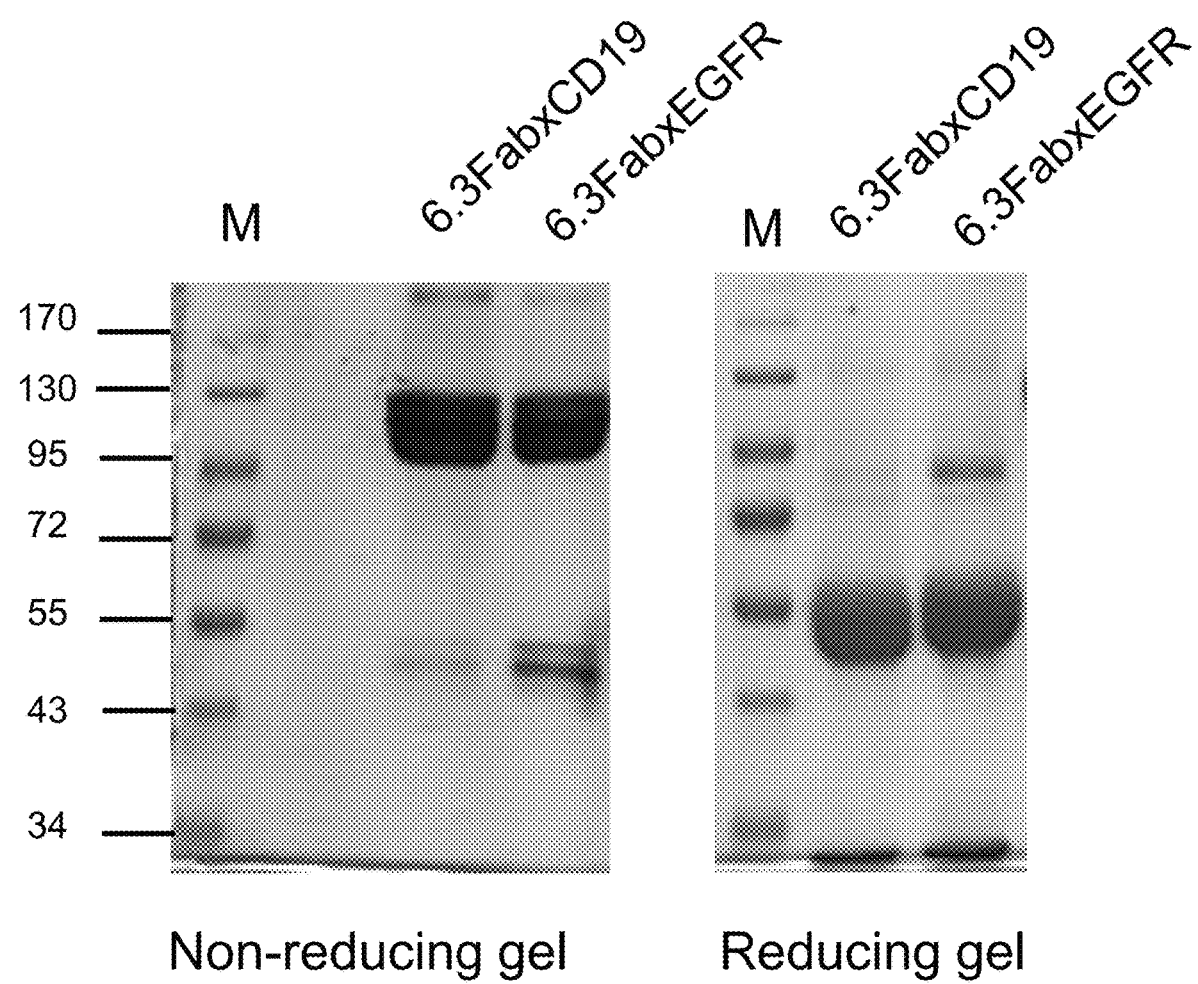
FIG. 13B illustrates the SDS-PAGE analysis of the humanized monovalent anti-PEG (h6.3) BsAbs of example 2.2 in reducing or non-reducing conditions in accordance with one embodiment of the present disclosure.

The humanized anti-PEG (h6.3) Fab was constructed as a single open reading frame by fusing $V_L$-Cκ and $V_H$-CH1 with a F2A (furin-2A) peptide linker, allowing the expression of light chain and heavy chain separately in accordance with procedures described in the "Materials and Methods" section. The single chain disulfide-stabilized variable fragments (dsFv) were linked to the C-termius of the CH1 domain in the 6.3Fab via a peptide linker to generate h6.3-11F8 (h6.3Fab×EGFR) and h6.3-hBU12 (h6.3Fab× CD19) BsAbs (FIG. 13A). These two BsAbs were then inserted into a lentiviral expression vector to generate stable 293FT producer cell lines. BsAbs (including h6.3Fab× EGFR and h6.3Fab×CD19) that were purified from the culture medium displayed the expected molecular sizes on a 10% SDS-PAGE (FIG. 13B).

Figure 14A:
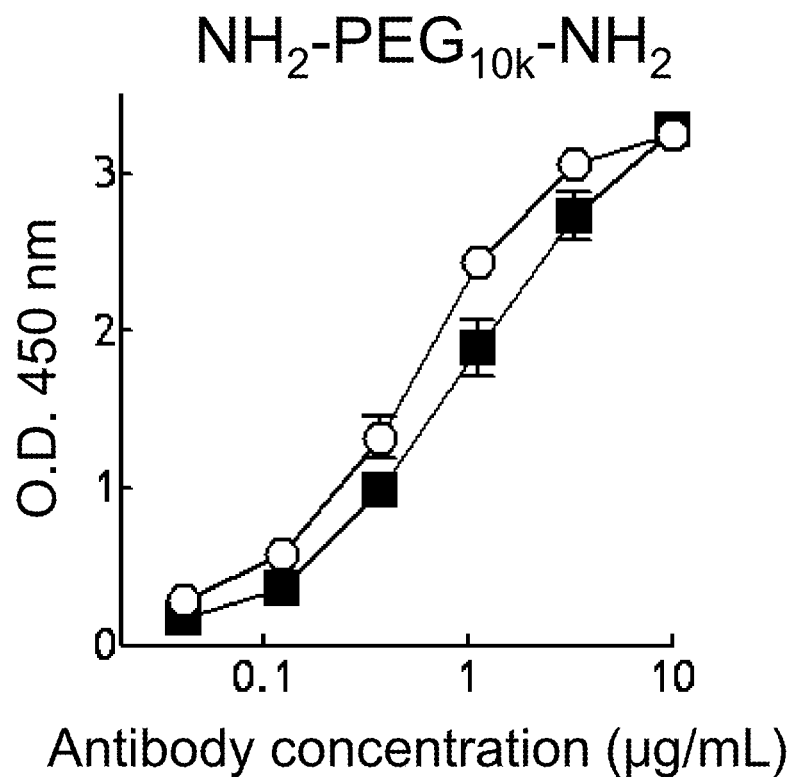
FIGS. 14A and 14B respectively illustrate the antigen-binding activity of the humanized monovalent anti-PEG (h6.3) BsAbs of example 2.2 towards (A) NH$_2$-PEG$_{10,000}$-NH$_2$ and (B) BSA in accordance with one embodiment of the present disclosure.
Figure 14B:
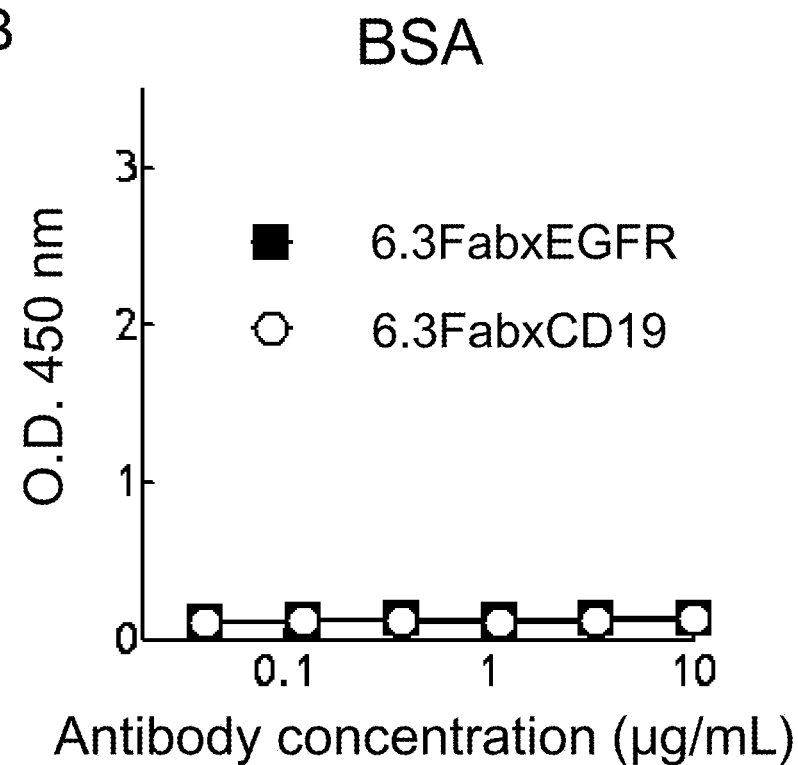
Figure 14C:
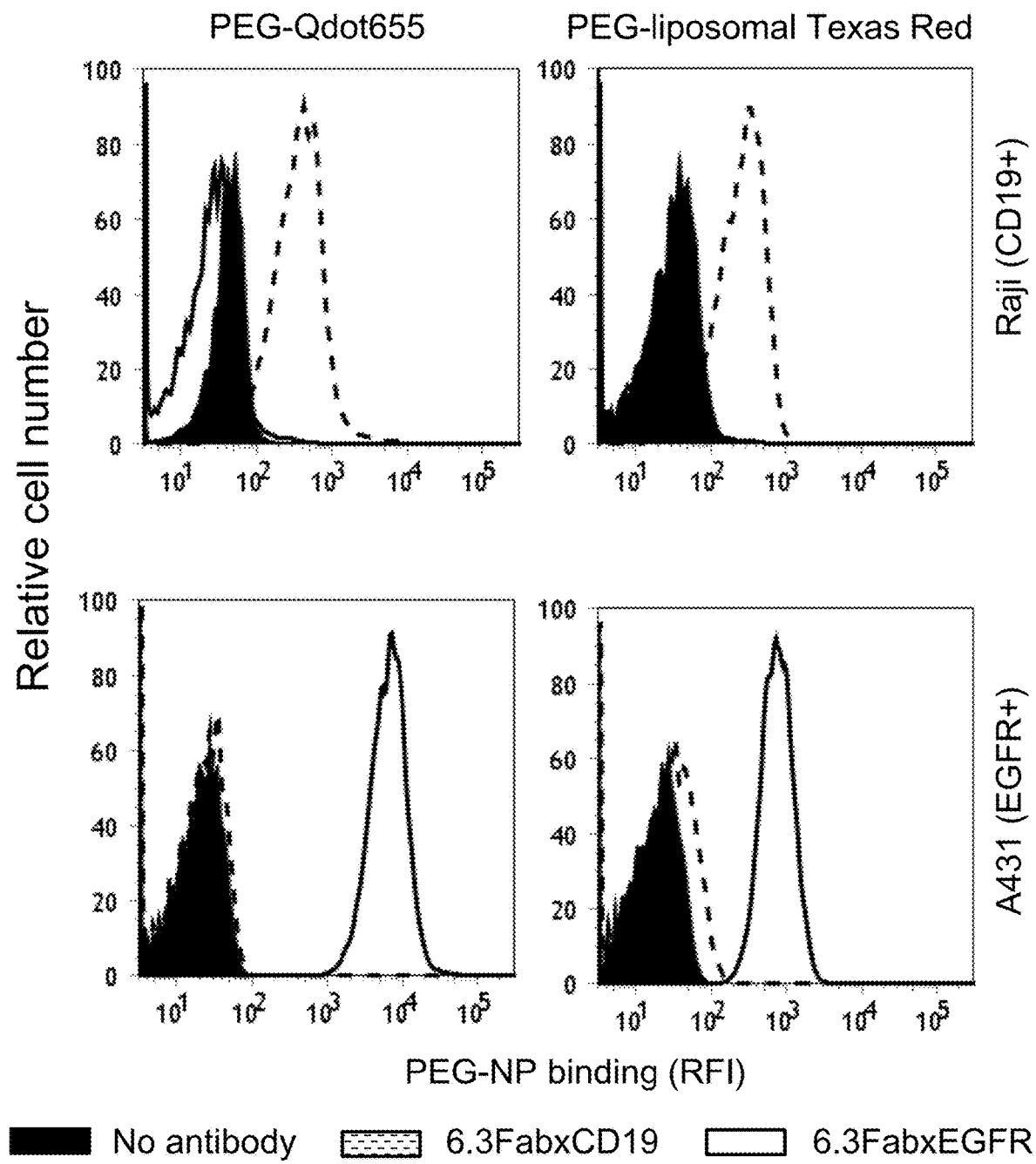
FIG. 14C illustrates the binding activities of the humanized monovalent anti-PEG (h6.3) BsAbs of example 2.2 with the PEGylated Quantum Dot (Qdot655) or PEGylated liposomal Texas Red in Raji (CD19+) or A431 (EGFR+) cells in accordance with one embodiment of the present disclosure.
Figure 14D:
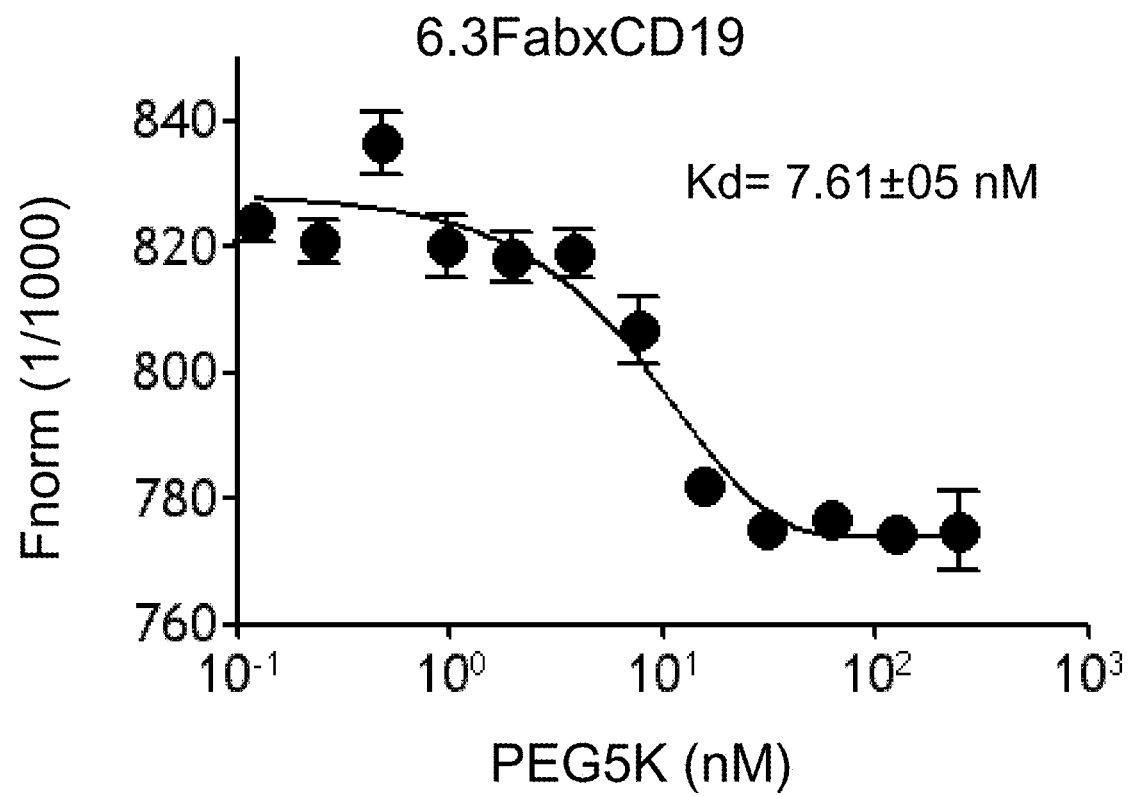
FIGS. 14D and 14E respectively illustrate the binding kinetics of the humanized monovalent anti-PEG (h6.3) and antiCD19 BsAbs of example 2.2 towards CH$_3$-PEG$_{5,000}$-Alexa647 in accordance with one embodiment of the present disclosure.
Figure 14E:
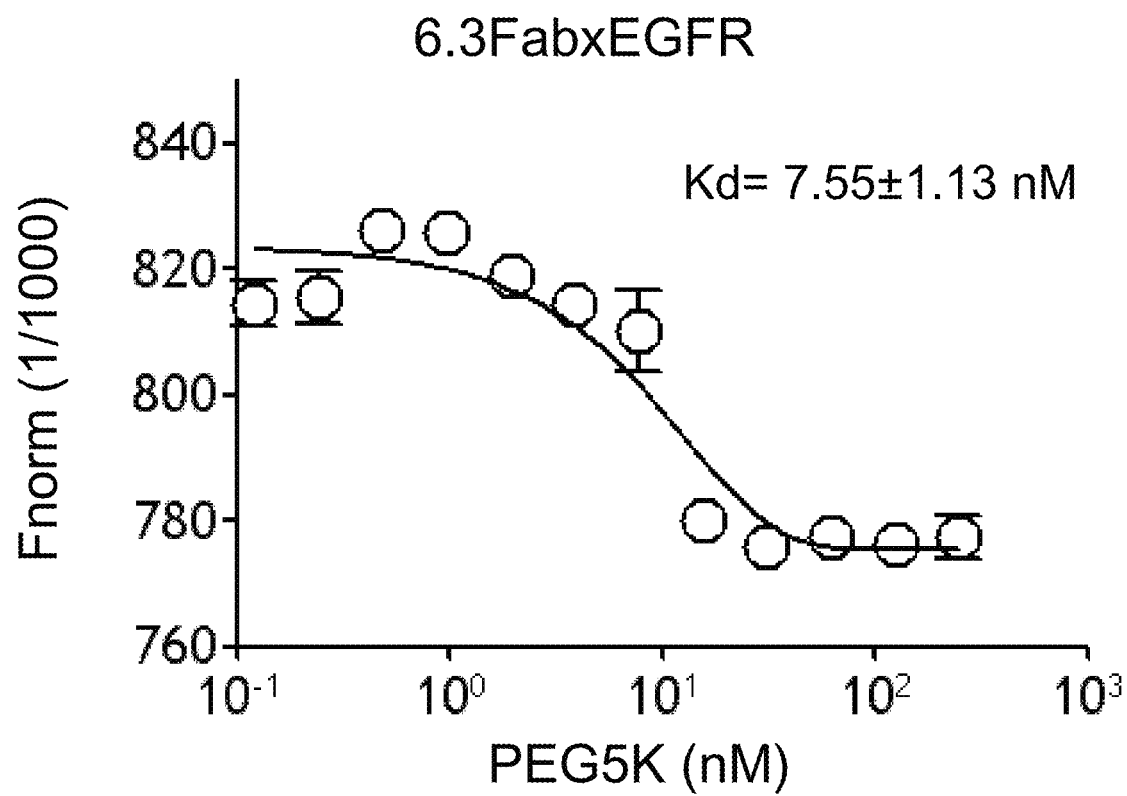

Further, both h6.3Fab×EGFR and h6.3Fab×CD19 BsAbs bound to the $NH_2$-$PEG_{10,000}$-NH2, but not to the control BSA protein, indicating their binding specificity toward PEG molecule (FIGS. 14A and 14B). As to their binding specificity toward the target antigen, flow cytometer analysis revealed that h6.3Fab×EGFR, but not h6.3Fab×CD19, was capable of directing the PEGylated substance (including PEG-liposome Texas Red and PEG-Qdot655) to A431 cells (EGFR+); whereas h6.3Fab×CD19, but not h6.3Fab×EGFR, was capable of directing PEGylated substance to Raji cells (CD19+) (FIG. 14C). The PEG-binding kinetics of h6.3Fab×EGFR and h6.3Fab×CD19 BsAbs were verified by Microscale Thermophoresis (MST) (FIGS. 14D and 14E).

Figure 15:
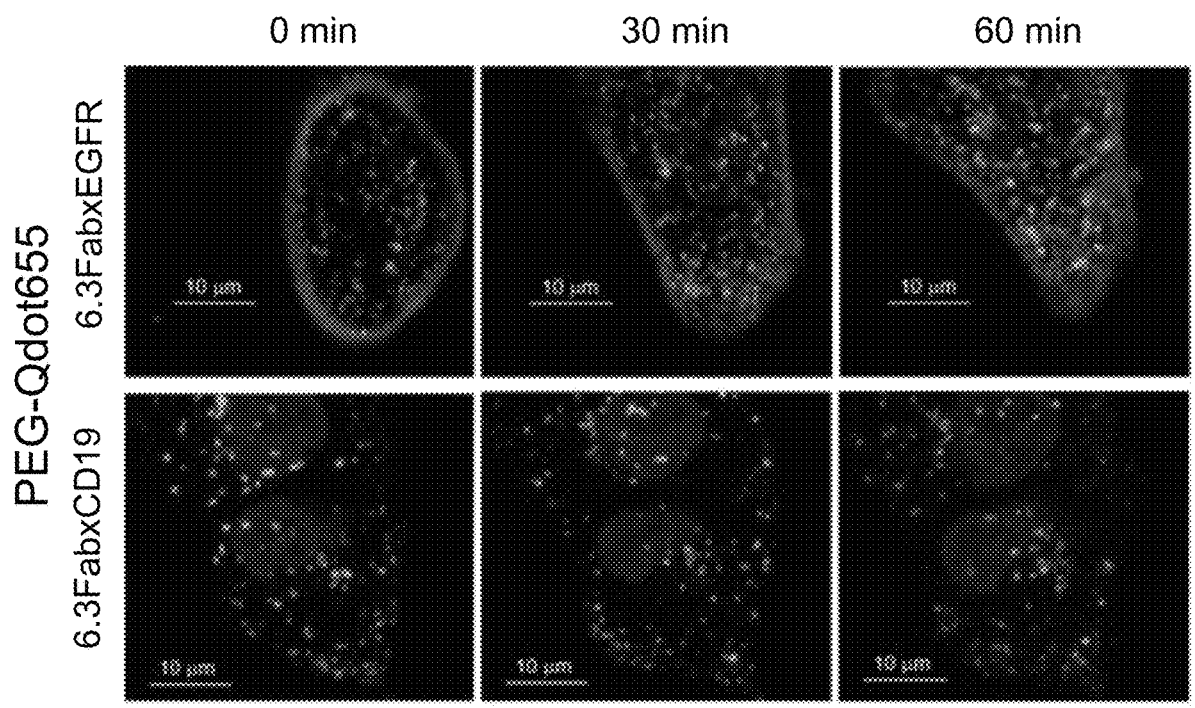
FIG. 15 is a panel of real-time images illustrating the endocytic activity of the humanized monovalent anti-PEG (h6.3) BsAbs of example 2.2 with the PEGylated Quantum Dot (Qdot655) in A431 (EGFR+) cells in accordance with one embodiment of the present disclosure.

To verify whether BsAb-targeted substance could be internalized by antigen-positive cancer cells, live cell imaging was performed by staining cells with lysosome tracker and BsAbs, followed by the addition and incubation of PEG-Qdot655. It was found that h6.3Fab×EGFR treated A431 cells displayed red fluorescence within endocytic vesicles, whereas h6.3Fab×CD19 treated A431 cells failed to produce PEG-Qdot655 signals (FIG. 15). This observation indicates that h6.3Fab×EGFR mediated EGFR endocytosis allows the uptake of PEG-substance into A431 cells.

Figure 16A:
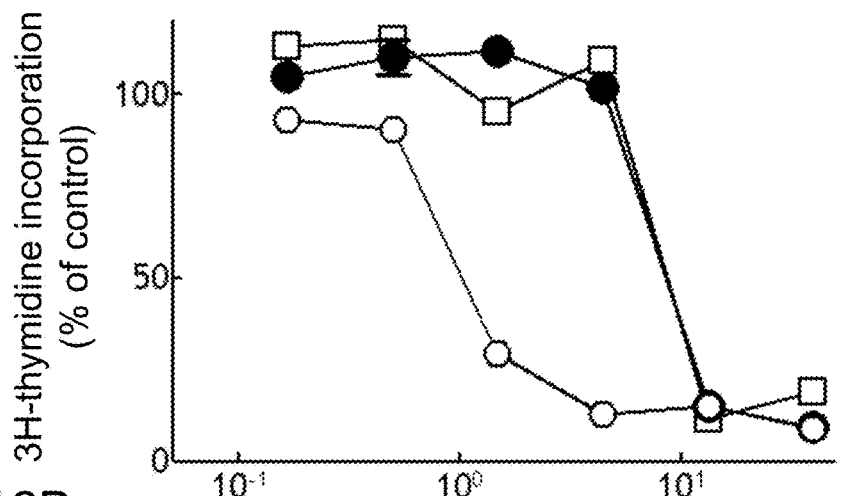
FIGS. 16A to 16C are line graphs respectively illustrate the enhanced in-vitro cytotoxicity of Lipo/DOX by the humanized monovalent anti-PEG (h6.3) BsAbs of example 2.2 in (A) A431 cells (EGFR$^+$), (B) MDA-MB-468 cells (EGFR$^+$) and (C) Raji cells (CD19+) in accordance with one embodiment of the present disclosure.
Figure 16B:
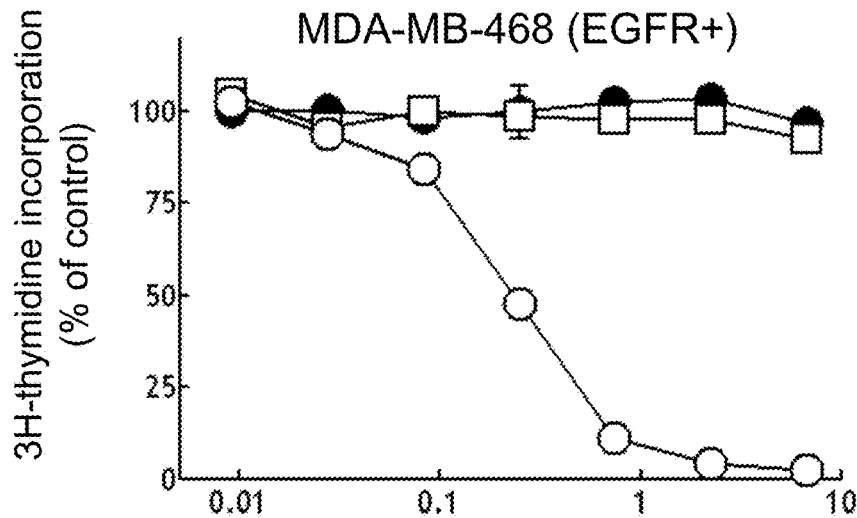
Figure 16C:
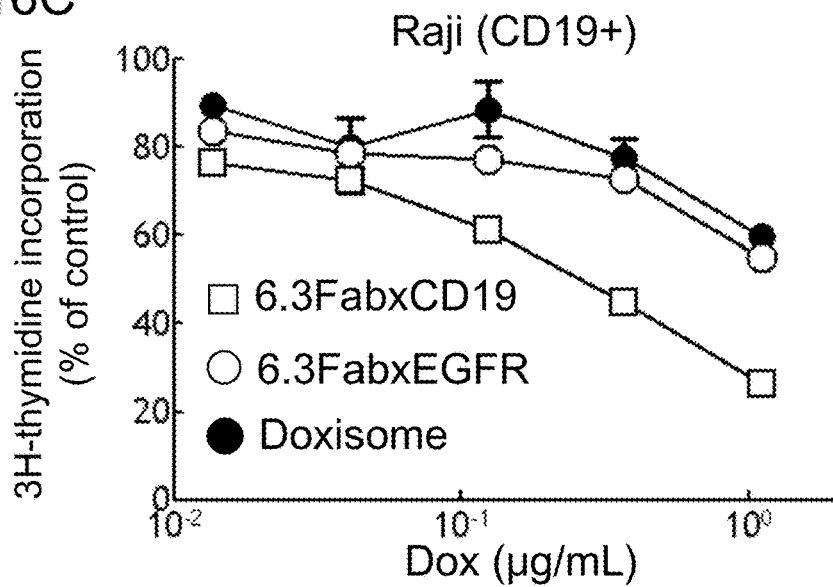

Next, the ability of whether h6.3Fab×CD19 and h6.3Fab× EGFR BsAbs could increase the cytotoxicity of the drug-loaded nanoparticles (NPs) to antigen-positive cancer cells was investigated. Raji (CD19$^+$) and A431 (EGFR$^+$) cells were incubated with h6.3Fab×CD19 and h6.3Fab×EGFR, followed by the addition of graded concentrations of Doxisome (i.e., PEGylated liposomal doxorubicin). When compared with Doxisome alone, both h6.3Fab×CD19 and h6.3Fab×EGFR enhanced cytotoxicity of Doxisome to Raji, MDA-MB-468 and A431 cells, respectively (FIGS. 16A to 16C). The results indicate that anti-PEG (h6.3) BsAbs may confer tumor selectivity and increase the cytotoxicity of a PEGylated NPs (e.g., doxisome) to antigen-positive cancer cells.

Figure 17:
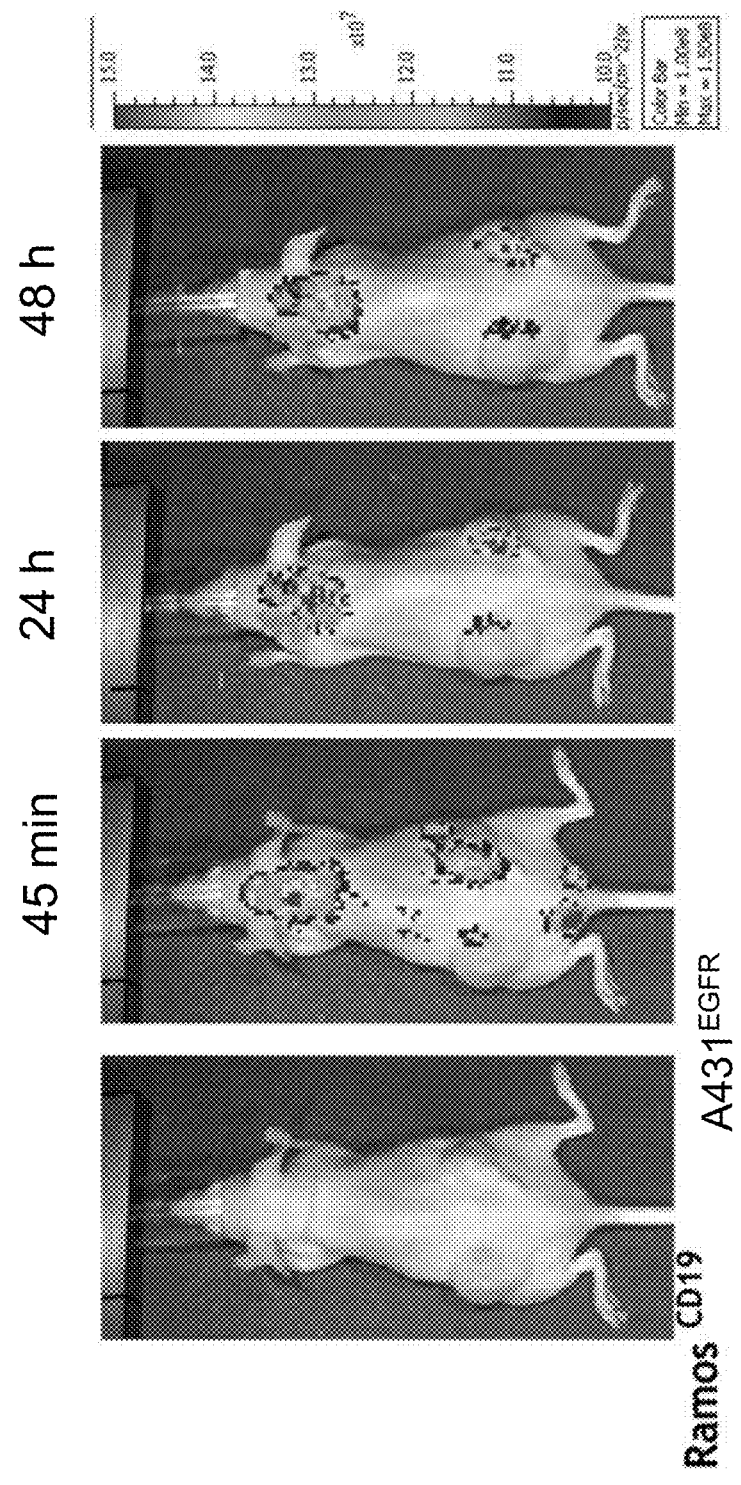
FIG. 17 illustrates the tumor imaging enhancement of the humanized monovalent anti-PEG (h6.3) BsAbs of example 2.2 targeted PEG-NIR797 against CD19 and EGFR tumor in accordance with one embodiment of the present disclosure.

To determine tumor targeting of anti-PEG (h6.3) BsAbs-NPs in vivo, BALB/c nude mice bearing Ramos (CD19, left side) and SW480 (EGFR, right side) tumors in their hind leg regions were intravenously injected with h6.3Fab×EGFR and PEG-NIR797 probes. The mice were then imaged at 45 min, 24 and 48 hours after injection using an IVIS spectrum optical imaging system. Enhanced signals of PEG-NIR797 were observed in A431 tumors but not in Ramos tumors (FIG. 17), demonstrating that h6.3FabxEGFR BsAbs preferentially deliver PEG probes to EGFR on antigen-positive tumors in vivo.

2.3 Production and Characterization of Monovalent Anti-mPEG (h15.2b) BsAbs

In this example, the DNA sequence of murine anti-mPEG mAb of example 1.1 was humanized and combined with another nucleic acid encoding a single chain variable fragment (scFv) of EGFR or HER2 in accordance with procedures described in the Materials and Methods section.

Figure 18A:
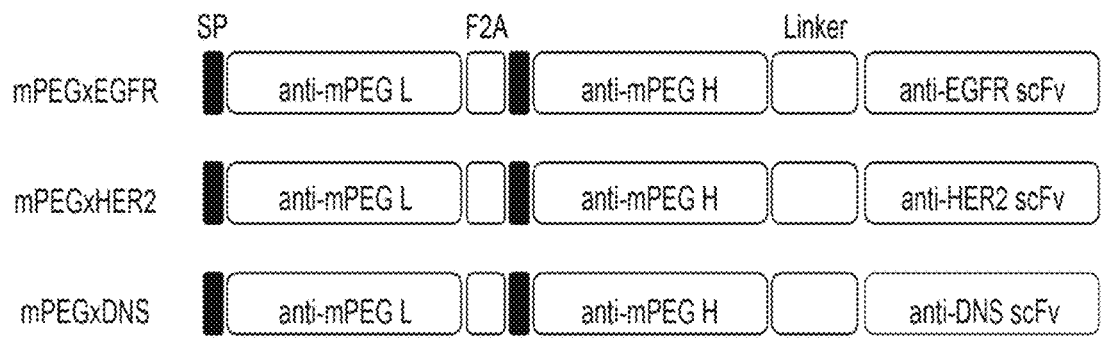
FIG. 18A is a schematic illustration of DNA constructs for humanized anti-mPEG BsAbs in accordance with one embodiment of the present disclosure.
Figure 18B:
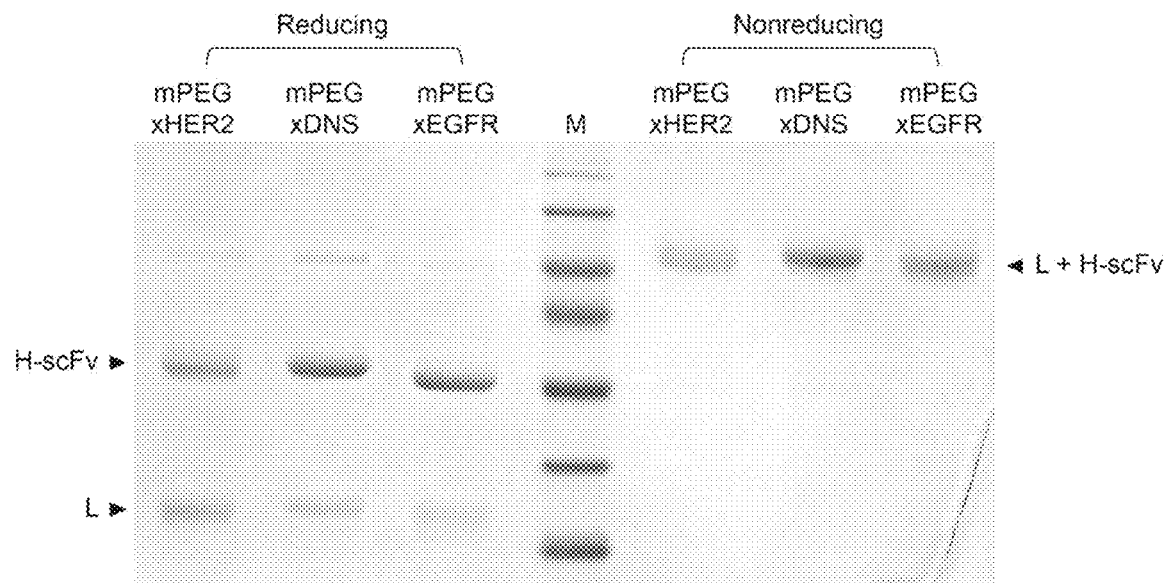
FIG. 18B illustrates the SDS-PAGE analysis of the humanized BsAbs of example 2.3 in reducing or non-reducing condition in accordance with one embodiment of the present disclosure.

FIG. 18A is a schematic illustration of the DNA constructs of the humanized bi-specific Abs prepared in this example, and 3 BsAbs including PEGxEGFR, PEGxHER2 and PEGxDNS were produced. In general, each construct encoded in sequence, a signal peptide (SP), HA epitope tag (HA), the anti-mPEG light chain, a F2A bicistronic element, the anti-mPEG heavy chain Fd fragment, a myc epitope tag, a 15 amino acid flexible linker peptide (L) and scFv against an anti-tumor marker sequence, such as anti-EGFR scFv for PEGxEGFR plasmid, and anti-HER2 scFv for PEGxHER2 plasmid, and anti-dansyl scFv for the control PEGxDNS plasmid. Accordingly, 3 BsAbs including PEGxEGFR, PEGxHER2 and PEGxDNS were produced. SDS-PAGE analysis indicated that BsAbs were composed by a Fd-scFv fragment (56 kDa) and light chain (35 kDa) under reducing condition; by contrast, a 91 kDa disulfide-linked BsAbs was observed under non-reducing condition (FIG. 18B).

The thus produced humanized BsAbs were then subjected to bi-functional activity assay in antigen-positive or antigen-deficient cancer cells. Briefly, cells with over expressed EGFR (i.e., SW480, EGFR$^+$) or HER2 (i.e., SK-BR-3, HER2$^+$) were first incubated with humanized BsAbs of this example, and the unbound BsAbs were washed out with a buffer solution, various PEG-NPs (i.e., Lipo/DOX, Lipo/IR780, SN38/PM, FeOdot, AuNP, and Qdot$_{565nm}$) were then added, and the respective binding activities of the BsAbs were detected by ELISA with an anti-mPEG antibody.

Figure 18C:
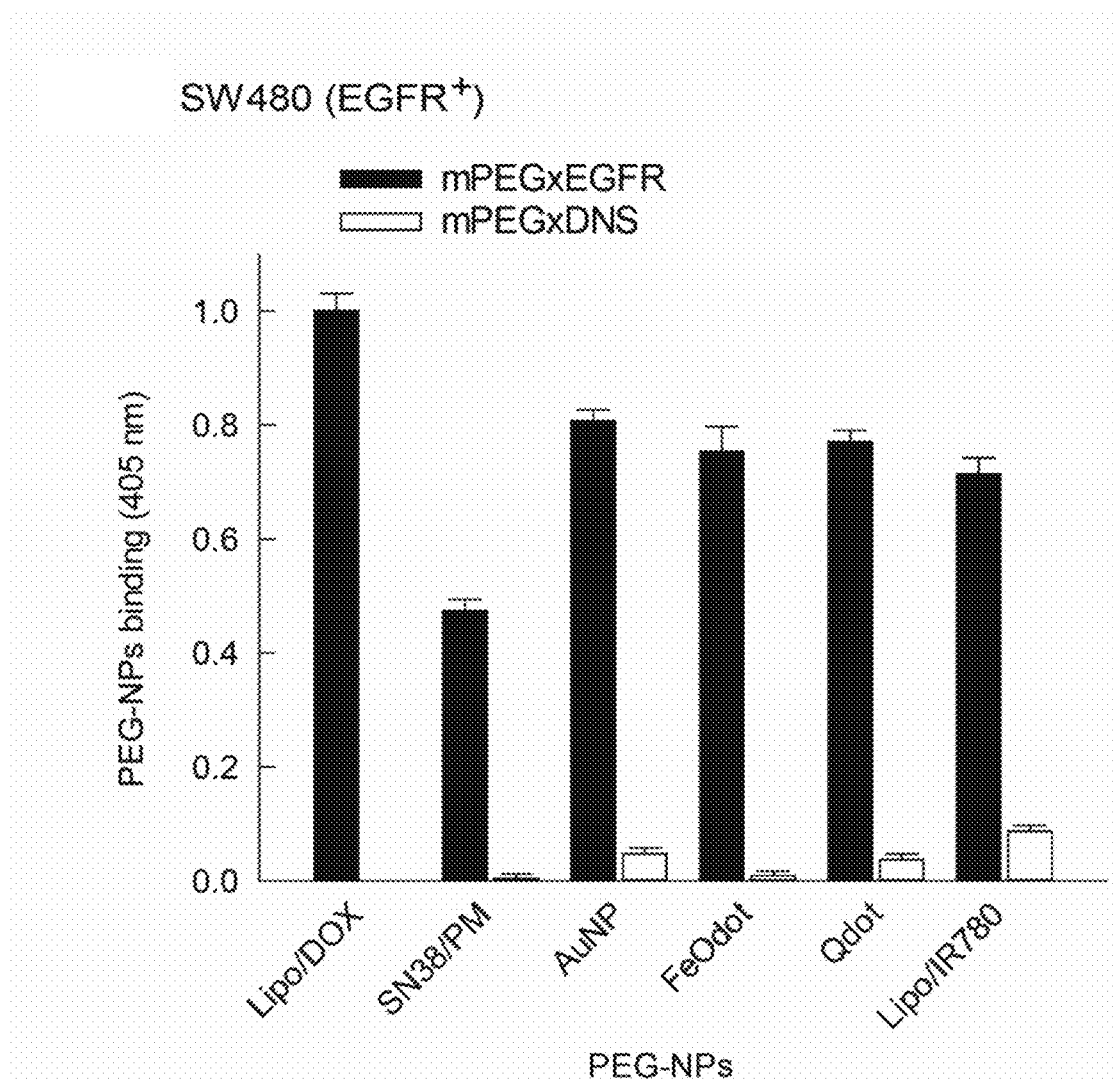
FIGS. 18C and 18D illustrate the respective binding activities of the humanized BsAbs of example 2.3 with the indicated PEG-NPs in SW480 cells (EGFR$^+$) (FIG. 2C) and SK-BR-3 cells (HER2$^+$) (FIG. 2D) in accordance with one embodiment of the present disclosure.
Figure 18D:
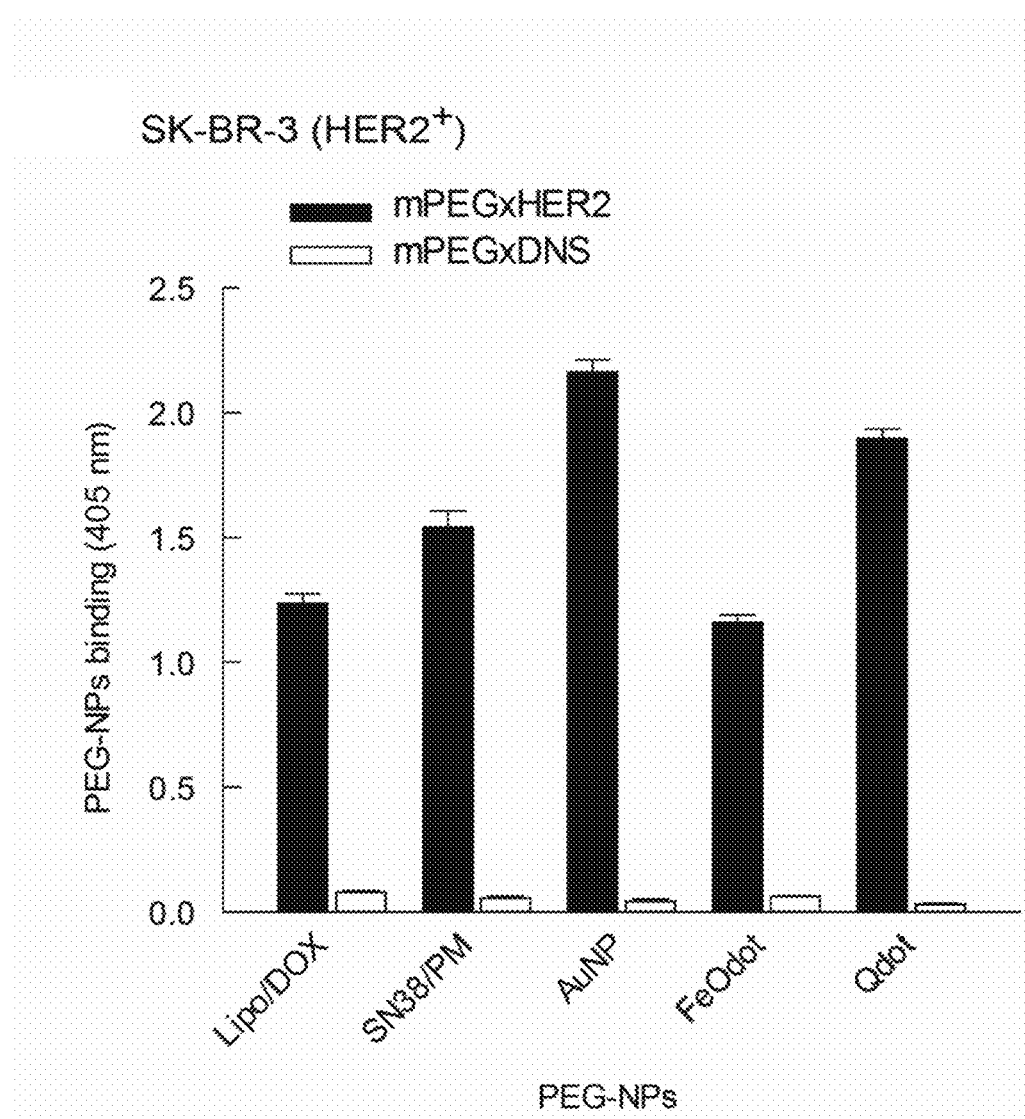

It is noted that PEGxEGFR, instead of the negative control PEGxDNS, mediated binding of all the tested PEG-NPs to EGFR$^+$ SW480 cancer cells (FIG. 18C). Likewise, PEGxHER2, but not PEGxDNS, mediated the binding of PEG-NPs to HER2$^+$ SK-BR-3 cancer cells (FIG. 18D). In sum, both PEGxEGFR and PEGxHER2 display bi-functional binding activity, and are capable of mediating the cross-linking of PEG-NPs to cells that express the EGFR or HER2 tumor markers.

Figure 19A:
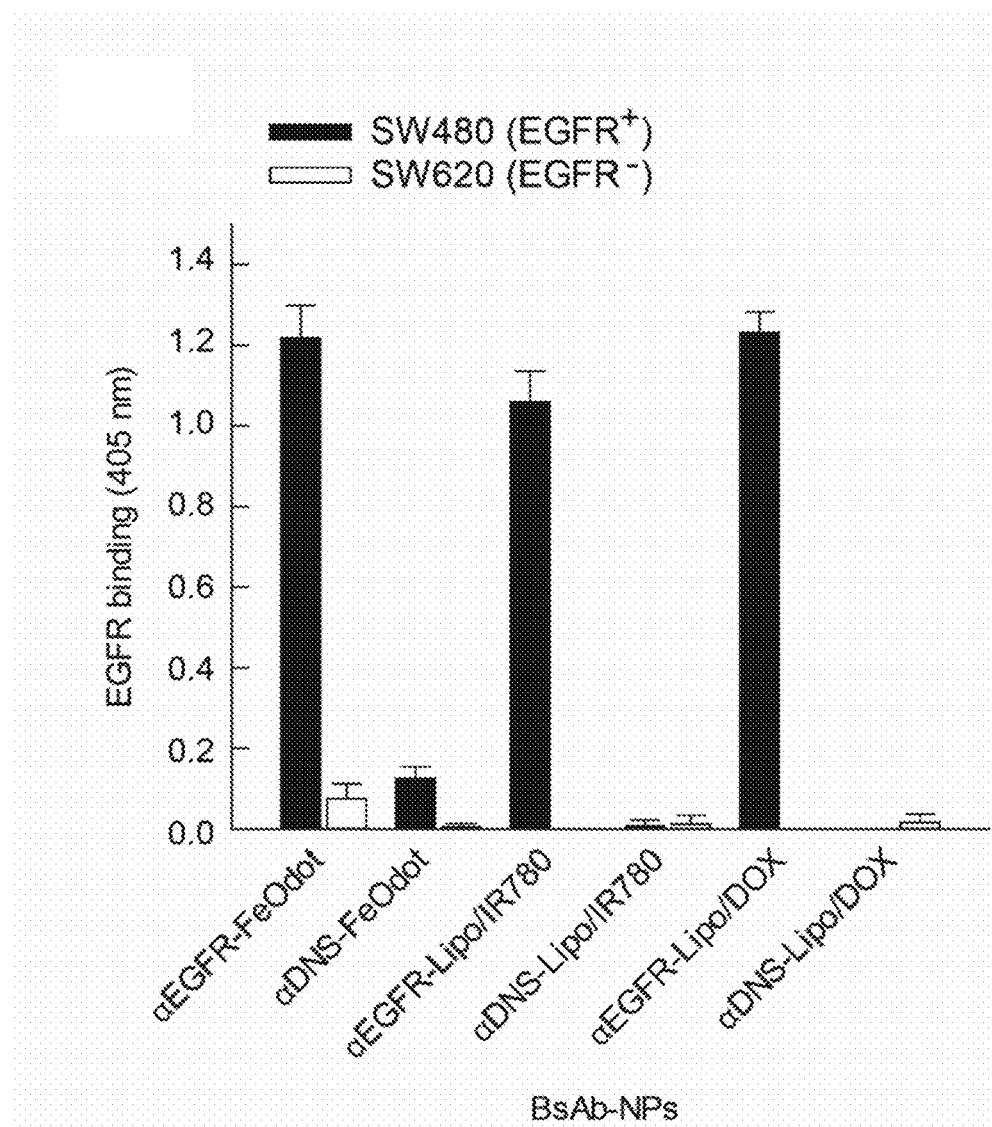
FIG. 19A illustrates the cancer cell selectivity of PEG-NPs treated with the humanized BsAbs of example 2.3 in SW480 cells (EGFR$^+$) and SW620 cells (EGFR$^-$) (FIG. 2C) in accordance with one embodiment of the present disclosure.
Figure 19B:
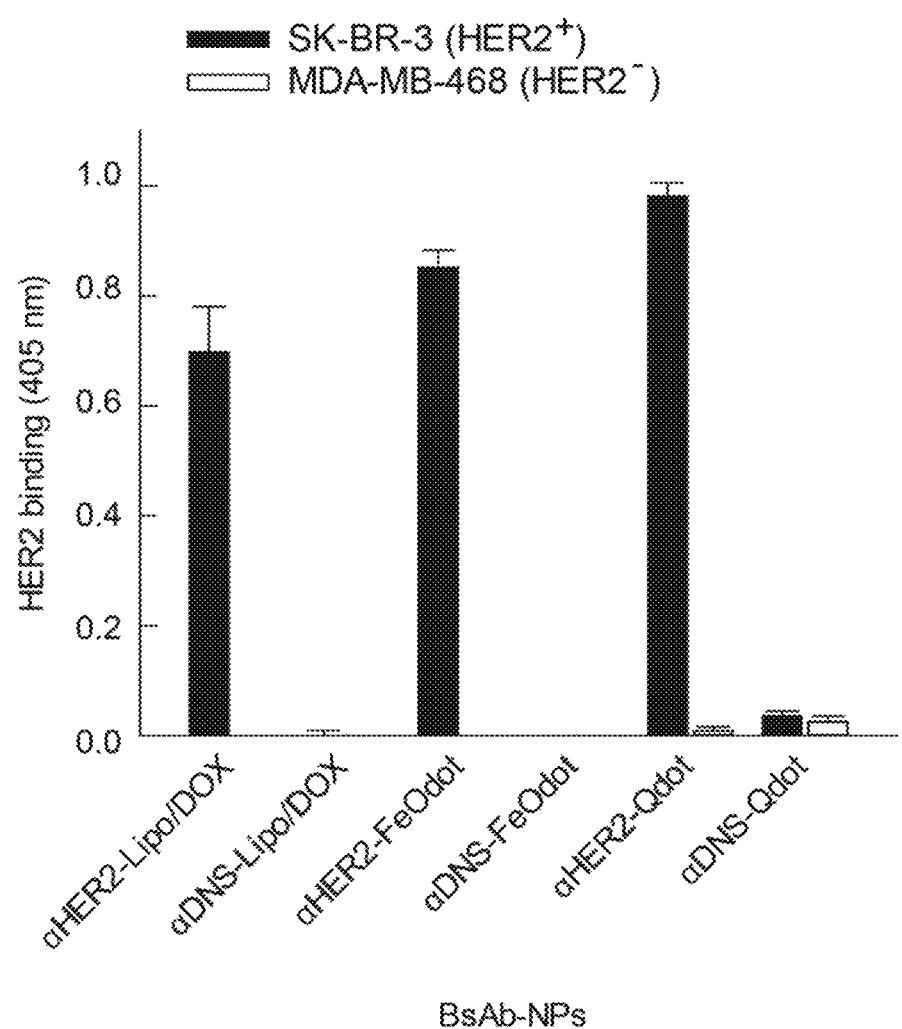
FIG. 19B illustrates the cancer cell selectivity of PEG-NPs treated with the PEG×EGFR or PEG×HER2 of example 2.3 in SK-BR-3 cells (HER2$^+$) and MDA-MB-468 cells (HER2$^-$) in accordance with one embodiment of the present disclosure.

To evaluate whether the BsAb of this example may confer cancer cell specificity to the PEG-NP, the BsAbs of this example were added to various PEG-NPs (e.g., Lipo/DOX, Lipo/IR780 and FeOdot) to generate targeted PEG-NPs. Binding specificity was then measured by ELISA. Results are depicted in FIGS. 19A and 19B. It is found that PEG-NPs targeting depends on the anti-EGFR portion of the BsAb, for the control αDNS-NPs failed to bind to either SW480 (EGFR$^+$) or SW620 (EGFR$^-$) tumor cells (FIG. 19A) Likewise, incubating PEG-NPs with PEGxHER2, allowed the NPs to bind with SK-BR-3 (HER2$^+$) tumor cells, but not MDA-MB-468 (HER2$^-$) tumor cells (FIG. 19B). These results demonstrate that mixing PEGxEGFR or PEGxHER2 with PEG-NPs can endow the NPs with specificity to EGFR or HER2 on cancer cells.

Figure 20A:
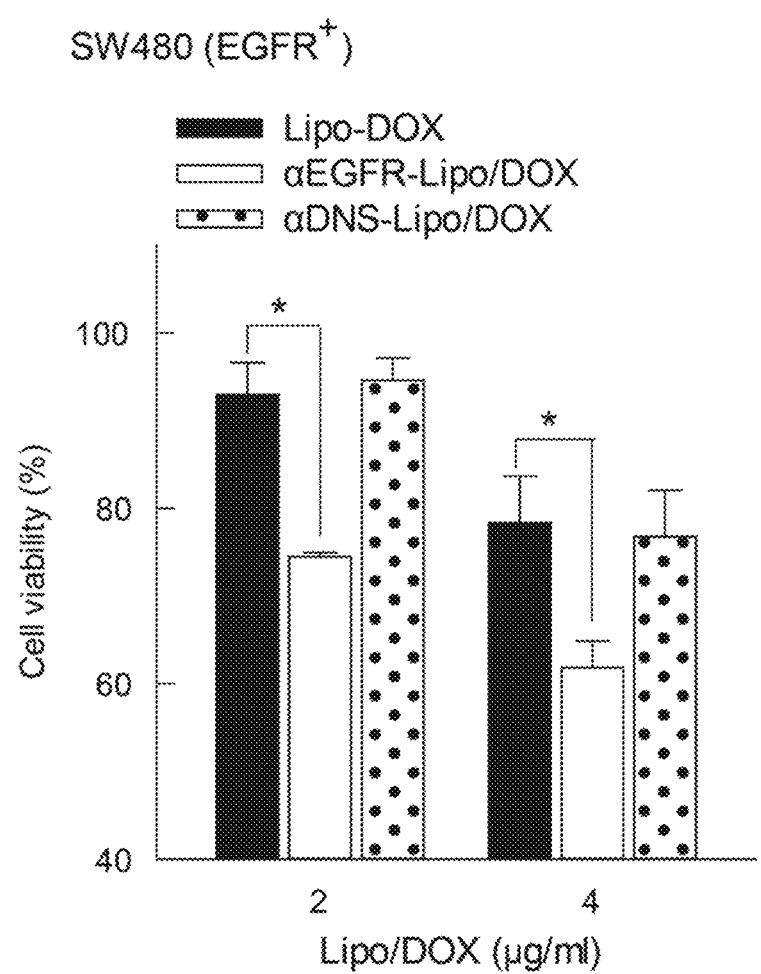
FIGS. 20A to 20D respectively illustrate the enhanced in-vitro cytotoxicity of Lipo/DOX by PEG×EGFR of example 2.3 in (A) SW480 cells (EGFR$^+$), (B) SW620 cells (EGFR$^-$), (C) SK-BR-3 cells (HER2$^+$), and (D) MDA-MB-468 cells (HER2$^-$) in accordance with one embodiment of the present disclosure.
Figure 20B:
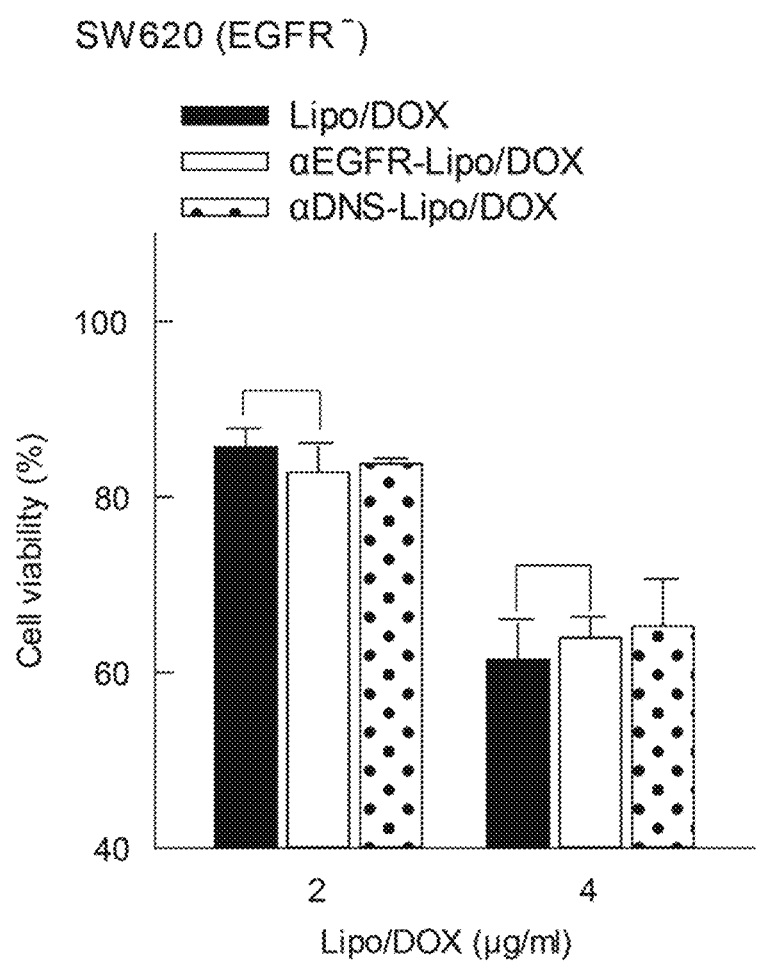
Figure 20C:
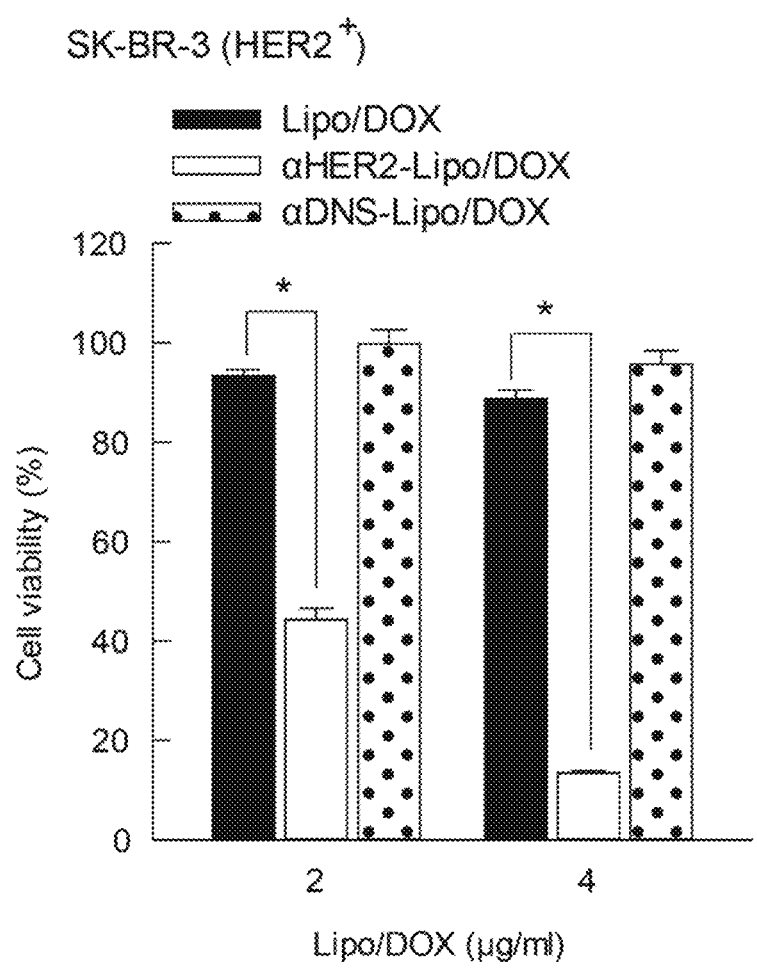
Figure 20D:
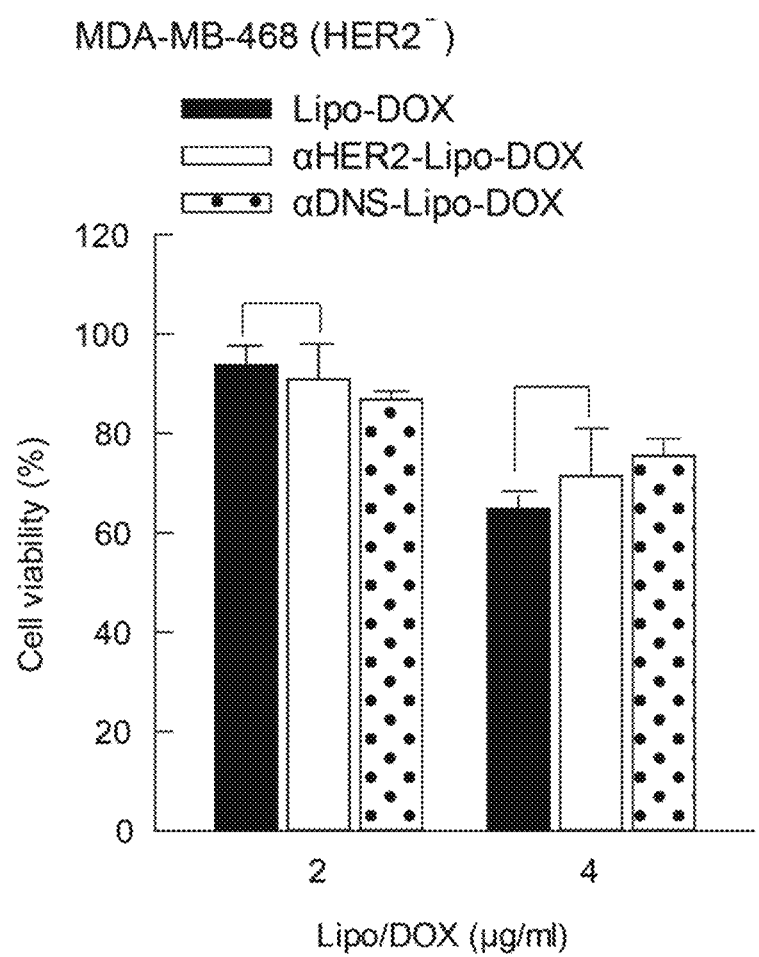

The ability of the targeted PEG-NP in killing antigen-positive cancer cells were further investigated, and results are provided in FIGS. 20A to 20D. As depicted in FIG. 20A, αEGFR-Lipo/DOX exhibited higher cytotoxicity to SW480 (EGFR$^+$) cancer cells, as compared with that of Lipo/DOX or αDNS-Lipo/DOX (FIG. 20A). By contrast, αEGFR-Lipo/DOX displayed similar cytotoxicity as to that of Lipo/DOX or αDNS-Lipo/DOX to SW620 (EGFR$^-$) tumor cells (FIG. 20B). Likewise, αHER2-Lipo/DOX was significantly more cytotoxic to SK-BR-3 (HER2$^+$) cancer cells than that caused by Lipo/DOX or αDNS-Lipo/DOX (FIG. 20C). However, αHER2-Lipo/DOX displayed similar cytotoxicity to MDA-MB-468 (HER2$^-$) cancer cells as compared with that of Lipo/DOX or αDNS-Lipo/DOX (FIG. 20D). Accordingly, it is reasonable to conclude that anti-mPEG BsAbs may confer tumor selectivity and increase the cytotoxicity of a PEG-NP (Lipo/DOX) to antigen-positive cancer cells.

Figure 21:
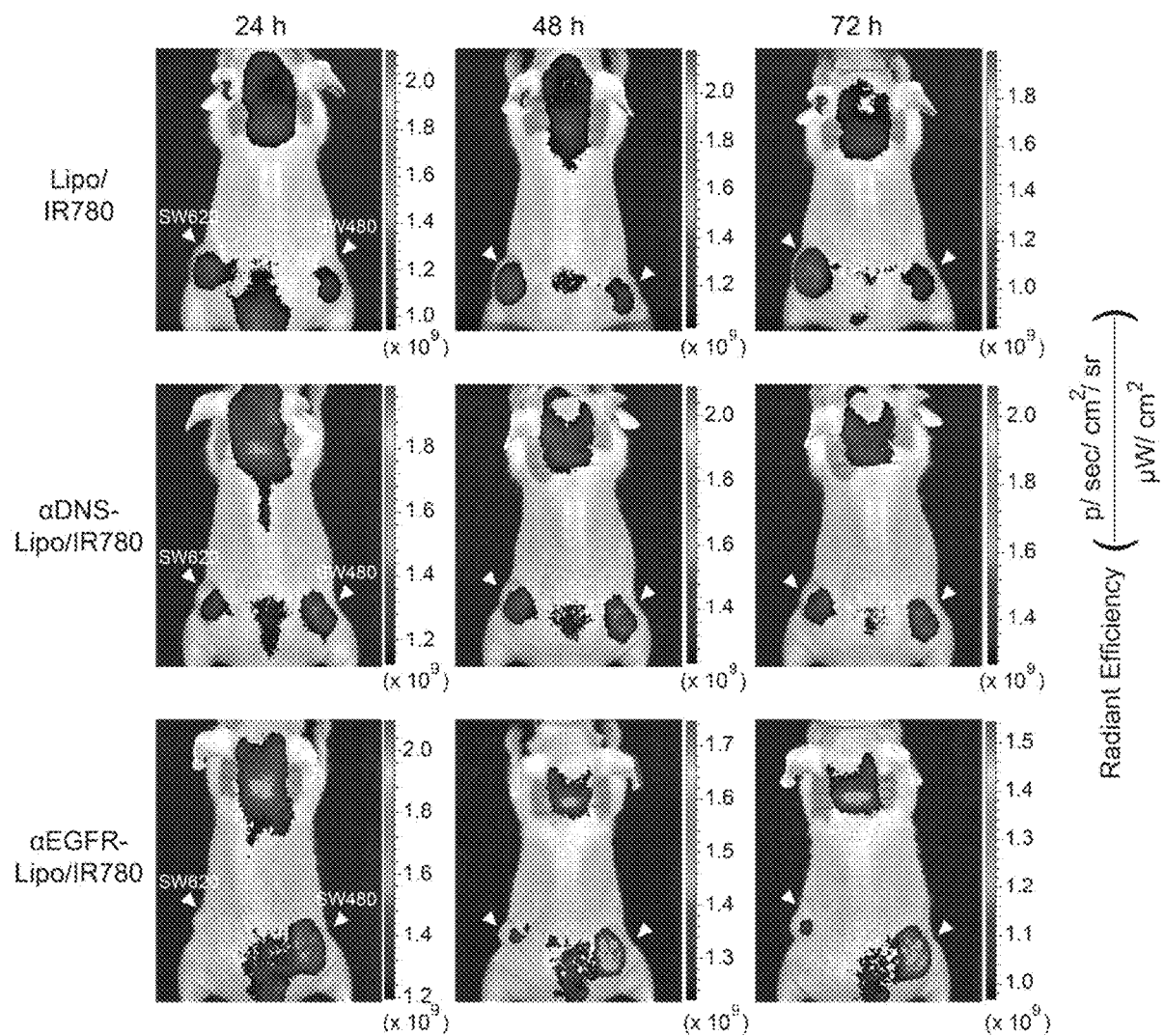
FIG. 21 is a panel of in vivo imaging of PEG×EGFR of example 2.3 targeting Lipo/IR780 in accordance with one embodiment of the present disclosure.

To investigate tumor targeting of BsAbs-NPs in vivo, BALB/c nude mice bearing EGFR$^-$ SW620 (left side) and EGFR SW480 (right side) tumors in their hind leg regions were intravenously injected with αEGFR-Lipo/IR780, αDNS-Lipo/IR780 or Lipo/IR780. The mice were imaged at 24, 48 and 72 hrs after injection with an IVIS spectrum optical imaging system. The fluorescent signal of αEGFR-Lipo/IR780 was enhanced in SW480 (EGFR$^+$) tumors as compared to SW620 (EGFR$^-$) tumors from 24 to 72 hrs after probe injection (FIG. 21, bottom row). The fluorescent intensity of αEGFR-Lipo/IR780 in SW480 (EGFR$^+$) tumor were 2.037, 2.318 and 2.328-fold greater at 24, 48 and 72 hrs than SW620 (EGFR$^-$) tumor, respectively (Table 28). By contrast, Lipo/IR780 and αDNS-Lipo/IR780 localized more strongly in SW620 tumors, presumably by the EPR effect. These data indicate that αEGFR-Lipo/IR780 possessed selectivity for EGFR cancer cells, thereby facilitating enhanced accumulation in EGFR$^+$ tumors.

TABLE 28

The region of interest (ROI) ratio of SW480 (EGFR$^+$) to SW620 (EGFR$^-$) tumors was determined at the indicated times

| | | Time | | |
| --- | --- | --- | --- | --- |
| i.v. injection | ROI ratio | 24 h | 48 h | 72 h |
| Lipo/IR780 | EGFR$^+$ | 0.93 | 0.93 | 0.92 |
| | EGFR$^-$ | | | |
| αDNS-Lipo/IR780 | EGFR$^+$ | 1.09 | 0.97 | 1.01 |
| | EGFR$^-$ | | | |
| αEGFR-Lipo/IR780 | EGFR$^+$ | 2.04 | 2.32 | 2.33 |
| | EGFR$^-$ | | | |

Figure 22A:
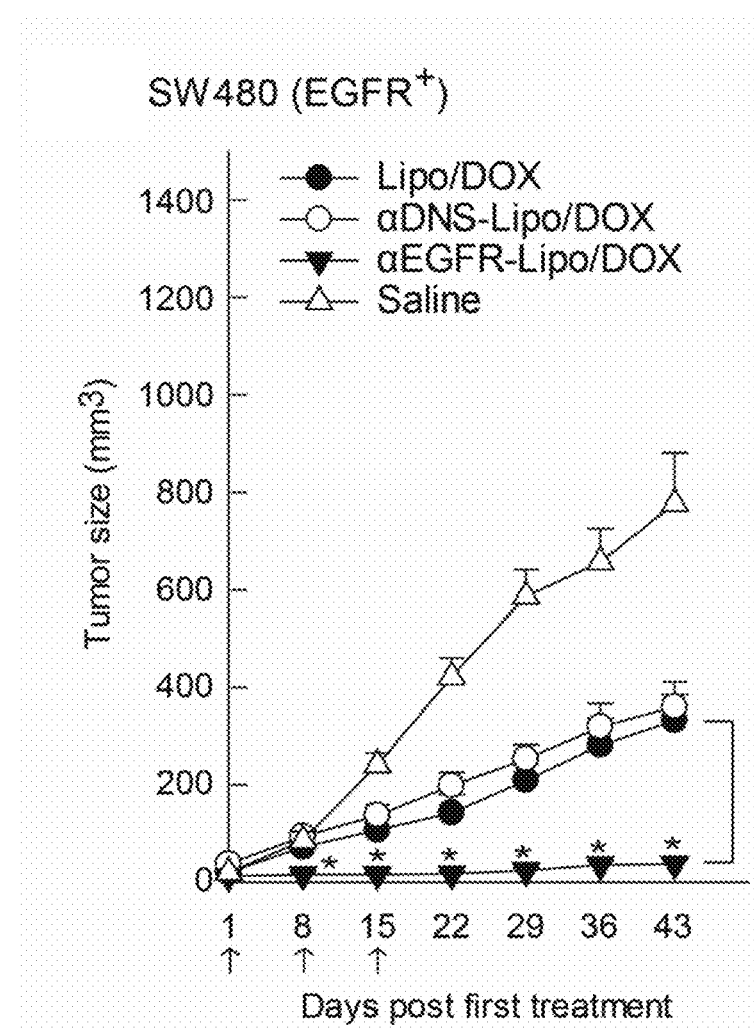
FIGS. 22A and 22B illustrate the respectively size of EGFR$^+$ and EGFR$^-$ tumors treated with PEG×EGFR targeted Lipo/Dox in accordance with one embodiment of the present disclosure.
Figure 22B:
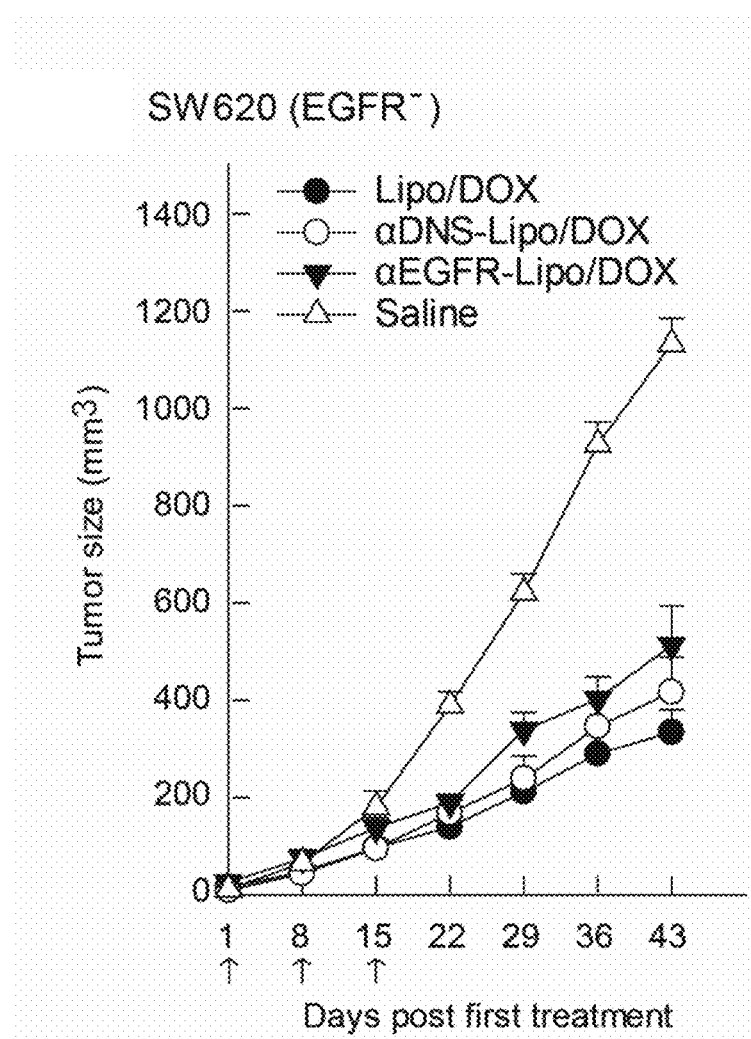
Figure 22C:
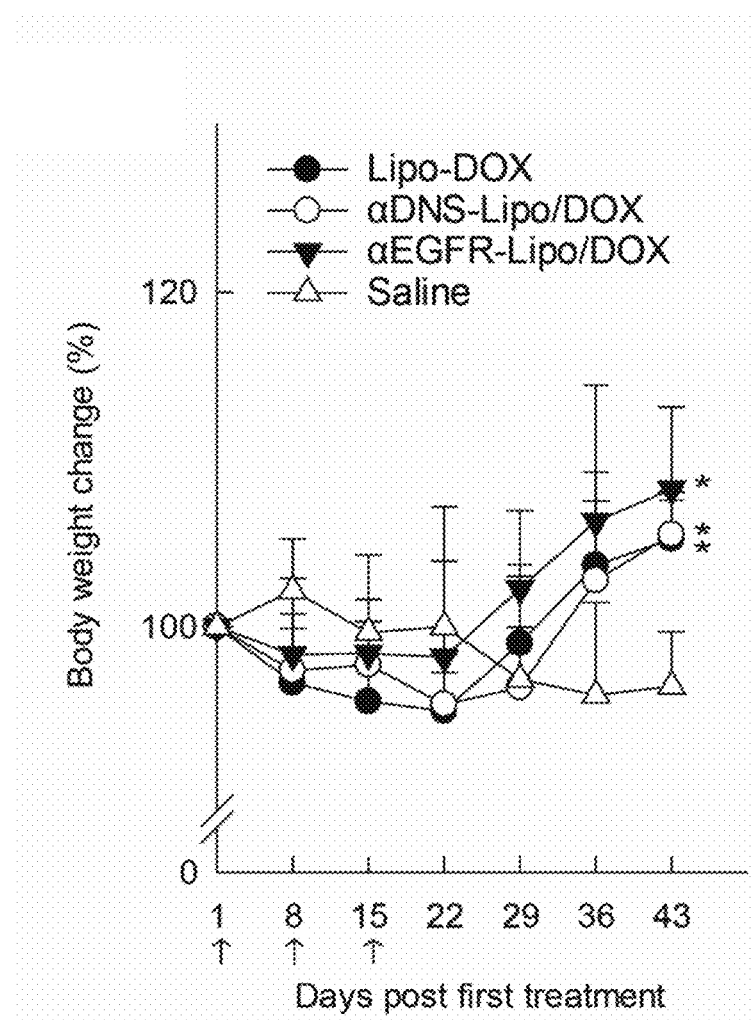
FIG. 22C is a line graph illustrating the changes in body weight of the test animals in FIGS. 22A and 22B.

To examine whether PEGxEGFR of this example may increase the therapeutic efficacy of Lipo/DOX to EGFR tumors in vivo, BALB/c nude mice bearing SW480 (EGFR$^+$) and SW620 (EGFR$^-$) tumor in their hind leg regions were treated with Lipo/DOX αEGFR-Lipo/DOX, αDNS-Lipo/DOX or saline. It was found that αEGFR-Lipo/DOX suppressed the growth of SW480 (EGFR$^+$) tumors significantly more than that treated by Lipo/DOX (P<0.01 on day 8 to 45) (FIG. 22A) without any apparent toxicity, as determined by mouse body weight (FIG. 22C). In the SW620 (EGFR$^-$) tumor model, there were no significant differences between tumor sizes in mice treated with αEGFR-Lipo/DOX, αDNS-Lipo/DOX or Lipo/DOX (FIG. 22B). Accordingly, it is reasonable to conclude that PEGxEGFR of this example may indeed enhance the anti-tumor efficacy of Lipo/DOX to EGFR tumors in vivo.

2.4 Production and Characterization of Monovalent Anti-mPEG (h15.2b) Anti-CD19 or Anti-CD20 BsAbs In this example, the humanized single chain variable fragment (scFv) of murine anti-mPEG mAb was combined with another nucleic acid encoding the monomeric IgG of CD19 or CD20 in accordance with procedures described in the Materials and Methods section.

Figure 23A:
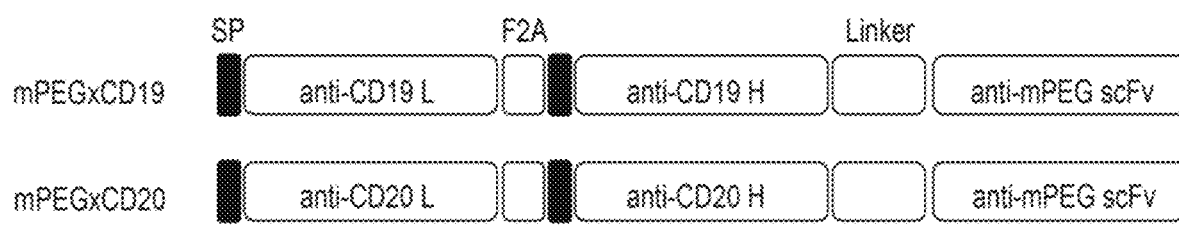
FIG. 23A is a schematic drawing of DNA constructs for humanized anti-mPEG (h15-2b) anti-CD19 BsAb and anti-mPEG (h15-2b) anti-CD20 BsAb in accordance with one embodiment of the present disclosure.
Figure 23B:
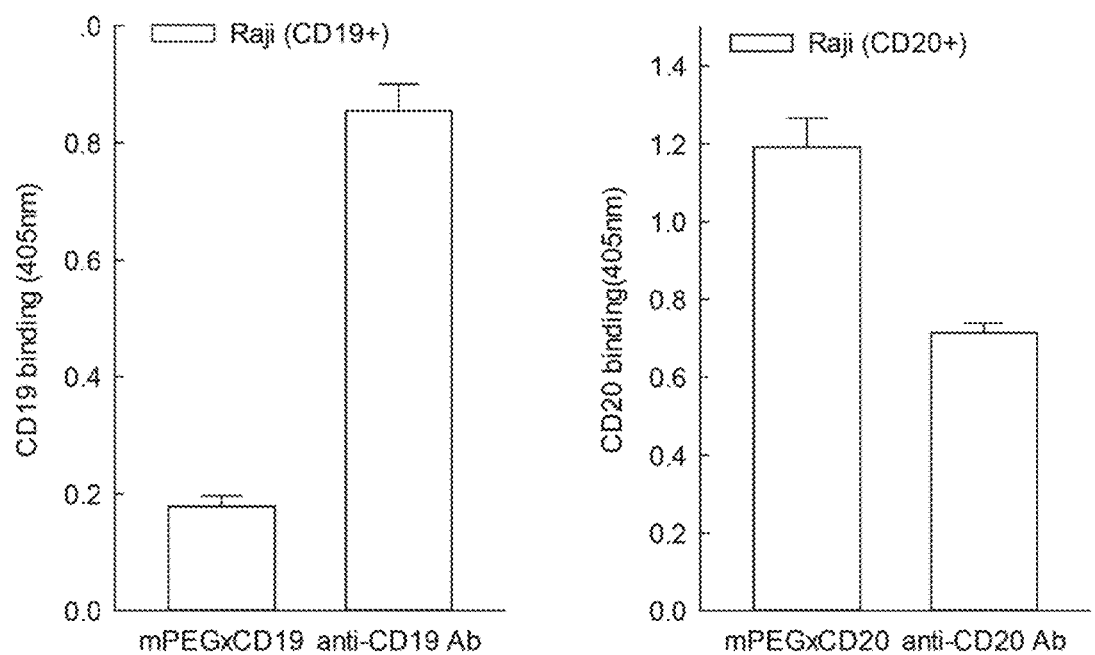
FIG. 23B illustrates the cancer cell selectivity of the BsAbs of example 2.4 in Raji cells in accordance with one embodiment of the present disclosure.
Figure 23C:
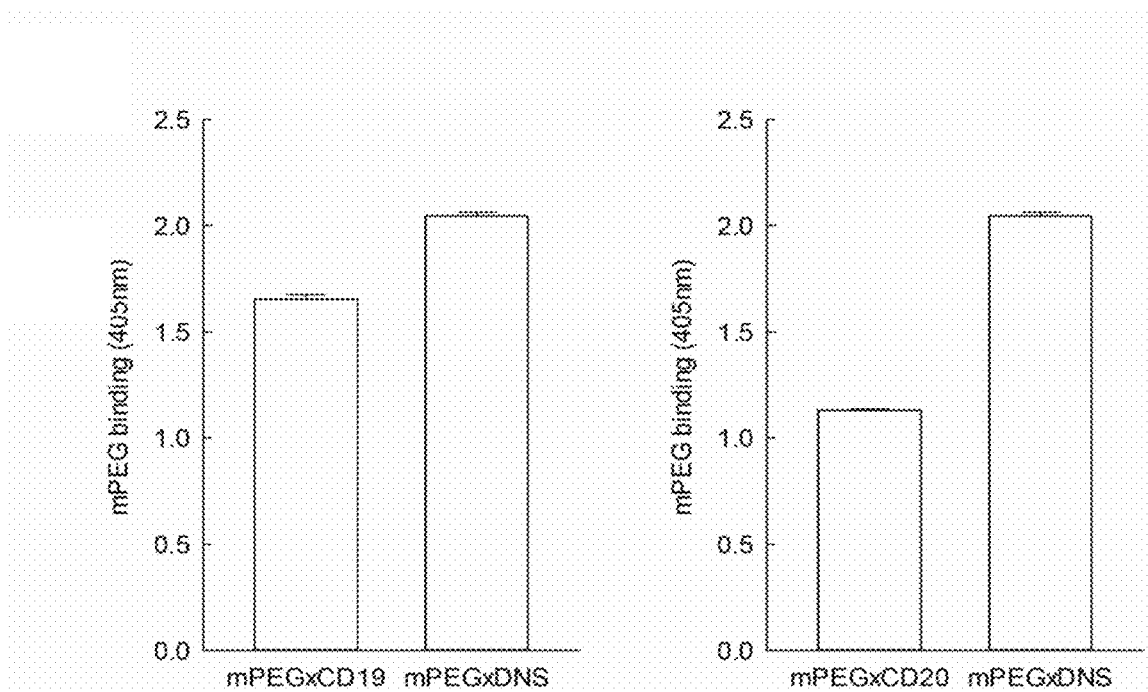
FIG. 23C illustrates the mPEG binding activity of the BsAbs of example 2.4 in accordance with one embodiment of the present disclosure.
Figure 23D:
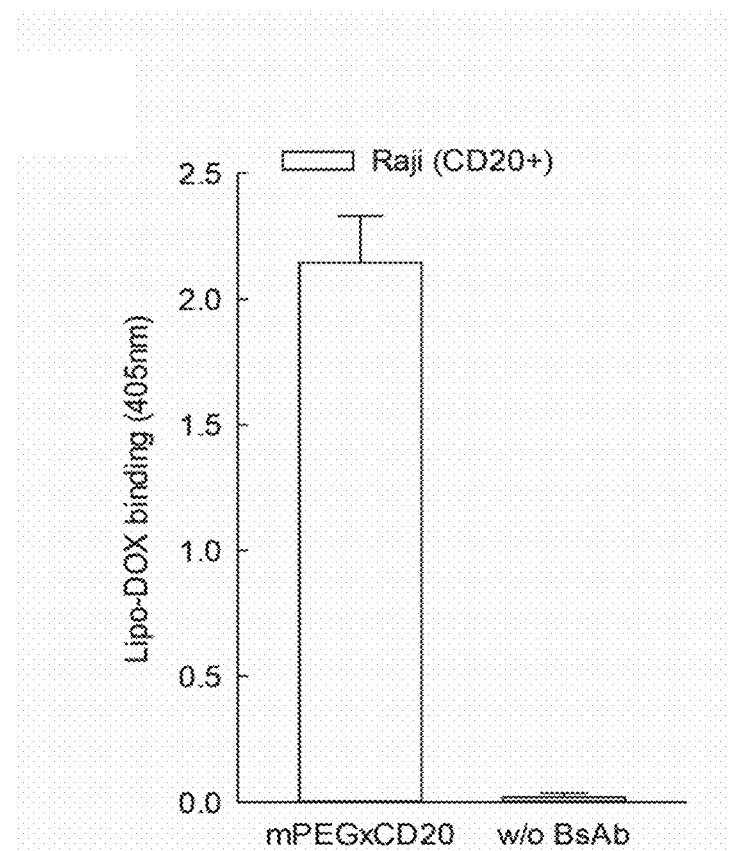
FIG. 23D illustrates the dual binding activity of the BsAbs of example 2.4 in accordance with one embodiment of the present disclosure.

FIG. 23A is a schematic illustration of the DNA constructs of the humanized bi-specific Abs prepared in this example. In general, each construct encoded in sequence, a signal peptide (SP), an anti-CD19 or anti-CD20 heavy chain sequence (VH-CH1), an anti-CD19 or anti-CD 20 light chain sequence (VL-Cκ), an amino acid flexible linker peptide (L), and the anti-mPEG scFv. Accordingly, 2 anti-mPEG BsAbs respectively directed to CD19 and CD20 were produced. Binding results confirmed that the anti-mPEG BsAbs of the present example specifically bound to cells that positively expressed CD19 and CD20 (e.g., Raji cells) (FIG. 23B), as well as the terminal methoxy or hydroxyl group of PEG molecules (FIG. 23C). Further, once the anti-mPEG BsAbs of the present example was mixed with therapeutic nanoparticles (e.g., Lipo/DOX), they were able to target deliver the therapeutic nanoparticles to CD19 or CD-20 positive cancer cells (FIG. 23D).

Example 3 Construction and Characterization of Dimeric Humanized Knob in Hole BsAbs 3.1 Production of Knob in Hole Anti-PEG (h6.3 or h15.2b) Anti-HER2 or Anti-CD19 BsAbs Recombinant DNA technology was utilized to create BsAbs derived from the cDNA coding regions of $V_H$ and $V_L$ of either an anti-HER2 antibody (C6) or an anti-CD19 antibodies (BU12), and the humanized anti-methoxy-PEG monoclonal h15-2b or the humanized anti-PEG antibody h6.3, with the employment of the "knobs-into-holes" strategy and immunoglobulin domain crossover approach, for heterodimer formation and correct antibody heavy chain and light assembly.

Figure 24A:
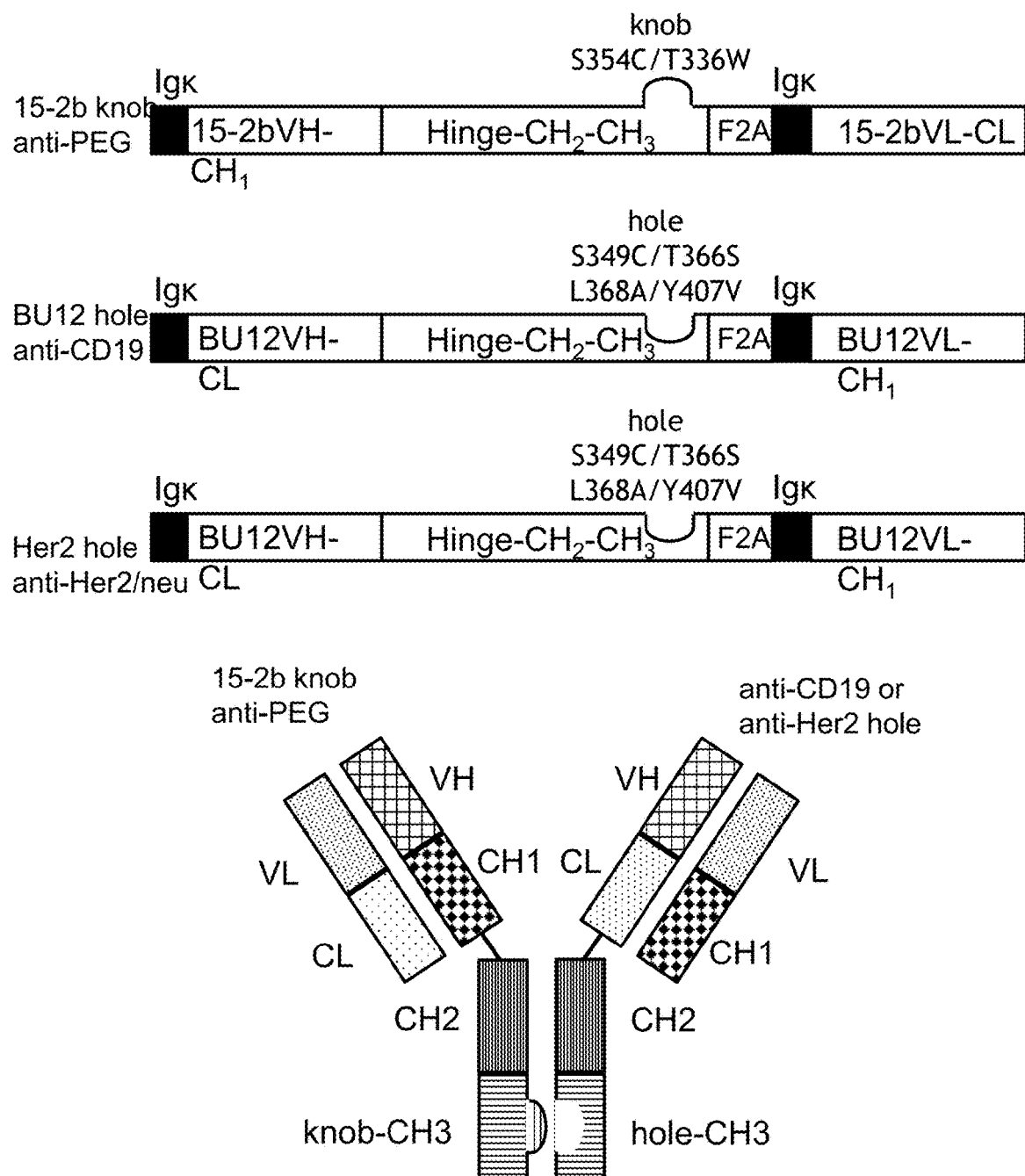
FIG. 24A is a schematic illustration of DNA constructs for humanized knob in hole anti-PEG (h15-2b) BsAbs of example 3.1 and the structures of the BsAbs in accordance with one embodiment of the present disclosure.

For generating correctly assembled antibody, the light chain Cκ domain and heavy chain CH1 domain within the antigen binding fragment (Fab) of either BU12 or C6 antibody were exchanged, while the anti-PEG antibodies were kept unmodified. In particular, Cκ of the tumor antigen antibodies BU12 and C6 was replaced with the partial $C_{H1}$ fragment and partial hinge of that antibody heavy chain, and the original $C_{H1}$ fragment site within antibody heavy chain was replaced with the Cκ sequence of the antibody light chain. This allows the light chain to pair with its cognate heavy chain, instead of pairing with the heavy chain of the anti-PEG-knob antibody. Also, for heavy-chain heterodimer formation, a knob structure (T366W and S354C) was introduced into the h15-2b and h6.3 CH3 region and a hole structure (T366S, L368A, Y407V and Y349C) was introduced into CH3 of C6 and BU12, respectively. The construction maps of BsAbs constructed from the anti-mPEG (h15-2b)-knob antibody and BU12-hole or anti-HER2-hole antibodies are depicted in FIG. 24A; whereas the DNA maps of BsAbs constructed from the anti-PEG antibody (h6.3)-knob and BU12-hole or anti-HER2-hole antibodies are illustrated in FIG. 24B.

Figure 24C:
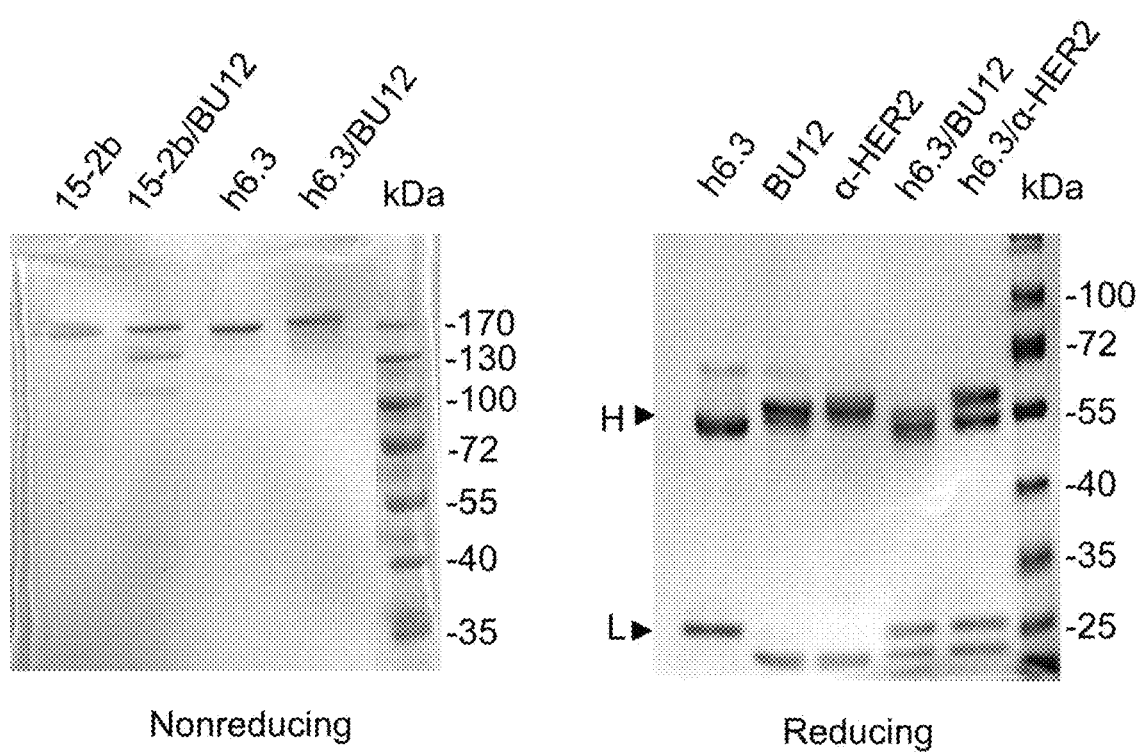
FIG. 24C illustrates the SDS-PAGE analysis of the humanized knob in hole anti-PEG (h15-2b or h6.3) BsAbs of example 3.1 in non-reducing condition in accordance with one embodiment of the present disclosure.

The DNA constructs of BsAbs were then inserted into a lentiviral expression vector to generate stable 293FT producer cell lines. BsAbs (including h15-2b knob+BU12-hole, h6.3+BU12-hole) that were purified from the culture medium displayed the expected molecular sizes on a 10% SDS-PAGE (FIG. 24C).

3.2 Characterization of Knob in Hole BsAbs of Example 3.1

In this example, the bi-specificity of the purified knob in hole BsAbs of example 3.1 was investigated. Briefly, Ramos cells (CD19⁺) and SKBR3 cells (HER2⁺) were used to verify whether purified BsAbs can bind to both PEG compounds and cancer cells that express the CD19 or Her2/neu tumor antigens. Briefly, Ramos cells (CD19⁺), Raji cells (CD19⁺) or SKBR3 cells (HER2⁺) were incubated with 10 µg/ml h15-2b-knob/BU12-hole or h15-2b-knob/anti-Her2-hole BsAbs, washed and incubated with 0.25 µg/ml FITC-labeled goat anti-human IgG or 10 nM methoxy-PEG Qdot 655 at 4° C. for 30 min. The surface fluorescence of viable cells was measured on a FACSCalibur. Results are illustrated in FIGS. 25 to 28.

Figure 25:
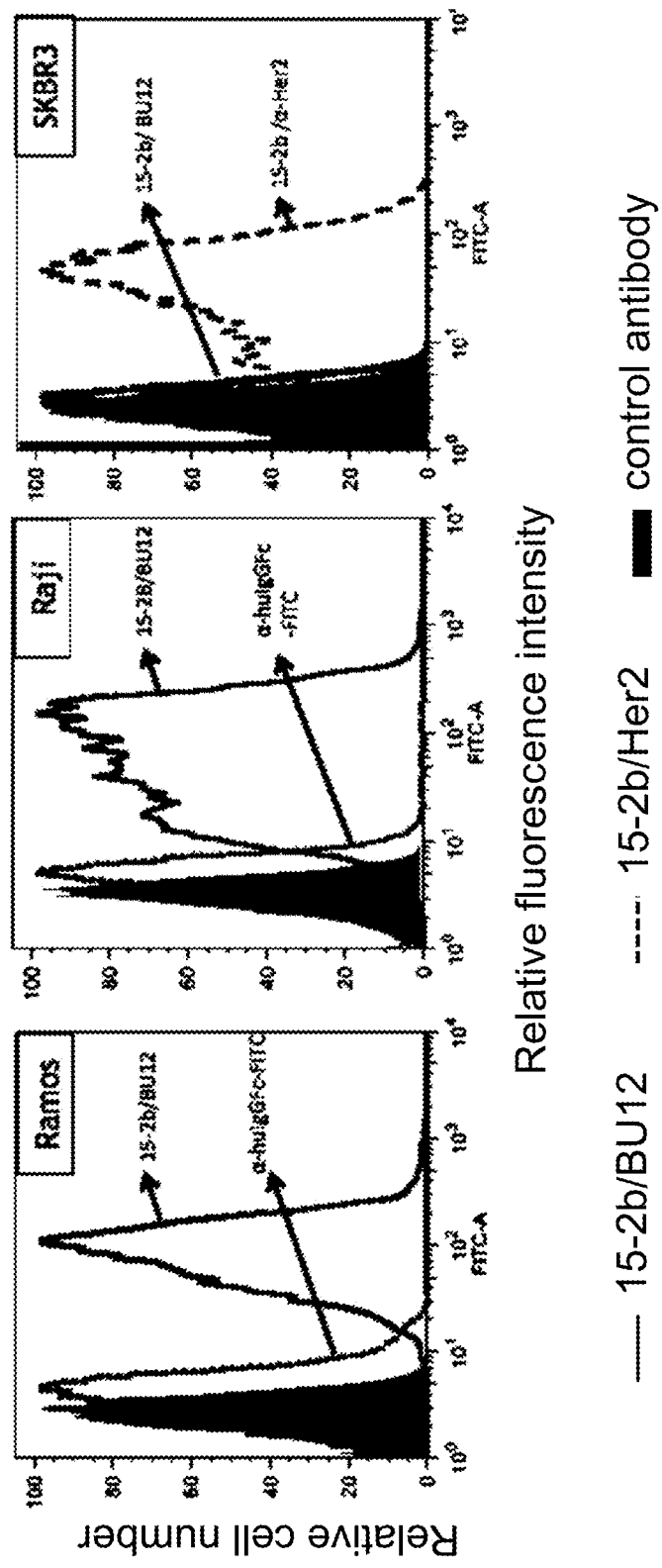
FIG. 25 illustrates the cancer cell selectivity of the humanized knob in hole anti-PEG (h15-2b) BsAbs of example 3.1 in Ramous (CD19$^+$), Raji (CD19$^+$) and SKBR3 (HER2$^+$) cells in accordance with one embodiment of the present disclosure.
Figure 26:
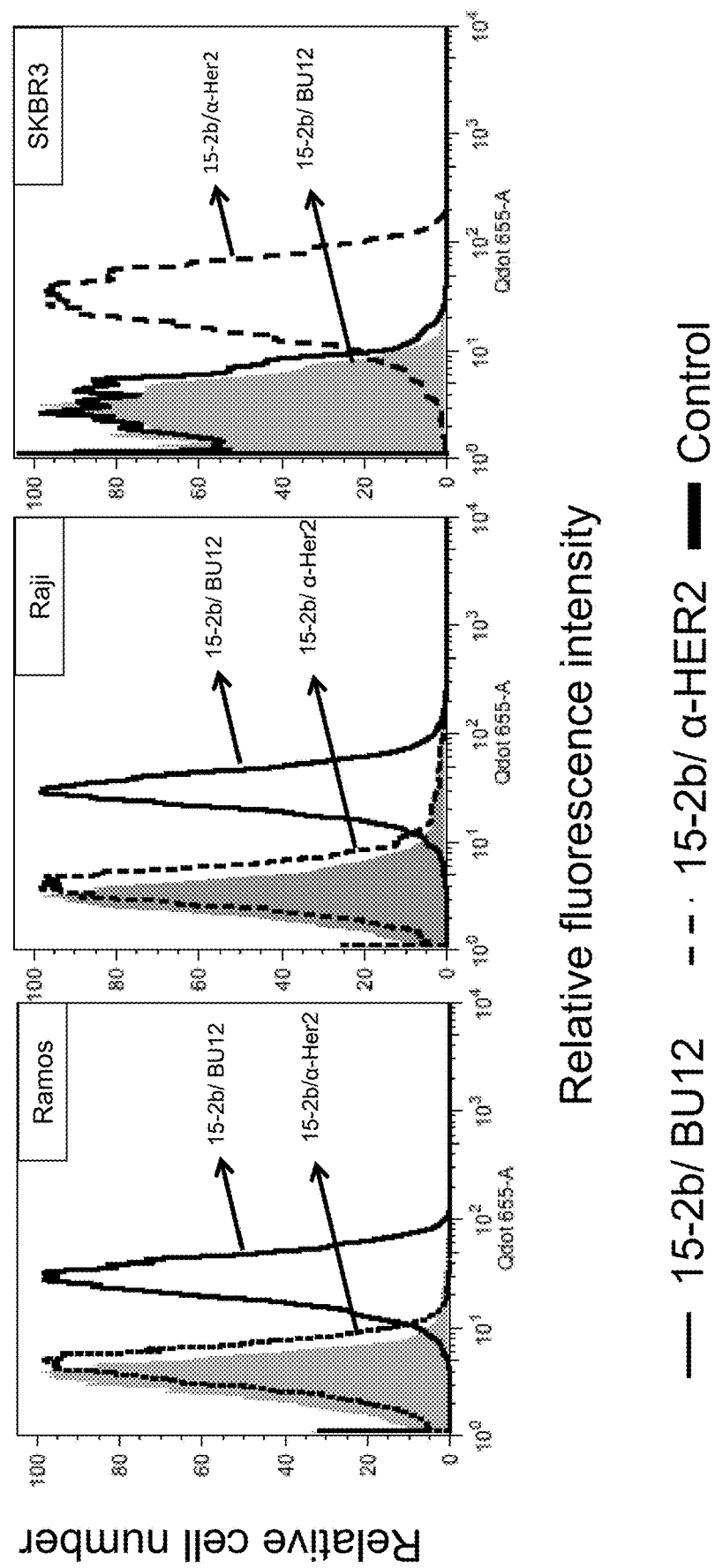
FIG. 26 illustrates the dual binding activities of the humanized knob in hole anti-PEG (15-2b) BsAbs of example 3.1 with the PEGylated Quantum Dot (Qdot655) in Ramos (CD19$^+$), Raji (CD19$^+$) and SKBR3 (HER2$^+$) cells in accordance with one embodiment of the present disclosure.
Figure 27:
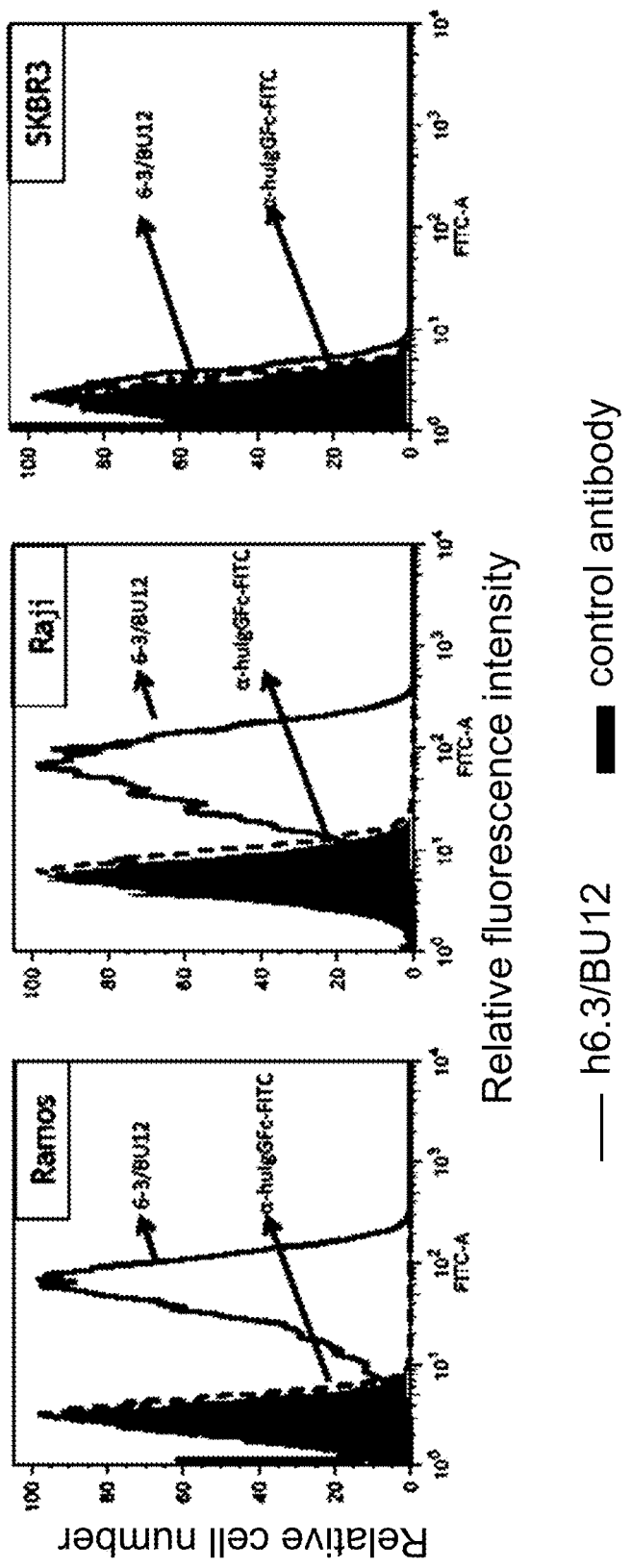
FIG. 27 illustrates the cancer cell selectivity of the humanized knob in hole anti-PEG (h6.3) BsAbs of example 3.1 in Ramos (CD19$^+$), Raji (CD19$^+$) and SKBR3 (HER2$^+$) cells in accordance with one embodiment of the present disclosure.
Figure 28:
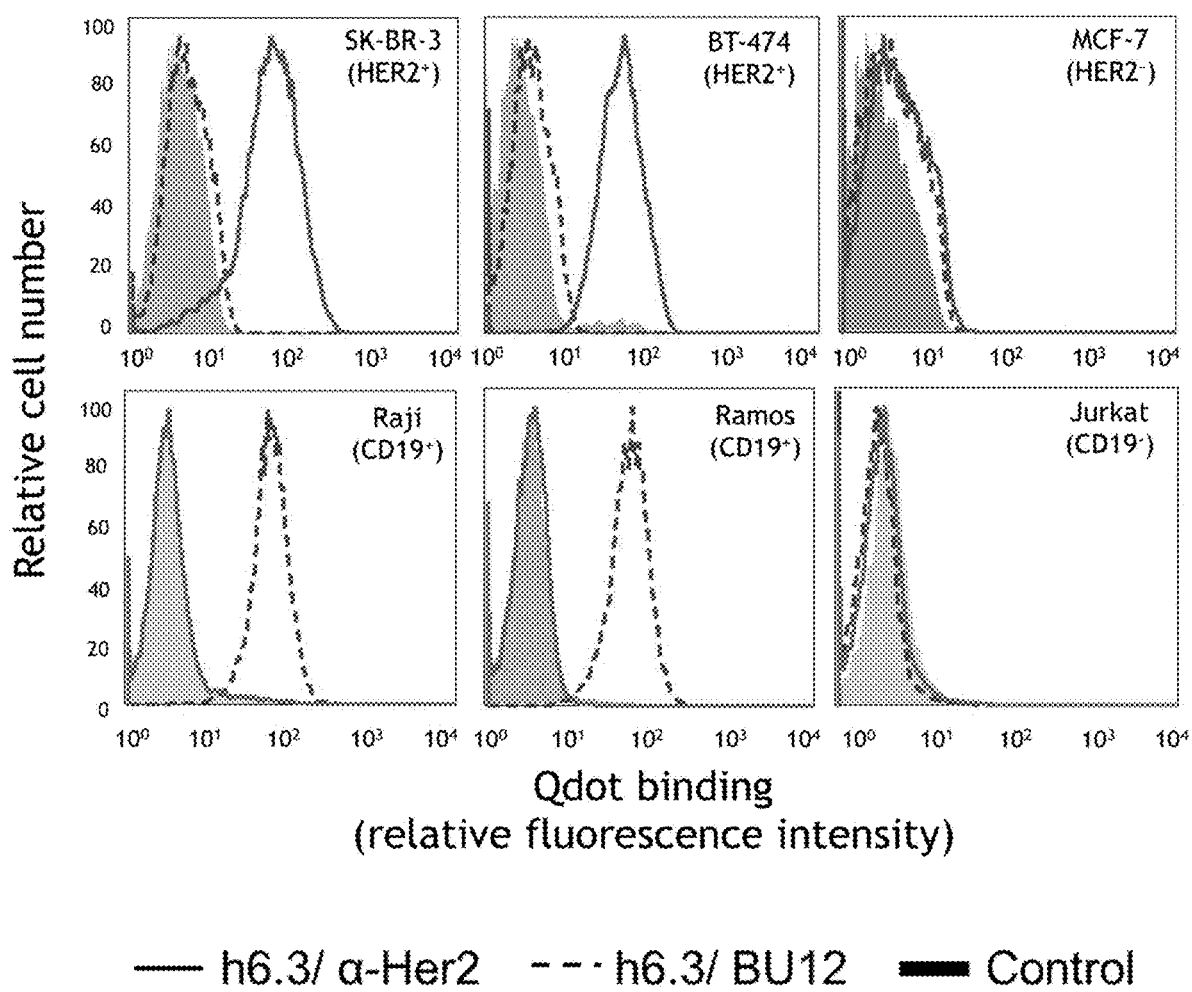
FIG. 28 illustrates the dual binding activities of the humanized knob in hole anti-PEG (h15-2b or h6.3) BsAbs of example 3.1 with the PEGylated Quantum Dot (Qdot655) in Raji (CD19$^+$) and SKBR3 (HER2$^+$) cells in accordance with one embodiment of the present disclosure.

It was found that h15-2b-knob/BU12-hole BsAbs bound to CD19-positive Ramos cells, but not to SKBR3 cells; whereas h15-2b-knob/anti-HER2-hole BsAbs bound to SKBR3 (Her2-positive) (FIG. 25). This indicates that h15-2b BsAbs retained the ability to specifically bind to cancer cells in an antigen-dependent fashion. More importantly, h15-2b-knob/BU12-hole could stably retain PEGylated Qdots at Ramos and Raji cells; and h15-2b-knob/anti-HER2-hole could retain the Qdots at SKBR3 cell (FIG. 26). Thus, these reagents acted as true bispecific molecules. Similar results were observed for h6.3-knob/BU12-hole BsAbs, which could bind to cells expressing CD19 (Ramos and Raji) as measured by FACs (FIG. 27). h6.3-knob/BU12-hole also effectively bound PEG-modified Qdots to Raji cells (FIG. 28), demonstrating that this BsAb could simultaneously bind to CD19 on cancer cells and the PEG molecule of a PEGylated nanoparticle.

Example 4 Construction and Characterization of Recombinant Intact Anti-Cancer BsAbs 4.1 Production of Herceptin/h-α-PEG and Erbitux/h-αPEG Abs To create reagents that may synergistically attack cancer cells, a functional and humanized anti-PEG single-chain Ab (h-αPEG scFv) was fused to the C-terminal of commercial available targeted antibodies (including Herceptin and Erbitux) to form bi-functional Herceptin/h-αPEG, and Erbitux/h-αPEG Abs (FIG. 29). Accordingly, not only have the original anticancer effects of the herceptin and/or Erbitux antibodies been retained, but the newly produced BsAbs can also actively bind to PEGylated drugs at tumor sites, to produce synergistic anticancer effects (i.e., double-attack strategy).

4.2 Characterization of the Function of BsAbs of Example 4.1

In this example, the bi-functional activity of BsAbs of example 4.1 was investigated. Briefly, SKBR-3 human breast adenocarcinoma cells, which overexpress the HER2/c-erb-2 gene product, were coated in 96-well microtiter plates; then Herceptin/h-αPEG antibodies and control Herceptin antibodies were added to the microtiter plates. After the unbound bi-functional antibodies were washed out, PEGylated liposomes containing doxorubicin therein (herein Lipo-DOX) were added to the wells. Binding of the PEGylated compounds was determined by ELISA.

Figure 30A:
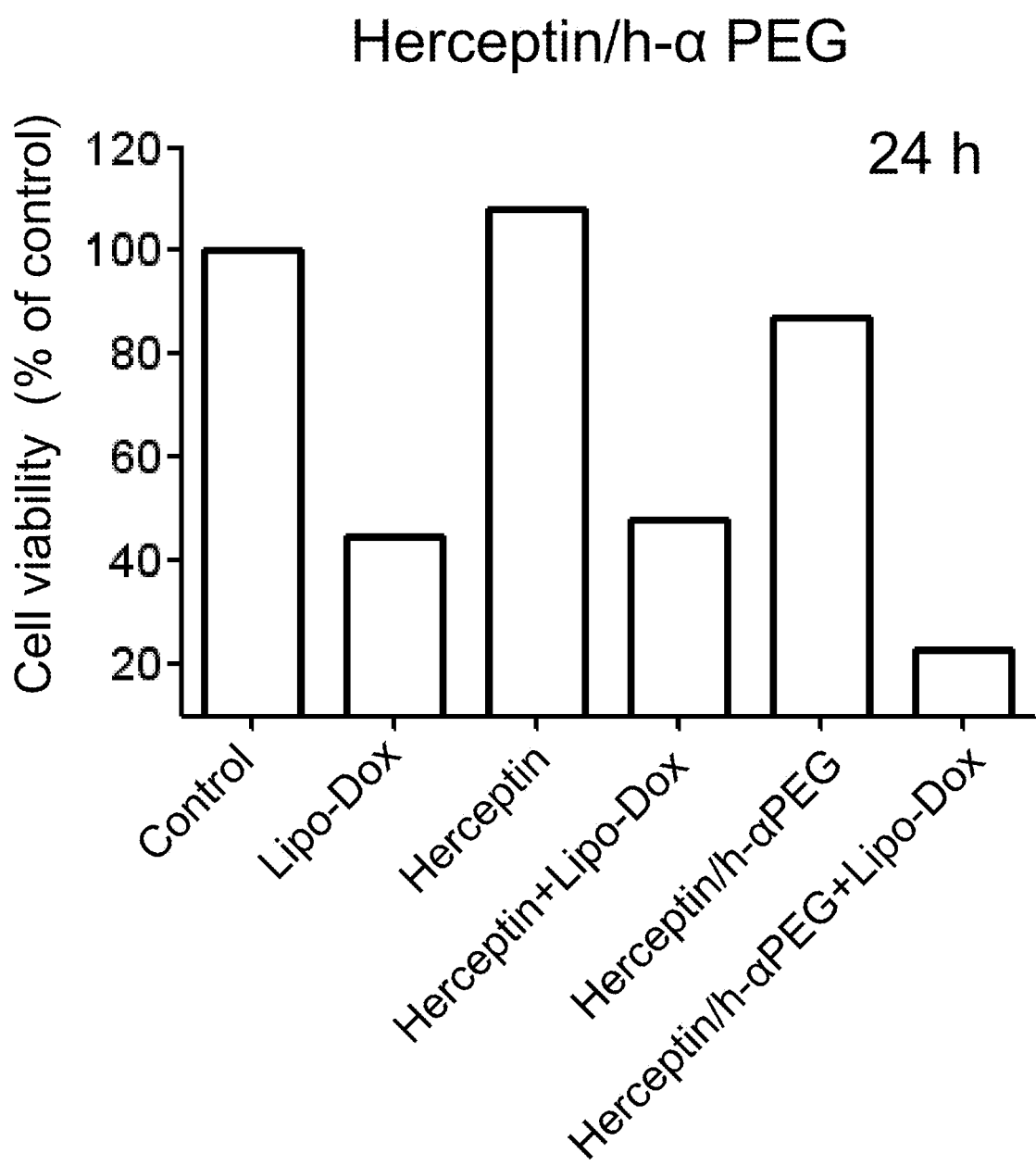
FIGS. 30A and 30B respectively illustrate the enhanced in-vitro cytotoxicity of Lipo/DOX by BsAbs of example 4.1 in (A) SKBR3 cells (HER2$^+$) and (B) A431 cells (EGFR$^+$) in accordance with one embodiment of the present disclosure.
Figure 30B:
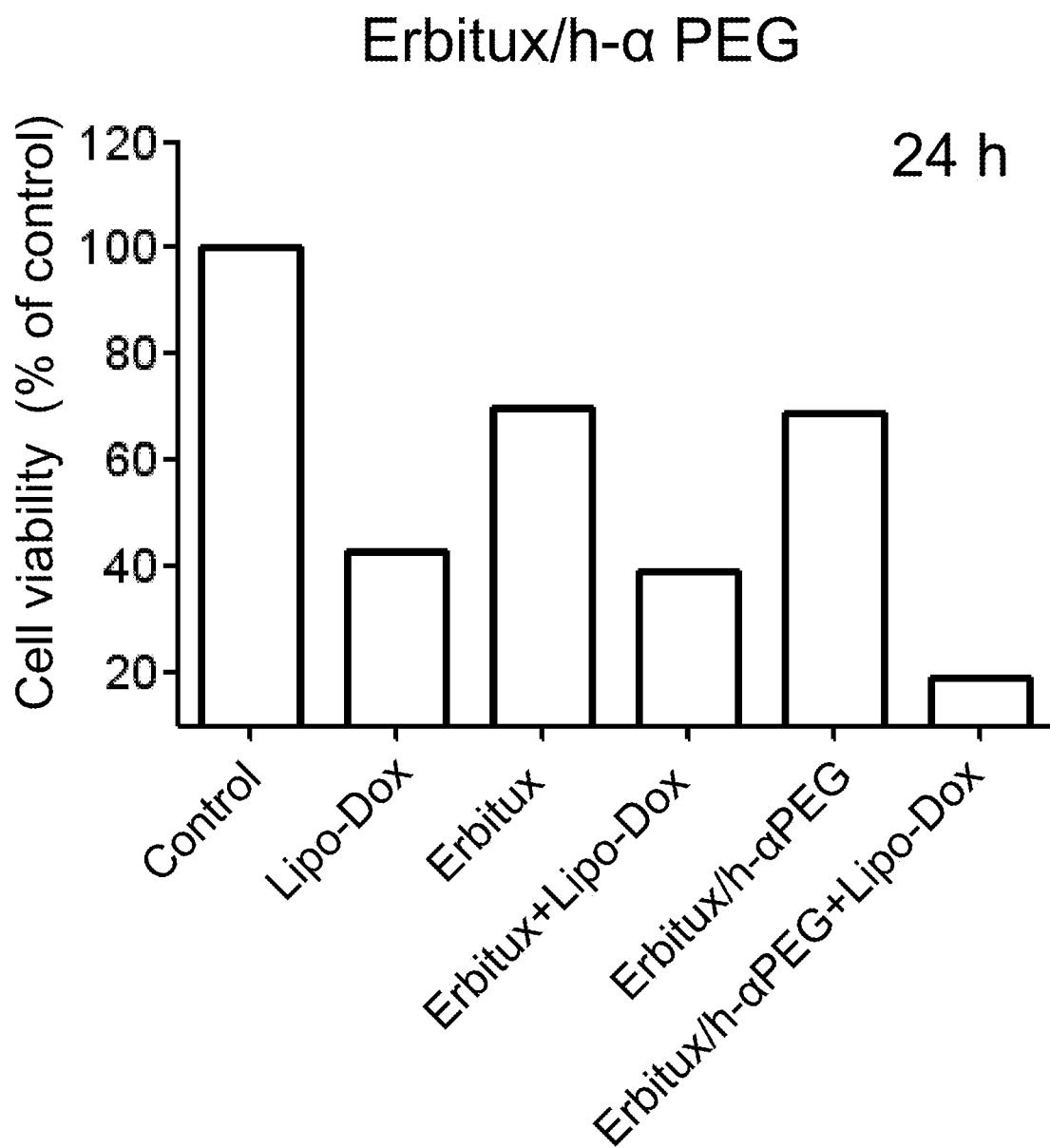

As expected, Herceptin/h-αPEG, but not control Herceptin antibodies, selectively bound Lipo-DOX to SKBR-3 cells (FIG. 30A). Similar results were also observed for A431 Human epithelial carcinoma cells, which exhibited an over expressed level of EGFR. Erbitux/h-αPEG, but not the control Erbitux antibodies, directed PEGylated compounds to be accumulated on the surface of A431 cells (EGFR+) (FIG. 30B).

Figure 31A:
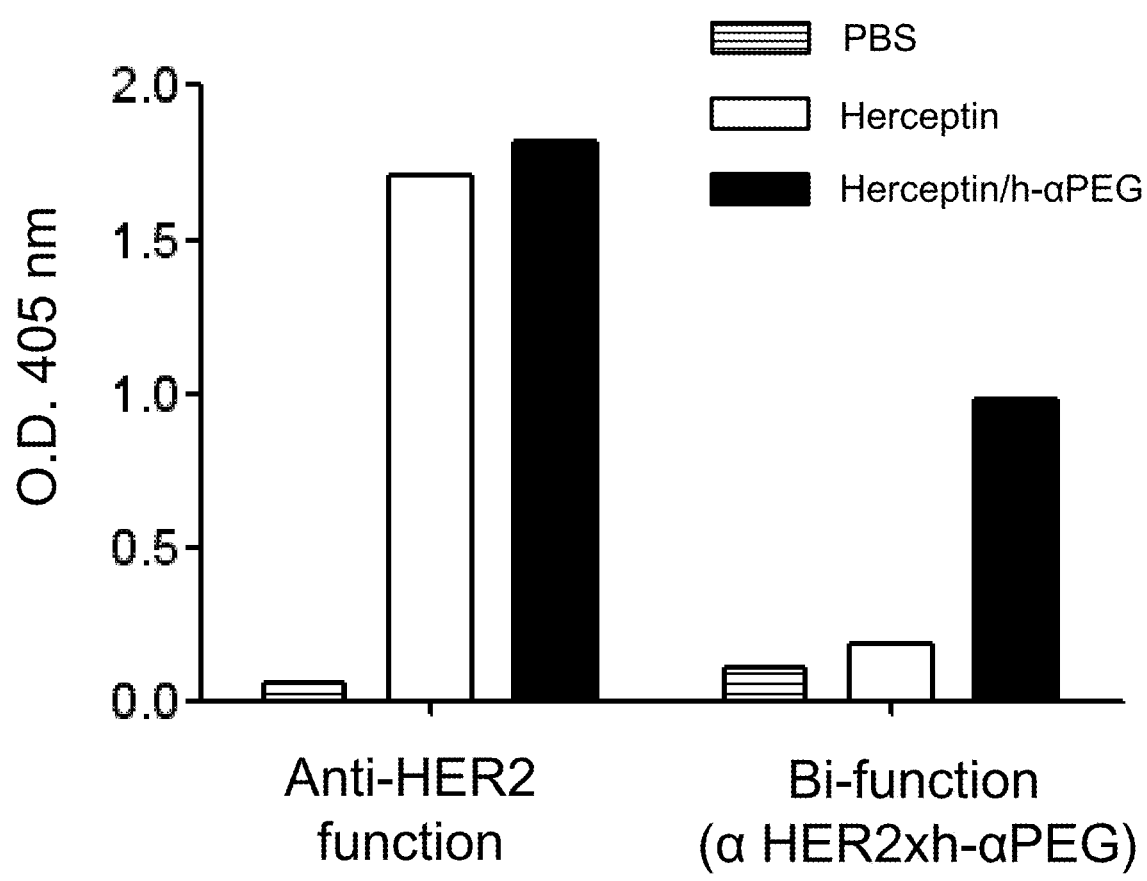
FIGS. 31A and 31B respectively illustrate the synergistic anti-cancer effects of Lipo/DOX by BsAbs of example 4.1 in (A) SKBR3 cells (HER2$^+$) and (B) A431 cells (EGFR$^+$) in accordance with one embodiment of the present disclosure.
Figure 31B:
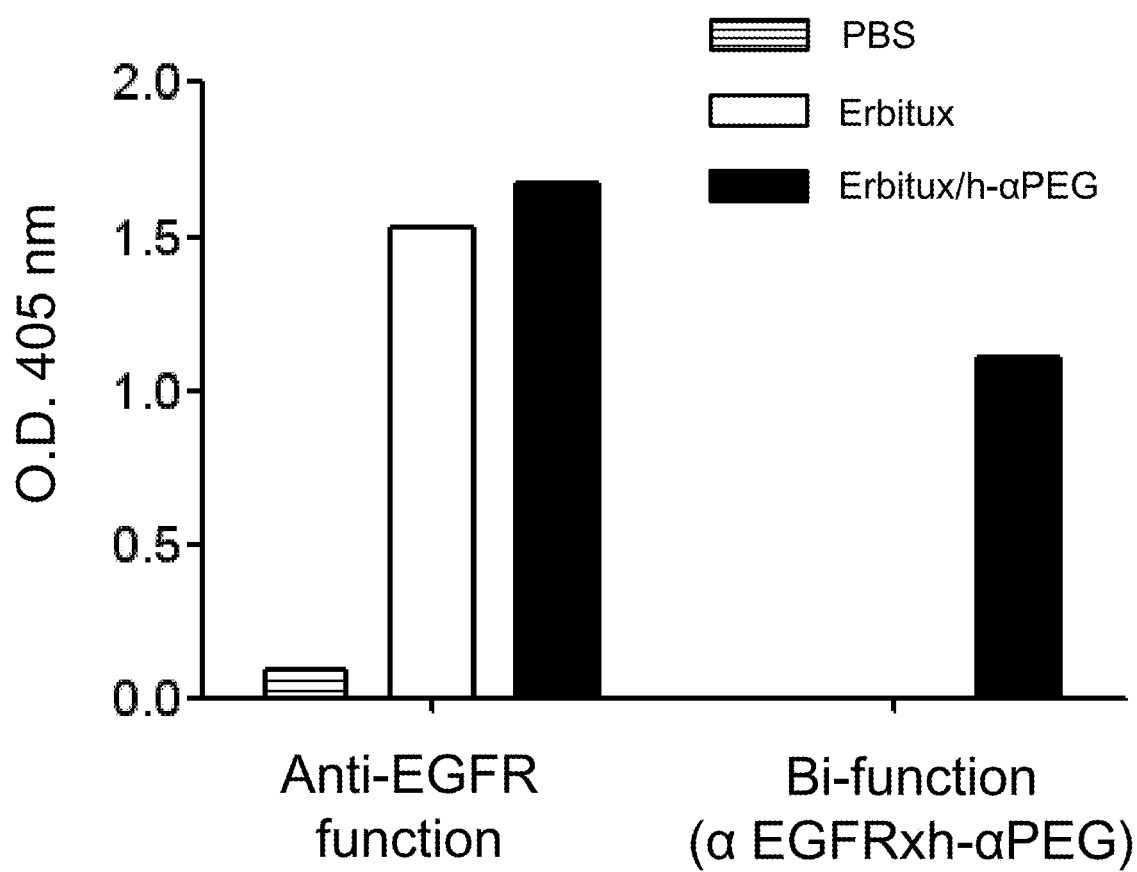

The anticancer effects of using BsAbs of example 4.1 to target Lipo-Dox to cancer cells was further examined in vitro. Results are depicted in FIGS. 31A and 31B.

It was confirmed that Herceptin/h-αPEG (FIG. 31A) and Erbitux/h-αPEG (FIG. 31B), but not control Abs, when respectively combined with Lipo-Dox exhibited synergistic anti-cancer effects, indicating that the double-attack strategy help attain a higher level of tumor-killing effect.

In a similar experiment, HER-2 positive SKBR-3 cells were pre-incubated with 5 μg/mL Herceptin/h-αPEG or Herceptin at 37° C. for 1 h. After washing to remove unbound Abs, cells were then treated with graded concentrations of Lipo-Dox (9, 3, and 0.33 μg/mL) in triplicate for 6 h. Drug-containing medium was then replaced with fresh medium and allowed the cells to continue incubation for an additional 72 hr. Cellular ATP synthesis in the drug-treated cells was then compared with that of the untreated cells.

Figure 32:
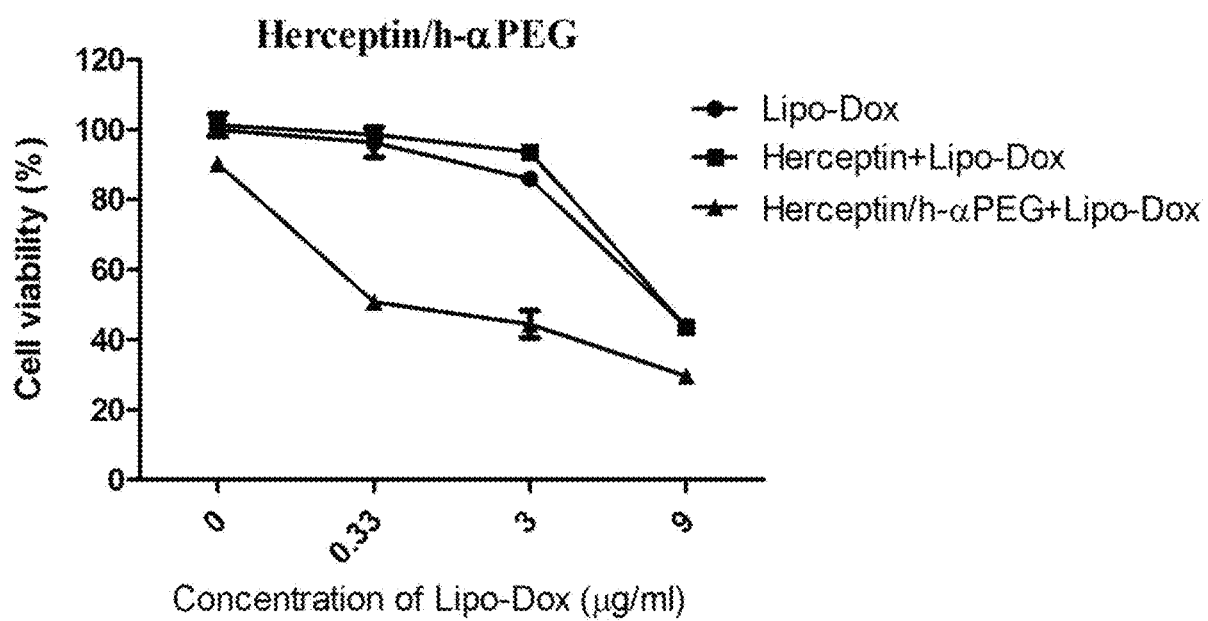
FIG. 32 illustrates the synergistic anti-cancer effects of Lipo/DOX by BsAbs of example 4.1 in SKBR3 cells (HER2$^+$) in accordance with one embodiment of the present disclosure.

It was found that cytotoxicity level was much higher in cells pre-treated with bi-specific Herceptin antibody and Lipo-Dox, than that of the cells treated with either Herceptin alone or Lipo-Dox alone (FIG. 32). The finding is in line with that of FIGS. 31A and 31B, in which a synergistic killing effect caused by Lipo-Dox and the anti-PEG BsAb was observed.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A humanized bi-specific antibody against the terminal methoxy or hydroxyl group of polyethylene glycol (PEG) and a target ligand on a cancer cell, comprising,
   a first antigen binding site that binds to the PEG, wherein the first antigen binding site comprises a first VL-Cκ domain and a first VH-CH1 domain; and
   a second antigen binding site that binds to the target ligand on the cancer cell, wherein the target ligand is HER2, EGFR, TAG-72, CD19 or CD20, wherein, the first VL-Cκ domain comprises a CDR1 having the sequence of SEQ ID NO: 221; a CDR2 having the sequence of SEQ ID NO: 222; and a CDR3 having the sequence of SEQ ID NO: 223; and
   the first VH-CH1 domain comprises a CDR1 having the sequence of SEQ ID NO: 224; a CDR2 having the sequence of SEQ ID NO: 225; and a CDR3 having the sequence of SEQ ID NO: 226; and
   the second antigen binding site comprises a single chain variable fragment (scFv).

2. The humanized bi-specific antibody of claim 1, wherein the first VL-Cκ domain has the sequence of SEQ ID NO: 12, and the first VH-CH1 domain has the sequence of SEQ ID NO: 13.

3. The humanized bi-specific antibody of claim 1, wherein the first antigen binding site further comprises a Knob Hinge CH2-CH3 domain connecting to the first VH-CH1 domain, wherein the Knob Hinge CH2-CH3 domain has the sequence of SEQ ID NO: 22.

4. The humanized bi-specific antibody of claim 1, wherein the first antigen binding site is Fab or single chain variable fragment (scFv).

5. A pharmaceutical kit comprising the humanized bi-specific antibody of claim 1; and a PEGylated substance, wherein the PEGylated substance is a protein, a peptide, and a nanoparticle, wherein the nanoparticle contains therein a chemotherapeutic drug or an imaging agent, wherein the protein is a chemokine or a cytokine; and the peptide is leuprolide, goserelin, octreotide, histrelin, abarelix, cetrorelix, degarelix, cilengtide, ATN-161 or IM862.

6. The pharmaceutical kit of claim 5, wherein the chemotherapeutic drug is adriamycin, amifostine, bleomycin, busulfan, cisplatin, carboplatin, oxaliplatin, camptothecin, CPT-11, cytosine arabinoside, chlorambucil, cyclophosphamide, cytarabine, daunorubicin, doxorubicin, docetaxel, dacarbazine, dactinomycin, etoposide, 5-fluorouracil (5-FU), fluoxuridine, gemcitabine, hydroxyurea, ifosfamide, idarubicin, interferon beta, irinotecan, L-asparaginase, L-aspartic acid, lomustine, mechlorethamine, mitomycin, methotrexate, mitoxantrone, megestrol, melphalan, mercaptopurine, mitotane, paclitaxel (taxol), plicamycin, pentostatin, streptozocin, topotecan, tamoxifen, teniposide, thioguanine, vinblastine, vincristine, SN38 or a combination thereof.

7. The pharmaceutical kit of claim 5, wherein the imaging agent is a quantum dot (QD), a microbubble contrast agent, a fluorescence dye, a chelated radioisotope a paramagnetic iron or a gold nanoparticle.

8. A method for treating a subject suffering from a cancer comprising:
   mixing a first amount of the humanized bi-specific antibody of claim 1 with a second amount of a PEGylated substance to form an assembly; and
   administering a therapeutically effective amount of the assembly either sequentially or concurrently to the subject to inhibit the growth of the cancer;
   wherein the PEGylated substance is therapeutic and is a protein, a peptide, and a nanoparticle, wherein the nanoparticle contains therein a chemotherapeutic drug, the protein is a chemokine or a cytokine; the peptide is leuprolide, goserelin, octreotide, histrelin, abarelix, cetrorelix, degarelix, cilengtide, ATN-161 or IM862; and the cancer is a cancer having the antigen of EGFR, HER2, TAG-72, CD19 or CD20.

9. The method of claim 8, wherein the chemotherapeutic drug is adriamycin, amifostine, bleomycin, busulfan, cisplatin, carboplatin, oxaliplatin, camptothecin, CPT-11, cytosine arabinoside, chlorambucil, cyclophosphamide, cytarabine, daunorubicin, doxorubicin, docetaxel, dacarbazine, dactinomycin, etoposide, 5-fluorouracil (5-FU), fluoxuridine, gemcitabine, hydroxyurea, ifosfamide, idarubicin, interferon beta, irinotecan, L-asparaginase, L-aspartic acid, lomustine, mechlorethamine, mitomycin, methotrexate, mitoxantrone, megestrol, melphalan, mercaptopurine, mitotane, paclitaxel (taxol), plicamycin, pentostatin, streptozocin, topotecan, tamoxifen, teniposide, thioguanine, vinblastine, vincristine, SN38 or a combination thereof.

10. The method of claim 8, wherein the cancer is breast cancer, colorectal cancer, colon cancer, hepatic cancer, non-Hodgkin's lymphoma, lymphoma, pancreatic cancer, lung cancer, gastric cancer, prostate cancer, brain tumor, retinoblastoma, ovary cancer, cervical cancer, hematopoietic malignances, esophageal cancer, renal cell carcinoma, squamous cell carcinoma, glioma, or leukemia.

11. A method of imaging tissues having an antigen of EGFR, HER2, TAG-72, CD19 or CD20 in a subject comprising:
   (a) mixing a first sufficient amount of the humanized bi-specific antibody of claim 1 and a second sufficient amount of a PEGylated imaging agent to form an assembly;
   (b) injecting the assembly of the step (a) to the subject so that the humanized bi-specific antibody of the assembly binds to the antigen of EGFR, HER2, TAG-72, CD19 or CD20 on the tissues; and
   (c) imaging the tissues having an antigen of EGFR, HER2, TAG-72, CD19 or CD20 of the subject by fluorescence imaging, electron spin resonance (ESR) imaging, X-ray imaging, computed tomography (CT), or magnetic resonance imaging (MRI);
   wherein the PEGylated imaging agent is a PEGylated fluorescence dye, a PEGylated microbubble contrast agent, a PEGylated chelated radioisotope, an PEGylated iron nanoparticle, a PEGylated gold nanoparticle, or a PEGylated quantum dot (QD).

* * * * *